US007919329B2

(12) United States Patent
Cowley et al.

(10) Patent No.: US 7,919,329 B2
(45) Date of Patent: Apr. 5, 2011

(54) METHOD FOR SCREENING FOR AGENTS THAT AFFECT FOOD INTAKE

(75) Inventors: Michael Cowley, Portland, OR (US); Roger Cone, Oregon City, OR (US); Malcolm Low, Lake Oswego, OR (US); Andrew Butler, Baton Rouge, LA (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 12/019,609

(22) Filed: Jan. 24, 2008

(65) Prior Publication Data
US 2008/0213803 A1 Sep. 4, 2008

Related U.S. Application Data

(63) Continuation of application No. 10/489,804, filed as application No. PCT/US02/30533 on Sep. 24, 2002, now abandoned.

(60) Provisional application No. 60/324,406, filed on Sep. 24, 2001, provisional application No. 60/392,109, filed on Jun. 28, 2002.

(51) Int. Cl.
G01N 33/566 (2006.01)
G01N 25/18 (2006.01)
G01N 27/00 (2006.01)
G01N 33/53 (2006.01)

(52) U.S. Cl. .................. 436/501; 436/149; 435/7.21

(58) Field of Classification Search .................. None
See application file for complete search history.

(56) References Cited

U.S. PATENT DOCUMENTS

| | | | |
|---|---|---|---|
| 4,175,122 A | 11/1979 | Lazarus | |
| 4,223,017 A | 9/1980 | Lazarus | |
| 4,355,025 A | 10/1982 | Lazarus | |
| 4,701,441 A | 10/1987 | Kalra | |
| 5,696,093 A | 12/1997 | Tseng et al. | |
| 5,912,227 A | 6/1999 | Croom, Jr. et al. | |
| 5,919,901 A | 7/1999 | Hu et al. | |
| 5,965,392 A | 10/1999 | Hu et al. | |
| 5,989,920 A | 11/1999 | Gerald et al. | |
| 6,001,970 A | 12/1999 | Cascieri et al. | |
| 6,316,203 B1 | 11/2001 | Gerald et al. | |
| 7,375,111 B2 | 5/2008 | Weber et al. | |
| 7,462,626 B2 | 12/2008 | Weber et al. | |
| 2002/0141985 A1 | 10/2002 | Pittner et al. | |

FOREIGN PATENT DOCUMENTS

| | | |
|---|---|---|
| WO | WO 97/46579 | 12/1997 |
| WO | WO 01/68699 A2 | 9/2001 |
| WO | WO 02/47712 | 6/2002 |
| WO | WO 03/026591 | 4/2003 |

OTHER PUBLICATIONS

Young et al. J. Neurosci., 1998, 18 (17), pp. 6631-6640.*
U.S. Appl. No. 60/256,216, filed Dec. 14, 2000, Pittner et al.
Adrian et al., *Gastroenterology* 89, 1070-1077 (1985).
Allen et al., *Digestion* 30:255-262, 1984.
Bagnol et al., *J Neurosci (Online)* 19, RC26 (1999).
Barrachina et al., *Am. J. Physiol.* 272, R1007-11 (1997).
Barsh et al., *Nature* 404, 644-651 (2000).
Batterham et al., *Nature* 418:650-654, 2002.
Broberger, et al., "Subtypes Y1 and Y2 of the Neuropeptide Y Receptor Are Respectively Expressed in Pro-Opiomelanocortin- and Neuropeptide-Y-Containing Neurons of the Rat Hypothalamic Arcuate Nucleus," *Neuroendocrinology*, 66:393-408 (1997).
Broberger-C et al., *Neuroendocrinology*, 66(393-408) 1997.
Butler et al., *Endocrinology* 141, 3518-21 (2000).
Butler et al., *Nature Neuroscience* 4, 605-611 (2001).
Butler, et al., "A unique metabolic syndrome causes obesity in the melanocortin-3 receptor-deficient mouse," *Endocrinology* 141(9):3518-3521, 2000.
Campfield et al., *Science* 269, 546-9 (1995).
Comuzzie et al., *Nature Genetics* 15:273-276, 1997.
Cone, *Trends Endocrinol Metab* 10, 211-216 (1999).
Cowley et al., *Neuron* 24, 155-63. (1999).
Cowley, et al., "Leptin activates anorexigenic POMC neurons through a neural network in the arcuate nucleus," *Nature* 411:480-484, 2001.
Csiffary et al., *Brain Res* 506, 215-22 (1990).
Edwards et al., *Am. J Physiol. Endocrinol. Metab.* 281, E155-E166, (2001).
Ekblad and Sundler, *Peptides* 23:251-261, 2002.
Elias et al., *Neuron* 23, 775-86 (1999).
Fan, et al., "Role of melanocortinergic neurons in feeding and the agouti obesity syndrome," *Nature* 385:165-168, 1997.
Farooqi et al., *N Engl J Med* 341, 879-84 (1999).
Glaum et al., *Mol Pharmacol* 50, 230-5 (1996).
Grandt et al., *Regul. Pept.* 51, 151-159 (1994).
Grieco et al., *J Med Chem* 43, 4998-5002 (2000).
Grove et al., *Neuroscience* 100, 731-40 (2000).
Hagan, "Peptide YY: a key mediator of orexigenic behavior," *Peptides* 23:377-382, 2002.
Hager et al., *Nature Genetics* 20:304-308, 1998.
Hakansson et al., *J Neurosci* 18, 559-72 (1998).
Halaas et al., *Proc Natl Acad Sci USA* 94, 8878-83 (1997).
Hammer et al., *Mol. Endocrin.* 4(11):1689-1697, 1990.
Harding and McDonald, "Identification and characterization of the emetic effects of peptide YY," *Peptides* 10:21-24, 1989.
Haynes et al. *J Clin Invest* 100, 270-8 (1997).
Haynes et al., *Hypertension* 33, 542-7 (1999).
Heisler, et al., "Activation of central melanocortin pathways by fenfluramine," *Science* 0:1-3, 2002.
Hoffman et al., *Front. Neuroendocrinol.* 14, 173-213 (1993).
Horvath et al., *Brain Res* 756, 283-6 (1997).

(Continued)

Primary Examiner — Olga N Chernyshev
(74) Attorney, Agent, or Firm — Klarquist Sparkman, LLP

(57) ABSTRACT

Screening methods of use in identifying agents that affect caloric intake, food intake, appetite, and energy expenditure are disclosed herein. These methods are used to identify agents of use in treating obesity, or that can be used to decrease the weight of a subject. These methods can also be used to identify agents of use in treating anorexia or cachexia and can be used to increase appetite and to increase the weight and lean body mass of a subject.

15 Claims, 13 Drawing Sheets

OTHER PUBLICATIONS

Horvath et al., *Neuroscience* 51, 391-9 (1992).
Ibrahim-N et al., *Society of Neuroscience*, Abstracts, 27(2)p. 1946, 2001.
Iyengar, et al., "Characterization of neuropeptide Y-induced feeding in mice: do Y1-Y6 receptor subtypes mediate feeding?" *The Journal of Pharmacology and Experimental Therapeutics* 289(2):1031-1040, 1999.
Kalra et al., *Endocr. Rev.* 20, 68-100 (1999).
Keire et al., *Am. J Physiol. Gastrointest. Liver Physiol.* 279, G126-131 (2000).
Kelly et al., *Neuroendocrinology* 52, 268-75 (1990).
Kim et al., *Diabetes* 49, 177-82 (2000).
Kim et al., *J Clin. Invest.* 105, 1005-11 (2000).
King et al., *J Neurochem* 73, 641-6 (1999).
Kirby et al., *J. Med. Chem.* 36:385-393, 1993.
Krude and Grüters, *TEM* 11(1):15-22, 2000.
Krude et al., *Nature Genetics* 19:155-157, 1998.
Lee et al., *J Physiol (Lond)* 515, 439-52 (1999).
Liu et al., *Biochem. J.* 312:827-832, 1995.
Liu et al., *Mol. & Cell.Biol.* 12(9):3978-3990, 1992.
Low et al., Chapter 15: "Transgenic Analysis of the Proopiomelanocortin Neuroendocrine System," in *Contemporary Endocrinology: Transgenics in Endocrinology*, Matzuk et al., eds., Humana Press, Totowa, NJ, 319-337, 2001.
Low et al., *J. Biol. Chem.* 268(33):24967-24975, 1993.
Low, M., Chapter 12: "The Identification of Neuropeptide Gene Regulatory Elements in Transgenic Mice," in *Methods in Molecular Biology*, vol. 13: *Protocols in Molecular Neurobiology*, Longstaff & Revest, eds., Humana Press, Totowa, NJ, 181-202, 1992.
Lyznicki et al., *Amer. Family Phys.* 63(11):2185-2196, 2001.
Malaisse-Lagae et al., *Experientia* 33(7):915-917, 1977.
Marks, et al., "Role of the central melanocortin system in cachexia," *Cancer Research* 61:1432-1438, 2001.
Moran, *Nutrition* 16, 858-865 (2000).
Naveilhan et al., *Peptides* 23(6):1087-1091, 2002.
Naveilhan, et al., "Normal feeding behavior, body weight and leptin response require the neuropeptide Y Y2 receptor," *Nature Medicine* 5(10):1188-1193, 1999.
Naveilhen et al., *J. Neurochem.* 78:1201-1207, 2001.
Okada et al., "Peripherally not centrally administered peptide YY (PYY) decreases high fat diet intake," Abstract 520, 75$^{th}$ Annual Meeting, The Endocrine Society, Las Vegas, Nevada, Jun. 9-12, 1993.
Pedersen-Bjergaard et al., *Scand. J Clin. Lab. Invest.* 56, 497-503 (1996).
Potter et al., *Eur. J. Pharmacol.* 267, 253-262 (1994).
Powis et al., *Am J Physiol* 274, R1468-72 (1998).
Raben et al., *Br. J Nutr.* 73, 517-30 (1995).
Rubinstein et al., *Neuroendocrinol.* 58:373-380, 1993.
Schwartz et al., *Nature* 404, 661-671 (2000).
Shiraishi et al., *Nutrition* 15, 576-9 (1999).
Slugg et al., *Neuroendocrinology* 72, 208-17 (2000).
Small et al., *Proc. Natl. Acad. Sci. USA* 94, 11686-91 (1997).
Smart & Low, Chapter 9: "Spontaneous and Induced Genetic Mutations of the POMC System," *Transgenic Models in Endocrinology*, Maria Castro, ed., U. of Manchester, UK, pp. 175-194, 2001.
Soderberg et al., *J. Neurochem.* 75, 908-18 (2000).
Spanswick et al., *Nature* 390:521-525, 1997.
Tarling et al., *Intensive Care Med.* 23, 256-260 (1997).
Tsukada et al., *DNA and Cell Biol.* 13(7):755-762, 1994.
Wang X et al., Abstract, *Life Science*, 1994;55(11)847.
Wardlaw, S., *J. Clin. Endocrin. & Metab.* 86(4):1442-1446, 2001.
Yoshinaga et al., *Am J Physiol Gastrointest Liver Physiol* 263: G695-G701, 1992.
Young-Ji et al., *Journal of Neuroscience*, 18(17)6631-6640, Sep. 1, 1998.
Zhang et al., [published erratum appears in Nature Mar. 30 1995;374(6521):479], *Nature* 372, 425-32 (1994).
Seeley, "Melanocortin receptors in leptin effect," *Nature*, 390:349 Nov. 27, 1997.
Yaswen et al. "Obesity in the mouse model of pro-opiomelanocortin deficiency responds to peripheral melanocortin," *Nature Medicine*, 5(9):1066-1070 Sep. 1999.
Cowley et al., "The Distribution and Mechanism of Action of Ghrelin in the CNS Demonstrates a Novel Hypothalamic Circuit Regulating Energy Homeostasis," *Neuron* 37:649-661, (Feb. 20, 2003).
Heisler et al., "Activation of Central Melanocortin Pathways by Fenfluramine," *Science* 297:609-611 (Jul. 26, 2002), with Supplemental Materials.
Nakazato et al., "A Role for Ghrelin in the Centralregulation of Feeding," *Nature* 409:194-198 (Jan. 11, 2001).

* cited by examiner

FIG. 1
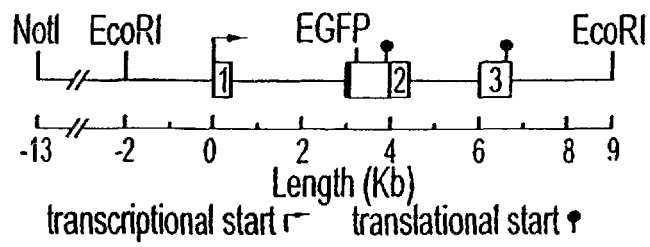
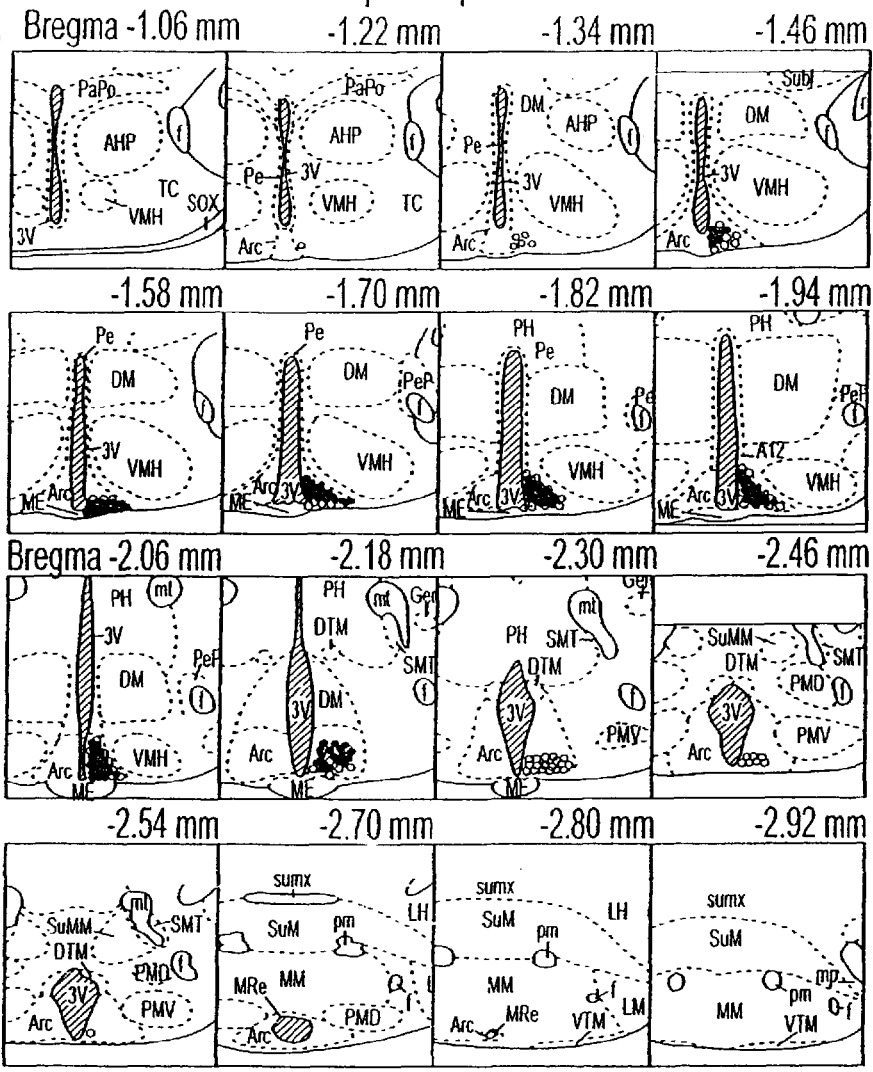

FIG. 10

FIG. 11 nPOMC 1 element

Mouse Chromosome 12 nucleotides 3,808,013 - 3,808,447

GACTGAGCTGAGTGCCTGTAAAAAGGCCACTTCAAGCCCCATTGTGGGGACAGCAGCAGGTGGGCA
AGTCTGAGCTTTGAATGCCTCTTCCCGTGATGCACTACGCTAATGGATGTGCATTAACAGTGTCCT
TCCTGGCCACCGCATCGCTCGCCTTTCCTCAGGCCCTGCTGGAGAACTCTGCATTCCTGAGGAAGG
GCAGCAGTCAGTGCCTAAAGGCCCCAGAATGGGGCCATTGTGGTCATCACTGAGTCACACTAGTGA
CTACTGGCACCTGAGCTCAGTCTGGAGTAAGTGGTTTCAGGGACGTCATCTGGGAGAGTCTGGTGC
GAGTCTAACGTCCAGGACATTTTCAGCAAAGACTGCACCTCCAGGAAGTCCATTCTGACTGCCCAG
AAACAAACCCTCATTTTGAAAAGAGAGTTTGGGCTAAGG nPOMC 1 element

Human Chromosome 2 nucleotides 2,324,416 - 2,323,942 (REVERSE
COMPLEMENT STRAND)

GACTGAGCTGAGTGCCTGTAAAAAGGCCACTTCAAGCCCCCTCCACGCAGCCATTGTTGGGTCTGG
AGGAAGGAGGACCGCTCGGAAGCTTCTGAATGCCGCCCTGTGATGCACTCACTAATGGATGTGCAT
TAGTGGCGTCCTTCCTGGCCACCACGTCACTCTCCCTACCTCAACTGCTGGCTGGAGAACTCCGCA
TTCTTCTGGAAAAGTAGCAGTCATGCTCGAGCCCCTAACAAAGGCCTGTCCCCCACAAAAGGACCA
TTATGACCACCGCTGAGTCAGAATGGTGGCCGCTGGCACCTGAGCTCTGTCTGGAAAGAGCGGCAG
CAGGGACGTCATCTAGCAGAGCCTGGTGTGTCTGTTATGTCCACAACATCTTCAGCAAAGACACTA
CTTCCAGGAAGTCTACTTGGATTGCAGAGGCGCAAGCCTTCATTGTGAAAAAGGGCTTGGGATAA
GG nPOMC 2 element

Mouse Chromosome 12 nucleotides 3,810,489 - 3,810,724
GGCTGGGGTGGGCTACTGTGCTAATACATGCATTAGTGGATGAAAGCCGTCTCAAGGGGCTCTTCA
CCAGGGCCCTTTGGCTGTAATAAAGCAAATTAAAACCCCATCCAAAGGTCAATTGAAATCTCTTTC
ATTCTTCTTCTCCACACAAATTGATTCCTCTTTGCCCTTGAGGTTGCACTGAATGCCATAAAGGGG
CCCAGCTGTAGCTGGATGGGAACAGCCTGAAAATGGCT nPOMC 2 element

Human Chromosome 2 nucleotides 2,322,890 - 2,322,659 (REVERSE
COMPLEMENT
STRAND)GGCTGCTGCACTAATGCGCGCATTAGTGGATAAAAGCAGTCTCAAGGGTCTCTTCACGA
GGTCCCTTTGGCTGGAATAAAGCAAATTAAAACCCCATTCAAAGGTCAATTGAAATCTCTTTCATT
CCAGTTCTCTGCACAAATTGATTCCTCTTTGCCCTTGAGGTCAAACCGAAGGCTGGTGAAGTAGCC
CAGCTGCAGTGCTGCATGAGAGAAGCTCAATGAAAAGGCT

METHOD FOR SCREENING FOR AGENTS THAT AFFECT FOOD INTAKE

PRIORITY CLAIM

This application is a continuation of U.S. application Ser. No. 10/489,804, filed Mar. 16, 2004 now abandoned, which is incorporated by reference in its entirety herein. U.S. application Ser. No. 10/489,804 is a §371 U.S. National Stage of International Application No. PCT/US02/30533, filed Sep. 24, 2003, which was published in English under PCT Article 21(2), which in turn claims the benefit of U.S. Provisional Application No. 60/324,406, filed Sep. 24, 2001, and U.S. Provisional Application No. 60/392,109, filed Jun. 28, 2002, which are incorporated by reference in their entirety herein.

STATEMENT OF GOVERNMENT SUPPORT

This invention was made with United States government support pursuant to grants TW001233, RR00163, DK51730 and DK55819, from the National Institutes of Health. The United States government has certain rights in the invention.

FIELD

This application relates to the field of weight gain and reduction, specifically to screening for agents that can be used to control appetite, food intake, and calorie intake. Methods for screening for agents that can be used to treat obesity, and related disorders, are disclosed. Methods are also disclosed for screening for agents that can be used to treat cachexia, anorexia, and other disorders of energy homeostasis.

BACKGROUND

According to the National Health and Nutrition Examination Survey (NHANES III, 1988 to 1994), between one third and one half of men and women in the United States are overweight. In the United States, sixty percent of men and fifty-one percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index. Indeed, this risk has been quantified as a five percent increase in the risk of cardiac disease for males, and a seven percent increase in the risk of cardiac disease for females, for each point of a BMI greater than 24.9 (see Kenchaiah et al., N. Engl. J. Med. 347:305, 2002; Massie, N. Engl. J. Med. 347: 358, 2002). In addition, there is substantial evidence that weight loss in obese persons reduces important disease risk factors. Even a small weight loss, such as 10% of the initial body weight, in both overweight and obese adults has been associated with a decrease in risk factors such as hypertension, hyperlipidemia, and hyperglycemia.

Although diet and exercise provide a simple process to decrease weight gain, overweight and obese individuals often cannot sufficiently control these factors to effectively lose weight. Weight loss surgery is an option in carefully selected patients with clinically severe obesity. However, these treatments are high-risk, and a suitable for use in only a limited number of patients. Limited pharmacotherapy is available; several weight loss drugs have been approved by the Food and Drug Administration that can be used as part of a comprehensive weight loss program. However, there remains a need for agents that can be used to effect weight loss in overweight and obese subjects.

Under normal circumstances, animals and humans respond to starvation with a complex neuroendocrine response that ultimately leads to an increase in appetite, a relative sparing of lean body mass and burning of fat stores, and an overall decrease in basal metabolic rate (Webber & Macdonald, 1994, Brit. J. Nutr. 71:437-447; Ahima et al., 1996, Nature 382:250-252). In contrast, in some diseases a devastating pathological state of malnutrition known as cachexia arises, brought about by a synergistic combination of a dramatic decrease in appetite and an increase in metabolic rate and metabolism of both fat and lean body mass, producing a relative wasting of lean body mass (Tisdale, 1997, J. Natl. Cancer Inst. 89:1763-1773; Inui, 1999, Cancer Res. 59:4493-4501; Fong et al., 1989, Amer. J. Phys. 256:R659-R665; Bruera, 1997, Brit. Med. J. 315:1219-1222; Emery, 1999, Nutrition 15:600-603). This combination is found in a number of disorders including cancer, cystic fibrosis, AIDS, rheumatoid arthritis, and renal failure (Tisdale, 1997, ibid.).

The severity of cachexia in many illnesses may be the primary determining factor in both quality of life, and in eventual mortality (Tisdale, 1997, ibid.; Larkin, 1998, Lancet 351:1336). Indeed, body mass retention in AIDS patients has a stronger correlation with survival than any other current measure of the disease (Kotler et al., 1989, Amer. J. Clin. Nutr. 50:444-447). Many different tumor types have been studied and it is a common finding that tumor-bearing animals die from cachexia and exhaustion of metabolic fuels, rather than from metastasis or infection (Svaninger et al., 1987, J. Natl. Cancer Inst. 78:943-950; Emery, 1999, Nutrition 15:600-603; Svaninger et al., 1989, Eur. J. Cancer Clin. Oncol. 25:1295-1302; Emery et al., 1984, Cancer Res. 44:2779-2784). Cachexia is commonly observed in patients with cancer, particularly in children and elderly individuals (Bruera, 1997, ibid.). The resulting malnutrition and loss of lean body mass reduces the quality of life for the affected individual and compromises recovery by decreasing tolerance to therapy and increasing post-surgical complications (Larkin, 1998, ibid.; Inui, 1999, ibid.).

Attempts at drug therapy for cachexia with a variety of agents has met with limited success (DeConno et al., 1998, Eur. J Cancer 34:1705-1709; Windisch et al., 1998, Ann. Pharmacother. 32:437-445; Rivandeneria et al., 1999, Nutr. Cancer 35:202-206; McCarthy, 1999, Res. Nurs. Health 22:380-387). The most widely utilized agent, megestrol acetate, has shown some promise in reversing weight loss, but this is primarily due to increases in fat mass and water retention, rather than preservation of lean body mass (Strang, 1997, Anticancer Res. 17:657-662). Thus, there is clearly a need to identify new agents that can be used in the treatment of cachexia and that may of use in treating other disorders, such as anorexia.

SUMMARY

Screening methods of use in identifying agents that affect caloric intake, food intake, appetite, and energy expenditure are disclosed herein. These methods are used to identify agents of use in treating obesity, or that can be used to decrease the weight of a subject. These methods are also of use to identify agents of use in treating cachexia or anorexia, or that can be used to increase the weight of a subject.

A method is disclosed herein for screening for an agent that affects caloric intake. The method includes contacting a histological section of an arcuate nucleus from a mouse expressing a marker in proopiomelanocortin neurons with an agent to be tested. The mouse comprises a transgene comprising a nucleic acid encoding the marker operably linked to a proopiomelanocortin nucleic acid sequence, wherein the proopiomelanocortin nucleic acid sequence directs expression of the marker in proopiomelanocortin neurons in the arcuate nucleus of the mouse. An electrophysiological response of a proopiomelanocortin neuron in the histological section is assessed, thereby determining if the agent affects caloric intake.

A method is disclosed herein for screening for an agent that affects food intake. The method includes contacting a histological section of an arcuate nucleus from a mouse expressing a marker in proopiomelanocortin neurons with an agent to be tested. The mouse comprises a transgene comprising a nucleic acid encoding the marker operably linked to a proopiomelanocortin nucleic acid sequence, wherein the proopiomelanocortin nucleic acid sequence directs expression of the marker in proopiomelanocortin neurons in the arcuate nucleus of the mouse. An electrophysiological response of a proopiomelanocortin neuron in the histological section is assessed, thereby determining if the agent affects food intake.

A method is disclosed herein for screening for an agent that affects appetite. The method includes contacting a histological section of an arcuate nucleus from a mouse expressing a marker in proopiomelanocortin neurons with an agent to be tested. The mouse comprises a transgene comprising a nucleic acid encoding the marker operably linked to a proopiomelanocortin nucleic acid sequence, wherein the proopiomelanocortin nucleic acid sequence directs expression of the marker in proopiomelanocortin neurons in the arcuate nucleus of the mouse. An electrophysiological response of a proopiomelanocortin neuron in the histological section is assessed, thereby determining if the agent affects appetite.

A method is disclosed herein for screening for an agent that affects caloric intake, appetite, energy expenditure or food intake. The method includes contacting a histological section of an arcuate nucleus, with an agent to be tested. Proopiomelanocortin neurons in the histological section express a heterologous marker that distinguishes the proopiomelanocortin neurons from other cells in the histological section. An electrophysiological response of a proopiomelanocortin neuron in the histological section is assessed, thereby determining if the agent affects caloric intake, appetite, energy expenditure, or food intake.

The foregoing and other features and advantages will become more apparent from the following detailed description of several embodiments, which proceeds with reference to the accompanying figures.

BRIEF DESCRIPTION OF THE FIGURES

FIG. 1 is a set of diagrams and digital images showing the generation of transgenic mice expressing EGFP in ARC POMC neurons. FIG. 1a is a schematic diagram of the structure of the POMC-EGFP transgene. FIG. 1b is a digital image showing the identification of a single POMC neuron (arrowhead on recording electrode tip) by EGFP fluorescence (upper) and IR-DIC microscopy (lower) in a living ARC slice prior to electrophysiological recordings. FIG. 1c is a set of digital images showing the co-localization (bright, on right) of EGFP (left) and β-endorphin immunoreactivity (middle) in ARC POMC neurons. Scale bars: b & c, 50 μm. FIG. 1d is a set of diagrams showing the distribution of EGFP-positive neuronal soma throughout the ARC nucleus. o=5 cells, ●=10 cells.

FIG. 2a is a tracing showing met-enkephalin hyperpolarizes POMC neurons and inhibits all action potentials. The horizontal bar indicates the time when 30 μM Met-Enk was bath-applied to the slice. FIG. 2b is a graph showing met-enkephalin current and reversal potential is shifted by extracellular $K^+$ concentration. FIG. 2c is a graph showing met-enkephalin activates MOP-Rs on POMC neurons. A Met-Enk (30 μM) current was observed and the MOP-R specific antagonist CTAP (1 μM) was applied for 1 minute. Following CTAP Met-Enk elicited no current. The figure is representative of three experiments.

FIG. 3a is a tracing demonstrating that leptin depolarizes POMC neurons and increases the frequency of action potentials within 1 to 10 minutes of addition. The figure is a representative example of recordings made from 77 POMC neurons. FIG. 3b is a graph showing that leptin causes a concentration dependent depolarization of POMC cells. The depolarization caused by leptin was determined at 0.1, 1, 10, 50, and 100 nM ($EC_{50}$=5.9 nM) in (8, 7, 9, 3, 45) cells respectively. FIG. 3c is a graph showing that leptin depolarizes POMC cells by activating a nonspecific cation current. The figure is representative of the response in 10 cells. FIG. 3d is a graph showing that leptin decreases the frequency of IPSCs in POMC cells. The figure is an example of 5 cells in which leptin (100 nM) decreased the frequency of IPSCs. FIG. 3e is a tracing demonstrating that leptin had no effect on 5 adjacent non-fluorescent ARC neurons. FIG. 3f is a tracing showing that leptin hyperpolarized 5 non-fluorescent ARC neurons.

FIG. 4a is a graph showing that NPY decreases the frequency of mini IPSCs in POMC neurons. FIG. 4b is a graph demonstrating that D-Trp$^8$-γMSH (7 nM), a dose that selectively activates MC3-R, increases the frequency of GABAergic IPSCs in POMC neurons. FIG. 4c is a tracing showing that D-Trp$^8$-γMSH hyperpolarizes POMC neurons. FIGS. 4a, 4b and 4c are representative. FIG. 4d is a set of digital images demonstrating that expression of NPY in nerve terminals adjacent to POMC neurons in the ARC. NPY nerve terminals (black, arrowheads); POMC neuronal soma (grey). Scale bar, 10 μm. FIG. 4e is a digital image showing expression of GABA and NPY in nerve terminals synapsing onto POMC neurons in the ARC. GABA immunoreactivity (10 nm gold particles, arrowheads without tail) and NPY immunoreactivity (25 nm gold particles, arrows with tail) are in separate vesicle populations co-localized within synaptic boutons that make direct contact with the soma of POMC neurons (DAB contrasted with uranyl acetate and lead citrate, diffuse black in cytoplasm). Scale bar, 1 μm. FIG. 4f is a diagram of the model of NPY/GABA and POMC neurons in the ARC.

FIGS. 5a and 5b are digital images of representative sections (bregma—1.4 mm) of c-fos expression in the arcuate nucleus of Pomc-EGFP mice response to intraperitoneal saline (FIG. 5a) or PYY$_{3-36}$ (5 μg/100 g) (FIG. 5b). Scale bar 100 μm. 3V, third ventricle; Arc, arcuate nucleus. FIGS. 5c and 5d are digital images of representative sections showing POMC-EGFP neurones (FIG. 5c) and c-fos immunoreactivity (FIG. 5d) either co-localising (bright arrows) or alone (single darker arrow). Scale bar 25 μm.

FIG. 6a is a tracing and bar graph showing the effect of PYY$_{3-36}$ (10 nM) on the frequency of action potentials in POMC neurons (whole-cell configuration recordings; n=22) *p<0.05. PYY$_{3-38}$ was administered at time D for 3 minutes; baseline, −3 to 0 minute; PYY$_{3-36}$, 2-5 minutes; and wash-out, 8-11 minutes. Inset shows a representative recording of membrane potential and action potential frequency. FIG. 6b is a graph of the effect if PYY$_{3-38}$ (10 nM) on the frequency of action potentials in loose cell-attached patch recordings (n=8). Data from individual cells were normalized to the firing rate for the 200 s before PYY$_{3-38}$ addition. FIG. 6c is a tracing and a graph of the effect of PYY$_{3-38}$ (50 nM) on spontaneous IPSCs onto POMC neurons (n=13). Inset shows a representative recording of IPSCs before and after PYY$_{3-36}$ (50 nM), respectively, results in FIG. 6a-6 c are expressed as mean±s.e.m.

FIG. 8a is a digital image showing fluorescence in POMC neurons of the arcuate nucleus of the hypothalamus in a −13/+8 POMC-EGFP (delta −6.5/0.8) transgenic mouse. FIG. 8b is a digital image showing immunofluorescence histochemistry using an antisera specific for human growth hormone. POMC neurons in the arcuate nucleus of a −13/−9 POMC-TKhGH transgenic mouse express the hGH marker. FIG. 8c is a digital image of higher power magnification of neuronal cell bodies and processes from FIG. 8b.

FIG. 9a is a PIP Maker multiple sequence alignment between 24 kb containing the human POMC gene, 4 kb of the mouse 5' flanking region located between 9 and 13 kb from the TATA box, and the three exons with short flanking sequences obtained from Genebank (J00610, J00611, and J00612). Conserved regions are indicated with horizontal black lines on gray shaded background. Exons 1, 2, and 3 are indicated; repetitive intergenic regions are present at −5 kb and −6 kb; two highly conserved intergenic regions longer than 100 bp are identified as nPOMC1 and nPOMC2. The gray and white horizontal boxes indicated GC-rich regions. FIG. 9b is a similar analysis performed with the Dotter program using the 4 kb between −13 and −9 of the mouse POMC gene and 15 kb of the human 5' flanking region. Diagonal lines inside the gray-shaded areas indicate the conserved sites nPOMC1 and nPOMC2.

FIG. 10 is the sequence alignments of nPOMC1 (5' half, human (SEQ ID NO: 336, cow (SEQ ID NO: 337), hamster (SEQ ID NO: 338), mouse (SEQ ID NO: 339), and rat (SEQ ID NO: 340)), nPOMC1 (3' half, human (SEQ ID NO: 341), mouse (SEQ ID NO: 342), and rat (SEQ ID NO: 343)) and nPOMC2 (human (SEQ ID NO: 344), Cow (SEQ ID NO: 345), mouse (SEQ ID NO: 346) and rabbit (SEQ ID NO: 347).

FIG. 11 is the nucleotide sequences of mouse and human nPOMC1 and nPOMC2 elements. nPOMC1 element from mouse chromosome 12 nucleotides 3,808,013-3,808,447 (SEQ ID NO: 348), nPOMC1 element from human chromosome 2 nucleotides 2,324,416-2,323,942 (SEQ ID NO: 349), nPOMC2 element from mouse chromosome 12 (SEQ ID NO: 350) and the nPOMC2 element from human chromosome 2 (SEQ ID NO: 351) are shown.

FIG. 12a is a graph demonstrating that Ghrelin increases the frequency of spontaneous synaptic GABA release onto POMC neurons. Results shown in the figure are representative of 18 experiments. Increased release of GABA from NPY neurons is shown, thus Ghrelin is increasing the activity of NPY neurons. FIG. 12b is a graph demonstrating that Ghrelin mildly hyperpolarizes POMC neurons and decreases the spontaneous activity of POMC neurons. Results shown in the figure are representative of 34 experiments. FIGS. 12a and 12b were recorded in conventional whole cell mode. FIG. 12c is a graph demonstrating that Ghrelin decreases the frequency of action potentials in POMC neurons, an effect that reverses with washout of the drug. Ghrelin induced a 50% decrease of the normalized mean (+/−s.e.m.) POMC neuron firing rate. These recordings were made in loose-cell-attached mode.

FIG. 13a shows the results obtained using a loose-cell-attached mode. d-FEN (20 microM) induced a doubling of the mean (+/−s.e.m.) POMC-neuron firing rate (n=3). This effect was reversed with drug washout. FIG. 13b is a graph of the mean (+/−s.e.m.) peak depolarization of POMC neurons (n=4-8 per dose) bathed with d-FEN, 5-HT mCPP or MK 212 using conventional whole cell recordings.

SEQUENCE LISTING

Figure 2:
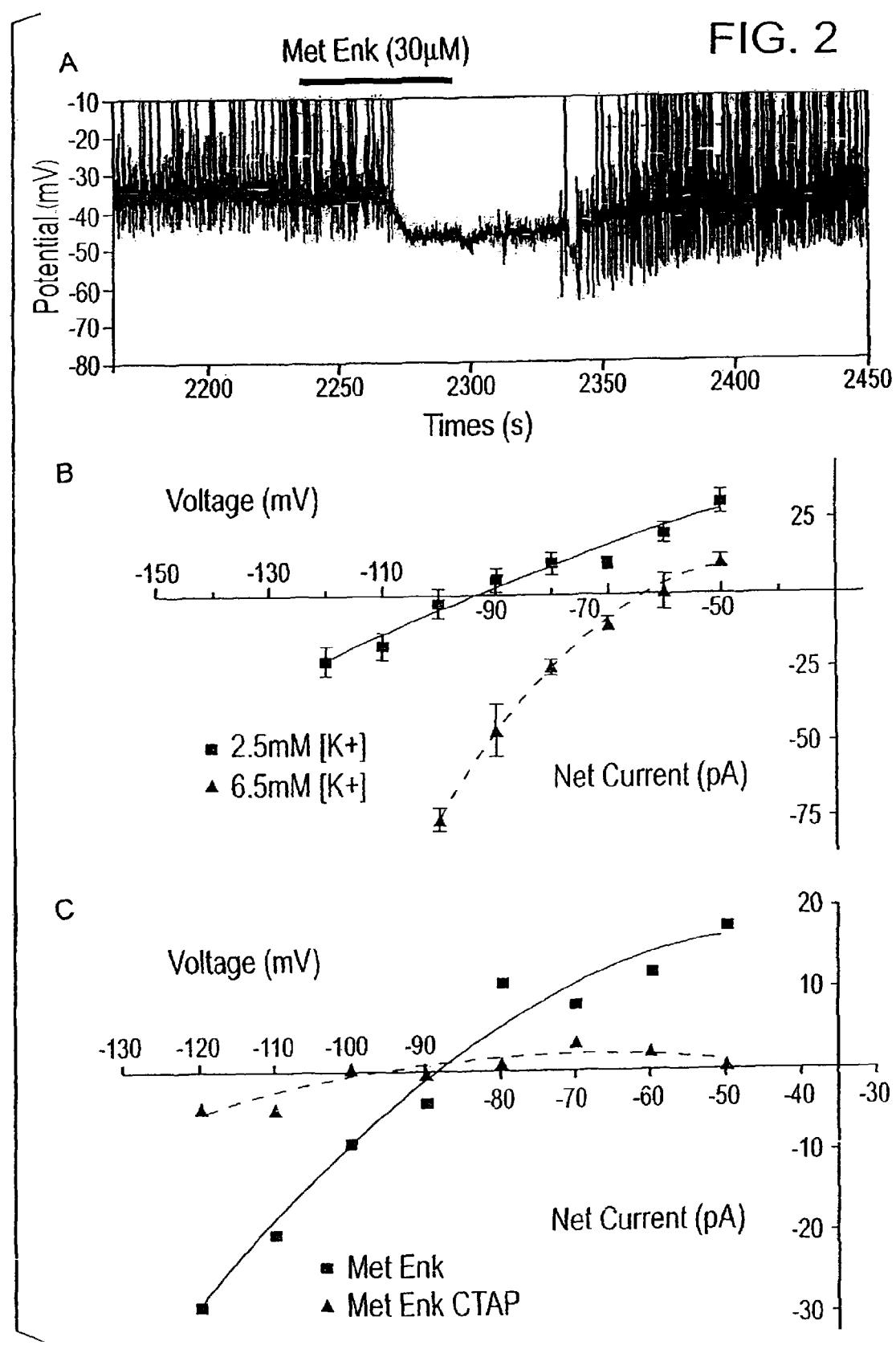
FIG. 2 is a tracing and graphs showing activation of MOP-Rs hyperpolarizes the EGFP-labeled POMC neurons by opening G protein-coupled inwardly-rectifying potassium channels.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

DETAILED DESCRIPTION

I. Abbreviations
  α-MSH: alpha melanocortin stimulating hormone
  Arc: arcuate nucleus of the hypothalamus
  CPP: m-CPP hydrochloride, 1-(3-Chlorophenyl)piperazine 5-HT$_{2B/2C}$ receptor agonist
  d-FEN: fenfluarmine
  EPSP: excitatory postsynaptic potential
  GABA: γaminobutyric acid
  GFP, EGFP: green fluorescent protein, enhanced green fluorescent protein
  IPSC: inhibitory postsynaptic current
  kb: kilobase
  kg: kilogram MOP-R: μ-opiod receptor
MK: MK212 hydrochloride, or 6-Chloro-2-(1-piperazinyl)pyrazine 5-$HT_{2C}$ serotonin receptor agonist.
MV: millivolts
nPOMC1: neural POMC regulatory element 1
nPOMC2: neural POMC regulatory element 2
NPY: neuropeptide Y
pmol: picomole
POMC: proopiomelanocortin
RIA: radioimmunoassay
RPA: RNase protection assay
s.e.m.: standard error of the mean
TH: tyrosine hydroxylase
μM: micromolar
V: volts
Y2A: N-acetyl ($Leu^{28}$, $Leu^{31}$) NPY (24-36)

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Action potential: A rapidly propagated electrical message that speeds along an axon of a neuron and over the surface membrane of many muscle and glandular cells. In axons they are brief, travel at constant velocity, and maintain a constant amplitude. Like all electrical messages of the central nervous system, the action potential is a membrane potential change caused by the flow of ions through ion channels in the membrane. In one embodiment, an action potential is a regenerative wave of sodium permeability.

Agent: Any polypeptide, compound, small molecule, organic compound, salt, polynucleotide, or other molecule of interest.

Animal: Living multi-cellular vertebrate organisms, a category that includes, for example, mammals and birds. The term mammal includes both human and non-human mammals. Similarly, the term "subject" includes both human and veterinary subjects.

Anorexia: A lack or loss of the appetite for food. In one embodiment, anorexia is a result of "anorexia nervosa." This is an eating disorder primarily affecting females, usually with onset in adolescence, characterized by refusal to maintain a normal minimal body weight, intense fear of gaining weight or becoming obese, and a disturbance of body image resulting in a feeling of being fat or having fat in certain areas even when extremely emaciated, undue reliance on body weight or shape for self-evaluation, and amenorrhea. Associated features often include denial of the illness and resistance to psychotherapy, depressive symptoms, markedly decreased libido, and obsessions or peculiar behavior regarding food, such as hoarding. The disorder is divided into two subtypes, a restricting type, in which weight loss is achieved primarily through diet or exercise, and a binge-eating/purging type, in which binge eating or purging behavior also occur regularly.

Antagonist: A substance that tends to nullify the action of another, as an agent that binds to a cell receptor without eliciting a biological response, blocking binding of substances that could elicit such responses.

Appetite: A natural desire, or longing for food. In one embodiment, appetite is measured by a survey to assess the desire for food. Increased appetite generally leads to increased feeding behavior.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Binding: A specific interaction between two molecules, such that the two molecules interact. Binding can be specific and selective, so that one molecule is bound preferentially when compared to another molecule. In one embodiment, specific binding is identified by a disassociation constant ($K_d$).

Body Mass Index (BMI): A mathematical formula for measuring body mass, also sometimes called Quetelet's Index. BMI is calculated by dividing weight (in kg) by $height^2$ (in $meters^2$). The current standards for both men and women accepted as "normal" are a BMI of 20-24.9 $kg/m^2$. In one embodiment, a BMI of greater than 25 $kg/m^2$ can be used to identify an obese subject. Grade I obesity corresponds to a BMI of 25-29.9 $kg/m^2$. Grade II obesity corresponds to a BMI of 30-40 $kg/m^2$; and Grade III obesity corresponds to a BMI greater than 40 $kg/m^2$ (Jequier, *Am. J. Clin. Nutr.,* 45:1035-47, 1987). Ideal body weight will vary among species and individuals based on height, body build, bone structure, and sex.

c-fos: The cellular homologue of the viral v-fos oncogene found in FBJ (Finkel-Biskis-Jinkins) and FBR murine osteosarcoma viruses (MSV). The human fos gene maps to chromosome 14q21-q31. Human fos has been identified as TIS-28.

C-fos is thought to have an important role in signal transduction, cell proliferation, and differentiation. It is a nuclear protein which, in combination with other transcription factors (for example, jun) acts as a trans-activating regulator of gene expression. C-fos is an immediate early response gene, which are believed to play a key role in the early response of cells to growth factors. C-fos is involved also in the control of cell growth and differentiation of embryonic hematopoietic cells and neuronal cells. The human c-fos coding amino acid and nucleic acid sequences are known (e.g. see Verma et al., Cold Spring Harb. Symp. Quant. Biol. 51, 949, 1986; GenBank Accession Nos. K00650 and M16287, and are available on the internet).

Cachexia: General physical wasting and malnutrition that is often associated with a chronic disease process. Cahexia is frequently seen in patients with cancer, AIDS, or other diseases. Cachexia includes, but is not limited to 1) cancerous cachexia, seen in cases of malignant tumor; 2) cardiac cachexia, an emaciation due to heart disease, usually caused by a combination of increased caloric expenditure and decreased caloric intake or utilization; 3) fluoric cachexia, seen in fluorosis; 4) hypophysial cachexia; 5) cachexia hypophysiopriva, a cluster of symptoms resulting from total deprivation of function of the pituitary gland, including phthisis, loss of sexual function, atrophy of the pituitary target glands, bradycardia, hypothermia, apathy, and coma; 6) malarial cachexia, a group of physical signs of a chronic nature that result from antecedent attacks of severe malaria; 7) cachexia mercurialis, seen in chronic mercury poisioning; 8) pituitary cachexia; 9) saturnine cachexia, seen in chronic lead poisioning; 10) cachexia suprarenalis, associated with Addison's disease; and 11) uremic cachexia, associated with other systemic symptoms of advanced renal failure.

Caloric intake or calorie intake: The number of calories (energy) consumed by an individual.

Calorie: A unit of measurement in food. A standard calorie is defined as 4.184 absolute joules, or the amount of energy it takes to raise the temperature of one gram of water from 15 to 16° C. (or 1/100th the amount of energy needed to raise the temperature of one gram of water at one atmosphere pressure from 0° C. to 100° C.), food calories are actually equal to 1,000 standard calories (1 food calorie=1 kilocalorie).

Conservative variation: The replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Non-limiting examples of conservative amino acid substitutions include those listed below:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Current: The amount of charge per unit time. Current is generated in a cell membrane of a neuron by an action potential or by opening of ion channels in the cell membrane and serves to depolarize or hyperpolarize adjacent membrane areas.

Deletion: The removal of a sequence of nucleic acid, such as DNA, the regions on either side being joined together.

DNA (deoxyribonucleic acid): DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine, and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Depolarization: An increase in the membrane potential of a cell. Certain stimuli reduce the charge across the plasma membrane. These can be electrical stimuli (which open or close voltage-gated channels), mechanical stimuli (which activate mechanically-gated channels) or certain neurotransmitters (which open ligand-gated channels). In each case, the facilitated diffusion of sodium into the cell increases the resting potential at that spot on the cell creating an excitatory postsynaptic potential (EPSP). Depolarizations can also be generated by decreasing the frequency of inhibitory postsynaptic currents (IPSCs), these are due to inhibitory neurotransmitters facilitating the influx of chloride ions into the cell, creating an IPSC. Depolarizations can also be induced by closing some ion channels. If the potential is increased to the threshold voltage (about −50 mV in mammalian neurons), an action potential is usually generated in the cell.

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Electroporation: A method of inducing or allowing a cell to take up macromolecules by applying electric fields to reversibly permeabilize the cell walls. Various methods and apparatuses used are further defined and described in: U.S. Pat. Nos. 4,695,547; 4,764,473; 4,882,28; and 4,946,793; 4,906, 576; 4,923,814; and 4,849,089.

Eukaryotic cell: A cell having an organized nucleus bounded by a nuclear membrane. These include simpler organisms such as yeasts, slime molds, and the like, as well as cells from multicellular organisms such as invertebrates, vertebrates, and mammals. Multicellular organisms include a variety of cell types, such as: endothelial cell, smooth muscle cell, epithelial cell, hepatocyte, cells of neural crest origin, tumor cell, hematopoietic cell, immunologic cell, T cell, B cell, monocyte, macrophage, dendritic cell, fibroblast, keratinocyte, neuronal cell, glial cell, adipocyte, myoblast, myocyte, chondroblast, chondrocyte, osteoblast, osteocyte, osteoclast, secretory cell, endocrine cell, oocyte, and spermatocyte. These cell types are described in standard histology texts, such as McCormack, Introduction to Histology, (c) 1984 by J.P. Lippincott Co.; Wheater et al., eds., Functional Histology, 2nd Ed., (c) 1987 by Churchill Livingstone; Fawcett et al., eds., Bloom and Fawcett: A Textbook of Histology, (c) 1984 by William and Wilkins.

Gene: A DNA sequence that comprises control and coding sequences necessary for the production of a polypeptide or protein. The polypeptide can be encoded by a full-length coding sequence or by any portion of the coding sequence in some embodiments, so long as at least a portion of the desired activity of the polypeptide is retained. A "foreign gene" is any nucleic acid (e.g., gene sequence) that is introduced into the genome of an animal by experimental manipulations and can include gene sequences found in that animal so long as the introduced gene contains some modification (e.g., a point mutation, the presence of a selectable marker gene, a non-native regulatory sequence, or a native sequence integrated into the genome at a non-native location, etc.) relative to the naturally-occurring gene.

Food intake: The amount of food consumed by an individual. Food intake can be measured by volume or by weight. In one embodiment, food intake is the total amount of food consumed by an individual. In another embodiment, food intake is the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Hyperpolarization: A decrease in the membrane potential of a cell. Inhibitory neurotransmitters inhibit the transmission of nerve impulses via hyperpolarization. This hyperpolarization is called an inhibitory postsynaptic potential (IPSP). Hyperpolarization may also be caused by opening or closing of ion channels. Although the threshold voltage of the cell is unchanged, a hyperpolarized cell requires a stronger excitatory stimulus to reach threshold.

Inhibitory Postsynaptic Current: A current that inhibits an electrophysiological parameter of a postsynaptic cell. The potential of a postsynaptic cell can be analyzed to determine an effect on a presynaptic cell. In one embodiment, the postsynaptic cell is held in voltage clamp mode, and postsynaptic currents are recorded. If necessary, antagonists of other classes of current can be added. In one specific, non-limiting example, to record GABAergic IPSCs, blockers of excitatory channels or receptors can be added. The instantaneous frequency over time is then determined.

In one embodiment, IPSCs give a measure of the frequency of GABA release from an NPY neuron. Thus, as NPY neurons release GABA onto POMC neurons, measurement of IPSC frequency is a gauge of the inhibitory tone that POMC neurons are receiving, and can be used to assess the effect of an agent that affects an NPY neuron, such as an antagonist or agonist of PYY.

Intron: An intragenic nucleic acid sequence in eukaryotes that is not expressed in a mature RNA molecule. Introns of the present disclosure include full-length intron sequences, or a portion thereof, such as a part of a full-length intron sequence.

In vitro amplification: Techniques that increases the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An isolated biological component (such as a nucleic acid, peptide or protein) has been substantially separated, produced apart from, or purified away from other biological components in the cell of the organism in which the component naturally occurs, i.e. other chromosomal and extrachromosomal DNA and RNA, and proteins. Nucleic acids, peptides and proteins that have been isolated include nucleic acids and proteins purified by standard purification methods. The term also embraces nucleic acids, peptides, and proteins prepared by recombinant expression in a host cell as well as chemically synthesized nucleic acids.

Marker: A protein, or a gene encoding a protein, for which a system is available to identify cells that produce the protein. Specific non-limiting examples of a marker include drug resistance markers, such as G148 or hygromycin. Additionally, a marker can be a protein or a gene encoding a protein for which negative selection can be used to identify the cell expressing the marker. A specific, non-limiting examples of a negative selection marker includes, but is not limited to, the HSV-tk gene. This gene will make the cells sensitive to agents such as acyclovir and gancyclovir. Another specific, non-limiting example of a selectable marker is a protein, or a gene encoding a protein, wherein selection can be made by using a cell surface marker, for example, to select overexpression of the marker by fluorescence activated cell sorting (FACS). In another specific, non-limiting example of a selectable marker is a protein, or a gene encoding a protein, that can be identified in a cell based on its fluorescent or enzymatic properties. Specific, non-limiting examples include, but are not limited to, enhanced fluorescent green protein (EGFP), alkaline phosphatase, or horseradish peroxidase. A marker can also be a polypeptide or antigenic epitope thereof, wherein an antibody that specifically binds the polypeptide can be used to identify cells that express the polypeptide or antigenic epitope. One specific, non-limiting example of a polypeptide of use is human growth Hormone (hGH).

Membrane potential: The electrical potential of the interior of the cell with respect to the environment, such as an external bath solution. One of skill in the art can readily assess the membrane potential of a cell, such as by using conventional whole cell techniques. Activation of a cell is associated with less negative membrane potentials (for example shifts from about −50 mV to about −40 mV). These changes in potential increase the likelihood of action potentials, and thus lead to an increase in the rate of action potentials.

The rate of action potentials can be assessed using many approaches, such as using conventional whole cell access, or using, for example, perforated-patch whole-cell and cell-attached configurations. In each event the absolute voltage or current is not assessed, rather the frequency of rapid deflections characteristic of action potentials is assessed, as a function of time (therefore this frequency is an instantaneous frequency, reported in "bins"). This time component can be related to the time at which a compound, such as a PYY agonist, is applied to the bath to analyze the effect of the compound, such as the PYY agonist, on action potential firing rate.

Neuropeptide Y (NPY): A 36-amino acid peptide that is a neuropeptide identified in the mammalian brain. NPY is believed to be an important regulator in both the central and peripheral nervous systems and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and have contributed to vasoconstriction. NPY binding sites have been identified in a variety of tissues, including spleen, intestinal membranes, brain, aortic smooth muscle, kidney, testis, and placenta. In addition, binding sites have been reported in a number of rat and human cell lines.

Neuropeptide Y (NPY) receptor has structure/activity relationships within the pancreatic polypeptide family. This family includes NPY, which is synthesized primarily in neurons; peptide YY (PYY), which is synthesized primarily by endocrine cells in the gut; and pancreatic polypeptide (PP), which is synthesized primarily by endocrine cells in the pancreas. These 36 amino acid peptides have a compact helical structure involving an amino acid structure, termed a "PP-fold" in the middle of the peptide.

NPY binds to several receptors, including the Y1, Y2, Y3, Y4 (PP), Y5, Y6, and Y7 receptors. These receptors are recognized based on binding affinities, pharmacology, and sequence (if known). Most, if not all of these receptors are G protein coupled receptors. The Y1 receptor is generally considered to be postsynaptic and mediates many of the known actions of neuropeptide Y in the periphery. Originally, this receptor was described as having poor affinity for C-terminal fragments of neuropeptide Y, such as the 13-36 fragment, but interacts with the full length neuropeptide Y and peptide YY with equal affinity (e.g. see Patent Cooperation Treaty publication WO 93/09227).

Pharmacologically, the Y2 receptor is distinguished from Y1 by exhibiting affinity for C-terminal fragments of neuropeptide Y. The Y2 receptor is most often differentiated by the affinity of neuropeptide Y(13-36), although the 3-36 fragment of neuropeptide Y and peptide YY provides improved affinity and selectivity (see Dumont et al., *Society for Neuroscience Abstracts*, 19:726, 1993). Signal transmission through both the Y1 and the Y2 receptors are coupled to the inhibition of adenylate cyclase. Binding to the Y-2 receptor was also found to reduce the intracellular levels of calcium in the synapse by selective inhibition of N-type calcium channels. In addition, the Y-2 receptor, like the Y1 receptors exhibits differential coupling to second messengers (see U.S. Pat. No. 6,355,478). Y2 receptors are found in a variety of brain regions, including the hippocampus, substantia nigra-lateralis, thalamus, hypothalamus, and brainstem. The human, murine, monkey and rat Y2 receptors have been cloned (e.g. see U.S. Pat. Nos. 6,420,352 and 6,355,478).

A Y2 receptor agonist is a peptide, small molecule, or chemical compound that preferentially binds to the Y2 receptor and stimulates intracellular signaling. In one embodiment, an agonist for the Y2 receptor binds to the receptor with an equal or greater affinity than NPY. In another embodiment, an agonist selectively binds the Y2 receptor, as compared to binding to another receptor.

One of skill in the art can readily determine the dissociation constant ($K_d$) value of a given compound. This value is dependent on the selectivity of the compound tested. For example, a compound with a $K_d$ which is less than 10 nM is generally considered an excellent drug candidate. However, a compound that has a lower affinity, but is selective for the particular receptor, can also be a good drug candidate. In one specific, non-limiting example, an assay, such as a competition assays, is used to determine if a compound of interest is a Y2 receptor agonist. Assays useful for evaluating neuropeptide Y receptor antagonists are also well known in the art (see U.S. Pat. No. 5,284,839, which is herein incorporated by reference, and Walker et al., *Journal of Neurosciences*, 8:2438-2446, 1988).

Normal Daily Diet: The average food intake for an individual of a given species. A normal daily diet can be expressed in terms of caloric intake, protein intake, carbohydrate intake, and/or fat intake. A normal daily diet in humans generally comprises the following: about 1,500, about 1,800, about 2,000, about 2, 400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102: E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. In one embodiment, the Body Mass Index (BMI) is used to assess obesity. In one embodiment, a BMI of 25.0 kg/m$^2$ to 29.9 kg/m$^2$ is overweight, while a BMI of 30 kg/m$^2$ is obese.

In another embodiment, waist circumference is used to assess obesity. In this embodiment, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Overweight: An individual who weighs more than their ideal body weight. An overweight individual can be obese, but is not necessarily obese. In one embodiment, an overweight individual is any individual who desires to decrease their weight. In another embodiment, an overweight individual is an individual with a BMI of 25.0 kg/m$^2$ to 29.9 kg/m$^2$ Pancreatic Polypeptide: A 36 amino acid peptide, produced by the pancreas that has homology to PYY and NPY.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "polypeptide fragment" refers to a portion of a polypeptide, for example such a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Promoter: An array of nucleic acid control sequences which directs transcription of a nucleic acid. In one embodiment, a promoter includes necessary nucleic acid sequences near the start site of transcription, such as, in the case of a polymerase II type promoter, a TATA element. In another embodiment, a promoter includes an enhancer. In another embodiment, a promoter includes a repressor element. Enhancer and repressor elements can be located adjacent to, or distal to the sequences necessary for the start site of transcription, and can be located as much as several thousand base pairs from the start site of transcription.

A promoter can be a "strong" promoter, which promotes transcription of RNA at high levels, for example at levels such that the transcriptional activity of the promoter generally accounts for about 25% of transcriptional activity of all transcription within a cell. The strength of a promoter is often tissue-specific and thus can vary from one cell type to another. For example, CMV is a classic strong promoter because it generates high levels of transcriptional activity in many cell types.

In other embodiments, the promoter is a "tissue-specific promoter," which promotes transcription in a single cell type or narrow range of tissues. In one embodiment, a tissue specific promoter promotes expression in the pituitary, but not in other tissues. In a further embodiment, a tissue specific promoter promotes expression in the hypothalamus, but not in other tissues (e.g., heart, lung, pancreas, intestines, skin, etc.)

In other embodiments, the promoter is a "minimal" promoter, which has very low intrinsic transcriptional activity in the absence of operably linked enhancer sequences. A minimal promoter is one that does not have inherent cell-specific or tissue-specific activity, but may direct transcriptional initiation in multiple eukaryotic cell types when operably linked to a cell- or tissue-specific enhancer sequence. One specific, non-limiting example of a minimal promoter is the minimal promoter sequences of the herpes simplex virus type 1 thymidine kinase (HSV1-tk) gene.

Proopiomelanocortin (POMC): A glycosylated protein of a molecular weight of 31 kDa protein. POMC is synthesized mainly in the anterior pituitary but also found in the hypothalamus and brainstem. This protein is a precursor protein, post-translational processing of POMC yields several neuroactive peptides upon specific cleavage. The POMC coding sequence includes the amino acid sequences of adrenocoroticotropic (ACTH) hormone and beta-lipotropin. ACTH is processed to produce the proteins melanotropin (msh), corticotrophin-like intermediate lobe peptide. Beta-lipotropin is processed to produce the proteins alpha-lipotropin, beta-endorphins, beta-melanocyte stimulating hormone (MSH), and met-enkephalin. The amino-terminal fragment of POMC is processed to a family of gamma-MSH peptides and to a peptide with putative mitogenic stimulatory activity of the adrenal cortical cells. The biological activity of POMC-derived peptides is further regulated in a tissue-specific manner by acetylation of the amino-terminal amino acid residue and/or amidation of the carboxyterminal amino acid residue by the enzyme peptidyl-α-monooxygenase (PAM).

The POMC gene (human chromosome 2p23) contains three exons and two large introns: one, of about 3.5 kb, interrupts the N-terminal fragment of the common precursor mostly encoded in exon 3. Exon 2 contains the sequence for a portion of the 5' untranslated portion of the mRNA, all of the signal sequence which directs insertion of the precursor protein into the endoplasmic reticulum, and 8 amino acids of the N-terminal fragment. The overall arrangement of introns and exons in the POMC gene is almost identical in all mammalian species. Hormonal control of POMC gene transcription and release of peptide products derived from the POMC precursor is tissue-specific; for example, glucocorticoids specifically inhibit anterior but not intermediate pituitary POMC transcription.

Purified: The term purified does not require absolute purity; rather, it is intended as a relative term. Thus, for example, a purified protein preparation is one in which the protein is more pure than the protein in its natural environment within a cell. Such proteins may be produced, for example, by standard purification techniques, or by recombinant expression. In some embodiments, a preparation of a protein is purified such that the protein represents at least 50%, for example at least 70%, of the total protein content of the preparation.

PYY: A peptide YY polypeptide obtained or derived from any species. Thus, PYY includes the human full length polypeptide (as set forth in SEQ ID NO: 1) and species variations of PYY, including e.g. murine, hamster, chicken, bovine, rat, and dog PYY. In one embodiment, PYY agonists do not include NPY. A "PYY agonist" is any compound which binds to a receptor that specifically binds PYY, and elicits an effect of PYY. In one embodiment, a PYY agonist is a compound that affects food intake, caloric intake, energy expenditure or appetite, and/or which binds specifically in a Y receptor assay or competes for binding with PYY, such as in a competitive binding assay with labeled PYY. PYY agonists include, but are not limited to, compounds that bind to the Y2 receptor.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g. by genetic engineering techniques, such as those described in Sambrook et al. (in *Molecular Cloning: A Laboratory Manual*, Cold Spring Harbor, N.Y., 1989).

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologues or variants of a POMC sequence will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16.10881, 1988; and Pearson and Lipman, *Proc. Natl. Acad. Sci. U.S.A.* 85:2444, 1988. Altschul et al., *Nature Genet.,* 6:119, 1994 presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available on the NCBI website on the internet. Other specific, non-limiting examples of sequence alignment programs specifically designed to identify homologous regions of intragenic DNA of greater than or equal to 100 nucleotides are PIPMaker and DOTTER.

Homologues and variants of a POMC sequence are typically characterized by possession of at least 75%, for example at least 80%, 90%, 95%, 98%, or 99%, sequence identity counted over the full length alignment with the originating POMC sequence using the NCBI Blast 2.0, set to default parameters. Methods for determining sequence identity over such short windows are available at the NCBI website on the internet. One of skill in the art will appreciate that these sequence identity ranges are provided for guidance only; it is entirely possible that strongly significant homologues could be obtained that fall outside of the ranges provided.

Substantially purified: A polypeptide which is substantially free of other proteins, lipids, carbohydrates or other materials with which it is naturally associated. For example, the polypeptide may be at least 50%, 80% or 90% free of other proteins, lipids, carbohydrates or other materials with which it is naturally associated.

Therapeutically effective amount: A dose sufficient to prevent advancement, or to cause regression of a disorder, or which is capable of relieving a sign or symptom of a disorder. In several embodiments, a therapeutically effect of PYY or an agonist thereof is an amount sufficient to inhibit or halt weight gain, or an amount sufficient to decrease appetite, or an amount sufficient to reduce caloric intake or food intake or increase energy expenditure.

Transduced and Transfected: A virus or vector transduces or transfects a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the terms transduced and transfected encompass all techniques by which a nucleic acid molecule might be introduced into such a cell, including transfection with viral vectors, transfection with plasmid vectors, and introduction of naked DNA by electroporation, lipofection, injection, and particle gun acceleration.

Transgene: A foreign gene that is placed into an organism by introducing the foreign gene into embryonic stem (ES) cells, newly fertilized eggs or early embryos. In one embodiment, a transgene is a gene sequence, for example a sequence that encodes a marker polypeptide that can be detected using methods known to one of skill in the art. In another embodiment, the transgene encodes a therapeutic polypeptide that can be used to alleviate or relieve a symptom of a disorder. In yet another embodiment, the transgene encodes a therapeutically effective oligonucleotide, for example an antisense oligonucleotide, wherein expression of the oligonucleotide inhibits expression of a target nucleic acid sequence. In a further embodiment, the transgene encodes an antisense nucleic acid or a ribozyme. In yet another embodiment, a transgene is a stop cassette.

In other embodiments, a transgene contains regulatory sequences operably linked to the transgene (e.g. a promoter, such as a POMC promoter). Thus, the transgene can include regulatory sequences operably linked to a nucleic acid sequence encoding a polypeptide, such as a marker.

Transgenic Cell: Cells that contain foreign, non-native DNA.

Transgenic Animal: An animal, for example, a non-human animal such as a mouse, that has had DNA introduced into one or more of its cells artificially. By way of example, this is commonly done by random integration or by targeted insertion. DNA can be integrated in a random fashion by injecting it into the pronucleus of a fertilized ovum. In this case, the DNA can integrate anywhere in the genome, and multiple copies often integrate in a head-to-tail fashion. There is no need for homology between the injected DNA and the host genome.

Targeted insertion, the other common method of producing transgenic animals, is accomplished by introducing the DNA into embryonic stem (ES) cells and selecting for cells in which the DNA has undergone homologous recombination with matching genomic sequences. For this to occur, there often are several kilobases of homology between the exogenous and genomic DNA, and positive selectable markers are often included. In addition, negative selectable markers are often used to select against cells that have incorporated DNA by non-homologous recombination (random insertion).

Vector: A nucleic acid molecule as introduced into a cell, thereby producing a transformed cell. A vector can include nucleic acid sequences that permit it to replicate in the cell, such as an origin of replication. A vector can also include one or more marker or therapeutic transgenes and other genetic elements known in the art.

In some embodiments, the vector is a non-viral vector, such as a bacterial vector. In other embodiments, the vector is a viral vector. Examples of viral vectors include, but are not limited to adenoviral vectors, retroviral vectors, and Herpes viral vectors.

Voltage: An electric potential or potential difference, expressed in volts.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addi- Screening Methods Methods for screening for an agent that affects caloric intake, food intake, appetite, and/or energy expenditure are disclosed herein. The methods include contacting a histological section of an arcuate nucleus from a non-human animal expressing a marker in proopiomelanocortin (POMC) neurons with the agent to be tested. The expression of the marker distinguishes the proopiomelanocortin neurons from the other neurons (and other cells) in the arcuate nucleus, such that electrophysiological measurements can be made on the POMC neurons. An electrophysiological parameter of the POMC neurons is measured. The effect of the agent on this parameter indicated if the agent has an effect on appetite, caloric intake, food intake, or energy expenditure upon administration of a therapeutically effective amount of the agent to a subject.

In one embodiment, in order to distinguish the POMC neurons from all other cells within the arcuate nucleus, a non-human animal is generated that carries a transgene comprising a nucleic acid encoding the marker operably linked to a POMC nucleic acid sequence. The POMC nucleic acid sequence directs expression of the marker in POMC neurons in the arcuate nucleus of the non-human animal. The marker can be any marker, including, but not limited to, fluorescent markers (e.g., green fluorescent protein, Aequoria Victoria, or Discosoma DSRed), antigenic markers (e.g., human growth hormone, human insulin, human HLA antigens), cell surface markers (e.g., CD4, or a any cell surface receptor), or enzymatic markers (e.g., lacZ).

Figure 10:
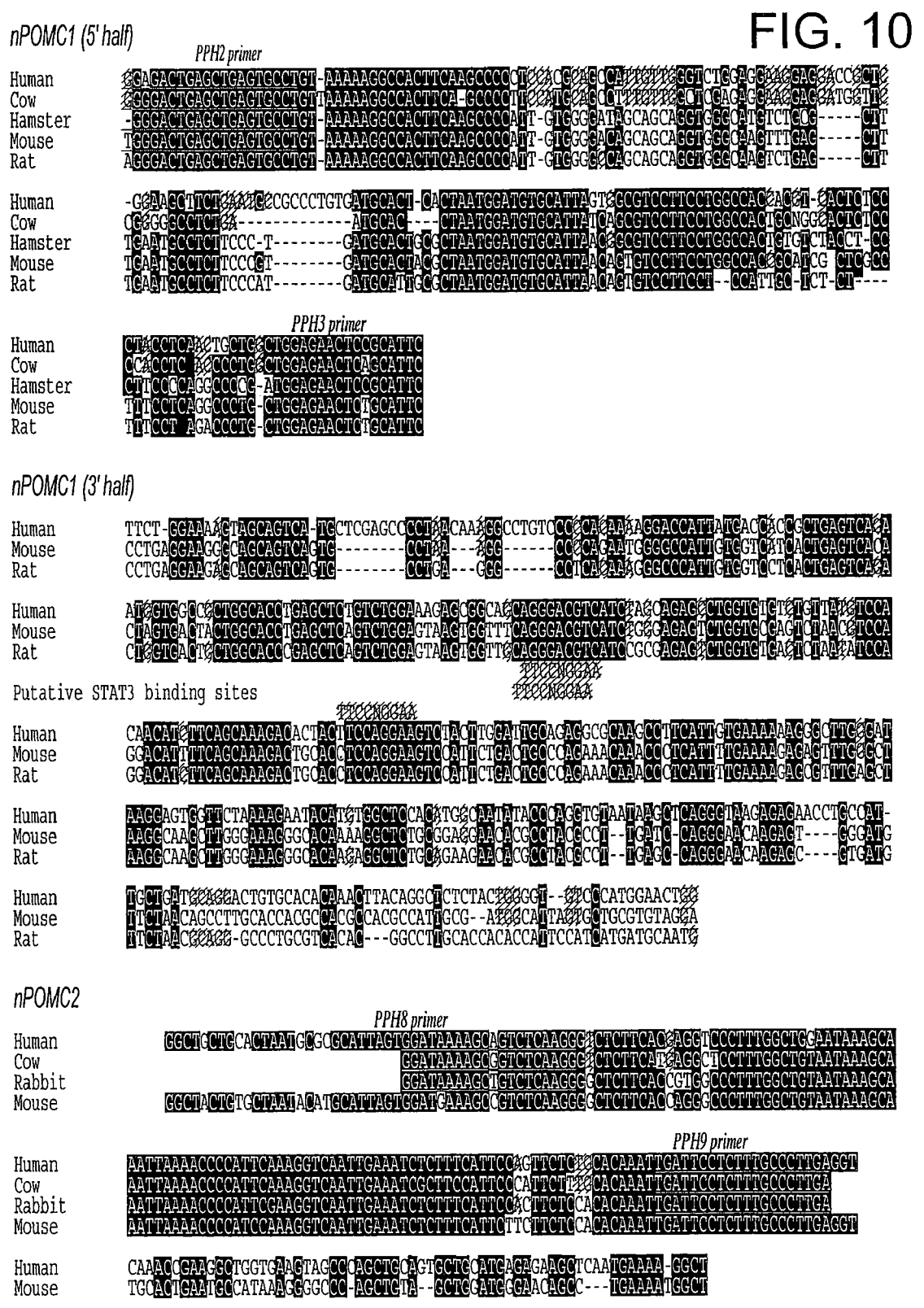

The cDNA that encodes the marker can be fused in proper reading frame under the transcriptional and translational control of regulatory sequence of interest, such as a POMC regulatory sequence that directs expression of the marker in the POMC neurons of the arcuate nucleus. The sequences include, but are not limited to, the regulatory and coding sequences of the POMC gene, and suitable fragments thereof, wherein the regulatory and/or coding POMC sequence directs expression of the marker in the POMC neurons of the arcuate nucleus. Specific, non-limiting examples of POMC sequences of use include, but are not limited to, transgenes carrying variable length or deletions of the 5' flanking sequences of a mammalian POMC gene, including, but not limited to, the mouse or human POMC gene. Specific, non-limiting examples of POMC sequences of use include, but are not limited to, murine, human, bovine, hamster, and rabbit POMC sequences. Variants of these POMC sequences, such as, but not limited to deletions, insertions, and additions are also of use, provided that these variants direct expression to the arcuate nucleus. In one embodiment, the POMC sequences can include the nPOMC1, nPOMC2 sequences, and/or the POMC promoter (see the Examples section below). Regions of homology for nPOMC1 and nPOMC2 are indicated in FIG. 10. In one embodiment, a POMC sequence of use includes the nPOMC1 and nPOMC2 and the POMC promoter, and is at least 70%, at least 80%, at least 90%, at least 95%, at least 98%, or at least 99% homologous with the corresponding originating POMC sequence. Additionally, such a sequence can include point mutation. Regions of homology for the human, cow, hamster, mouse, rabbit, and rat the nPOMC1 and nPOMC2 regions are shown in FIG. 10. One of skill in the art can readily use this information to design suitable sequences of interest. For example, conserved regions (shown in black) can be retained, while non-conserved regions (shown in grey or white) can be substituted. Additional exemplary sequences are described in the Examples section below.

This construct can be introduced into a vector to produce a product that is then amplified, for example, by preparation in a bacterial vector, according to conventional methods (see, for example, Sambrook et al., *Molecular Cloning: a Laboratory Manual*, Cold Spring Harbor Press, 1989). The amplified construct is thereafter excised from the vector and purified for use in producing transgenic animals.

Any animal can be of use in the methods disclosed herein, provided the animal is any non-human animal. A "non-human animal" includes, but is not limited to, a non-human primate, a farm animal such as swine, cattle, and poultry, a sport animal or pet such as dogs, cats, horses, hamsters, rodents, or a zoo animal such as lions, tigers, or bears. In one specific, non-limiting example, the non-human animal is a transgenic animal, such as, but not limited to, a transgenic mouse, cow, sheep, or goat.

A transgenic animal contains cells that bear genetic information received, directly or indirectly, by deliberate genetic manipulation at the subcellular level, such as by microinjection or infection with recombinant virus, such that a recombinant DNA is included in the cells of the animal. This molecule can be integrated within the animal's chromosomes, or can be included as an extrachromosomally replicating DNA sequences, such as might be engineered into yeast artificial chromosomes. A transgenic animal can be a "germ cell line" transgenic animal, such that the genetic information has been taken up and incorporated into a germ line cell, therefore conferring the ability to transfer the information to offspring. If such offspring in fact possess some or all of that information, then they, too, are transgenic animals.

Transgenic animals can readily be produced by one of skill in the art. For example, transgenic animals can be produced by introducing into single cell embryos DNA encoding a marker, in a manner such that the polynucleotides are stably integrated into the DNA of germ line cells of the mature animal and inherited in normal Mendelian fashion. Advances in technologies for embryo micromanipulation permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In one non-limiting method, developing embryos are infected with a retrovirus containing the desired DNA, and transgenic animals produced from the infected embryo.

In another, specific, non-limiting example, the appropriate DNA(s) are injected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., *Manipulating the Mouse Embryo*, Cold Spring Harbor Press, 1986; Krimpenfort et al., *Bio/Technology* 9:86, 1991; Palmiter et al., *Cell* 41:343, 1985; Kraemer et al., *Genetic Manipulation of the Early Mammalian Embryo*, Cold Spring Harbor Laboratory Press, 1985; Hammer et al., *Nature*, 315:680, 1985; Purcel et al., *Science*, 244:1281, 1986; Wagner et al., U.S. Pat. No. 5,175, 385; Krimpenfort et al., U.S. Pat. No. 5,175,384.

A histological section of the arcuate nucleus from a non-human animal expressing a marker in the POMC neurons is prepared using methods known to one of skill in the art, and the section is contacted with a test agent of interest. An electrophysiological parameter of a POMC neuron is then assessed. Suitable electrophysiological parameters include, but are not limited to, hyperpolarization of the membrane potential of the POMC neuron and/or an increase in IPSCs in the POMC neuron. In one non-limiting example, an agonist is selected that causes hyperpolarization of the membrane potential of a POMC neuron, and increases IPSCs in a POMC neuron.

One of skill in the art can readily assesses neuron firing rate, membrane voltage, depolarization, action potentials, and IPSC frequency. Exemplary methods are described in the examples section below. However, the methods disclosed herein are not limited to the devices and measurements described in the Examples section. For example, any electrophysiology amplifier can be utilized, such as, but not limited to, devices produced by Dagan Instruments, Minneapolis, Minn., or Heka Elektronik, Lambrecht/Pfalz, Germany.

In one embodiment, the membrane potential, action potential rate, and/or the frequency of IPSCs in a POMC neuron treated with an agent is compared to a control. Suitable controls include, but are not limited to, a section contacted with a buffer alone, in the absence of an agent, a sample contact with a control agent, such as an agent known to have an effect on the frequency of IPSCs, action potential rate, or to alter membrane potential of a POMC neuron, or an agent known not to have an effect on IPSCs, action potential rate, or membrane potential of a POMC neuron.

In one specific, non-limiting example, a section of the arcuate nucleus is contacted with an agent, and the effect on the membrane potential of a POMC neuron is measured. In this example, a change in the membrane potential of about 2 to about 50 mV indicates that the agent affects food intake, caloric intake, appetite, and/or energy expenditure. In another specific, non-limiting example, a change in IPSC frequency is measured. In this example, a change in the IPSC frequency is measured. In this example, a change of the IPSC frequency from about 2% to a ten fold increase, or completely stopping IPSCs indicates that the agent affects food intake, caloric intake, appetite, and/or energy expenditure. In another embodiment, a change in the action potential rate of a POMC neuron is measured. In this example, a change in the action potential rate of about 2% to completely stopping, or a change in the action potential rate of greater than, or equal to, about a 1-fold, about a 2-fold, about a 20-fold, about a 50-fold, or about a 100-fold, increase indicates that the agent affects food intake, caloric intake, appetite, and/or energy expenditure. Alternatively, a change from no firing to activity of a POMC neuron indicates that the agent affects food intake, caloric intake, appetite, and/or energy expenditure. Other approaches to measuring activity includes, but not be limited to, an analysis of the expression of c-fos.

One of skill in the art can readily identify a statistically analysis of use in assessing data obtained from the methods disclosed herein. The statistical analyses are standard, such as tests for repeatability, for example analysis of variance, or wilcoxin signed rank test, are performed, using an appropriate confidence level, such as, but not limited to, $p<0.05$.

It should be noted that parameters of a POMC neuron, such as, but not limited to, ion fluxes (e.g., a potassium flux), enzyme activation (e.g., a serine/threonine kinase), changes in cyclic nucleotides (e.g., cAMP, cADP, cGMP, cGDP, etc.), among others, can also be measured. A specific, nonlimiting example of a signaling event is the generation of a $K^+$ flux following the interaction of an agent with a POMC neuron. A "physiological indicator," which is any compound in which a measurable property changes in a response to a physical parameter of the cell, can be used to measure the signaling event. One specific, non-limiting example of a measurable property is a change is in fluorescence of a physiological indicator in response to an ion flux.

Fluorescence is one spectral property of which can be used as the means of detecting a physiological parameter of a cell. A "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between a cell contacted with an agent as compared to a control cell suffices to identify a compound as being of interest. A measurable difference can be determined by determining the amount of any quantitative fluorescent property, e.g., the amount of fluorescence at a particular wavelength, or the integral of fluorescence over the emission spectrum. Optimally, the physiological indicator is selected to have fluorescent properties that are easily distinguishable. A specific, non-limiting example of a fluorescent indicator of use is fura-2. This dye measures intracellular calcium. Increased intracellular calcium is an indicator of increased neuronal activity, while decreased intracellular calcium is an indicator of decreased neural activity.

Any agent can be screened using the methods disclosed herein to determine if it affects appetite, food intake, caloric intake, and/or energy metabolism. Suitable test agents include, but are not limited to, agents that bind, or are suspected of binding a receptor on either a POMC neuron, or a NPY neuron, or both. Receptors on a POMC neuron include, but are not limited to a melanocortin receptor, a μ-opioid receptor, a leptin receptor, and an insulin receptor. Receptors on a NPY neuron include, but are not limited to, a Y2 receptor, a leptin receptor, an insulin receptor, a melanocortin receptor, or an opiod receptor. In one specific, non-limiting example the agent is a receptor agonist, or is suspected of being a receptor agonist. In another specific, non-limiting example, the agent is a Y2 receptor agonist, or is suspected of being a Y2 receptor agonist.

In one specific, non-limiting example, the agent is an antagonist for a receptor on an NPY neuron, or a POMC neuron. Thus, the agent can be, but is not limited to, an antagonist of a Y2 receptor. An electrophysiological property of the POMC neurons is measured. Increased activity of NPY neurons, measured as increased frequency of IPSCs in POMC neurons, hyperpolarization of POMC neurons, and/or a decrease in the action potential firing rate of POMC neurons indicates the antagonist is of use in increasing feeding behavior. Without being bound by theory, antagonists, such as Y2 antagonists, can stimulate NPY neurons by reducing the tonic inhibition of those neurons mediated by the Y2 R and as such will be of use in treating anorexia and cachexia. Thus, the methods described herein can be use to screen for agents that increase appetite, food intake, caloric intake and decrease energy expenditure.

Agents that can be tested using the methods disclosed herein include polypeptides, chemical compounds; biological agents such as, but not limited to polypeptides, cytokines, and small molecules, peptidomimetics; antibodies; and synthetic ligands, amongst others. Receptor agonists and antagonists can be screened.

"Incubating" includes conditions that allow contact between the test compound and the histological section.

"Contacting" includes in solution and solid phase. The test compound may also be a combinatorial library for screening a plurality of compounds. Compounds identified in the method of the invention can be further evaluated, detected, cloned, sequenced, and the like, either in solution of after binding to a solid support, by any method usually applied to the detection of a specific DNA sequence, such as PCR, oligomer restriction (Saiki et al., *Bio/Technology* 3:1008-1012, 1985), allele-specific oligonucleotide (ASO) probe analysis (Conner et al., *Proc. Natl. Acad. Sci. U.S.A.* 80:278, 1983), oligonucleotide ligation assays (OLAs) (Landegren et al., *Science* 241:1077, 1988), and the like. Molecular techniques for DNA analysis have been reviewed (Landegren et al., *Science* 242:229-237, 1988).

The binding affinities of receptor agonists (or antagonists) can also be determined in either cells or a membrane preparation expressing the receptor. For example, assays are utilized in which a labeled ligand is employed. A number of labels have been indicated previously (e.g., radiolabels, fluorescence labels, among others) to be of use. The candidate compound is added in an appropriate buffered medium. After an incubation to ensure that binding has occurred, the surface may be washed free of any nonspecifically bound components of the assay medium, particularly any nonspecifically bound labeled ligand, and any label bound to the surface determined. The label may be quantitatively measured. By using standards, the relative binding affinity of a candidate compound can be determined.

Following screening using the methods disclosed herein, further testing can be performed, either in animal models or in clinical trials, to confirm that the agent affects food intake, caloric intake, appetite, or energy expenditure. Exemplary in vivo assays are described in the Examples section below. However, one of skill in the art can readily design alternative in vivo assays or clinical trials.

PYY Agonists

A PYY agonist can be screened using the methods disclosed herein, in order to determine if the PYY agonist will affect caloric intake, food intake, appetite, and/or energy metabolism. A PYY agonist is a molecule that binds to a receptor that specifically binds PYY, and elicits an effect of PYY. Suitable PYY agonists that can be screened using the methods disclosed herein include compounds that bind specifically in a Y receptor assay or competes for binding with PYY, such as in a competitive binding assay with labeled PYY. Suitable PYY agonists include, but are not limited to, compounds that bind to the Y2 receptor.

Thus, in one embodiment, a PYY agonist is selected using the methods disclosed herein that binds to a NPY neuron in the arcuate nucleus, and results in an electrophysiological effect on an NPY neuron. The electrophysiological effect on the NYP neuron can result in a further electrophysiological effect on a POMC neuron. Thus, one specific, non-limiting example, a PYY agonist is selected, using the methods disclosed herein, that causes depolarization of the membrane potential of a POMC neuron. In another specific, non-limiting example, a PYY agonist is selected using the method disclosed herein that causes an decrease in IPSCs in a POMC neuron, and/or an increased activity of a POMC neuron. In several non-limiting examples, agonists that cause hyperpolarization of the membrane potential of a POMC neuron, increase in IPSCs in a POMC neuron, are selected using the methods disclosed herein.

In one embodiment, these PYY agonists do not include NPY. In another specific, non-limiting example, a PYY agonist is tested using the methods disclosed herein that binds NPY neurons, but does not cross the blood/brain barrier. The arcuate nucleus neurons upon which PYY exerts its effects are not protected by the blood/brain barrier, and thus are readily accessible to peripherally available molecules. In addition, other brain sites that express the Y2 receptor are protected by the blood/brain barrier. Without being bound by theory, agents able to bind to the arcuate Y2R, but that do not cross the blood/brain barrier following peripheral administration, are selected using the methods disclosed herein. In one embodiment, the ability of an agent to cross the blood brain barrier is assessed by the ability of the agent to induce the expression of c-fos in the arcuate nucleus following peripheral administration of the agent to a subject.

PYY and agonists that can be screened using the methods disclosed herein include, but are not limited to, polypeptides comprising, or alternatively consisting of, the amino acid sequence for PPY and agonists thereof, e.g., mutants, fragments and/or variants thereof. Variants include deletions, insertions, inversions, repeats and substitutions (e.g., conservative substitutions and non-conservative substitutions; see, e.g., Tables 1 and 2, infra). More than one amino acid (e.g., 2, 3, 4, 5, 6, 7, 8, 9, 10, etc.) can be deleted or inserted or substituted with another amino acid. Typically conservative substitutions are the replacements, one for another, among the aliphatic amino acids Ala, Val, Leu and Ile; interchange of Ser and Thr containing hydroxy residues, interchange of the acidic residues Asp and Glu, interchange between the amide residues Asn and Gln, interchange of the basic residues Lys and Arg, interchange of the aromatic residues Phe and Tyr, and interchange of the small-sized amino acids Ala, Ser, Thr, Met and Gly.

As another example, polypeptide fragments may contain a continuous series of deleted residues from the amino (N)- or the carboxyl (C)-terminus, or both (see, e.g., Tables 1 and 2, infra). Any number of amino acids, ranging from 1 to 24, can be deleted from the N-terminus, the C-terminus or both.

Furthermore, the agonist polypeptides that are screened using the methods disclosed herein, also include, but are not limited to, polypeptides comprising, or alternatively consisting of, internal deletions of the amino acid sequences for PPY and/or agonist thereof (see, e.g., Table 2, infra). Such deletions may comprise one or more amino acid residue deletions (e.g., one, two, three, four, five, six, seven, eight, nine, ten, etc.) and may begin at any amino acid position (e.g., two, three, four, five, six, seven, eight, nine, ten, etc.). In addition, polypeptides can be screened that contain one or more such internal deletions. Such deletions are can be made in PPY, NPY and PP.

Also contemplated is the screening of agonist peptides that are PPY, NPY and/or PP chimeras having high affinity and/or selectivity for the Y2 receptor. These chimeras may comprise amino acid substitutions of one or more amino acids (e.g., 1, 2, 3, 4, 5, 6, 7, 8, 9, 10, etc.) from PPY, NPY and/or PP, variants, mutants and/or deletions thereof, with one or more amino acids (e.g., 1, 2, 3, 4, 5, 6, 7, 8, 9, 10, etc.) from a second PPY, NPY, or PP, variants, mutations and/or deletions thereof. These substitutions may begin at any amino acid position (e.g., two, three, four, five, six, seven, eight, nine, ten, etc.).

In one embodiment, the agents that are screened using the methods disclosed herein are selective for the Y2 receptor. That is, they bind with higher affinity to Y2 compared to other receptors, such as Y1, Y2, Y3, Y4, Y5 and Y6. In another embodiment, the peptides are selective for the Y2 and Y5 receptors over the Y1, Y3, Y4 and Y6 receptors.

Other polypeptide fragments that can be screened are fragments comprising structural or functional domain of the polypeptides of this disclosure. Such fragments include amino acid residues that comprise a polyproline-type II helix (residues 1-8), beta-turn (residues 9-14), amphipathic alpha-helix (residues 15-32) and/or a C-terminal turn structure (residues 33-36). See, Kirby et al., *J Med Chem* 36:385-393, 1993.

In addition, this disclosure includes the screening of a polypeptide or agonist comprising, or alternatively consisting of, the amino acid sequence for PPY, NPY and PP species variants (see Table 1, infra) and/or mutants, and fragments thereof.

Also contemplated is the screening of fusion proteins, whereby a PYY or PYY agonist will be fused to another protein or polypeptide (the fusion partner) using recombinant methods known in the art, to identify fusion proteins of use in reducing appetite, caloric intake, food intake, and/or energy expenditure. These fusion proteins can be synthetically synthesized by any known method. Any known peptide or protein can be used as the fusion partner (e.g., serum albumin, carbonic anhydrase, glutathione-S-transferase or thioredoxin, etc.). Such fusion proteins can be designed linking the carboxy-terminus of the fusion partner to the amino-terminus of the PYY or agonist peptide, or vice versa. Optionally, a cleavable linker region can be used linking the PYY or PYY agonist to the fusion partner, and can be cleaved in vivo thereby resulting in the release of an active form of PYY or a PYY agonist. Examples of such cleavage regions include, but are not limited to, the linker regions D-D-D-D-Y (SEQ ID NO: 330), G-P-R (SEQ ID NO: 331), A-G-G (SEQ ID NO: 332) and H-P-F-H-L (SEQ ID NO 333), which can be cleaved by enterokinase, thrombin, ubiquitin cleaving enzyme and renin, respectfully. See, e.g., U.S. Pat. No. 6,410,707.

Also contemplated is the screening of PYY agonists that Y2 specific peptide agonists as described in U.S. Pat. Nos. 5,026,685; 5,574,010; 5,604,203; 5,696,093; 6,046,167.

PPY agonists that can be screened using the assays disclosed herein are described herein as follows.

TABLE 1

PYY: Variation Among Species

| PEPTIDE YY | AA SEQUENCE | |
| --- | --- | --- |
| Human | YPIKPEAPGEDASPEELNRYYASLRHYLNLVTRQRY | (SEQ ID NO: 1) |
| Rat | YPAKPEAPGEDASPEELSRYYASLRHYLNLVTRQRY | (SEQ ID NO: 5) |
| Pig | YPAKPEAPGEDASPEELSRYYASLRHYLNLVTRQRY | (SEQ ID NO: 6) |
| Guinea pig | YPSKPEAPGSDASPEELARYYASLRHYLNLVTRQRY | (SEQ ID NO: 7) |
| Frog | YPPKPENPGEDASPEEMTKYLTALRHYINLVTRQRY | (SEQ ID NO: 8) |
| Raja | YPPKPENPGDDAAPEELAKYYSALRHYINLITRQRY | (SEQ ID NO: 9) |
| Dogfish | YPPKPENPGEDAPPEELAKYYSALRHYINLITRQRY | (SEQ ID NO: 10) |
| Lampetra | FPPKPDNPGDNASPEQMARYKAAVRHYINLITRQRY | (SEQ ID NO: 11) |
| Petromyzon | MPPKPDNPSPDASPEELSKYMLAVRNYINLITRQRY | (SEQ ID NO: 12) |
| NEUROPEPTIDE Y | AA SEQUENCE | |
| Human | YPSKPDNPGEDAPAEDMARYYSALRHYINLITRQRY | (SEQ ID NO: 2) |
| Rat | YPSKPDNPGEDAPAEDMARYYSALRHYINLITRQRY | (SEQ ID NO: 13) |
| Rabbit | YPSKPDNPGEDAPAEDMARYYSALRHYINLITRQRY | (SEQ ID NO: 14) |
| Dog | YPSKPDNPGEDAPAEDMARYYSALRHYINLITRQRY | (SEQ ID NO: 15) |
| Pig | YPSKPDNPGEDAPAEDLARYYSALRHYINLITRQRY | (SEQ ID NO: 16) |
| Cow | YPSKPDNPGEDAPAEDLARYYSALRHYINLITRQRY | (SEQ ID NO: 17) |
| Sheep | YPSKPDNPGDDAPAEDLARYYSALRHYINLITRQRY | (SEQ ID NO: 18) |
| Guinea pig | YPSKPDNPGEDAPAEDMARYYSALRHYINLITRQRY | (SEQ ID NO: 19) |
| Avian | YPSKPDSPGEDAPAEDMARYYSALRHYINLITRQRY | (SEQ ID NO: 20) |
| Rana | YPSKPDNPGEDAPAEDMAKYYSALRHYINLITRQRY | (SEQ ID NO: 21) |
| Goldfish | YPTKPDNPGEGAPAEELAKYYSALRHYINLITRQRY | (SEQ ID NO: 22) |
| Dogfish | YPSKPDNPGEGAPAEDLAKYYSALRHYINLITRQRY | (SEQ ID NO: 23) |
| Lampetra | PPNKPDSPGEDAPAEDLARYLSAVRHYINLITRQRY | (SEQ ID NO: 24) |
| PANCREATIC POLYPEPTIDE | AA SEQUENCE | |
| Human | ASLEPEYPGDNATPEQMAQYAAELRRYINMLTRPRY | (SEQ ID NO: 3) |
| Sheep | APLEPVYPGDNATPEQMAQYAADLRRYINMLTRPRY | (SEQ ID NO: 25) |

TABLE 1-continued

| PYY: Variation Among Species | | |
|---|---|---|
| Pig | APLEPVYPGDDATPEQMAQYAAELRRYINMLTRPRY | (SEQ ID NO: 26) |
| Dog | APLEPVYPGDDATPEQMAQYAAELRRYINMLTRPRY | (SEQ ID NO: 27) |
| Cat | APLEPVYPGDNATPEQMAQYAAELRRYINMLTRPRY | (SEQ ID NO: 28) |
| Cow | APLEPEYPGDNATPEQMAQYAAELRRYINMLTRPRY | (SEQ ID NO: 29) |
| Rat | APLEPMYPGDYATHEQRAQYETQLRRYINTLTRPRY | (SEQ ID NO: 30) |
| Mouse | APLEPMYPGDYATPEQMAQYETQLRRYINTLTRPRY | (SEQ ID NO: 31) |
| Guinea pig | APLEPVYPGDNATPEQQMAQYAAEMRRYINMLTRPRY | (SEQ ID NO: 32) |
| Chicken | GPSQPTYPGDDAPVEDLIRFYNDLQQYLNVVTRHRY | (SEQ ID NO: 33) |
| Alligator | TPLQPKYPGDGAPVEDLIQFYNDLQQYLNVVTRPRF | (SEQ ID NO: 34) |
| Bullfrog | APSEPHHPGDQATPDQLAQYYSDLYQYITFITRPRF | (SEQ ID NO: 35) |

Ref: Beck-Sickinger, A.G., Jung, G., Biopolymers 37: 123-142, 1995.

TABLE 2

| PEPTIDE AGONIST OF PPY | |
|---|---|
| PEPTIDE | SEQUENCE |
| PPY(3-36)(human) | IKPEAPGEDASPEELNRYYASLRHYLNLVTRQRY (SEQ ID NO: 1) |

Ref: Eberlein et al., Peptides 10: 797-803, 1989; Grandt et al., Peptides 15(5): 815-20, 1994.

Variations of PPY(3-36)

N-Terminal Deletions of PYY, including but not limited to: PYY(26-36), PYY(25-36), PYY(24-36), PYY(23-36), PYY(22-36), PYY(21-36), PYY(20-36), PYY(19-36), PYY(18-36), PYY(17-36), PYY(16-36), PYY(15-36), PYY(14-36), PYY(13-36), PYY(12-36), PYY(11-36), PYY(10-36), PYY(9-36), PYY(8-36), PYY(7-36), PYY(6-36), PYY(5-36), PYY(4-36), PYY(3-36).
Ref: See, e.g., Balasubramaniam et al., Pept Res 1(1): 32-5, Sep-Oct 1998; Liu et al., J Gastrointest Surg 5(2): 147-52, Mar-Apr 2001.

| NPY (human) | YPSKPDNPGEDAPAEDMARYYSALRHYINLITRQRY (SEQ ID NO: 2) |
|---|---|

Ref: Tatemoto et al., Proc Natl Acad Sci U.S.A. 79: 5485-9, 1982.

Variations of NPY

N-Terminal Deletions of NPY, including but not limited to: NPY(26-36), NPY(25-36), NPY(24-36), NPY(23-36), NPY(22-36), NPY(21-36), NPY(20-36), NPY(19-36), NPY(18-36), NPY(17-36), NPY(16-36), NPY(15-36), NPY(14-36), NPY(13-36), NPY(12-36), NPY(11-36), NPY(10-36), NPY(9-36), NPY(8-36), NPY(7-36), NPY(6-36), NPY(5-36), NPY(4-36), NPY(3-36).
Ref: See e.g., Gehlert et al., Proc Soc Exp Biol Med 218: 7-22, 1998; Sheikh et al., Am J Physiol 261: G701-15, Nov. 1991.

Internal Deletions, including but not limited to: (1-4)-Aca-(14-36)pNPY, (1-4)-Aca-(15-36)pNPY, (1-4)-Aca-(16-36)pNPY, (1-4)-Aca-(17-36)pNPY, (1-4)-Aca-(18-36)pNPY, (1-4)-(31-36)pNPY11, (1-4)-Aca-(31-36)pNPY, (4-1)-(31-36)pNPY, (4-1)-Aca-(31-36)pNPY, (4-1)$_D$-(31-36)pNPY, (4-1)$_D$-Aca-(31-36)pNPY.
Ref: Fournier et al., Mol Pharmacol 45(1): 93-101, Jan 1994.

Additional Internal Deletion Mutants, including but not limited to: des-AA$^{10-17}$-NPY, des-AA-$^{10-17}$, Ac-[D-Lys$^9$(ε-Ac-Ala)]NPY, des-AA-$^{10-17}$, Ac[D-Lys$^9$(ε-Ac-Ala)]NPY, des-AA$^{10-17}$[Ala$^{7,21}$]NPY, des-AA$^{10-17}$[Cys$^{7,21}$]NPY, des-AA$^{10-17}$[Glu$^7$, Lys$^{21}$]NPY, des-AA$^{11-17}$[D-Lys$^{10}$(ε-Ac), Cys$^{7,21}$]NPY, des-AA$^{10-17}$[D-Cys$^7$, D-Lys(ε-Ac), Cys$^{21}$]NPY, des-AA$^{10-17}$[D-Cys$^7$, Lys$^9$(ε-Ac), Cys$^{21}$]NPY, des-AA$^{10-17}$[Cys$^{7,21}$, Pro$^{34}$]NPY, des-AA$^{10-17}$[Asp$^7$, Dpr$^{21}$, Pro$^{34}$]NPY, des-AA-$^{10-17}$[Glu$^7$, Lys$^{21}$, Pro$^{34}$]NPY, des-AA$^{10-17}$[Cys$^{7,21}$, Leu$^{31}$, Pro$^{34}$]NPY, des-AA$^{10-20}$[Cys$^{7,21}$, Pro$^{34}$]NPY, des-AA$^{10-17}$[Cys$^{2,27}$]NPY, des-AA$^{10-17}$[Cys$^2$, D-Cys$^{27}$]NPY.
Ref: Kirby et al., J Med Chem 38: 4579-86, 1995.

Cyclic agonist of NPY, including but not limited to: [Lys 25-Glu 29]NPY(Ac-25-36), [Glu 25-Lys 29]NPY(Ac-25-36), [Lys 26-Glu31]NPY(Ac-25-36), [Glu 27-Lys 31]NPY(Ac-25-36), [Lys28-Glu 32]NPY(Ac-25-36), [Lys27-Glu34]NPY(Ac-25-36).
Ref: Rist et al., Eur J Biochem 247: 1019-1028, 1997.

TABLE 2-continued

PEPTIDE AGONIST OF PPY

| PEPTIDE | SEQUENCE | |
|---|---|---|
| D-amino acid substitutions: [D-Tyr$^1$]NPY, [D-Pro]NPY, [D-Ser$^3$]NPY, [D-Lys$^4$]NPY, [D-Pro$^5$]NPY, [D-Asp$^6$]NPY, [D-Asn$^7$]NPY, [D-Pro$^8$]NPY, [D-Ala$^9$]NPY, [D-Glu$^{10}$]NPY, [D-Asp$^{11}$]NPY, [D-Ala$^{12}$]NPY, [D-Pro$^{13}$]NPY, [D-Ala$^{14}$]NPY, [D-Glu$^{15}$]NPY, [D-Asp$^{16}$]NPY, [D-Leu$^{17}$]NPY, [D-Ala$^{18}$]NPY, [D-Arg$^{19}$]NPY, [D-Tyr$^{20}$]NPY, [D-Tyr$^{21}$]NPY, [D-Ser$^{22}$]NPY, [D-Ala$^{23}$]NPY, [D-Leu$^{24}$]NPY, [D-Arg$^{25}$]NPY, [D-His$^{26}$]NPY, [D-Tyr$^{27}$]NPY, [D-Ile$^{28}$]NPY, [D-Asn$^{29}$]NPY, [D-Leu$^{30}$]NPY, [D-Ile$^{31}$]NPY, [D-Thr$^{32}$]NPY, [D-Arg$^{33}$]NPY, [D-Gln$^{34}$]NPY, [D-Arg$^{35}$]NPY, [D-Tyr$^{36}$]NPY, [D-Tyr$^1$, D-Pro$^2$]NPY, [D-Ser$^3$, D-Lys$^4$]NPY, [D-Pro$^5$, D-Asp$^6$]NPY, [D-Asn$^7$, D-Pro$^8$]NPY, [D-Glu$^{10}$, D-Asp$^{11}$]NPY, D-Ala$^{12}$]NPY, [D-Pro$^{13}$, D-Ala$^{14}$]NPY, [D-Glu$^{15}$, D-Asp$^{16}$]NPY, [D-Met$^{17}$, D-Ala$^{18}$]NPY, [D-Arg$^{19}$, D-Tyr$^{20}$]NPY, [D-Tyr$^{21}$, D-Ser$^{22}$]NPY, [D-Ala$^{23}$, D-Leu$^{24}$]NPY, [D-Arg$^{25}$, D-His$^{26}$]NPY, [D-Tyr$^{27}$, D-Ile$^{28}$]NPY, [D-Asn$^{29}$, D-Leu$^{30}$]NPY, [D-Ile$^{31}$, D-Thr$^{32}$]NPY, [D-Arg$^{33}$, D-Gln$^{34}$]NPY, [D-Arg$^{35}$, D-Tyr$^{36}$]NPY. Ref: Kirby et al., J Med Chem 36: 3802-08, 1993; Grundemar et al., Regulatory Peptides 62: 131-136, 1996. | | |
| Other NPY Agonist and Analogs | | |
| NPY(3-36) Ref: Grandt et al., Regulatory Peptides 67(1): 33-7, 1996. | SKPDNPGEDAPAEDMARYYSALRHYINLITRQRY | (SEQ ID NO: 5) |
| N-Acetyl NPY(24-36) Ref: Potter et al., Eur J Pharmacol 267(3): 253-262, May 17, 1994. | LRHYINLITRQRY | (SEQ ID NO: 213) |
| N-Acetyl [Leu$^{28}$, Leu$^{31}$]NPY(24-36) Ref: Potter et al., Eur J Pharmacol 267(3): 253-262, May 17, 1994. | LRHYLNLLTRQRY | (SEQ ID NO: 214) |
| [Leu$^{28}$, Leu$^{31}$]NPY(24-36) Ref: Potter et al., Eur J Pharmacol 267(3): 253-262, May 17, 1994. | LRHYLNLLTRQRY | (SEQ ID NO: 215) |
| [Leu$^{17}$, Gln$^{19}$, Ala$^{21}$, Ala$^{22}$, Glu$^{23}$, Leu$^{28}$, Leu$^{31}$] NPY(13-36) Ref: Potter et al., Eur J Pharmacol 267(3): 253-262, May 17, 1994. | PAEDLAQYAAELRHYLNLLTRQRY | (SEQ ID NO: 216) |
| Cyclo S-S [Cys$^{20}$, Cys$^{24}$]pNPY Ref: Soll et al., Eur J Biochem 268(10): 2828-37, May 2001. | SKPDNPGEDAPAEDMARCYSACRHYINLITRQRY | (SEQ ID NO: 315) |
| Cyclo-(28/32)-Ac-[Lys$^{28}$-Glu$^{32}$]-(25-36)-pNPY Ref: Cabrele et al., J Pept Sci 6(3): 97-122, Mar 2000. | RHYLNLIGRQRY | (SEQ ID NO: 316) |
| Cyclo-(27/31)-Ac-[Glu$^{27}$-Lys$^{31}$]-(25-36)-pNPY Ref: Cabrele et al., J Pept Sci 6(3): 97-122, Mar 2000. | RHGLNLLGRQRY | (SEQ ID NO: 317) |
| [Tyr$^{32}$, Leu$^{34}$]NPY(27-36) Ref: Leban et al., J Med Chem 38: 1150-57, 1995. | YINLIYRLRY | (SEQ ID NO: 318) |
| [Tyr$^{32}$, Leu$^{34}$]NPY(26-36) Ref: Leban et al., J Med Chem 38: 1150-57, 1995. | HYINLIYRLRY | (SEQ ID NO: 319) |
| [Tyr$^{32}$, Leu$^{34}$]NPY(25-36) Ref: Leban et al., J Med Chem 38: 1150-57, 1995. | RHYINLIYRLRY | (SEQ ID NO: 320) |
| [Leu$^{31}$]NPY(27-36) Ref: Leban et al., J Med Chem 38: 1150-57, 1995. | YINLLYRQRY | (SEQ ID NO: 321) |
| [Tyr$^{32}$, Leu$^{34}$](1-4)-Ahr-(27-36)NPY Ref: Leban et al., J Med Chem 38: 1150-57, 1995. | YPSL-Aha-YINLIYRLRY | (S[D ID NO: 322) |
| [Tyr$^{32}$, Leu$^{34}$]NPY(28-36) Ref: Leban et al., J Med Chem 38: 1150-57, 1995. | INLIYRLRY | (SEQ ID NO: 323) |
| PP (human) Ref: Kimmel et al., Endocrinology 83: 1323-30, 1968. | ASLEPEYPGDNATPEQMAQYAAELRRYINMLTRPRY | (SEQ ID NO:323) |

Variations of PP

N-Terminal Deletions including but not limited to: PP(26-36), PP(25-36), PP(24-36), PP(23-36), PP(22-36), PP(21-36), PP(20-36), PP(19-36), PP(18-36), PP(17-36), PP(16-36), PP(15-36), PP(14-36), PP(13-36), PP(12-36), PP(11-36), PP(10-36), PP(9-36), PP(8-36), PP(7-36), PP(6-36), PP(5-36), PP(4-36), PP(3-36).

TABLE 3

EXAMPLES OF CONSERVATIVE AMINO ACID SUBSTITUTIONS OF PYY

| PEPTIDE | SEQUENCE |
|---|---|
| Single point mutations of PYY(25-36) | |
| [Lys$^{25}$]PPY(25-36) | KHYLNLVTRQRY (SEQ ID NO: 36) |
| [Thr$^{27}$]PPY(25-36) | RHTLNLVTRQRY (SEQ ID NO: 37) |
| [Phe$^{27}$]PPY(25-36) | RHFLNLVTRQRY (SEQ ID NO: 38) |
| [Ile$^{28}$]PYY(25-36) | RHYINLVTRQRY (SEQ ID NO: 39) |
| [Val$^{28}$]PYY(25-36) | RHYVNLVTRQRY (SEQ ID NO: 40) |
| [Gln$^{29}$]PYY(25-36) | RHYLQLVTRQRY (SEQ ID NO: 41) |
| [Ile$^{30}$]PYY(25-36) | RHYLNIVTRQRY (SEQ ID NO: 42) |
| [Val$^{30}$]PYY(25-36) | RHYLNVVTRQRY (SEQ ID NO: 43) |
| [Ile$^{31}$]PYY(25-36) | RHYLNLITRQRY (SEQ ID NO: 44) |
| [Leu$^{31}$]PYY(25-36) | RHYLNLLTRQRY (SEQ ID NO: 45) |
| [Ser$^{32}$]PYY(25-36) | RHYLNLVSRQRY (SEQ ID NO: 46) |
| [Lys$^{33}$]PYY(25-36) | RHYLNLVTKQRY (SEQ ID NO: 47) |
| [Asn$^{34}$]PYY(25-36) | RHYLNLVTRNRY (SEQ ID NO: 48) |
| [Lys$^{35}$]PYY(25-36) | RHYLNLVTRQKY (SEQ ID NO: 49) |
| [Thr$^{36}$]PYY(25-36) | RHYLNLVTRQRT (SEQ ID NO: 50) |
| [Phe$^{36}$]PYY(25-36) | RHYLNLVTRQRF (SEQ ID NO: 51) |
| Double point mutations | |
| [Lys$^{25}$, Thr$^{27}$]PPY(25-36) | KHTLNLVTRQRY (SEQ ID NO: 52) |
| [Lys$^{25}$, Phe$^{27}$]PPY(25-36) | KHFLNLVTRQRY (SEQ ID NO: 53) |
| [Lys$^{25}$, Ile$^{28}$]PPY(25-36) | KHYINLVTRQRY (SEQ ID NO: 54) |
| [Lys$^{25}$, Val$^{28}$]PPY(25-36) | KHYVNLVTRQRY (SEQ ID NO: 55) |

TABLE 3-continued

EXAMPLES OF CONSERVATIVE AMINO ACID SUBSTITUTIONS OF PYY

| PEPTIDE | SEQUENCE |
|---|---|
| [Lys$^{25}$, Gln$^{29}$]PPY(25-36) | KHYLQLVTRQRY (SEQ ID NO: 56) |
| [Lys$^{25}$, Ile$^{30}$]PPY(25-36) | KHYLNIVTRQRY (SEQ ID NO: 57) |
| [Lys$^{25}$, Val$^{30}$]PPY(25-36) | KHYLNVVTRQRY (SEQ ID NO: 58) |
| [Lys$^{25}$, Ile$^{31}$]PPY(25-36) | KHYLNLITRQRY (SEQ ID NO: 59) |
| [Lys$^{25}$, Leu$^{31}$]PPY(25-36) | KHYLNLLTRQRY (SEQ ID NO: 60) |
| [Lys$^{25}$, Ser$^{32}$]PPY(25-36) | KHYLNLVSRQRY (SEQ ID NO: 61) |
| [Lys$^{25}$, Lys$^{33}$]PPY(25-36) | KHYLNLVTKQRY (SEQ ID NO: 62) |
| [Lys$^{25}$, Asn$^{34}$]PPY(25-36) | KHYLNLVTRNRY (SEQ ID NO: 63) |
| [Lys$^{25}$, Lys$^{35}$]PPY(25-36) | KHYLNLVTRQKY (SEQ ID NO: 64) |
| [Lys$^{25}$, Thr$^{36}$]PPY(25-36) | KHYLNLVTRQRT (SEQ ID NO: 65) |
| [Lys$^{25}$, Phe$^{36}$]PPY(25-36) | KHYLNLVTRQRF (SEQ ID NO: 66) |
| [Thr$^{27}$, Ile$^{28}$]PPY(25-36) | RHTINLVTRQRY (SEQ ID NO: 67) |
| [Thr$^{27}$, Val$^{28}$]PPY(25-36) | RHTVNLVTRQRY (SEQ ID NO: 68) |
| [Thr$^{27}$, Gln$^{29}$]PPY(25-36) | RHTLQLVTRQRY (SEQ ID NO: 69) |
| [Thr$^{27}$, Ile$^{30}$]PPY(25-36) | RHTLNIVTRQRY (SEQ ID NO: 70) |
| [Thr$^{27}$, Val$^{30}$]PPY(25-36) | RHTLNVVTRQRY (SEQ ID NO: 71) |
| [Thr$^{27}$, Ile$^{31}$]PPY(25-36) | RHTLNLITRQRY (SEQ ID NO: 72) |
| [Thr$^{27}$, Leu$^{31}$]PPY(25-36) | RHTLNLLTRQRY (SEQ ID NO: 73) |
| [Thr$^{27}$, Ser$^{32}$]PPY(25-36) | RHTLNLVSRQRY (SEQ ID NO: 74) |
| [Thr$^{27}$, Lys$^{33}$]PPY(25-36) | RHTLNLVTKQRY (SEQ ID NO: 75) |
| [Thr$^{27}$, Asn$^{34}$]PPY(25-36) | RHTLNLVTRNRY (SEQ ID NO: 76) |
| [Thr$^{27}$, Lys$^{35}$]PPY(25-36) | RHTLNLVTRQKY (SEQ ID NO: 77) |
| [Thr$^{27}$, Thr$^{36}$]PPY(25-36) | RHTLNLVTRQRT (SEQ ID NO: 78) |
| [Thr$^{27}$, Phe$^{36}$]PPY(25-36) | RHTLNLVTRQRF (SEQ ID NO: 79) |
| [Phe$^{27}$, Ile$^{28}$]PPY(25-36) | RHFINLVTRQRY (SEQ ID NO: 80) |

TABLE 3-continued

EXAMPLES OF CONSERVATIVE AMINO ACID SUBSTITUTIONS OF PYY

| PEPTIDE | SEQUENCE |
|---|---|
| [Phe$^{27}$, Val$^{28}$]PPY(25-36) | RHFVNLVTRQRY (SEQ ID NO: 81) |
| [Phe$^{27}$, Gln$^{29}$]PPY(25-36) | RHFLQLVTRQRY (SEQ ID NO: 82) |
| [Phe$^{27}$, Ile$^{30}$]PPY(25-36) | RHFLNIVTRQRY (SEQ ID NO: 83) |
| [Phe$^{27}$, Val$^{30}$]PPY(25-36) | RHFLNVVTRQRY (SEQ ID NO: 84) |
| [Phe$^{27}$, Ile$^{31}$]PPY(25-36) | RHFLNLITRQRY (SEQ ID NO: 85) |
| [Phe$^{27}$, Leu$^{31}$]PPY(25-36) | RHFLNLLTRQRY (SEQ ID NO: 86) |
| [Phe$^{27}$, Ser$^{32}$]PPY(25-36) | RHFLNLVSRQRY (SEQ ID NO: 87) |
| [Phe$^{27}$, Lys$^{33}$]PPY(25-36) | RHFLNLVTKQRY (SEQ ID NO: 88) |
| [Phe$^{27}$, Asn$^{34}$]PPY(25-36) | RHFLNLVTRNRY (SEQ ID NO: 89) |
| [Phe$^{27}$, Lys$^{35}$]PPY(25-36) | RHFLNLVTRQKY (SEQ ID NO: 90) |
| [Phe$^{27}$, Thr$^{36}$]PPY(25-36) | RHFLNLVTRQRT (SEQ ID NO: 91) |
| [Phe$^{27}$, Phe$^{36}$]PPY(25-36) | RHFLNLVTRQRF (SEQ ID NO: 92) |
| [Gln$^{29}$, Ile$^{30}$]PYY(25-36) | RHYLQIVTRQRY (SEQ ID NO: 93) |
| [Gln$^{29}$, Val$^{30}$]PYY(25-36) | RHYLQVVTRQRY (SEQ ID NO: 94) |
| [Gln$^{29}$, Ile$^{31}$]PYY(25-36) | RHYLQLITRQRY (SEQ ID NO: 95) |
| [Gln$^{29}$, Leu$^{31}$]PYY(25-36) | RHYLQLLTRQRY (SEQ ID NO: 96) |
| [Gln$^{29}$, 5er$^{32}$]PYY(25-36) | RHYLQLVSRQRY (SEQ ID NO: 97) |
| [Gln$^{29}$, Leu33]PYY(25-36) | RHYLQLVTKQRY (SEQ ID NO: 98) |
| [Gln$^{29}$, Asn$^{34}$]PYY(25-36) | RHYLQLVTRNRY (SEQ ID NO: 99) |
| [Gln$^{29}$, Leu35]PYY(25-36) | RHYLQLVTRQKY (SEQ ID NO: 100) |
| [Gln$^{29}$, Thr$^{36}$]PYY(25-36) | RHYLQLVTRQRT (SEQ ID NO: 101) |
| [Gln$^{29}$, Phe$^{36}$]PYY(25-36) | RHYLQLVTRQRF (SEQ ID NO: 102) |
| [Ile$^{30}$, Ile$^{31}$]PYY(25-36) | RHYLNIITRQRY (SEQ ID NO: 103) |
| [Ile$^{30}$, Leu$^{31}$]PYY(25-36) | RHYLNILTRQRY (SEQ ID NO: 104) |
| [Ile$^{30}$, Ser$^{32}$]PYY(25-36) | RHYLNIVSRQRY (SEQ ID NO: 105) |
| [Ile$^{30}$, Lys$^{33}$]PYY(25-36) | RHYLNIVTKQRY (SEQ ID NO: 106) |
| [Ile$^{30}$, Asn$^{34}$]PYY(25-36) | RHYLNIVTRNRY (SEQ ID NO: 107) |
| [Ile$^{30}$, Lys$^{35}$]PYY(25-36) | RHYLNIVTRQKY (SEQ ID NO: 108) |
| [Ile$^{30}$, Thr$^{36}$]PYY(25-36) | RHYLNIVTRQRT (SEQ ID NO: 109) |
| [Ile$^{30}$, Phe$^{36}$]PYY(25-36) | RHYLNIVTRQRF (SEQ ID NO: 110) |
| [Val$^{30}$, Ile$^{31}$]PYY(25-36) | RHYLNVITRQRY (SEQ ID NO: 111) |
| [Val$^{30}$, Leu$^{31}$]PYY(25-36) | RHYLNVLTRQRY (SEQ ID NO: 112) |
| [Val$^{30}$, Ser$^{32}$]PYY(25-36) | RHYLNVVSRQRY (SEQ ID NO: 113) |
| [Val$^{30}$, Lys$^{33}$]PYY(25-36) | RHYLNVVTKQRY (SEQ ID NO: 114) |
| [Val$^{30}$, Asn$^{34}$]PYY(25-36) | RHYLNVVTRNRY (SEQ ID NO: 115) |
| [Val$^{30}$, Lys$^{35}$]PYY(25-36) | RHYLNVVTRQKY (SEQ ID NO: 116) |
| [Val$^{30}$, Thr$^{36}$]PYY(25-36) | RHYLNVVTRQRT (SEQ ID NO: 117) |
| [Val$^{30}$, Phe$^{36}$]PYY(25-36) | RHYLNVVTRQRF (SEQ ID NO: 118) |
| [Ile$^{31}$, Ser$^{32}$]PYY(25-36) | RHYLNLISRQRY (SEQ ID NO: 119) |
| [Ile$^{31}$, Lys$^{33}$]PYY(25-36) | RHYLNLITKQRY (SEQ ID NO: 120) |
| [Ile$^{31}$, Asn$^{34}$]PYY(25-36) | RHYLNLITRNRY (SEQ ID NO: 121) |
| [Ile$^{31}$, Lys$^{35}$]PYY(25-36) | RHYLNLITRQKY (SEQ ID NO: 122) |
| [Ile$^{31}$, Thr$^{36}$]PYY(25-36) | RHYLNLITRQRT (SEQ ID NO: 123) |
| [Leu$^{31}$, Phe$^{36}$]PYY(25-36) | RHYLNLITRQRF (SEQ ID NO: 124) |
| [Leu$^{31}$, Ser$^{32}$]PYY(25-36) | RHYLNLLSRQRY (SEQ ID NO: 125) |
| [Val$^{31}$, Lys$^{33}$]PYY(25-36) | RHYLNLLTKQRY (SEQ ID NO: 126) |
| [Leu$^{31}$, Asn$^{34}$]PYY(25-36) | RHYLNLLTRNRY (SEQ ID NO: 127) |
| [Leu$^{31}$, Lys$^{35}$]PYY(25-36) | RHYLNLLTRQKY (SEQ ID NO: 128) |
| [Leu$^{31}$, Thr$^{36}$]PYY(25-36) | RHYLNLLTRQRT (SEQ ID NO: 129) |
| [Leu$^{31}$, Phe$^{36}$]PYY(25-36) | RHYLNLLTRQRF (SEQ ID NO: 130) |

TABLE 3-continued

EXAMPLES OF CONSERVATIVE AMINO ACID SUBSTITUTIONS OF PYY

| PEPTIDE | SEQUENCE |
|---|---|
| [Ser$^{32}$, Lys$^{33}$]PYY(25-36) | RHYLNLVSKQRY (SEQ ID NO: 131) |
| [Ser$^{32}$, Asn$^{34}$]PYY(25-36) | RHYLNLVSRNRY (SEQ ID NO: 132) |
| [Ser$^{32}$, Lys$^{35}$]PYY(25-36) | RHYLNLVSRQKY (SEQ ID NO: 133) |
| [Ser$^{32}$, Thr$^{36}$]PYY(25-36) | RHYLNLVSRQRT (SEQ ID NO: 134) |
| [Ser$^{32}$, Phe$^{36}$]PYY(25-36) | RHYLNLVSRQRY (SEQ ID NO: 135) |
| [Lys$^{33}$, Asn$^{34}$]PYY(25-36) | RHYLNLVTKNRY (SEQ ID NO: 136) |
| [Lys$^{33}$, Lys$^{35}$]PYY(25-36) | RHYLNLVTKQKY (SEQ ID NO: 137) |
| [Lys$^{33}$, Thr$^{36}$]PYY(25-36) | RHYLNLVTKQRT (SEQ ID NO: 138) |
| [Lys$^{33}$, Phe$^{36}$]PYY(25-36) | RHYLNLVTKQRF (SEQ ID NO: 139) |
| [Asn$^{34}$, Lys$^{35}$]PYY(25-36) | RHYLNLVTRNKY (SEQ ID NO: 140) |
| [Asn$^{34}$, Thr$^3{}_6$]PYY(25-36) | RHYLNLVTRNRT (SEQ ID NO: 141) |
| [Asn$^{34}$, Phe$^{36}$]PYY(25-36) | RHYLNLVTRNRF (SEQ ID NO: 142) |
| [Lys$^{35}$, Thr$^3{}_6$]PYY(25-36) | RHYLNLVTRQKT (SEQ ID NO: 143) |
| [Lys$^{35}$, Phe$^{36}$]PYY(25-36) | RHYLNLVTRQKF (SEQ ID NO: 144) |

Point Mutations of PYY(24-36)

| PYY(24-36) | LRHYLNLVTRQRY (SEQ ID NO: 145) |
|---|---|
| [Ile$^{24}$]PYY(24-36) | IRHYLNLVTRQRY (SEQ ID NO: 146) |
| [Val$^{24}$]PYY(24-36) | VRHYLNLVTRQRY (SEQ ID NO: 147) |

Also included as PYY(24-36) mutations are polypeptide variations (amino acid sequence variations) resulting from the combination of any of these three mutants with any of the above listed mutants for PYY(25-36), e.g., [Lys$^2$]PPY(24-36) (Amino acid sequence=LKHYLNLVTRQRY (SEQ ID NO: 191)) would result from combining the mutations from SEQ ID NO: 36 with SEQ ID NO: 145.

Point Mutations of PYY(23-36)

| PEPTIDE | SEQUENCE |
|---|---|
| PYY(23-36) | SLRHYLNLVTRQRY (SEQ ID NO: 148) |
| [Thr$^{23}$]PYY(23-36) | TLRHYLNLVTRQRY (SEQ ID NO: 149) |

Also included as PYY(23-36) mutations are polypeptide variations (amino acid sequence variations) resulting from the combination of either of these two mutants with any of the above listed mutants for PYY(25-36), and/or any of the above listed mutants for PYY(24-36), e.g., [Lys$^{25}$]PPY(23-36) (Amino acid sequence=SLKHYLNLVTRQRY (SEQ ID NO: 192)) would result from combining the mutations from SEQ ID NO: 36 with SEQ ID NO: 148.

Point Mutations of PYY(22-36)

| PEPTIDE | SEQUENCE |
|---|---|
| PYY(22-36) | ASLRHYLNLVTRQRY (SEQ ID NO: 150) |
| [Ser$^{22}$)PYY(22-36) | SSLRHYLNLVTRQRY (SEQ ID NO: 151) |

Also included as PYY(22-36) mutations are polypeptide variations (amino acid sequence variations) resulting from the combination of either of these two mutants with any of the above listed mutants for PYY(25-36), and/or any of the above listed mutants for PYY(23-36), e.g., [Lys$^{25}$]PPY(22-36) (Amino acid sequence=ASLKHYLNLVTRQRY (SEQ ID NO: 193)) would result from combining the mutations from SEQ ID NO: 36 with SEQ ID NO: 150.

Point Mutations of PYY(21-36)

| PEPTIDE | SEQUENCE |
|---|---|
| PYY(21-36) | YASLRHYLNLVTRQRY (SEQ ID NO: 152) |
| [Thr$^{21}$]PYY(21-36) | TASLRHYLNLVTRQRY (SEQ ID NO: 153) |
| [Phe$^{21}$]PYY(21-36) | FASLRHYLNLVTRQRY (SEQ ID NO: 154) |

Also included as PYY(21-36) mutations are polypeptide variations (amino acid sequence variations) resulting from the combination of any of these three mutants with any of the above listed mutants for PYY(25-36), and/or any of the above listed mutants for PYY(22-36), e.g., [Lys$^{25}$]PPY(21-36) (Amino acid sequence=YASLKHYLNLVTRQRY (SEQ ID NO: 194)) would result from combining the mutations from SEQ ID NO: 36 with SEQ ID NO: 152.

| Point Mutations of PYY(20-36) | |
|---|---|
| PEPTIDE | SEQUENCE |
| PYY(20-36) | YYASLRHYLNLVTRQRY (SEQ ID NO: 155) |
| [Thr$^{20}$]PYY(20-36) | TYASLRHYLNLVTRQRY (SEQ ID NO: 156) |
| [Phe$^{20}$]PYY(20-36) | FYASLRHYLNLVTRQRY (SEQ ID NO: 157) |

Also included as PYY(20-36) mutations are polypeptide variations (amino acid sequence variations) resulting from the combination of any of these three mutants with any of the above listed mutants for PYY(25-36), and/or any of the above listed mutants for PYY(21-36), e.g., [Lys$^{25}$]PPY(20-36) (Amino acid sequence=YYASLKHYLNLVTRQRY (SEQ ID NO: 195)) would result from combining the mutations from SEQ ID NO: 36 with SEQ ID NO: 155.

| Point Mutations of PYY(19-36) | |
|---|---|
| PEPTIDE | SEQUENCE |
| PYY(19-36) | RYYASLRHYLNLVTRQRY (SEQ ID NO: 158) |
| [Lys$^{19}$]PYY(19-36) | KYYASLRHYLNLVTRQRY (SEQ ID NO: 159) |

Also included as PYY(19-36) mutations are polypeptide variations (amino acid sequence variations) resulting from the combination of either of these two mutants with any of the above listed mutants for PYY(25-36), and/or any of the above listed mutants for PYY(20-36), e.g., [Lys$^{25}$]PPY(19-36) (Amino acid sequence=RYYASLKHYLNLVTRQRY (SEQ ID NO: 196)) would result from combining the mutations from SEQ ID NO: 36 with SEQ ID NO: 158.

| Point Mutations of PYY(18-36) | |
|---|---|
| PEPTIDE | SEQUENCE |
| PYY(18-36) | NRYYASLRHYLNLVTRQRY (SEQ ID NO: 160) |
| [Gln$^{18}$]PYY(18-36) | QRYYASLRHYLNLVTRQRY (SEQ ID NO: 161) |

Also included as PYY(18-36) mutations are polypeptide variations (amino acid sequence variations) resulting from the combination of either of these two mutants with any of the above listed mutants for PYY(25-36), and/or any of the above listed mutants for PYY(19-36), e.g., [Lys$^{25}$]PPY(18-36) (Amino acid sequence=NRYYASLKHYLNLVTRQRY (SEQ ID NO: 197)) would result from combining the mutations from SEQ ID NO: 36 with SEQ ID NO: 160.

| Point Mutations of PYY(17-36) | |
|---|---|
| PEPTIDE | SEQUENCE |
| PYY(17-36) | LNRYYASLRHYLNLVTRQRY (SEQ ID NO: 162) |
| [Ile$^{17}$]PYY(17-36) | INRYYASLRHYLNLVTRQRY (SEQ ID NO: 163) |
| [Val$^{17}$]PYY(17-36) | VNRYYASLRHYLNLVTRQRY (SEQ ID NO: 164) |

Also included as PYY(17-36) mutations are polypeptide variations (amino acid sequence variations) resulting from the combination of any of these three mutants with any of the above listed mutants for PYY(25-36), and/or any of the above listed mutants for PYY(18-36), e.g., [Lys$^{25}$]PPY(17-36) (Amino acid sequence=LNRYYASLKHYLNLVTRQRY (SEQ ID NO: 198)) would result from combining the mutations from SEQ ID NO: 36 with SEQ ID NO: 162.

| Point Mutations of PYY(16-36) | |
|---|---|
| PEPTIDE | SEQUENCE |
| PYY(16-36) | ELNRYYASLRHYLNLVTRQRY (SEQ ID NO: 165) |
| [Asp$^{16}$]PYY(16-36) | DLNRYYASLRHYLNLVTRQRY (SEQ ID NO: 166) |

Also included as PYY(16-36) mutations are polypeptide variations (amino acid sequence variations) resulting from the combination of either of these two mutants with any of the above listed mutants for PYY(25-36), and/or any of the above listed mutants for PYY(17-36), e.g., [Lys$^{25}$]PPY(16-36) (Amino acid sequence=ELNRYYASLKHYLNLVTRQRY (SEQ ID NO: 199)) would result from combining the mutations from SEQ ID NO: 36 with SEQ ID NO: 165.

| Point Mutations of PYY(15-36) | |
|---|---|
| PEPTIDE | SEQUENCE |
| PYY(15-36) | EELNRYYASLRHYLNLVTRQRY (SEQ ID NO: 167) |
| [Asp$^{15}$]PYY(15-36) | DELNRYYASLRHYLNLVTRQRY (SEQ ID NO: 168) |

Also included as PYY(15-36) mutations are polypeptide variations (amino acid sequence variations) resulting from the combination of either of these two mutants with any of the above listed mutants for PYY(25-36), and/or any of the above listed mutants for PYY(16-36), e.g., [Lys$^{25}$]PPY(15-36) (Amino acid sequence=EELNRYYASLKHYLNLVTRQRY (SEQ ID NO: 200)) would result from combining the mutations from SEQ ID NO: 36 with SEQ ID NO: 167.

| Point Mutations of PYY(14-36) | |
| --- | --- |
| PEPTIDE | SEQUENCE |
| PYY(14-36) | PEELNRYYASLRHYLNLVTRQRY (SEQ ID NO: 169) |

Also included as PYY(14-36) mutations are polypeptide variations (amino acid sequence variations) resulting from the combination of this PYY(14-36) mutant with any of the above listed mutants for PYY(25-36), and/or any of the above listed mutants for PYY(15-36), e.g., [Lys$^{25}$]PPY(23-36) (Amino acid sequence=PEELNRYYASLKHYLNLVTRQRY (SEQ ID NO: 201) would result from combining the mutations from SEQ ID NO: 36 with SEQ ID NO: 169.

| Point Mutations of PYY(13-36) | |
| --- | --- |
| PEPTIDE | SEQUENCE |
| PYY(13-36) | SPEELNRYYASLRHYLNLVTRQRY (SEQ ID NO: 170) |
| [Thr$^{13}$]PYY(13-36) | TPEELNRYYASLRHYLNLVTRQRY (SEQ ID NO: 171) |

Also included as PYY(13-36) mutations are polypeptide variations (amino acid sequence variations) resulting from the combination of either of these two mutants with any of the above listed mutants for PYY(25-36), and/or any of the above listed mutants for PYY(14-36), e.g., [Lys$^{25}$]PPY(13-36) (Amino acid sequence=SEELNRYYASLKHYLNLVTRQRY (SEQ ID NO: 202)) would result from combining the mutations from SEQ ID NO: 36 with SEQ ID NO: 170.

| Point Mutations of PYY(12-36) | |
| --- | --- |
| PEPTIDE | SEQUENCE |
| PYY(12-36) | ASPEELNRYYASLRHYLNLVTRQRY (SEQ ID NO: 172) |
| [Ser$^{12}$]PYY(12-36) | SSPEELNRYYASLRHYLNLVTRQRY (SEQ ID NO: 173) |

Also included as PYY(12-36) mutations are polypeptide variations (amino acid sequence variations) resulting from the combination of either of these two mutants with any of the above listed mutants for PYY(25-36), and/or any of the above listed mutants for PYY(13-36), e.g., [Lys$^{25}$]PPY(12-36) (Amino acid sequence=ASEELNRYYASLKHYLNLVTRQRY (SEQ ID NO: 203)) would result from combining the mutations from SEQ ID NO: 36 with SEQ ID NO: 172.

| Point Mutations of PYY(11-36) | |
| --- | --- |
| PEPTIDE | SEQUENCE |
| PYY(11-36) | DASPEELNRYYASLRHYLNLVTRQRY (SEQ ID NO: 174) |
| [Glu$^{11}$]PYY(11-36) | EASPEELNRYYASLRHYLNLVTRQRY (SEQ ID NO: 175) |

Also included as PYY(12-36) mutations are polypeptide variations (amino acid sequence variations) resulting from the combination of either of these two mutants with any of the above listed mutants for PYY(25-36), and/or any of the above listed mutants for PYY(12-36), e.g., [Lys$^{25}$]PPY(11-36) (Amino acid sequence=DASEELNRYYASLKHYLNLVTRQRY (SEQ ID NO: 204)) would result from combining the mutations from SEQ ID NO: 36 with SEQ ID NO: 174.

| Point Mutations of PYY(10-36) | |
| --- | --- |
| PEPTIDE | SEQUENCE |
| PYY(10-36) | EDASPEELNRYYASLRHYLNLVTRQRY (SEQ ID NO: 176) |
| [Asp$^{10}$]PYY(10-36) | DDASPEELNRYYASLRHYLNLVTRQRY (SEQ ID NO: 177) |

Also included as PYY(10-36) mutations are polypeptide variations (amino acid sequence variations) resulting from the combination of either of these two mutants with any of the above listed mutants for PYY(25-36), and/or any of the above listed mutants for PYY(11-36), e.g., [Lys$^{25}$]PPY(10-36) (Amino acid sequence=EDASEELNRYYASLKHYLNLVTRQRY (SEQ ID NO: 205)) would result from combining the mutations from SEQ ID NO: 36 with SEQ ID NO: 176.

| Point Mutations of PYY(9-36) | |
| --- | --- |
| PEPTIDE | SEQUENCE |
| PYY(9-36) | GEDASPEELNRYYASLRHYLNLVTRQRY (SEQ ID NO: 178) |

Also included as PYY(9-36) mutations are polypeptide variations (amino acid sequence variations) resulting from the combination of this PPY(9-36) mutant with any of the above listed mutants for PYY(25-36), and/or any of the above listed mutants for PYY(10-36), e.g., [Lys$^{25}$]PPY(9-36) (Amino acid sequence=GEDASPEELNRYYASLKHYLNLVTRQRY (SEQ ID NO: 206)) would result from combining the mutations from SEQ ID NO: 36 with SEQ ID NO: 178.

Point Mutations of PYY(8-36)

| PEPTIDE | SEQUENCE |
|---|---|
| PYY(8-36) | PGEDASPEELNRYYASLRHYLNLVTRQRY (SEQ ID NO: 179) |

Also included as PYY(8-36) mutations are polypeptide variations (amino acid sequence variations) resulting from the combination of this PPY(8-36) mutant with any of the above listed mutants for PYY(25-36), and/or any of the above listed mutants for PYY(9-36), e.g., [Lys$^{25}$]PPY(8-36) (Amino acid sequence=SEQ ID NO: 207)) would result from combining the mutations from SEQ ID NO: 36 with SEQ ID NO: 179.

Point Mutations of PYY(7-36)

| PEPTIDE | SEQUENCE |
|---|---|
| PYY(7-36) | APGEDASPEELNRYYASLRHYLNLVTRQRY (SEQ ID NO: 180) |
| [Ser$^9$]PYY(7-36) | SPGEDASPEELNRYYASLRHYLNLVTRQRY (SEQ ID NO: 181) |

Also included as PYY(7-36) mutations are polypeptide variations (amino acid sequence variations) resulting from the combination of either of these two mutants with any of the above listed mutants for PYY(25-36), and/or any of the above listed mutants for PYY(8-36), e.g., [Lys$^{25}$]PPY(7-36) (Amino acid sequence=APGEDASEELNRYYASLKHYLNLVTRQRY (SEQ ID NO: 208)) would result from combining the mutations from SEQ ID NO: 36 with SEQ ID NO: 180.

Point Mutations of PYY(6-36)

| PEPTIDE | SEQUENCE |
|---|---|
| PYY(6-36) | EAPGEDASPEELNRYYASLRHYLNLVTRQRY (SEQ ID NO: 182) |
| [Asp$^6$]PYY(6-36) | DAPGEDASPEELNRYYASLRHYLNLVTRQRY (SEQ ID NO: 183) |

Also included as PYY(6-36) mutations are polypeptide variations (amino acid sequence variations) resulting from the combination of either of these two mutants with any of the above listed mutants for PYY(25-36), and/or any of the above listed mutants for PYY(7-36), e.g., [Lys$^{25}$]PPY(6-36) (Amino acid sequence=EAPGEDASEELNRYYASLKHYLNLVTRQRY (SEQ ID NO: 209)) would result from combining the mutations from SEQ ID NO: 36 with SEQ ID NO: 182.

Point Mutations of PYY(5-36)

| PEPTIDE | SEQUENCE |
|---|---|
| PYY(5-36) | PEAPGEDASPEELNRYYASLRHYLNLVTRQRY (SEQ ID NO: 184) |

Also included as PYY(5-36) mutations are polypeptide variations (amino acid sequence variations) resulting from the combination of this PPY(5-36) mutant with any of the above listed mutants for PYY(25-36), and/or any of the above listed mutants for PYY(6-36), e.g., [Lys$^{25}$]PPY(5-36) (Amino acid sequence=PEAPGEDASPEELNRYYASLKHYLNLVTRQRY (SEQ ID NO: 210)) would result from combining the mutations from SEQ ID NO: 36 with SEQ ID NO: 184.

Point Mutations of PYY(4-36)

| PEPTIDE | SEQUENCE |
|---|---|
| PYY(4-26) | KPEAPGEDASPEELNRYYASLRHYLNLVTRQRY (SEQ ID NO: 185) |
| [Arg$^4$]PYY(4-36) | RPEAPGEDASPEELNRYYASLRHYLNLVTRQRY (SEQ ID NO: 186) |
| [Gln$^4$]PYY(4-36) | QPEAPGEDASPEELNRYYASLRHYLNLVTRQRY (SEQ ID NO: 187) |
| [Asn$^4$]PYY(4-36) | NPEAPGEDASPEELNRYYASLRHYLNLVTRQRY (SEQ ID NO: 188) |

Also included as PYY(4-36) mutations are polypeptide variations (amino acid sequence variations) resulting from the combination of any of these four mutants with any of the above listed mutants for PYY(25-36), and/or any of the above listed mutants for PYY(5-36), e.g., [Lys$^{25}$]PPY(4-36) (Amino acid sequence=KPEAPGEDASEELNRYYASLKHYLNLVTRQRY (SEQ ID NO: 211)) would result from combining the mutations from SEQ ID NO: 36 with SEQ ID NO: 185.

Point Mutations of PYY(3-36)

| PEPTIDE | SEQUENCE |
|---|---|
| PYY(3-36) | IKPEAPGEDASPEELNRYYASLRHYLNLVTRQRY (SEQ ID NO: 1) |
| [Leu$^3$]PYY(3-36) | LKPEAPGEDASPEELNRYYASLRHYLNLVTRQRY (SEQ ID NO: 189) |
| [Val$^3$]PYY(3-36) | VKPEAPGEDASPEELNRYYASLRHYLNLVTRQRY (SEQ ID NO: 190) |

Also included as PYY(3-36) mutations are polypeptide variations (amino acid sequence variations) resulting from the combination of any of these three mutants with any of the above listed mutants for PYY(25-36), and/or any of the above listed mutants for PYY(4-36), e.g., [Lys$^{25}$]PPY(3-36) (Amino acid sequence=IKPEAPGEDASEELNRYYASLKHYLNLVTRQRY (SEQ ID NO: 212)) would result from combining the mutations from SEQ ID NO: 36 with SEQ ID NO: 1.

Also contemplated are PYY agonists (NPY analogs) having the formula:

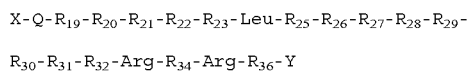

$X$-$Q$-$R_{19}$-$R_{20}$-$R_{21}$-$R_{22}$-$R_{23}$-Leu-$R_{25}$-$R_{26}$-$R_{27}$-$R_{28}$-$R_{29}$-$R_{30}$-$R_{31}$-$R_{32}$-Arg-$R_{34}$-Arg-$R_{36}$-Y wherein X is H or C$^\alpha$ Me or N$^\alpha$ Me or desamino or an acyl group having 7 carbon atoms or less; Q is $R_{17}$-$R_{18}$, $R_{18}$ or desQ; $R_{17}$ is Met, Arg, Nle, Nva, Leu, Ala or D-Ala; $R_{18}$ is Ala, Ser, Ile, D-Ala, D-Ser or D-Ile; $R_{19}$ is Arg, Lys or Gln; $R_{20}$ is Tyr or Phe; $R_{21}$ is Tyr, Glu, His or Ala; $R_{22}$ is Ser, Ala, Thr, Asn or Asp; $R_{23}$ is Ala, Asp, Glu, Gln, Asn or Ser; $R_{25}$ is Arg or Gln; $R_{26}$ is His, Arg or Gln; $R_{27}$ is Phe or Tyr; $R_{28}$ is Ile, Leu, Val or Arg; $R_{29}$ is Asn or Ile; $R_{30}$ is Leu, Met, Thr or Val; $R_{31}$ is Ile, Val or Leu; $R_{32}$ is Thr or Phe; $R_{34}$ is Gln, Pro or His; $R_{36}$ is Phe or Tyr; and Y is $NH_2$ or OH; provided that when Q is $R_{18}$, then at least one of $R_{27}$ and $R_{36}$ is Phe. Analogs of NPY have the following applications: potent postsynaptic treatment of hypertension and cardiogenic shock, the treatment of acute cardiovascular circulatory failure, and the elevation of intracellular calcium. See U.S. Pat. No. 5,026,685.

Certain preferred NPY analogs have the formula: X-$R_{18}$-Arg-Tyr-Tyr-$R_{22}$-$R_{23}$-Leu-Arg-His-Tyr-$R_{28}$-Asn-Leu-$R_{31}$-Thr-Arg-Gln-Arg-Tyr-$NH_2$, wherein X is H or $C^a$ Me or $N^a$ Me or desamino or an acyl group having 7 carbon atoms or less; $R_{18}$ is Ala or Ser; $R_{22}$ is Ser or Ala; $R_{23}$ is Ala or Ser; $R_{27}$ is Phe or Tyr; $R_{28}$ is Ile or Leu; $R_{31}$ is Ile or Val; and $R_{36}$ is Phe or Tyr; provided that at least one of $R_{27}$ and $R_{36}$ is Phe. See U.S. Pat. No. 5,026,685.

Other contemplated NPY analogs have the formula:

X-$R_{17}$-$R_{18}$-Arg-Tyr-Tyr-Ser-Ala-Leu-Arg-His-$R_{27}$-Ile-Asn-Leu-Ile-Thr-Arg-Gln-Arg-$R_{36}$-$NH_2$, wherein $R_{17}$ is Arg or Leu and $R_{18}$ is Ser or Ala or Ile; and wherein X, $R_{27}$ and $R_{36}$ are as previously indicated.

Still other preferred NPY analogs have the formula:

X-$R_{18}$-Arg-Tyr-Tyr-Ala-Ser-Leu-$R_{25}$-His-$R_{27}$-Leu-Asn-Leu-Val-Thr-Arg-Gln-Arg-$R_{36}$-$NH_2$, wherein X is desamino or $C^a$ Me or $N^a$ Me and wherein $R_{18}$, $R_{25}$, $R_{27}$ and $R_{36}$ are as previously indicated.

Examples of such NPY agonists include:
pNPY (17-36) having the formula:

(SEQ ID NO: 217)
H-Leu-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide hNPY (17-36) having the formula:

(SEQ ID NO: 218)
H-Met-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide [Phe$^{27}$]-NPY (18-36) having the formula:

(SEQ ID NO: 219)
H-Ala-Arg-Tyr-Tyr-Ser-Ala-Leu-Arg-His-Phe-Ile-Asn-Leu-Ile-Thr-Arg-Gln-Arg-Tyr-$NH_2$

The peptide [Ac-D-Ala$^{17}$]-NPY (17-36) having the formula:

(SEQ ID NO: 220)
Ac-D-Ala-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide NPY (19-36) having the formula:

(SEQ ID NO: 221)
H-Arg-Tyr-Tyr-Ser-Ala-Leu-Arg-His-Tyr-Ile-Asn-Leu-Ile-Thr-Arg-Gln-Arg-Tyr-$NH_2$

The peptide [Nle$^{17}$]-NPY (17-36) having the formula:

(SEQ ID NO: 222)
H-Nle-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide [D-Ser$^{18}$]-NPY (18-36) having the formula:

(SEQ ID NO: 223)
H-D-Ser-Arg-Tyr-Tyr-Ser-Ala-Leu-Arg-His-Tyr-Ile-Asn-Leu-Ile-Thr-Arg-Gln-Arg-Tyr-$NH_2$

The peptide [Ala$^{17}$, His$^{21}$]-NPY (17-36) having the formula:

(SEQ ID NO: 224)
H-Ala-Ala-Arg-Tyr-His-Ser-Ala-Leu-Arg-His-Tyr-Ile-Asn-Leu-Ile-Thr-Arg-Gln-Arg-Tyr-$NH_2$

The peptide [D-Ile$^{18}$]-NPY (18-36) having the formula:

(SEQ ID NO: 225)
D-Ile-Arg-Tyr-Tyr-Ser-Ala-Leu-Arg-His-Tyr-Ile-Asn-Leu-Ile-Thr-Arg-Gln-Arg-Tyr-$NH_2$

The peptide [Ac-Arg$^{17}$]-NPY (17-36) having the formula:

(SEQ ID NO: 226)
Ac-Arg-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide [Gln$^{19}$]-NPY (19-36) having the formula:

(SEQ ID NO: 227)
H-Gln-Tyr-Tyr-Ser-Ala-Leu-Arg-His-Tyr-Ile-Asn-Leu-Ile-Thr-Arg-Gln-Arg-Tyr-$NH_2$

The peptide [Phe$^{20}$]-NpY (18-36) having the formula:

(SEQ ID NO: 228)
H-Ala-Arg-Phe-Tyr-Ser-Ala-Leu-Arg-His-Tyr-Ile-Asn-Leu-Ile-Thr-Arg-Gln-Arg-Tyr-$NH_2$

The peptide [$C^a$ MeLeu$^{17}$]-pNPY (17-36) having the formula:

(SEQ ID NO: 229)
H-$C^a$ MeLeu-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide [N$^a$ MeLeu$^{17}$]-pNPY (17-36) having the formula:

(SEQ ID NO: 230)
H-N$^a$ MeLeu-Ala-Arg-Tyr-Tyr-Ser-Ala-Leu-Arg-His-

Tyr-Ile-Asn-Leu-Ile-Thr-Arg-Gln-Arg-Tyr-NH$_2$

The peptide [desamino Ala$^{18}$]-NpY (18-36) having the formula:

(SEQ ID NO: 231)
desamino-Ala-Arg-Tyr-Tyr-Ser-Ala-Leu-Arg-His-Tyr-

Ile-Asn-Leu-Ile-Thr-Arg-Gln-Arg-Tyr-NH$_2$

The peptide [For-Ala$^{18}$, Glu$^{23}$, Arg$^{26}$]-NPY (18-36) having the formula:

(SEQ ID NO: 232)
For-Ala-Arg-Tyr-Tyr-Ser-Glu-Leu-Arg-Arg-Tyr-Ile-

Asn-Leu-Ile-Thr-Arg-Gln-Arg-Tyr-NH$_2$

The peptide [Nva$^{17}$, Ala$^{21}$, Leu$^{28}$]-NPY (17-36) having the formula:

(SEQ ID NO: 233)
H-Nva-Ala-Arg-Tyr-Ala-Ser-Ala-Leu-Arg-His-Tyr-Leu-

Asn-Leu-Ile-Thr-Arg-Gln-Arg-Tyr-NH$_2$

The peptide [Thr$^{22}$, Gln$^{23}$]-NPY (18-36) having the formula:

(SEQ ID NO: 234)
H-Ala-Arg-Tyr-Tyr-Thr-Gln-Leu-Arg-His-Tyr-Ile-Asn-

Leu-Ile-Thr-Arg-Gln-Arg-Tyr-NH$_2$

The peptide [desamino Leu$^{17}$, Asn$^{23}$, Val$^{30}$]-NPY (17-36) having the formula:

(SEQ ID NO: 235)
H-desamino Leu-Ala-Arg-Tyr-Tyr-Ser-Asn-Leu-Arg-

His-Tyr-Ile-Asn-Val-Ile-Thr-Arg-Gln-Arg-Tyr-NH$_2$

The peptide [Asp$^{22}$, Ser$^{23}$, Thr$^{30}$]-NPY (18-36) having the formula:

(SEQ ID NO: 236)
H-Ala-Arg-Tyr-Tyr-Asp-Ser-Leu-Arg-His-Tyr-Ile-Asn-

Thr-Ile-Thr-Arg-Gln-Arg-Tyr-NH$_2$

The peptide [Gln$^{25}$, Leu$^{31}$, Pro$^{34}$]-NPY (18-36) having the formula:

(SEQ ID NO: 237)
H-Ala-Arg-Tyr-Tyr-Ser-Ala-Leu-Gln-His-Tyr-Ile-Asn-

Leu-Leu-Thr-Arg-Pro-Arg-Tyr-NH$_2$

The peptide [Gln$^2$ Phe$^{36}$]-NPY (17-36) having the formula:

(SEQ ID NO: 238)
H-Leu-Ala-Arg-Tyr-Tyr-Ser-Ala-Leu-Arg-Gln-Tyr-Arg-

Asn-Leu-Ile-Thr-Arg-Gln-Arg-Phe-NH$_2$

The peptide [Phe$^{36}$]-pPYY (19-36) having the formula:

H-Arg-Tyr-Tyr-Ala-Ser-Leu-Arg-His-Tyr-Leu-Asn-Leu-

Val-Thr-Arg-Gln-Arg-Phe-NH$_2$

The peptide pPYY (18-36) having the formula:

(SEQ ID NO: 240)
H-Ser-Arg-Tyr-Tyr-Ala-Ser-Leu-Arg-His-Tyr-Leu-Asn-

Leu-Val-Thr-Arg-Gln-Arg-Tyr-NH$_2$

The peptide [Ac-Ser$^{18}$, Phe$^{27}$]-pPYY (18-36) having the formula:

(SEQ ID NO: 241)
Ac-Ser-Arg-Tyr-Tyr-Ala-Ser-Leu-Arg-His-Phe-Leu-

Asn-Leu-Val-Thr-Arg-Gln-Arg-Tyr-NH$_2$

The peptide [Nle$^{17}$, Asn$^{22}$, Phe$^{27}$]-NPY (17-36) having the formula:

(SEQ ID NO: 242)
H-Nle-Ala-Arg-Tyr-Tyr-Asn-Ala-Leu-Arg-His-Phe-Ile-

Asn-Leu-Ile-Thr-Arg-Gln-Arg-Tyr-NH$_2$

The peptide [D-Ala$^{18}$, Glu$^{21}$, His$^{34}$]-NPY (18-36) having the formula:

(SEQ ID NO: 243)
H-D-Ala-Arg-Tyr-Glu-Ser-Ala-Leu-Arg-His-Tyr-Ile-

Asn-Leu-Ile-Thr-Arg-His-Arg-Tyr-NH$_2$

The peptide [Bz-Leu$^{17}$, Pro$^{34}$, Phe$^{36}$]-pNPY (17-36) having the formula:

(SEQ ID NO: 244)
Bz-Leu-Ala-Arg-Tyr-Tyr-Ser-Ala-Leu-Arg-His-Tyr-

Ile-Asn-Leu-Ile-Thr-Arg-Pro-Arg-Phe-NH$_2$

The peptide [Lys$^{19}$, Phe$^{27}$, Val$^{28}$]-NpY (18-36) having the formula:

(SEQ ID NO: 245)
H-Ala-Lys-Tyr-Tyr-Ser-Ala-Leu-Arg-His-Phe-Val-Asn-

Leu-Ile-Thr-Arg-Gln-Arg-Tyr-NH$_2$

The peptide [D-Ala$^{17}$, Val$^{28}$, Phe$^{32}$]-NPY (17-36) having the formula:

(SEQ ID NO: 246)
D-Ala-Arg-Tyr-Tyr-Ser-Ala-Leu-Arg-His-Tyr-Val-Asn-

Leu-Ile-Phe-Arg-Gln-Arg-Tyr-NH$_2$

The peptide [C$^\alpha$ MeSer$^{18}$, Met$^{30}$, Phe$^{36}$]-NPY (18-36) having the formula:

(SEQ ID NO: 247)
H-C$^\alpha$ MeSer-Tyr-Tyr-Ser-Ala-Leu-Arg-His-Tyr-Ile-

Asn-Met-Ile-Thr-Arg-Gln-Arg-Phe-NH$_2$

The peptide [Arg$^{17}$, Ile$^{18}$, Phe$^{27,36}$]-NPY (17-36) having the formula:

(SEQ ID NO: 248)
H-Arg-Ile-Arg-Tyr-Tyr-Ser-Ala-Leu-Arg-His-Phe-Ile-

Asn-Leu-Ile-Thr-Arg-Gln-Arg-Phe-NH$_2$

The peptide [Ser$^{18}$, Phe$^{27}$]-pNPY (17-36) having the formula:

(SEQ ID NO: 249)
H-Leu-Ser-Arg-Tyr-Tyr-Ser-Ala-Leu-Arg-His-Phe-Ile-

Asn-Leu-Ile-Thr-Arg-Gln-Arg-Tyr-NH$_2$

The peptide [N$^\alpha$ MeIle$^{18}$, Gln$^{25}$, Phe$^{27}$]-NPY (18-36) having the formula:

(SEQ ID NO: 250)
N$^\alpha$ MeIle-Arg-Tyr-Tyr-Ser-Ala-Leu-Gln-His-Phe-Ile-

Asn-Leu-Ile-Thr-Arg-Gln-Arg-Tyr-NH$_2$

The peptide [D-Ser$^{18}$, Phe$^{36}$]-NPY (18-36) having the formula:

(SEQ ID NO: 251)
H-D-Ser-Arg-Tyr-Tyr-Ser-Ala-Leu-Arg-His-Tyr-Ile-

Asn-Leu-Ile-Thr-Arg-Gln-Arg-Phe-NH$_2$

The peptide [Asp$^{23}$, Arg$^{26}$]hNPY (17-36) having the formula:

(SEQ ID NO: 252)
H-Met-Ala-Arg-Tyr-Tyr-Ser-Asp-Leu-Arg-Arg-Tyr-Ile-

Asn-Leu-Ile-Thr-Arg-Gln-Arg-Tyr-NH$_2$

The peptide [Glu$^{23}$, Ile$^{29}$]-NPY (18-36) having the formula:

(SEQ ID NO: 253)
H-Ala-Arg-Tyr-Tyr-Ser-Glu-Leu-Arg-His-Tyr-Ile-Ile-

Leu-Ile-Thr-Arg-Gln-Arg-Tyr-NH$_2$

The peptide [D-Ala$^{17}$]-NPY(17-36)-OH having the formula:

(SEQ ID NO: 254)
D-Ala-Ala-Arg-Tyr-Tyr-Ser-Ala-Leu-Arg-His-Tyr-Ile-

Asn-Leu-Ile-Thr-Arg-Gln-Arg-Tyr-OH.

Other peptide YY agonists have the formula:

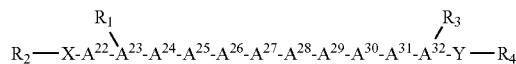

wherein:

X is a chain of 0-5 amino acids, inclusive, the N-terminal one of which is bonded to $R_1$ and $R_2$ Y is a chain of 0-4 amino acids, inclusive, the C-terminal one of which is bonded to $R_3$ and $R_4$ $R_1$ is H, $C_1$-$C_2$ alkyl (e.g., methyl), $C_6$-$C_{18}$ aryl (e.g., phenyl, napthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$R_2$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$A^{22}$ is an aromatic amino acid, Ala, Aib, Anb, N-Me-Ala, or is deleted;

$A^{23}$ is Ser, Thr, Ala, N-Me-Ser, N-Me-Thr, N-Me-Ala, or is deleted;

$A^{24}$ is Leu, lie, Vat, Trp, Gly, Aib, Anb, N-Me-Leu, or is deleted;

$A^{25}$ is Arg, Lys, homo-Arg, diethyl-homo-Arg, Lys-ε-NH—R (where R is H, a branched or straight chain $C_1$-$C_{10}$ alkyl group, or an aryl group), Orn, or is deleted;

$A^{26}$ is His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$-$C_{10}$ alkyl group, or an aryl group), Orn, or is deleted;

$A^{27}$ is an aromatic amino acid other than Tyr;

$A^{28}$ is Leu, Ile, Vat, Trp, Aib, Aib, Anb, or N-Me-Leu;

$A^{29}$ is Asn, Ala, Gln, Gly, Trp, or N-Me-Asn;

$A^{30}$ is Leu, Ile, Val, Trp, Aib, Anb, or N-Me-Leu;

$A^{31}$ is Vat, Ile, Trp, Aib, Anb, or N-Me-Val;

$A^{32}$ is Thr, Ser, N-Me-Set, or N-Me-Thr;

$R_3$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$R_4$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl), or a pharmaceutically acceptable salt thereof. See U.S. Pat. No. 5,574,010.

Particularly preferred agonists of this formula to be used in the method of the disclosure include:

N-α-Ala-Ser-Leu-Arg-His-Trp-Leu-Asn-Leu-Val-Thr-Arg-Gln-Arg-Tyr-NH$_2$ (SEQ ID NO: 255).

Other peptide YY agonists have the formula:

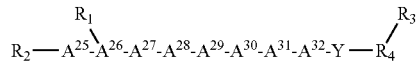

wherein:
the N-terminal amino acid bonds to $R_1$ and $R_2$;
Y is a chain of 0-4 amino acids, inclusive the C-terminal one of which bonds to $R_3$ and $R_4$;
$R_1$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl;
$R_2$ is H, $C_1$-$C_{12}$alkyl, $C_6$-$C_{18}$ aryl, $C_1$-$C_{12}$ acyl, $C_7$-$C_{18}$ aralkyl, or $C_7$-$C_{18}$ alkaryl;
$A^{25}$ is Arg, Lys, homo-Arg, diethyl-homo-Arg, Lys-ε-NH—R (where R is H, a branched or straight chain $C_1$-$C_{10}$ alkyl group, or an aryl group), Orn, or is deleted;
$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$-$C_{10}$ alkyl group, or an aryl group), Orn or is deleted;
$A^{27}$ is an aromatic amino acid;
$A^{28}$ is Leu, Ile, Val, Trp, Aib, Anb, or N-Me-Leu;
$A^{29}$ is Asn, Ala, Gln, Gly, Trp, or N-Me-Asn;
$A^{30}$ is Leu, Ile, Val, Trp, Aib, Anb, or N-Me-Leu;
$A^{31}$ is Val, Ile, Trp, Aib, Anb, or N-Me-Val;
$A^{32}$ is Thr, Set, N-Me-Set, or N-Me-Thr or D-Trp;
$R_3$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl; and
$R_4$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl, or a pharmaceutically acceptable salt thereof. Note that, unless indicated otherwise, for all peptide YY agonists described herein, each amino acid residue, e.g., Leu and $A^1$, represents the structure of NH—C(R)H—CO—, in which R is the side chain. Lines between amino acid residues represent peptide bonds which join the amino acids. Also, where the amino acid residue is optically active, it is the L-form configuration that is intended unless D-form is expressly designated.
Other PYY agonists have the formula:

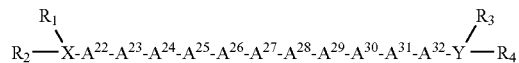

wherein:
X is a chain of 0-5 amino acids, inclusive, the N-terminal one of which is bonded to $R_1$ and $R_2$;
Y is a chain of 0-4 amino acids, inclusive, the C-terminal one of which is bonded to $R_3$ and $R_4$;
$R_1$ is H, $C_1$-$C_{12}$ alkyl (e.g. methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);
$R_2$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);
$A^{22}$ is an aromatic amino acid, Ala, Aib, Anb, N-Me-Ala, or is deleted;
$A^{23}$ is Ser, Thr, Ala, Aib, N-Me-Ser, N-Me-Thr, N Me-Ala, or is deleted;
$A^{24}$ is leu, Ile, Val, Trp, Gly, Nle, Nva, Aib, Anb, N-Me-Leu, or is deleted;
$A^{25}$ is Arg, Lys, homo-Arg, diethyl-homo-Arg, Lye-ε-NH—R (where R is H, a branched or straight chain $C_1$-$C_{10}$ alkyl group, or an aryl group), Orn, or is deleted;
$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$-$C_{10}$ alkyl groups or an aryl group), Orn, or is deleted;
$A^{27}$ is an aromatic amino acid other than Tyr;
$A^{28}$ is Leu, Ile, Val, Trp, Nle, Nva, Aib, Anb, or N-Me-Leu;
$A^{29}$ is Asn, Ala, Gln, Gly, Trp, or N-Me-Asn;
$A^{30}$ is Leu, Ile, Val, Trp, Nle, Nva, Aib, Anb, or N-Me-Leu;
$A^{31}$ is Val, Leu, Ile, Trp, Nle, Nva, Aib, Anb, or N-Me-Val;
$A^{32}$ is Thr, Ser, N-Me-Ser, N-Me-Thr, or D-Trp;
$R_3$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl); and
$R_4$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl), or a pharmaceutically acceptable salt thereof.
In preferred embodiments, $A^{27}$ is Phe, NaI, Bip, Pcp, Tic, Trp, Bth, Thi, or Dip.
In preferred embodiments X is $A^{17}$-$A^{18}$-$A^{19}$-$A^{20}$-$A^{21}$ wherein
$A^{17}$ is Cys, Leu, Ile, Val, Nle, Nva, Aib, Anb, or N-Me-Leu;
$A^{18}$ is Cys, Ser, Thr, N-Me-Ser, or N-Me-Thr;
$A^{19}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn;
$A^{20}$ is an aromatic amino acid, or Cys; and
$A^{21}$ is an aromatic amino acid, Cys, or a pharmaceutically acceptable salt thereof. In yet other preferred embodiments, Y is $A^{33}$-$A^{34}$-$A^{35}$-$A^{36}$ wherein
$A^{33}$ is Arg, Lys, homo-Arg, diethyl-homo-Arg, Lys-ε-NH—R (where R is H, a branched or straight chain $C_1$-$C_{10}$ alkyl group, or an aryl group), Cys, or Orn;
$A^{34}$ is Cys, Gln, Asn, Ala, Gly, N-Me-Cln, Aib, or Anb;
$A^{35}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn; and
$A^{36}$ is an aromatic amino acid, Cys or a pharmaceutically acceptable salt thereof. See U.S. Pat. No. 5,604,203.
Particular embodiments include compounds has the formula: N-α-Ac-Ala-Ser-Leu-Arg-His-Phe-Leu-Asn-Leu-Val-Thr-Arg-Gln-Arg-Tyr-$NH_2$ (SEQ. ID. NO: 325), H-Ala-Ser-Leu-Arg-His-Phe-Leu-Asn-Leu-Val-Thr-Arg-Gln-Arg-Tyr-$NH_2$ (SEQ. ID. NO: 326), N-α-Ac-Ala-Ser-Leu-Arg-Thr-Arg-Gln-Arg-Tyr-$NH_2$ (SEQ. ID. NO: 327), N-α-Ac-Ala-Ser-Leu-Arg-His-Thi-Leu-Asn-Leu-Val-Thr-Arg-Gln-Arg-Tyr-$NH_2$ (SEQ. ID. NO: 328), N-α-Ac-Tyr-Ser-Leu-Arg-His-Phe-Leu-Asn-Leu-Val-Thr-Arg-Gln-Arg-Tyr-$NH_2$ (SEQ. ID. NO: 329) or a pharmaceutically acceptable salt thereof.
Other PYY agonists have the formula:

(Formula II)
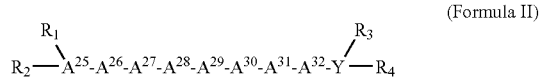

wherein the N-terminal amino acid is bounded to $R_1$ and $R_2$; Y is a chain of 0-4 amino acids, inclusive the C-terminal one of which is bonded to $R_3$ and $R_4$;
$R_1$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);
$R_2$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$A^{25}$ is Arg, Lys, homo-Arg, diethyl-homo-Arg, Lys-ε-NH—R (where R is H, a branched or straight chain $C_1$-$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$-$C_{10}$ alkyl groups or an aryl group), Orn, or is deleted;

$A^{27}$ is an aromatic amino acid;

$A^{28}$ is Leu, Ile, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Ile, Trp, Nle, Nva, Aib, Anb, or N-Me-Val;

$A^{32}$ is Thr, Ser, N-Me-Ser, N-Me-Thr, or D-Trp;

$R_3$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl); and $R_4$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl), or a pharmaceutically acceptable salt thereof. See U.S. Pat. No. 5,604,203.

In particular embodiments, $A^{27}$ is Phe, NaI, Bip, Pcp, Tic, Trp, Bth, Thi, or Dip.

In particular embodiments X is $A^{33}$-$A^{34}$-$A^{35}$-$A^{36}$ wherein $A^{33}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn;

$A^{34}$ is Gln, Asn, Ala, Gly, N-Me-Gln, Aib, Cys, or Anb;

$A^{35}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn; and $A^{36}$ is an aromatic amino acid, Cys, or a pharmaceutically acceptable salt thereof.

Preferably, the compound has the formula: N-α-Ac-Arg-His-Phe-Leu-Asn-Leu-Val-Thr-Arg-Gln-Arg-Tyr-NH$_2$ (SEQ. ID. NO: 324).

Exemplary PYY agonists include:

```
                                     (SEQ ID NO: 256)
YPAKEAPGEDASPEELSTYYASLR [im-DNP-His26]
YLNLVTRZRY-NH2
PYY(22-36)

(SEQ ID NO: 257)
ASLRHYLNLVTRQRY-NH2
[Ala32]PYY (SEQ ID NO: 258)
ASLRHYLNLV[Ala]RQRY-NH2
[Ala23,32]PYY (SEQ ID NO: 259)
A[Ala]LRHYLNLV[Ala]RQRY-NN2
[Glu28]PYY(22-36)

(SEQ ID NO: 260)
ASLRHY[Glu]NLVTRQRY-NH2
N-α-Ac-PYY(22-36)

(SEQ ID NO: 261)
N-α-Ac-ASLRHYLNLVTRORY-NH2
N-α-Ac[p.CL.Phe26]PYY (SEQ ID NO: 262)
N-α-Ac-ASLR[p.CL.Phe26]YLNLVTRQRY-NH2
N-α-Ac[Glu28]PYY (SEQ ID NO: 263)
N-α-Ac-ASLRHY[Glu]NLVTRQRY-NH2
N-α-Ac[Phe27]PYY
```

-continued

```
                                     (SEQ ID NO: 264)
N-α-Ac-ASLRH[Phe]ENLVTRQR[N-Me-Tyr]-NH2
N-α-Ac]8N-Me-Tyr36]PYY (SEQ ID NO: 265)
N-α-Ac-ASLRHYENLVTR0R[N-Me-Tyr]-NH2
N-α-myristoyl-PYY(2214 36)

(SEQ ID NO: 266)
N-α-myristoyl-ASLRHYLNLVTRQRY-NH2
N-α-naphthateneacetyl-PYY(22-36)

(SEQ ID NO: 267)
N-α-naphthateneacetyl-ASLRHYLNLVTRQRY-NH2
N-α-Ac[Phe27]PYY (SEQ ID NO: 268)
N-α-Ac-ASLRH[Phe]ENLVTR0R[N-Me-Tyr]-NH2
N-α-Ac-PYY (22-36)

(SEQ ID NO: 269)
N-α-Ac-ASLRHYLNLVTRQRY-NH2
N-α-Ac-[Bth27]PYY (22-36)

(SEQ ID NO: 270)
N-α-Ac-ASLRH[Bth]LNLVTRQRY-NH2

(SEQ ID NO: 271)
N-α-Ac-[Bip27]PYY (22-36)

(SEQ ID NO: 272)
N-α-Ac-ASLRH[Bth]LNLVTRQRY-NH2
N-α-Ac-[Nal27]PYY (22-36)

(SEQ ID NO: 273)
N-α-Ac-ASLRH[Bth]LNLVTRQRY-NH2

(SEQ ID NO: 274)
N-α-Ac-[Trp27]PYY (22-36)

(SEQ ID NO: 275)
N-α-Ac-ASLRH[Trp]LNLVTRQRY-NH2
N-α-Ac-[Thi27]PYY (22-36)

(SEQ ID NO: 276)
N-α-Ac-ASLRN[Thi]LNLVTRQRY-NH2
N-α-Ac-[Tic27]PYY (22-36)

(SEQ ID NO: 277)
N-α-Ac-ASLRH[Tic]LNLVTRQRY-NH2
N-α-Ac-[Phe27]PYY (25-36)

(SEQ ID NO: 279)
N-α-Ac-H[Phe]LNLVTRQRY-NH2
N-α-Ac-[Phe27, Thi27]PYY (22-36)

(SEQ ID NO: 280)
N-α-Ac-ASLRH[Phe]LNLVTRQR[Thi]-NH2
N-α-Ac-[Thz26, Phe27]PYY (22-36)

(SEQ ID NO: 281)
N-α-Ac-ASLRH[Thz][Phe]LNLVTRQRY-NH2
N-α-Ac-[Phe27]PYY (22-36)

(SEQ ID NO: 282)
N-α-Ac-ASLRH[Thz][Phe]LNLVTRQRY-NH2
N-α-Ac-[Phe27]PYY (22-36)

(SEQ ID NO: 289)
N-α-Ac-[Phe]SLRN[Phe]LNLVTRQRY-NH2
N-α-Ac-[Tyr22, Phe27]PYY (22-36)

(SEQ ID NO: 290)
N-α-Ac-[Tyr]SLRH[Phe]LNLVTRQRY-NH2
N-α-Ac-[Trp28]PYY (22-36)

(SEQ ID NO: 291)
N-α-Ac-ASLRHY[Trp]NLVTRQRY-NH2
N-α-Ac-[Trp28]PYY (22-36)
```

```
                                                  (SEQ ID NO: 292)
N-α-Ac-ASLRHYLN[Trp]VTRQRY-NH2
N-α-Ac-[Ala26, Phe27]PYY (22-36)

(SEQ ID NO: 293)
N-α-Ac-ASLR[Ala][Phe]LNLVTRQRY-NH2
N-α-Ac-[Bth27]PYY (22-36)

(SEQ ID NO: 294)
N-α-Ac-ASLR[Bth]LNLVTRQRY-NH2
N-α-Ac-[Phe27]PYY (22-36)

(SEQ ID NO: 295)
N-α-Ac-ASLRH[Phe]LNLVTRQRY-NH2
N-α-Ac-[Phe27,36]PYY (22-36)

(SEQ ID NO: 296)
N-α-Ac-ASLRH[Phe]LNLVTRQR[Phe]-NH2
N-α-Ac-[Phe27, D-Trp32]PYY (22-36)

(SEQ ID NO: 297)
N-α-Ac-ASLRH[Phe]LNLV[D-Trp]RQRY-NH2
```

Other PYY agonists include neurophilic Y Y2 receptor specific peptides having the formula:

```
X1(-X2-X3-X4-X5-X6-X7-X8-X9-X10-X11-X12-
    X13-X14)n-X15
``` wherein
X1 is NH, CH$_3$CO or one or two naturally occurring amino acids.
X2 is Leu, Ile or Val.
X3 is Arg, Lys or His.
X4 is His, Lys or Arg.
X5 is Tyr or Phe.
X6 is Leu, Ile or Val.
X7 is Asn or Gln.
X8 is Leu, Ile or Val.
X9 is Leu, Ile or Val.
X10 is Thr or Ser.
X11 is Arg, His or Lys.
X12 is Gln or Asn.
X13 is Arg, His or Lys.
X14 is Tyr or Phe.
X15 is COOH, NH$_2$ or one or two naturally occurring amino acids with the terminal amino acid being in the normal or carboxamide form; and
n is 1 to 5. See U.S. Pat. No. 5,696,093.
Exemplary agonists include:

```
                                                  (SEQ ID NO: 298)
CH3CO-L-R-H-Y-L-N-L-L-T-R-Q-R-Y-NH2

(SEQ ID NO: 299)
CH3CO-L-R-H-Y-I-N-L-I-T-R-Q-R-Y-NH2

(SEQ ID NO: 300)
NH2-L-R-H-Y-L-N-L-L-T-R-Q-R-Y-NH2

(SEQ ID NO: 301)
NH2-L-R-H-Y-I-N-L-I-T-R-Q-R-Y-NH2
```

Other PYY agonists have the formula:
N-α-R$^1$-[Nle$^{24,28,30}$, Trp$^{27}$, Nva$^{31}$, ψ$^{35/36}$]PYY(22-36)-NH$_2$,
N-α-R$^1$-[Nle$^{24,28}$, Trp$^{27,30}$, Nva$^{31}$, ψ$^{35/36}$]PYY(22-36)-NH$_2$,
N-α-R$^1$-[Nle$^{24,28,30}$, Phe$^{27}$, Nva$^{31}$, ψ$^{35/36}$]PYY(22-36)-NH$_2$,
N-α-R$^1$-[Nle$^{24,28}$, Phe$^{27}$, Trp$^{30}$, Nva$^{31}$, ψ$^{35/36}$]PYY(22-36)-NH$_2$,
N-α-R$^1$-[Trp$^{30}$, ψ$^{35/36}$]PYY(25-36)-NH$_2$,
N-α-R$^1$-[Trp$^{30}$]PYY(25-36)-NH$_2$,
N-α-R$^1$-[Nle$^{24,28}$, Trp$^{30}$, Nva$^{31}$, W$^{35/36}$]PYY(22-36)-NH$_2$ and
N-α-R$^1$-[Nle$^{28}$, Trp$^{30}$, Nva$^{31}$, ψ$^{35/36}$]PYY(22-36)-NH$_2$ or a pharmaceutically-acceptable salt thereof,
wherein R$^1$ is H, (C$_1$-C$_{12}$)alkyl or (C$_1$-C$_{12}$)acyl; and
ψ is a pseudopeptide bond selected from the group consisting of —CH$_2$—NH—CH$_2$—S—, —CH$_2$—CH$_2$—, —CH$_2$—O— and —CH$_2$—CO—. See U.S. Pat. No. 6,046,162.

Particular compounds of the immediately foregoing group of compounds are where R$^1$ is acetyl and W is —CH$_2$—NH—.

A particular group of compounds is selected from a group consisting of

N-α-Ac-[Nle$^{24,28,30}$ Trp$^{27}$, Nva$^{31}$, ψ$^{35/36}$]PYY(22-36)-NH$_2$, (SEQ ID NO: 302)
N-α-Ac-[Nle$^{24,28}$, Trp$^{27,30}$, Nva$^{31}$, ψ$^{35/36}$]PYY(22-36)-NH$_2$, (SEQ ID NO: 303)
N-α-Ac-[Nle$^{24,28,30}$ Phe$^{27}$, Nva$^{31}$, ψ$^{35/36}$]PYY(22-36)-NH$_2$, (SEQ ID NO: 304)
N-α-Ac-[Nle$^{24,28}$, Phe$^{27}$, Trp$^{30}$, Nva$^{31}$, ψ$^{35/36}$]PYY(22-36)-NH$_2$, (SEQ ID NO: 305)
N-α-Ac-[Trp$^{30}$, ψ$^{35/36}$]PYY(25-36)-NH$_2$, (SEQ ID NO: 306)
N-α-Ac-[Trp$^{30}$]PYY(25-36)-NH$_2$ (SEQ ID NO: 307) and
N-α-Ac-[Nle$^{28}$, Trp$^{30}$, Nva$^{31}$, ψ$^{35/36}$]PYY(22-36)-NH$_2$, (SEQ ID NO: 308) or
a pharmaceutically acceptable salt thereof.

Another particular compound has the formula N-α-Ac-[Nle$^{24,28}$, Trp$^{30}$, Nva.sup.$^{31}$, ψ$^{35/36}$]PYY(22-36)-NH$_2$ (SEQ. ID. NO: 309) or a pharmaceutically acceptable salt thereof.

Another PYY agonist has the formula (A),

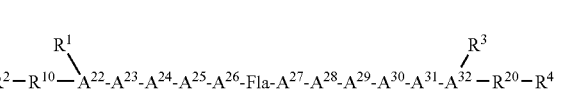

having one or two pseudopeptide bonds where each pseudopeptide bond is independently selected from the group consisting of —CH$_2$—NH—, —CH$_2$—S—, —CH$_2$—CH$_2$—, —CH$_2$—O— and —CH$_2$—CO—; wherein:

R$^{10}$ is a chain of 0-5 amino acids, inclusive, where the N-terminal amino acid is bonded to R$^1$ and R$^2$ by the side chain of the N-terminal amino acid or by the nitrogen of the amino group of the N-terminal amino acid;

R$^{20}$ is a chain of 0-4 amino acids, inclusive, where the C-terminal amino acid is bonded to R$^3$ and R$^4$ by the side chain of the C-terminal amino acid or by the carbon of the carboxyl group of the C-terminal amino acid;

R$^1$, R$^2$, R$^3$ and R$^4$ are each independently selected from the group consisting of H, (C$_1$-C$_{12}$)alkyl, (C$_6$-C$_{18}$)aryl, (C$_1$-C$_{12}$) acyl, phenyl(C$_1$-C$_{12}$)alkyl and ((C$_1$-C$_{12}$)alkyl)$_{1-5}$-phenyl;

A$^{22}$ is an aromatic amino acid, Ala, Aib, Anb, N-Me-Ala or is deleted;

A$^{23}$ is Ser, Thr, Ala, N-Me-Ser, N-Me-Thr, N-Me-Ala or is deleted;

A$^{24}$ is Leu, Ile, Nle, Val, Trp, Gly, Aib, Anb, N-Me-Leu or is deleted;

A$^{25}$ is Arg, Lys, homo-Arg, diethyl-homo-Arg, Lys-p.epsilon.-NH-Z, Orn or is deleted;

A$^{26}$ is His, Thr, 3-Me-His, 1-Me-His, β-pyrazolylalanine, N-Me-His, Arg, Lys, homo-Arg, diethyl-homo-Arg, Lys-ε-NH-Z, Orn or is deleted;

A$^{28}$ is Leu, Ile, Nle, Val, Trp, Aib, Anb or N-Me-Leu;

A$^{29}$ is Asn, Ala, Gln, Gly, Trp or N-Me-Asn;

A³⁰ is Leu, Ile, Nle, Fla, Val, Trp, Aib, Anb or N-Me-Leu;
A³¹ is Val, Nva, Ile, Trp, Aib, Anb or N-Me-Val; and
A³² is Thr, Ser, N-Me-Ser or N-Me-Thr;
where Z for each occurrence is independently selected from the group consisting of H, $(C_1-C_{10})$alkyl and $(C_6-C_{18})$ aryl; or a pharmaceutically acceptable salt thereof. See U.S. Pat. No. 6,046,167.

A particular group of compounds of the immediately foregoing group of compounds is where $R^{10}$ is $A^{17}$-$A^{18}$-$A^{19}$-$A^{20}$-$A^{21}$;

where $A^{17}$ is Cys, Leu, Ile, Val, Nle, Nva, Aib, Anb or N-Me-Leu;

$A^{18}$ is Cys, Ser, Thr, N-Me-Ser or N-Me-Thr;

$A^{19}$ is Arg, Lys, homo-Arg, diethyl-homo-Arg, Lys-ϵ-NH—R.sup.5, Cys or Orn;

$A^{20}$ is an aromatic amino acid or Cys;

$A^{21}$ is an aromatic amino acid or Cys;

$R^{20}$ is $A^{33}$-$A^{34}$-$A^{35}$-$A^{36}$, $A^{33}$ is Arg, Lys, homo-Arg, diethyl-homo-Arg, Lys-β-NH—$R^5$, Cys or Orn;

$A^{34}$ is Cys, Gln, Asn, Ala, Gly, N-Me-Gln, Aib or Anb;

$A^{35}$ is Arg, Lys, homo-Arg, diethyl-homo-Arg, Lys-ϵ-NH—$R^5$, Cys or Orn; and $A^{36}$ is an aromatic amino acid or Cys;

where $R^5$ for each occurrence is independently selected from the group consisting of $H_1$ $(C_1-C_{10})$alkyl and $(C_6-C_{18})$ aryl.

A particular group of compounds of the foregoing group of compounds are the compounds of the formula N-α-Ac-[Fla²⁷)]PYY(25-36)-NH₂ and N-α-Ac-[Fla²⁷]PYY(22-36)-NH₂ or a pharmaceutically acceptable salt thereof.

Another group of PYY agonist has the formula:

$$(R^1R^2)\text{-}A^1\text{-}A^2\text{-}A^3\text{-}A^4\text{-}A^5\text{-}A^6\text{-}A^7\text{-}A^8\text{-}A^9\text{-}A^{10}\text{-}R^{30}, \quad (I)$$

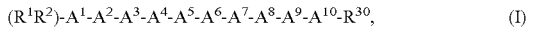
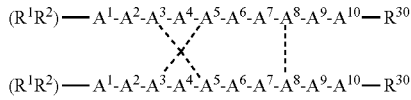
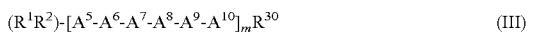

$$(R^1R^2)\text{-}[A^5\text{-}A^6\text{-}A^7\text{-}A^8\text{-}A^9\text{-}A^{10}]_m R^{30} \quad (III)$$

or a pharmaceutically acceptable salt thereof wherein

---- represents an optional bond between the amino acids shown connected where each bond is independently selected from the group consisting of —S—S— only when the amino acids connected are Cys-Cys, —CO—NH—, —CH₂—NH— and

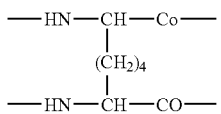

provided that when the optional bond is

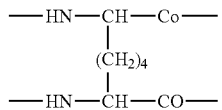

it replaces the two amino acids that the optional bond is attached to; q is 1-4;

m is 1 to 4;

$R^{30}$ is OH or —O—R', provided that when $A^1$ to $A^7$ are deleted then $R^{30}$ is also NH—$R^1$, where $R^{30}$ is attached to the carbon atom of the carboxyl of the C-terminal amino acid;

$R^1$ and $R^2$ for each occurrence are each independently selected from the group consisting of H, $(C_1-C_{12})$alkyl, $(C_6-C_{18})$aryl, $(C_1-C_{12})$acyl, phenyl$(C_1-C_{12})$alkyl and $((C_1-C_{12})$alkyl$)_{1-5}$-phenyl where $R^1$ and $R^2$ are attached to the nitrogen of the amine of the N-terminal amino acid;

$A^1$ is deleted or D- or L- of the following amino acids: Trp, Tyr, Fla, Bth, NaI, Tic, Tic-OH, Dip, Bip or optionally substituted Phe where the Phe is optionally substituted with one to five substituents selected from the group consisting of $(C_1-C_4)$alkyl, halo, $(C_1-C_4)$alkoxy, amino and nitro;

$A^2$ is deleted or D- or L- of the following amino acids: Ile, Val, Leu, Nle, Anb, Aib, Pro, Gln or Asn;

$A^3$ is deleted or D- or L- of the following amino acids: Asn, Gln, Glu, Asp, Orn, Lys, Dpr or Cys;

$A^4$ is deleted or D- or L- of the following amino acids: Ile, Val, Leu, Nle, Anb, Aib or Pro;

$A^5$ is deleted or D- or L- of the following amino acids: Ile, Val, Leu, Nle, Anb, Aib, Pro, Glu, Asp, Orn, Lys, Dpr or Cys;

$A^6$ is deleted or D- or L- of the following amino acids: Thr, Ser, Trp, Tyr, Fla, Bth, NaI, Tic, Tic-OH, Dip, Bip or optionally substituted Phe where the Phe is optionally substituted with one to five substituents selected from the group consisting of $(C_1-C_4)$alkyl, halo, $(C_1-C_4)$alkoxy, amino and nitro;

$A^7$ is deleted or D- or L- of the following amino acids: Arg, Lys, homo-Arg, dialkyl-homo-Arg, Lys-ϵ-NH—$R^7$ or Orn;

$A^8$ is deleted or D- or L- of the following amino acids: Nva, Val, Ile, Leu, Nle, Anb, Aib, Pro, Gln, Asn, Glu, Asp, Orn, Lys, Dpr or Cys;

$A^9$ is deleted or D- or L- of the following amino acids: Arg, Lys, homo-Arg, dialkyl-homo-Arg, Lys-ϵ-NH—$R^7$ or Orn; and $A^{10}$ is deleted or D- or L- of the following amino acids: Tyr, Trp, Fla, Bth, NaI, Tic, Tic-OH, Dip, Bip, tyramine or optionally substituted Phe where the Phe is optionally substituted with one to five substituents selected from the group consisting of $(C_1-C_4)$alkyl, halo, $(C_1-C_4)$alkoxy, amino and nitro, or the corresponding decarboxylated optionally substituted Phe;

where $R^7$ for each occurrence is independently selected from the group consisting of H.sub.₁ $(C_1-C_{10})$alkyl and $(C_6-C_{18})$ aryl, provided that not all of $A_1$ to $A_{10}$ are deleted at the same time. See U.S. Pat. No. 6,046,167.

A particular group of compounds of the immediately foregoing group of compounds is

```
H--Ile--Asn--Pro--Ile--Tyr--Arg--Leu--Arg--Tyr--OMe     (SEQ ID NO: 310)

H--Ile--Asn--Pro--Cys--Tyr--Arg--Leu--Arg--Tyr-Ome       (SEQ ID NO: 311)
                          |
H--Ile--Asn--Pro--Cys--Tyr--Arg--Leu--Arg--Tyr--Ome,
```

-continued

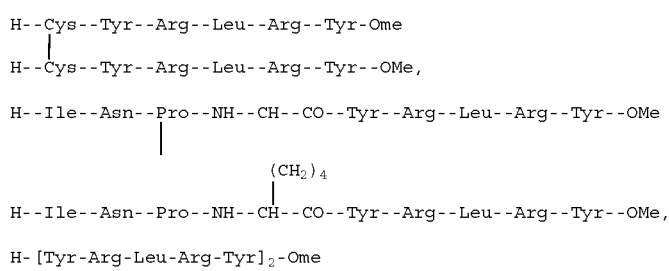

```
H--Cys--Tyr--Arg--Leu--Arg--Tyr-Ome
   |
H--Cys--Tyr--Arg--Leu--Arg--Tyr--OMe,
```
(SEQ ID NO: 312)

```
H--Ile--Asn--Pro--NH--CH--CO--Tyr--Arg--Leu--Arg--Tyr--OMe
                      |
                    (CH2)4
                      |
H--Ile--Asn--Pro--NH--CH--CO--Tyr--Arg--Leu--Arg--Tyr--OMe,
```
(SEQ ID NO: 313)

H-[Tyr-Arg-Leu-Arg-Tyr]$_2$-Ome (SEQ ID NO: 314)

or a pharmaceutically acceptable salt thereof.

PYY and PYY agonists may be modified by well known processes such as amidation, glycosylation, acylation (e.g. acetylation), sulfation, phosphylation, cyclization, lipidization and pegylation. Methods for lipidization with fatty acid derivatives of sulfhydryl-containing compounds are disclosed in U.S. Pat. Nos. 5,936,092; 6,093,692; and 6,225,445. Fatty acid derivatives of sulfhydryl-containing PYY and PYY agonists comprising fatty acid-conjugated products with a disulfide linkage are employed for delivery of the PYY and PYY agonists to neuronal cells and tissues. This modification markedly increases the absorption of the compounds relative to the rate of absorption of the unconjugated compounds, as well as prolonging blood and tissue retention of the compounds. Moreover, the disulfide linkage in the conjugate is quite labile in the cells and thus facilitates intracellular release of the intact compounds from the fatty acid moieties.

Fatty acids, as constituents of phospholipids, make up the bulk of cell membranes. Due to their lipidic nature, fatty acids can easily partition into and interact with the cell membrane in a non-toxic way. Therefore, fatty acids represent potentially a useful carrier ligand for the delivery of proteins and peptides. Strategies that may use fatty acids in the delivery of proteins and peptides include the covalent modification of proteins and peptides and the use of fatty acid emulsions.

To prepare such conjugates, a sulfhydryl-containing PYY and PYY agonist is attached to a fatty acid derivative via a reversible, biodegradable disulfide bond. Such a conjugate is expected to bind to the apical side of a cell membrane, reach the basolateral membrane of the GI-epithelium as a result of membrane transport and turnover, and become released into interstitial fluid as the result of disulfide bond reduction.

Such lipidized PYY and PYY agonist compounds have the general formula

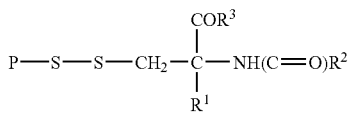

$$P-S-S-CH_2-\underset{R^1}{\underset{|}{C}}-NH(C=O)R^2$$
$$\quad\quad\quad\quad\;\;|$$
$$\quad\quad\quad\;\;COR^3$$

in which P is a residue derived from a PYY or PYY agonist; R$^1$ is hydrogen, lower alkyl or aryl; R$^2$ is a lipid-containing moiety and R$^3$ is —OH, a lipid-containing moiety or an amino acid chain comprising one or 2 amino acids and terminating in —CO$_2$H or —COR$^2$. See U.S. Pat. No. 5,936,092. These conjugates are particularly useful for increasing the absorption and prolonging blood and tissue retention of PYY and PYY agonists.

Typical alkyl groups include C$_{1-6}$ alkyl groups including methyl, ethyl, propyl, isopropyl, butyl, isobutyl, sec-butyl, tert-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl, and the like.

Preferred aryl groups are C$_{6-14}$ aryl groups and typically include phenyl, naphthyl, fluorenyl, phenanthryl, and anthracyl groups.

The term "lipid-containing moiety" refers to either a lipid group per se or a hydrocarbon-based group (in particular, one or more amino acids) comprising a lipid group. By the term "lipid group" is meant a hydrophobic substituent consisting of 4 to 26 carbon atoms, preferably 5 to 19 carbon atoms. Suitable lipid groups include, but are not limited to, the following: palmityl (C$_{15}$H$_{31}$,), oleyl (C$_{15}$H$_{29}$), stearyl (C$_{17}$H$_{35}$), cholate; and deoxycholate.

PCT Application No. WO 00/34236 describes drug-carrier conjugates and synthetic strategies for their production, as well as synthetic methods, intermediates, and final products useful for the uptake and release of biologically-active amino group containing compounds. Such lipidized PYY and PYY agonist compounds have general Formula I

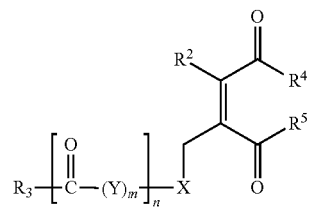

in which R$^2$ is selected from the group consisting of hydrogen, halo, alkyl, or aryl, wherein the alkyl or aryl groups are optionally substituted with one or more alkoxy, alkoxyalkyl, alkanoyl, nitro, cycloalkyl, alkenyl, alkynyl, alkanoyloxy, alkyl or halogen atoms;

R$^3$ is a lipophilic group; one of R$^4$ and R$^5$ is a PYY or a PYY agonist and the other of R$^4$ and R$^5$ is OR$^6$ where R$^6$ is hydrogen, an alkali metal or a negative charge;

X is oxygen or sulfur;

Y is a bridging natural or unnatural amino acid; n is zero or 1; and m is an integer from zero to 10.

Typical alkyl groups include C$_{1-6}$ alkyl groups including methyl, ethyl, propyl, isopropyl, butyl, isobutyl, sec-butyl, tert-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl, and the like.

Typical alkoxy groups include oxygen substituted by any of the alkyl groups mentioned above.

Typical alkoxyalkyl groups include any of the above alkyl groups substituted by an alkoxy group, such as methoxymethyl, ethoxymethyl, propoxymethyl, butoxymethyl, pentoxymethyl, hexoxymethyl, methoxyethyl, methoxypropyl, methoxybutyl, methoxypentyl, methoxyhexyl, and the like.

Preferred aryl groups are $C_{6-14}$ aryl groups and typically include phenyl, naphthyl, fluorenyl, phenanthryl, and anthracyl groups.

Typical alkoxy substituted aryl groups include the above aryl groups substituted by one or more of the above alkoxy groups, e.g., 3-methoxyphenyl, 2-ethoxyphenyl, and the like.

Typical alkyl substituted aryl groups include any of the above aryl groups substituted by any of the $C_{1-6}$ alkyl groups, including the group $Ph(CH_2)n$, where n is 1-6, for example, tolyl, o-, m-, and p-xylyl, ethylphenyl, 1-propylphenyl, 2-propylphenyl, 1-butylphenyl, 2-butylphenyl, t-butylphenyl, 1-pentylphenyl, 2-pentylphenyl, 3-pentylphenyl.

Typical alkenyl groups include $C_{2-6}$ alkenyl groups, e.g. ethenyl, 2-propenyl, isopropenyl, 2-butenyl, 3-butenyl, 4-pentenyl, 3-pentenyl, 2-pentenyl, 5-hexenyl, 4-hexenyl, 3-hexenyl, and 2-hexenyl groups.

Typical alkynyl groups include $C_{2-6}$ alkynyl groups e.g. enthynyl, 2-propenyl, 2-butynyl, 3-butynyl, 4-pentynyl, 3-pentynyl, 2-pentynyl, 5-hexynyl, 4hexynyl, 3-hexynyl, and 2-hexynyl groups.

Typical alkenyl or alkynyl substituted aryl groups include any of the above $C_{6-14}$ aryl groups substituted by any of the above $C_{2-6}$ alkenyl or $C_{2-6}$ alkynyl groups, e.g., ethenylphenyl, 1-propenylphenyl, 2-propenylphenyl, 1butenylphenyl, 2-butenylphenyl, 1-pentenylphenyl, 2-pentenylphenyl, 3-pentenylphenyl, 1-hexenylphenyl, 2-hexenylphenyl, 3-hexenylphenyl, ethynylphenyl, 1-propynylphenyl, 2-propynylphenyl, 1-butynylphenyl, 2-butynylphenyl, 1-pentynylphenyl, 2-pentynylphenyl, 3-pentynylphenyl, 1-hexynylphenyl, 2-hexynylphenyl, 3-hexynylphenyl groups.

Typical halo groups include fluorine, chlorine, bromine, and iodine.

Typical halo substituted alkyl groups include $C_{1-6}$ alkyl groups substituted by one or more fluorine, chlorine, bromine, or iodine atoms, e.g., fluoromethyl, difluoromethyl, trifluoromethyl, pentafluoroethyl, 1,1-difluoroethyl, and trichloromethyl groups.

Typical alkanoyl groups include $C_{1-5}C(=O)$— alkanoyl groups, e.g., acetyl, propionyl, butanoyl, pentanoyl, and hexanoyl groups, or by an arylalkanoyl group, e.g., a $C_{1-5}C(=O)$— alkanoyl group substituted by any of the above aryl groups.

Typical cycloalkyl groups include $C_{3-8}$ cycloalkyl groups including cyclopropyl, cyclobutyl, cyclopentyl, cyclohexyl, cycloheptyl and cyclooctyl groups.

The term "lipophilic group" as used herein refers to either a naturally occurring lipid per se, a hydrophobic branched or unbranched hydrocarbon comprising about 4 to about 26 carbon atoms, preferably about 5 to about 19 carbon atoms, a fatty acid or ester thereof, or a surfactant. Suitable lipophilic groups include, but are not limited to, long chain alkanoyl groups including: palmityl ($C_{15}H_{31}$), oleyl ($C_{15}H_{29}$), stearyl ($C_{17}H_{35}$), lauryl ($C_{11}H_{23}$), cholyl, and myristyl ($C_{13}H_{27}$)

The term "natural or unnatural amino acid" as used herein refers to any of the 21 naturally occurring amino acids as well as D-form amino acids, blocked L-and D-form amino acids such as those blocked by amidation or acylation, substituted amino acids (e.g., those substituted with a sterically hindered alkyl group or a cycloalkyl group such as cyclopropyl or cyclobutyl) in which the substitution introduces a conformational restraint in the amino acid. The preferred naturally occurring amino acids for use in the present disclosure as amino acids or components of a peptide or protein are alanine, arginine, asparagine, aspartic acid, citrulline, cysteine, cystine, y-glutamic acid, glutamine, glycine, histidine, isoleucine, norleucine, leucine, lysine, methionine, ornithine, phenylalanine, proline, hydroxyproline, serine, threonine, tryptophan, tyrosine, valine, γ-carboxyglutamate, or O-phosphoserine. The preferred non-naturally occurring amino acids for use in the present disclosure as amino acids or components of peptides or proteins are any of the β-amino acids, e.g., α-alanine, γ-amino butyric acid, γ-amino butyric acid, γ-(aminophenyl)butyric acid, α-amino isobutyric acid, ε-amino caproic acid, 7-amino heptanoic acid, amino benzoic acid, aminophenyl acetic acid, aminophenyl butyric acid, cysteine (ACM), methionine sulfone, phenylglycine, norvaline, ornithine, δ-ornithine, p-nitro-phenylalanine, 1,2,3,4-terahydroisoquinoline-3-carboxylic acid and thioproline.

The present disclosure is also directed to methods of preparing lipidized conjugates of PYY and PYY agonists, pharmaceutical compositions comprising lipidized conjugates of PYY and PYY agonists, and methods of increasing the delivery of amino group-containing PYY and PYY agonists into a cell.

Also provided by the disclosure are chemically modified derivatives of PYY and PYY agonists which may provide additional advantages such as increased solubility, stability and circulating time of the polypeptide, or decreased immunogenicity (see U.S. Pat. No. 4,179,337). Such modified derivatives include PYY and PYY agonists modified by pegylation. The terms "pegylated" and "pegylation" refer to the process of reacting a poly(alkylene glycol), preferably an activated poly(alkylene glycol), with a facilitator such as an amino acid, e.g. lysine, to form a covalent bond. Although "pegylation" is often carried out using poly(ethylene glycol) or derivatives thereof, such as methoxy poly(ethylene glycol), the term is not intended to be so limited here, but is intended to include any other useful poly(alkylene glycol), such as, for example poly(propylene glycol).

The chemical moieties for derivatization may also be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72, 1996; Vorobjev et al., *Nucleosides Nucleotides* 18:2745-2750, 1999; and Caliceti et al., *Bioconjug. Chem.* 10:638-646, 1999.

The polyethylene glycol molecules (or other chemical moieties) should be attached to the polypeptides or proteins with consideration of effects on functional or antigenic domains of the polypeptides or proteins. There are a number of attachment methods available to those skilled in the art, e.g., EP 0 401 384 (coupling PEG to G-CSF), see also Malik et al., *Exp. Hematol.* 20:1028-1035, 1992 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins and polypeptides via linkage to any of a number of amino acid residues. For example, polyethylene glycol can be linked to proteins and polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the polypeptide or protein or to more than one type of amino acid residue (e.g., lysine, histidine, aspartic acid, glutamic acid, cysteine and combinations thereof) of the protein or polypeptide.

One may specifically desire proteins and polypeptides chemically modified at the N-terminus. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins and polypeptides may be accomplished by any number of means. For example, polyethylene glycol may be attached to the protein or polypeptide either directly or by an intervening linker. Linkerless systems for attaching polyethylene glycol to proteins and polypeptides are described in Delgado et al., *Crit. Rev. Thera. Drug Carrier Sys.* 9:249-304, 1992; Francis et al., *Intern. J. of Hematol.* 68:1-18, 1998; U.S. Pat. Nos. 4,002,531; 5,349,052; WO 95/06058; and WO 98/32466.

One system for attaching polyethylene glycol directly to amino acid residues of proteins and polypeptides without an intervening linker employs tresylated MPEG, which is produced by the modification of monmethoxy polyethylene glycol (MPEG) using tresylchloride ($ClSO_2CH_2CF_3$). Upon reaction of the protein or polypeptide with tresylated MPEG, polyethylene glycol is directly attached to amine groups of the protein or polypeptide. Thus, the disclosure includes protein-polyethylene glycol conjugates produced by reacting proteins and polypeptides with a polyethylene glycol molecule having a 2,2,2-trifluoreothane sulphonyl group.

Polyethylene glycol can also be attached to proteins and polypeptides using a number of different intervening linkers. For example, U.S. Pat. No. 5,612,460 discloses urethane linkers for connecting polyethylene glycol to proteins. Protein-polyethylene glycol conjugates wherein the polyethylene glycol is attached to the protein or polypeptide by a linker can also be produced by reaction of proteins or polypeptides with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to proteins and polypeptides are described in WO 98/32466.

The number of polyethylene glycol moieties attached to each protein or polypeptide (i.e., the degree of substitution) may also vary. For example, the pegylated proteins and polypeptides may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein or polypeptide molecule. Methods for determining the degree of substitution are discussed, for example, in Delgado et al., *Crit. Rev. Thera. Drug Carrier Sys.* 9:249-304, 1992.

The proteins and polypeptides containing substantially non-antigenic polymers, preferably poly(alkylene glycols) may be prepared, for example, as described in U.S. Pat. Nos. 5,428,128; 6,127,355; and 5,880,131.

To effect covalent attachment of poly(ethylene glycol) (PEG) to a protein or polypeptide, the hydroxyl end groups of the PEG must first be converted into reactive functional groups. This process is frequently referred to as "activation" and the product is called "activated PEG." Methoxy poly (ethylene glycol) (mPEG), distally capped with a reactive functional group is often used. One such activated PEG is succinimidyl succinate derivative of PEG (SS-PEG). See also Abuchowski et al., *Cancer Biochem. Biophys.* 7:175-186, 1984; and U.S. Pat. No. 5,122,614 which discloses poly(ethylene glycol)-N-succinimide carbonate and its preparation.

Alternative substantially non-antigenic polymers that may be employed in the practice of the present disclosure include materials such as dextran, polyvinyl pyrrolidones, polysaccharides, starches, polyvinyl alcohols, polyacrylamides, or other similar non-immunogenic polymers. Those of ordinary skill in the art will realize that the foregoing is merely illustrative and not intended to restrict the type of polymeric substances suitable for use herein.

In one aspect of the disclosure, the polymer is introduced into the peptide or protein molecule after being functionalized or activated for reaction and attachment to one or more amino acids. By activation, it is understood by those of ordinary skill in the art that the polymer is functionalized to include a desired reactive group. See, for example, U.S. Pat. Nos. 4,179,337 and 5,122,614. In this embodiment, the hydroxyl end groups of poly(alkylene glycols) are converted and activated into reactive functional groups.

In another aspect of the disclosure, the polymer is conjugated to a facilitator moiety prior to being introduced into the polypeptide or protein molecule. The facilitator moiety is preferably an amino acid such as lysine, however, non-amino acid moieties are also contemplated. Within the aspect, there are included multifunctionalized organic moieties such as alkyls or substituted alkyls. Such moieties can be prepared to have a nucleophilic functional group such as an amine and an electrophilic group such as an acid as well as a suitably functionalized region for conjugating with the desired polymer or polymers.

The facilitator moieties allow easier inclusion of a polymer into the peptide or protein molecule during synthesis. For example, poly(alkylene glycols) coupled to facilitator amino acids or amino acid residues in polypeptides or proteins by means of suitable coupling agents are illustrative. A useful review of a number of coupling agents known in the art appears in Dreborg et al., *Critical Reviews in Therapeutic Drug Carrier Systems* 6(4):315-165, 1990, see especially, pp. 317-320.

Pegylated PYY peptides and agonists can also be of the general formula

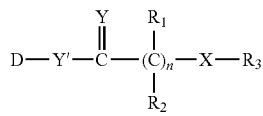

wherein:

D is a residue of a PYY peptide or agonist;

X is an electron withdrawing group;

Y and Y' are independently O or S;

(n) is zero (0) or a positive integer, preferably from 1 to about 12;

$R_1$ and $R_2$ are independently selected from the group consisting of H, $C_{1-6}$ alkyls, aryls, substituted aryls, aralkyls, heteroalkyls, substituted heteroalkyls, and substituted $C_{1-6}$ alkyls;

$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

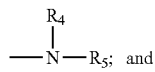

$R_4$ and $R_5$ are independently selected from the group consisting of H, $C_{1-6}$ alkyls, aryls, substituted aryls, aralkyls, heteroalkyls, substituted heteroalkyls and substituted $C_{1-6}$ alkyls or jointly form a cyclic $C_5$-$C_7$ ring. See U.S. Pat. No. 6,127,355.

Typical alkyl groups include $C_{1-6}$ alkyl groups including methyl, ethyl, propyl, isopropyl, butyl, isobutyl, sec-butyl, tert-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl, and the like.

Preferred aryl groups are $C_{6-14}$ aryl groups and typically include phenyl, naphthyl, fluorenyl, phenanthryl, and anthracyl groups.

Typical alkyl substituted aryl groups include any of the above aryl groups substituted by any of the $C_{1-6}$ alkyl groups, including the group $Ph(CH_2)_n$, where n is 1-6, for example, tolyl, o-, m-, and p-xylyl, ethylphenyl, 1-propylphenyl, 2-propylphenyl, 1-butylphenyl, 2-butylphenyl, t-butylphenyl, 1-pentylphenyl, 2-pentylphenyl, 3-pentylphenyl.

Typical cycloalkyl groups include $C_{3-8}$ cycloalkyl groups including cyclopropyl, cyclobutyl, cyclopentyl, cyclohexyl, cycloheptyl and cyclooctyl groups.

Typical electron withdrawing groups include O, $NR_1$, S, SO and $SO_2$, wherein $R_1$ is defined above.

PYY Antagonists

Also contemplated, are the use of Y receptor antagonist. A Y receptor antagonist is a substance (typically a ligand) which binds to a Y receptor and blocks the physiological effect of a Y receptor agonist (such as, PYY, NPY, or PP (see Tables 1-3, infra). These antagonists could be either peptide antagonist or non-peptide antagonist of PYY, NPY, or PP.

Peptide antagonist include modifications, mutants, fragments, and/or variants thereof, of the PYY, NPY, or PP peptide's natural amino acid sequence (e.g., by deletions, amino acid substitutions, deletions, insertions, and modifications of the N-terminal amino and/or C-terminal carboxyl group) resulting in a peptide which acts as an antagonist to a Y receptor. In addition, PYY, NPY, or PP amino acid sequences may be fusion or chimera proteins which act as antagonists at the Y receptor. These peptides may also be modified by processes such as, lipidation, pegylation, amidation, glycosylation, acylation, sulfation, phosphorylation, acetylation and cyclization.

Many non-peptide antagonist of the Y receptors are known in the art and are contemplated for use with this invention. (See Table 5, infra). Any known PYY, NPY, or PP non-peptide antagonist may be useful in this invention.

Table 5—PYY and NPY Antagonist

Exemplary antagonists of the Y receptor include, but are not limited to the following:

BIBO3304

Ref: Berglund, M M. *Biochem Pharmacol* 60(12):1815-22, Dec. 15, 2000.

SR120819A

1-[2-[2-(2-naphtylsulfamoyl)-3-phenylpropionamido]-3-[4-[N-[4-(dimethylaminomethyl)-cis-cyclohexylmethyl] amidino]phenyl]propionyl]pyrrolidine, (S,R) stereoisomer Ref: Berglund, M M. *Biochem Pharmacol* 60(12):1815-22, Dec. 15, 2000.

BIIE0246

(S)-N2-[[1-[2-[4-[(R,S)-5,11-dihydro-6(6h)-oxodibenz[b,e] azepin-11-yl]-1-piperazinyl]-2-oxoethyl]cyclopentyl] acetyl]-N-[2-[1,2-dihydro-3,5(4H)-dioxo-1,2-diphenyl-3H-1,2,4-triazol-4-yl]ethyl]-argininamid Ref: Malmstrom, *Life Sci* 69(17):1999-2005, Sep. 14, 2001.

BIBP 3226

[(R)-N2-(diphenylacetyl)-N-[(4-hydroxyphenyl)methyl]-D-arginine-amide], and a recently described peptidic structure [Ile-Glu-Pro-Orn-Tyr-Arg-Leu-Arg-Tyr-NH2, cyclic (2,4'), (2',4)-diamide].

Ref: Doods, H. N. *J Pharmacol Exp Ther* 275(1):136-42, October, 1995.

BIBP 3435

Ref: Lundberg J. M., Modin A. *Br J Pharmacol* 116(7):2971-82, December, 1995.

H 394/84

1,4-Dihydro-4-[3-[[[[3-[spiro(indene-4,1'-piperidin-1-yl)] propyl]amino]carbonyl]amino]phenyl]-2,6-dimethyl-3,5-pyridine dicarboxylic acid, dimethylester Ref: Malmstrom, R. E. *Eur J Pharmacol* 418(1-2):95-104, Apr. 20, 2001.

H 409/22
(2R)-5-([amino(imino)methyl]amino)-2-[(2,2-diphenylacetyl)amino]-N-[(1R)-1-(4-hydroxyphenyl)ethyl]-pentanamide
Ref: Malmstrom, R. E. *Life Sci* 69(17):1999-2005, Sep. 14, 2001.
1229U91
Ref: Schober, D A. *Peptides* 19(3):537-42, 1998.
L-152,804
Ref: Kanatani, A. *Biochem Biophys Res Commun* 272(1): 169-73, May 27, 2000.

Aminoalkyl substituted
pyrazolo[1,5,-a]-1,5-pyrimidines and
pyrazolo[1,5-a]-1,3,5-triazines Ref: U.S. Pat. No. 6,372,743

Alkyl and cycloalkyl derivatives of
1,4-dihydropyridine (e.g., 1,4-dihydro-2,6-dimethyl-4-[4-[[[[3-[4-(3-methoxyphenyl)-1-piperidinyl]propyl]amino]carbonyl]amino]butyl]-3,5-pyridine dicarboxylic acid, dimethyl ester)
Ref: U.S. Pat. No. 6,444,675

4-(3-substituted-phenyl)-1,4-dihydropyridine
derivatives

Ref: U.S. Pat. No. 5,635,503

Squarate derivatives of
4-phenyl-1,4-dihydropyridines e.g., 1,4-dihydro-4-[3-[[2-[[3-[4-(3-methoxyphenyl)-1-piperidinyl]propyl]amino]-3,4-dioxo-1-cyclobuten-1-yl]amino]phenyl]-2,3-dimethyl-3,5-pyridinedicarboxylic acid, dimethyl ester
Ref: U.S. Pat. No. 6,432,960
Substituted amide Y receptor antagonist, such as:
N-(4-Diethylamino-phenyl)-2-phenyl-2-pyridin-4-yl-acetamide;
2-(4-Fluoro-phenyl)-2-pyridin-4-yl-N-(3,4,5,6-tetrahydro-2H-[1,2']bipyridinyl-5'-yl)-acetamide;
2-Phenyl-2-pyridin-4-yl-N-(3,4,5,6-tetrahydro-2H-[1,2']bipyridinyl-5'-yl)-acetamide;
N-(4-Diethylamino-phenyl)-2-phenyl-2-pyridin-2-yl-acetamide;
N-(6-Diethylamino-pyridin-3-yl)-2,2-diphenylacetamide;
N-(4-Diethyl-sulfamoyl-phenyl)-2-phenyl-2-pyridin-4-yl-acetamide;
2,2-Diphenyl-N-(6-pyrrolidin-1-yl-pyridin-3-yl)-acetamide;
2,2-Diphenyl-N-(3,4,5,6-tetrahydro-2H-[1,2']bipyridinyl-5'-yl)-acetamide;
N-[6-(2,5-Dimethyl-pyrrolidin-1-yl)-pyridin-3-yl]-2,2-diphenyl-acetamide;
N-(4-Diethylsulfamoyl-phenyl)-2,2-diphenyl-acetamide; and
N-(4-Dimethylsulfamoyl-phenyl)-2,2-diphenyl-acetamide.
Ref: U.S. Pat. No. 6,407,120
Carbazole Y receptor antagonist, such as:
2-Dimethylamino-N-(9-ethyl-9H-carbazol-3-yl)-acetamide;
3-Diethylamino-N-(9-ethyl-9H-carbazol-3-yl)-propionamide;
N-(9-Ethyl-9H-carbazol-3-yl)-2-fluoro-benzamide;
4-Dimethylamino-N-(9-ethyl-9H-carbazol-3-yl)-butyramide;
N-(9-Ethyl-9H-carbazol-3-yl)-2-hydroxy-2,2-diphenyl-acetamide;
N-(9-Ethyl-9H-carbazol-3-yl)-2-hydroxy-2-methyl-propionamide;
N-(9-Ethyl-9H-carbazol-3-yl)-2-hydroxy-2-methyl-butyramide;
N-(9-Ethyl-9H-carbazol-3-yl)-2-hydroxy-2-phenyl-propionamide;
(R)-N-(9-Ethyl-9H-carbazol-3-yl)-2-hydroxy-2-phenyl-propionamide;
2-Bromo-N-(9-ethyl-9H-carbazol-3-yl)-acetamide; and
3-Dimethylamino-N-(9-ethyl-9H-carbazol-3-yl)-propionamide.
2-[Bis-(2-hydroxy-ethyl)-amino]-N-(9-ethyl-9H-carbazol-3-yl)-acetamide;
2-Benzylamino-N-(9-ethyl-9H-carbazol-3-yl)-acetamide;
3-Diphenylamino-N-(9-ethyl-9H-carbazol-3-yl)-propionamide; and
N-(9-Ethyl-9H-carbazol-3-yl)-3-(4-piperidin-1-ylmethyl-phenoxy)-propionamide;
N-(9-Ethyl-9H-carbazol-3-yl)-3-[methyl-(1,2,3,4-tetrahydro-naphthalen-2-yl)-amino]-propionamide;
N-(9-Ethyl-9H-carbazol-3-yl)-3-(quinolin-7-yloxy)-propionamide; and
2-[Bis-(2-hydroxy-ethyl)-amino]-N-(9-ethyl-9H-carbazol-3-yl)-acetamide.
3-Bromo-N-(9-ethyl-9H-carbazol-3-yl)-propionamide;
N-(9-Isopropyl-9H-carbazol-3-yl)-trifluoroacetamide;
4-Dimethylamino-N-(9-ethyl-9H-carbazol-3-yl)-N-methyl-butyramide;
N-(9-Methyl-9H-carbazol-3-yl)-trifluoroacetamide;
1-Hydroxy-cyclopropanecarboxylic acid (9-ethyl-9H-carbazol-3-yl)-amide; and
2-(4-Chloro)-benzylamino-N-(9-ethyl-9H-carbazol-3-yl)-acetamide.
2-(4-fluoro)-benzylamino-N-(9-ethyl-9H-carbazol-3-yl)-acetamide;
(R)-N-(9-Ethyl-9H-carbazol-3-yl)-2-(1-phenyl-ethylamino)-acetamide;
(R)-N-(9-Ethyl-9H-carbazol-3-yl)-2-(1-(4-chloro)-phenyl-ethylamino)-acetamide;
2-(3-Diethylamino-2-hydroxy-propylamino)-N-(9-ethyl-9H-carbazol-3-yl)-acetamide;
2-(Benzyl-isopropyl-amino)-N-(9-ethyl-9H-carbazol-3-yl)-acetamide;
N-3-Bromo-(9-ethyl-9H-carbazol-6-yl)-trifluoroacetamide;
N-(9-Ethyl-6-formyl-9H-carbazol-3-yl)-trifluoroacetamide;
N-(9-Ethyl-6-hydroxymethyl-9H-carbazol-3-yl)-trifluoroacetamide;
N-(9-Ethyl-9H-carbazol-3-yl)-methanesulfonamide;
N-(9-Ethyl-9H-carbazol-3-yl)-chloromethanesulfonamide;
2-Bromo-N-(9-ethyl-9H-carbazol-3-yl)-acetamide; and
3-Dimethylamino-N-(9-ethyl-9H-carbazol-3-yl)-propionamide.
2-[Bis-(2-hydroxy-ethyl)-amino]-N-(9-ethyl-9H-carbazol-3-yl)-acetamide;
2-Benzylamino-N-(9-ethyl-9H-carbazol-3-yl)-acetamide;
3-Diphenylamino-N-(9-ethyl-9H-carbazol-3-yl)-propionamide;
N-(9-Ethyl-9H-carbazol-3-yl)-3-(4-piperidin-1-ylmethyl-phenoxy)-propionamide;
N-(9-Ethyl-9H-carbazol-3-yl)-3-[methyl-(1,2,3,4-tetrahydro-naphthalen-2-yl)-amino]-propionamide;
N-(9-Ethyl-9H-carbazol-3-yl)-3-(quinolin-7-yloxy)-propionamide;
2-[Bis-(2-hydroxy-ethyl)-amino]-N-(9-ethyl-9H-carbazol-3-yl)-acetamide;

3-Bromo-N-(9-ethyl-9H-carbazol-3-yl)-propionamide; and
N-(9-Isopropyl-9H-carbazol-3-yl)-acetamide.
4-Dimethylamino-N-(9-ethyl-9H-carbazol-3-yl)-N-methyl-butyramide;
N-(9-Methyl-9H-carbazol-3-yl)-trifluoroacetamide;
1-Hydroxy-cyclopropanecarboxylic acid (9-ethyl-9H-carbazol-3-yl)-amide;
2-(4-Chloro)-benzylamino-N-(9-ethyl-9H-carbazol-3-yl)-acetamide; and
2-(4-fluoro)-benzylamino-N-(9-ethyl-9H-carbazol-3-yl)-acetamide.
(R)-N-(9-Ethyl-9H-carbazol-3-yl)-2-(1-phenyl-ethylamino)-acetamide;
(R)-N-(9-Ethyl-9H-carbazol-3-yl)-2-(1-(4-chloro)-phenylethylamino)-acetamide;
(R)-, (S)- or a mixture of (R)-and (S)-2-(3-Diethylamino-2-hydroxy-propylamino)-N-(9-ethyl-9H-carbazol-3-yl)-acetamide;
(S)-N-(6-tert-Butyl-9-ethyl-9H-carbazol-3-yl)-2-(3-diethylamino-2-hydroxy-propylamino)-acetamide, 2-(Benzyl-isopropyl-amino)-N-(9-ethyl-9H-carbazol-3-yl)-acetamide;
N-3-Bromo-(9-ethyl-9H-carbazol-6-yl)-trifluoroacetamide;
N-(9-Ethyl-6-formyl-9H-carbazol-3-yl)-trifluoroacetamide; and
N-(9-Ethyl-6-hydroxymethyl-9H-carbazol-3-yl)-trifluoroacetamide.
N-(9-Ethyl-9H-carbazol-3-yl)-methanesulfonamide; and
N-(9-Ethyl-9H-carbazol-3-yl)-chloromethanesulfonamide.
Ref: U.S. Pat. No. 6,399,631
Various Dihydropyridine Derivatives:
Ref: U.S. Pat. No. 4,829,076

Cyanoguanidine derivatives of the
4-(3-substituted-phenyl)-1,4-dihydropyridines

Ref: U.S. Pat. No. 6,001,836
Amide derivatives that are NPY Y5 receptor antagonists
Ref: U.S. Pat. No. 6,410,792
Thiourea linked piperazine and piperidine derivatives of
4-phenyl-1,4-dihydropyridines, such as:
1,4-dihydro-4-[3-[[[[3-[4-(3-methoxyphenyl)piperidinyl]propyl]amino]carbonothioyl]amino]phenyl]-2,6-dimethyl-3,5-pyridine dicarboxylic acid, dimethyl ester,
1,4-dihydro-4-[3-[[[[3-(4-phenylpiperidinyl)propyl]amino]carbonothioyl]amino]phenyl]-2,6-dimethyl-3,5-pyridine dicarboxylic acid, dimethyl ester, and
1,4-dihydro-4-[4-[[[[3-(4-cyclohexyl-1-piperazinyl)propyl]amino]carbonothioyl]amino]phenyl]-2,6-dimethyl-3,5-pyridine dicarboxylic acid, dimethyl ester.
1,4-dihydro-4-[4-fluoro-3-[[[[3-(4-phenylpiperidinyl)propyl]amino]carbonothioyl]amino]phenyl]-2,6-dimethyl-3,5-pyridine dicarboxylic acid, dimethyl ester,
1,4-dihydro-4-[3-[[[[3-(4-methyl-1-piperidinyl)propyl]amino]carbonothioyl]amino]-4-fluorophenyl)-2,6-dimethyl-3,5-pyridine dicarboxylic acid, dimethyl ester,
1,4-dihydro-4-[3-[[[[3-(4-ethyl-1-piperidinyl]propyl]amino]carbonothioyl]amino]-4-fluorophenyl]-2,6-dimethyl-3,5-pyridine dicarboxylic acid, dimethyl ester,
1,4-dihydro-4-[3-[[[[3-(4-propyl-1-piperidinyl)propyl]amino]carbonothioyl]amino]-4-fluorophenyl]-2,6-dimethyl-3,5-pyridine dicarboxylic acid, dimethyl ester,
1,4-dihydro-4-[3-[[[[3-[4-1,1-dimethylethyl)-1-piperidinyl]propyl]amino]carbonothioyl]amino]-4-fluorophenyl]-2,6-dimethyl-3,5-pyridine dicarboxylic acid, dimethyl ester,
1,4-dihydro-4-[3-[[[[3-[4-(1-methylethyl)-1-piperidinyl]propyl]amino]carbonothioyl]amino]-4-fluorophenyl]-2,6-dimethyl-3,5-pyridine dicarboxylic acid, dimethyl ester, and
1,4-dihydro-4-[4-[[[[3-(4-cyclohexyl-1-piperazinyl)propyl]amino]carbonothioyl]amino]-4-fluorophenyl]-2,6-dimethyl-3,5-pyridine dicarboxylic acid, dimethyl ester.
Ref: U.S. Pat. No. 6,391,881
Novel Aryl Sulfonamide and Sulfamide Compounds
Ref: U.S. Pat. No. 6,391,877
Amine and amide derivative Y receptor antagonist, such as:
Amino-6-[(2-fluorophenylsulfonyl)amino]-N-[cis-1,2,3,4-tetrahydro-6-methoxy-1-(3-pyridinylmethyl)-2-naphthenyl]-(2S)-hexanamide bis-hydrochloride, N-[5-amino-6-[[cis-1,2,3,4-tetrahydro-6-methoxy-1-(3-pyridinylmethyl)-2-naphthalenyl]amino]hexyl]-2-fluorobenzenesulfonamide tris-hydrochloride, N-[5-amino-6-[[cis-1,2,3,4-tetrahydro-6-hydroxy-1-(3-pyridinylmethyl)-2-naphthalenyl]amino]hexyl]-2-fluorobenzenesulfonamide tris-hydrochloride, (2S)-2-(Acetylamino)-6-[(2-fluorophenylsulfonyl)amino]-N-[cis-1,2,3,4-tetrahydro-6-methoxy-1-(3-pyridinylmethyl)-2-naphthenyl]hexanamide bis-hydrochloride, (2S)-2-(Acetylamino)-6-[(2-fluorophenylsulfonyl)amino]-N-[cis-1,2,3,4-tetrahydro-6-hydroxy-1-(3-pyridinylmethyl)-2-naphthenyl]hexanamide bis-hydrochloride, 3-[(Phenylsulfonyl)amino]-N-[cis-1,2,3,4-tetrahydro-6-fluoro-1-(3-pyridinylmethyl)-2-naphthalenyl]-1-pyrrolidineacetamide bis-trifluoroacetate, 4-Oxo-1-phenyl-N-[cis-1,2,3,4-tetrahydro-1-(3-pyridinylmethyl)-2-naphthalenyl]-1,3,8-triazaspiro[4.5]decane-8-acetamide bis-hydrochloride, trans-N-[2-(4-fluorophenyl)-3-(3-pyridinyl)propyl]-4-[((2-fluorophenylsulfonyl)amino)methyl]-1-cyclohexanamide hydrochloride, trans-N-[[[[[2-(4-fluorophenyl)-3-(3-pyridinyl)propyl]amino]methyl]-4-cyclohexyl]methyl]2-fluorobenzenesulfonamide bis-hydrochloride.
Ref: U.S. Pat. No. 6,380,224.
Alkylene diamine-substituted pyrazlo (1,5-a)-1,5-pyrimidines and pyrazolo (1,5-a) 1,3,5-triazines, such as:
2-{2-[3-(2,6-dichloro-4-methoxy-phenyl)-2,5-dimethyl-pyrazolo[1,5-a]pyrimidin-7-ylamino]-ethylamino}-butan-1-ol;
N-{2-[3-(2,6-dichloro-4-methoxy-phenyl)-2,5-dimethyl-pyrazolo[1,5-a]pyrimidin-7-ylamino]-ethyl}-N'-methyl-cyclohexane-1,4-diamine;
N-{2-[3-(2,6-dichloro-4-methoxy-phenyl)-2,5-dimethyl-pyrazolo[1,5-a]pyrimidin-7-ylamino]-ethyl}-N'-ethyl-cyclohexane-1,4-diamine;
N-[3-(2,6-dichloro-4-methoxy-phenyl)-2,5-dimethyl-pyrazolo[1,5-a]pyrimidin-7-yl]-N-(4-morpholin-4-yl-cyclohexyl)-ethane-1,2-diamine;
4-{2-[3-(2,6-dichloro-4-methoxy-phenyl)-2,5-dimethyl-pyrazolo[1,5-a]pyrimidin-7-ylamino]-ethylamino}-cyclohexanol;
3-{2-[3-(2,6-dichloro-4-methoxy-phenyl)-2,5-dimethyl-pyrazolo[1,5-a]pyrimidin-7-ylamino]-ethylamino}-propane-1,2-diol;
N-{2-[3 (2,6-dichloro-4-methoxy-phenyl)-2,5-dimethyl-pyrazolo[1,5-a]pyrimidin-7-ylamino]-ethyl}-N'-isobutyl-cyclohexane-1,4-diamine;
N-{2-[3-(2,6-dichloro-4-methoxy-phenyl)-2,5-dimethyl-pyrazolo[1,5-a]pyrimidin-7-ylamino]-ethyl}-N-isobutyl-cyclohexane-1,4-diamine;
4-{2-[3-(2,6-dichloro-4-ethoxy-phenyl)-2,5-dimethyl-pyrazolo[1,5-a]pyrimidin-7-ylamino]-1-methyl-ethylamino}-cyclohexanol;

2-{2-[3-(2,6-dichloro-4-ethoxy-phenyl)-2,5-dimethyl-pyrazolo[1,5-a]pyrimidin-7-ylamino]-ethylamino}-cyclohexanol;

N-[3-(2,6-dichloro-4-methoxy-phenyl)-2,5-dimethyl-pyrazol[1,5-a]pyrimidin-7-yl]-N-(4,4,4-trifluoro-butyl)-ethane-1,2-diamine;

N-[3-(2,6-dichloro-4-ethoxy-phenyl)-2,5-dimethyl-pyrazolo[1,5-a]pyrimidin-7-yl]-N-(2,2,2-trifluoro-ethyl)-ethane-1,2-diamine;

N-[3-(2,6-dichloro-4-methoxy-phenyl)-2,5-dimethyl-pyrazolo[1,5-a]pyrimidin-7-yl]-N-(2-trifluoromethyl-cyclohexyl)-ethane-1,2-diamine;

N-[3-(2,6-dichloro-4-methoxy-phenyl)-2,5-dimethyl-pyrazolo[1,5-a]pyrimidin-7-yl]-N-(4-trifluoromethyl-cyclohexyl)-ethane 1,2-diamine;

N-[3-(2,6-dichloro-4-methoxy-phenyl)-2,5-dimethyl-pyrazolo[1,5-a]pyrimidin-7-yl]-N-(2,2-difluoro-ethyl)-ethane-1,2-diamine;

N-[3-(2,6-dichloro-4-methoxy-phenyl)-2,5-dimethyl-pyrazolo[1,5-a]pyrimidin-7-yl]-N-(2-fluoro-1-methyl-ethyl)-ethane-1,2-diamine;

N-[3-(2,6-dichloro-4-methoxy-phenyl)-2,5-dimethyl-pyrazolo[1,5-a]pyrimidin-7-yl]-N-(2-fluoro-cyclohexyl)-ethane-1,2-diamine.

N-[3-(2,6-dichloro-phenyl)-2,5-dimethylpyrazolo[1,5-a]pyrimidin-7-yl]-N-(1-ethyl-piperidin-5-a]pyrimidin-7-yl]-N-(2,2,66-tetramethyl-piperidin-4-yl)-ethane-1,2diamine;

N-[3-(2,6-dichloro-phenyl)-2,5-dimethyl-pyrazolo[1,5-a]pyrimidin-7-yl]-N-19 piperidin-4-yl-ethane-1,2-diamine;

N-[3-(2,6-dichloro-phenyl)-2,5-dimethyl-pyrazolo[1,5-a]pyrimidin-7-yl]-N-(1-ethyl-piperidin-3-yl)-ethane-1,2-diamine;

N-(1 benzyl-pyrrolidin-3-yl)-N'-[3-(2,6-dichloro-phenyl)-2,5-dimethyl-pyrazolo[1,5-a]pyrimidin-7-yl]-ethane-1,2-diamine;

N-[3-(2,6-dichloro-phenyl)-2,5-dimethyl-pyrazolo[1,5-a]pyrimidin-7-yl]-N'-pyrimidin-2-yl-ethane-1,2-diamine;

N-(1-benzylpiperidin-4-yl)-N'-[3-(2,4-dichloro-6-methoxy-phenyl)-2,5-diethyl-pyrazolo[1,5-a]pyrimidin-7-yl]-ethane-1,2-diamine;

N-(1-benzyl-piperidin-4-yl)-N'-[3-(2,6-dichloro-4-methoxy-phenyl)-2,5-dimethyl-pyrazolo[1,5-a]pyrimidin-7-yl]-ethane-1,2-diamine;

N-[3(2,6-dichloro-4-methoxy-phenyl)-2,5-dimethyl-pyrazolo[1,5-a]pyrimidin-7-yl]-N-(1-methyl-piperidin-4-yl)-ethane-1,2-diamine;

N-[3-(2,6-dichloro-4-methoxy-phenyl)-2,5 dimethyl-pyrazolo[1,5-a]pyrimidin-7-yl]-N-(1-ethyl-piperidin-4-yl)-ethane-1,2-diamine;

N-[3-(2,6-dichloro-4-methoxy-phenyl)-2,5-dimethyl-pyrazolo[1,5-a]pyrimidin-7-yl]-N-(1-isopropyl-piperidin-4-yl)-ethane-1,2-diamine;

N-[3-(2,6-dichloro-4-methoxy-phenyl)2,5-dimethyl-pyrazolo[1,5-a]pyrimidin-7-yl]-N-(2,2,6,6-tetramethyl-piperidin-4-yl)ethane-1,2-diamine;

N-[3-(2,6-dichloro-4-methoxy-phenyl)-2,5-dimethyl-pyrazolo[1,5-a]pyrimidin-7-yl]-N-(1-ethyl-piperidin-3-yl)-ethane-1,2-diamine;

N-[3-(2,6-dichloro-4-methoxy-phenyl)-2,5-dimethyl-pyrazol to [1,5-a]pyrimidin-7-yl]-N'-piperidin-4-yl-ethane 1,2-diamine;

N.sup.2-(1-Benzyl-piperidin-4-yl)-N'-[3-(2,6-dichloro-phenyl)-2,5-dimethyl-pyrazolo[1,5-a]pyrimidin-7-yl]-propane-1,2-diamine;

N-[3-(2,6-Dichloro-4-methoxy-phenyl)-2,5-dimethyl-pyrazolo[1,5-a]pyrimidin-7-yl]-N'-(1-pyridin-3-ylmethyl-piperidin-4-yl)-ethane-1,2-diamine;

N-[3-(2,6-Dichloro-4-methoxyphenyl)-2,5-dimethyl-pyrazolo[1,5-a]pyrimidin-7-yl]-N'-(1-pyridin-4-ylmethyl-piperidin-4-yl)-ethane-1,2-diamine;

3,5-Dichloro-4-12,5-dimethyl-7-[2-(1-phenyl-pyrrolidin-3-ylamino)-ethylamino]-pyrazolo[1,5-a]pyrimidin-3-yl]-phenol;

N-[3-(2,6-dichloro-4-methoxy-phenyl)-2,5-dimethyl-pyrazolo[1,5-a]pyrimidin-7-yl]-N'-(1-pyridin-2-ylmethyl-piperidin-4-yl)-ethane-1,2-diamine;

3,5-dichloro-4-(2,5-dimethyl-7-[2-(1-pyrimidin-2-yl-piperidin-4-ylamino)-ethylamino]-pyrazolo[1,5-a]pyrimidin-3-yl}-benzonitrile;

N-[3-(2,6-dichloro-4-ethoxy-phenyl)-2,5-dimethyl-pyrazolo[1,5a]pyrimidin-7-yl]-N'-(1-pyrimidin-2-yl-piperidin-4-yl)-ethane-1,2-diamine;

N-[3-(2,6-dichloro-4-methoxy-phenyl)-2,5-dimethyl-pyrazolo[1,5-a]pyrimidin-7-yl]-N'-(1-pyrimidin-2-yl-piperidin-4-yl)-ethane-1,2-diamine;

N-(1-benzyl-piperidin-4-yl)-N'-[3(2,6-dichloro-4-ethoxy-phenyl)-2,5-dimethyl-pyrazolo[1,5-a]pyrimidin-7-yl]-ethane-1,2-diamine;

N-[3-(2,6-dichloro-phenyl)-5-ethyl-2-methyl-pyrazolo[1,5-a]pyrimidin-7-yl]-N'-(1-pyrimidin-2-yl-piperidin-4-yl)-ethane-1,2-diamine;

N-[3-(2,6-dichloro-phenyl)-5 isopropyl-2-methyl-pyrazolo[1,5-a]pyrimidin-7-yl]-N'-(1-pyrimidin-2-yl-piperidin-4-yl)ethane-1,2-diamine;

N-[3-(2,4-dichloro-phenyl)-5-isopropyl-2-methyl-pyrazolo[1,5a]pyrimidin-7-yl]-N'-(1-pyrimidin-2-yl-piperidin-4-yl)-ethane-1,2-diamine;

N-[3-(2,6-dichloro-4-ethoxy-phenyl)-2,5-dimethyl-pyrazolo[1,5-a]pyrimidin-7-yl]-N-(1-pyrimidin-2-yl-piperidin-4-yl)-propane-1,2-diamine;

N-[3-(2,6-dichloro-4-methoxy-phenyl)-5 isopropyl-2-methyl-pyrazolo[1,5-a]pyrimidin-7-yl]-N2-(1-pyrimidin-2-yl-piperidin-4-yl)propane-1,2-diamine;

N-[3-(2,6-dichloro-4-methoxy-phenyl)-5-ethyl-2-methylpyrazoto [1,5-a]pyrimidin-7-yl]-N-(1-pyrimidin-2-yl-piperidin-4-yl)-ethane-1,2-diamine;

N-[3-(2,6-dichloro-4-methoxy-phenyl)-2-methyl-5-propyl-pyrazolo[1,5-a]pyrimidin-7-yl]-N-(1-pyrimidin-2-yl-piperidin-4-yl)-propane-1,2-diamine;

N-[3-(2,6-dichloro-4-methoxy-phenyl)-5-ethyl-2-methylpyrazolo[1,5-a]pyrimidin-7-yl]-N-(1-pyrimidin-2-ylpiperidin-4-yl)-propane-1,2-diamine;

N-[3-(2,6-dichloro-phenyl)-2-methyl-5-propylpyrazoto [1,5-a]pyrimidin-7-yl]-N'-(1-pyrimidin-2-yl-piperidin-4-yl)-ethane-1,2-diamine;

N-[3-(2,6-dichloro-phenyl)-2-methyl-5-propyl-pyrazolo[1,5-a]pyrimidin-7-yl ]-N2-(1-pyrimidin-2-yl-piperidin-4-yl)-propane-1,2-diamine;

N-[3-(2,6-dichloro-phenyl)-5-ethyl-2-methyl-pyrazolo[1,5-a]pyrimidin-7-yl]-N.sup.2-(1-pyrimidin-2-yl-piperidin-4-yl)-propane 1,2-diamine;

N-[5-ethyl-2-methyl-3-(2,4,6-trimethyl-phenyl)-pyrazolo[1,5-a]pyrimidin-7-yl]-N'-(1-pyrimidin-2-yl-piperidin-4-yl)-ethane-1,2-diamine;

N-[5-ethyl-2-methyl-3-(2,4,6-trimethyl-phenyl)-pyrazolo[1,5-a]pyrimidin-7-yl]-N-(1-pyrimidin-2-yl-piperidin-4-yl)-propane-1,2-diamine;

N-[3-(2,6-dichloro-4-ethynyl-phenyl)-2,5-dimethylpyrazolo[1,5-a]pyrimidin-7-yl]-N'-(1-pyrimidin-2-yl-piperidin-4-yl)-ethane-1,2-diamine;

N-[2-methyl-5-propyl-3-(2,4,6-trimethyl-phenyl)-pyrazolo [1,5-a]pyrimidin-7-yl]-N'-(1pyrimidin-2-yl-piperidin-4-yl)-ethane-1,2-diamine;

N-[2,5-dimethyl-3-(2,4,6-trimethylphenyl)-pyrazolo[1,5-a] pyrimidin-7-yl]-N'-(1-pyridin-2-yl-piperidin-4-yl)-ethane-1,2-diamine;

N-[3-(2,6-Dimethyl-phenyl)-5-ethyl-2-methyl-pyrazolo[1,5-a]pyrimidin-7-yl]-N-(1-pyrimidin-2-yl-piperidin-4-yl)-propane-1,2-diamine;

N-[3-(2,6-dimethyl-phenyl)-2-methyl-5-propyl-pyrazolo[1,5-a]pyrimidin-7-yl]-N-(1-pyrimidin-2-yl-piperidin-4-yl)-ethane-1,2-diamine;

N-[3-(2,6-Dimethyl-phenyl)-2-methyl-5-propyl-pyrazolo[1,5-a]pyrimidin-7-yl]-NZ-(1-pyrimidin-2-yl-piperidin-4-yl)-propane-1,2-diamine;

N-[3-(2,6-dimethyl-phenyl)-2,5-dimethyl-pyrazolo[1,5-a] pyrimidin-7-yl]-N-(1-pyrimidin-2-ylpiperidin-4-yl)-propane-1,2-diamine;

N-[3-(2,4-dimethyl-phenyl)-5-ethyl-2-methyl-pyrazolo[1,5-a]pyrimidin-7-yl]-N-(1-pyrimidin-2-yl-piperidin-4-yl)-ethane-1,2-diamine;

N-[3-(2,4-dimethyl-phenyl)-2-methyl-5-propyl-pyrazolo[1,5-a]pyrimidin-7-yl]-N-(1-pyrimidin-2-yl-piperidin-4-yl)-ethane-1,2-diamine; and 1-[4-(1-{[3-(2,6-dichloro-4-methoxyphenyl)-2,5-dimethyl-pyrazolo[1,5-a]pyrimidin-7-ylamino]-methyl}-propylamino)piperidin-1-yl]-ethanone.

N-[2,5-dimethyl-3-(2,4,6-trimethylphenyl)-pyrazolo[1,5-a] pyrimidin-7-yl]-N-[2-(4-methoxy-phenyl)-ethyl]-ethane-1,2diamine;

N-[3-(2,6-dichloro-4-methoxy-phenyl)-2,5-dimethyl-pyrazolo1,5-a]pyrimidin-7-yl]-N-[2-(4-methoxy-phenyl)-ethyl]-ethane-1,2-diamine;

N-[3-(2,6-dichloro-4-methoxy-phenyl)-2,5-dimethyl-pyrazolo[1,5-a]pyrimidin-7-yl]-N'-[2-(3-ethoxy-4-methoxyphenyl)-ethyl]-ethane-1,2-diamine;

N-[3-(2,6-dichloro-4-methoxy-phenyl)-2,5-dimethyl-pyrazolo1,5-a]pyrimidin-7-yl]-N-[2-(4-ethoxy-3-methoxyphenyl)-ethyl]-ethane-1,2-diamine;

N-[3-(2,6-dichloro-4-methoxy-phenyl)-2,5-dimethyl-pyrazolo[1,a]pyrimidin-7-yl]-N'-(1,2,3,4-tetrahydro-naphthalen-2-yl)-ethane-1,2-diamine;

N-[3-(2,6-dichloro-4-methoxy-phenyl)-2,5-dimethyl-pyrazolo[1,5-a]pyrimidin-7-yl]-N-(2-pyridin-2-yl-ethyl)-ethane-1,2-diamine;

N-[3-(2,6-dichloro-4-methoxy-phenyl)-2,5-dimethyl-pyrazolo[1,5-a]pyrimidin-7-yl]-N-(2-pyridin-3-yl-ethyl)-ethane-1,2-diamine; and N-[3-(2,6-dichloro-4-methoxy-phenyl)-2,5-dimethyl-pyrazolo[1,5-a]pyrimidin-7-yl]-N-(2-pyridin4-yl-ethyl)-ethane-1,2-diamine.

Ref: U.S. Pat. No. 6,372,743

Spiroisoquinolinone derivative Y antaponist, such as:

2-(3-Chloropropyl)-2-phenyl-1,3-dioxolane,
2-(3-Chloropropyl)-2-(4-methoxyphenyl)-1,3-dioxolane,
2-(3-Chloropropyl)-2-(4-phenoxyphenyl)-1,3-dioxolane,
2-(3-Chloropropyl)-2-(4-bromophenyl)-1,3-dioxolane,
2-(3-Chloropropyl)-2-(4-chlorophenyl)-1,3-dioxolane,
N-3-Chloropropyl-N-methylbenzenemethanamine Hydrochloride,
N-(3-Chloropropyl)-N-(phenylmethyl)benzenemethanamine Hydrochloride,
N-(2-Hydroxyethyl)-N-methylbenzenemethanamine,
Chloro-1-(4-phenoxyphenyl)ethanone,
3-Chloro-1-(4-phenoxyphenyl)propanone,
1'-[3-(4-Phenoxyphenyl)-3-oxopropyl]spiro[isoquinoline-1-(2H)-4'-piperidine-3-(4H)-one Hydrochloride,
1'-[3-(4-Bromophenyl)-3-oxopropyl]spiro[isoquinoline-1-(2H)-4'-piperidine-3-(4H)-one],
1'-[2-[(1,1'-Biphenyl)-4-yl]-2-oxoethyl]spiro[isoquinoline-1-(2H)-4'-piperidine-3-(4H)-one],
1'-[2-(4-Bromophenyl)-2-oxoethyl]spiro[isoquinoline-1-(2H)-4'-piperidine-3-(4H)-one],
1'-[2-(4-Phenoxyphenyl)-2-oxoethyl]spiro[isoquinoline-1-(2H-4'-piperidine-3-(4H)-one], Hydrochloride,
1'-[2-[Bis(phenylmethyl)amino]ethyl]spiro[isoquinoline-1-(2H)-4'-piperidine-3-(4H)-one]Dihydrochloride,
1'-(4-Phenyl-4-oxobutyl)spiro[isoquinoline-1-(2H)-4'-piperidine-3-(4H)-one]Hydrochloride,
1'-[4-(4-Methoxyphenyl)-4-oxobutyl]spiro[isoquinoline-1-(2H)-4'-piperidine-3-(4H)-one]Hydrochloride,
1'-[4-(4-Phenoxyphenyl)-4-oxobutyl]spiro[isoquinoline-1-(2H)-4'-piperidine-3-(4H)-one]Hydrochloride,
1'-[4-(4-Bromophenyl)-4-oxobutyl]spiro[isoquinoline-1-(2H)-4'-piperidine-3-(4H)-one],
1'-[4-(4-Chlorophenyl)-4-oxobutyl]spiro[isoquinoline-1-(2H)-4'-piperidine-3-(4H)-one]Hydrochloride,
1'-[2-[(1,1'-Biphenyl)-3-yl]-2-oxoethyl]spiro[isoquinoline-1-(2H)-4'-piperidine-3-(4H)-one]Hydrochloride,
1'-[3-[(1,1'-Biphenyl)-4-yl]-3-oxopropyl]spiro[isoquinoline-1-(2H)-4'-piperidine-3-(4H)-one]Hydrochloride,
1'-[4-[(1,1'-Biphenyl)-4-yl]-4-oxobutyl]spiro[isoquinoline-1-(2H)4'-piperidine-3-(4H)-one]Hydrochloride,
1'-[2-[(1,1'-Biphenyl)-4-yl]-2-hydroxyethyl]spiro[isoquinoline-1-(2H)-4'-piperidine-3-(4H-one]Hydrochloride, Ref: U.S. Pat. No. 6,348,472

Triazine derivative Y receptor antagonists, such as:

N1-{[4-({[4-(Isopropylamino)-6-(methylamino)-1,3,5-triazin-2-yl]amino}methyl)cyclohexyl]methyl}-1-naphthalenesulfonamide, N1-[4-([4-(ethylamino)-6-(isopropylamino)-1,3,5-triazin-2-yl]aminomethyl)cyclohexyl]methyl-1-naphthalenesulfonamide)-6-(isopropylamino)-1,3,5-triazin-2-yl] amino}methyl)cyclohexyl]methyl}-1-naphthalenesulfenamideN1-{[4-({[4,6-Di(isopropylamino)-1,3,5-triazin-2-yl]amino}methyl) cyclohexyl]methyl}-1-naphthalenesulfonamide, N1-[4-([4-(isopropylamino)-6-(propylamino)-1,3,5-triazin-2-yl]aminomethyl)cyclohexyl3methyl-1-naphthalenesulfonamide, N1-[4-([4-(butylamino)-6-(isopropylamino)-1,3,5-triazin-2-yl]aminomethyl)cyclohexyl]methyl-1-naphthalenesulfonamide, N1-[4-([4-(cyclobutylamino)-6-(isopropylamino)-1,3,5-triazin-2-yl]aminomethyl)cyclohexyl]methyl-1-naphthalenesulfonamide, N1-[4-([4-(cyclopropylamino)-6-(isopropylamino)-1,3,5-triazin-2-yl]aminomethyl)cyclohexyl]methyl-1-naphthalenesulfonamide, N1-[4-([4-(isopropylamino)-6-(pentylamino)-1,3,5-triazin-2-yl]aminomethyl)cyclohexyl]methyl-1-naphthalenesulfonamide, N1-[4-([4-[(2-cyanoethyl)amino]-6-(isopropylamino)-1,3,5-triazin-2-yl]aminomethyl)cyclohexyl]methyl-1-naphthalenesulfonamide, N1-[4-([4-[(2-hydroxyethyl)amino]-6-(isopropylamino)-1,3,5-triazin-2-yl]aminomethyl)cyclohexyl]methyl-1-naphthalenesulfonamide, N1-(4-[(4-(isopropylamino)-6-((2-methoxyethyl)amino]-1,3,5-triazin-2-yl]amino)methyl]cyclohexylmethyl)-1-naphthalenesulfonamide, N1-(4-[(4-(isopropylamino)-6-[(3-methoxypropyl)amino]-1,3,5-triazin-2-ylamino)methyl]cyclohexylmethyl)-1-naphthalenesulfonamide, N1-{[4-({[4-}2-(dimethylamino)ethyl]amino}-6-(isopropylamino)-1,3,5-triazin-2-yl]amino}methyl)cyclohexyl]methyl}-1-naphthalenesulfonamide, N1-[4-([4-[3-(1H-1-imidazolyl)propyl]amino-6-(isopropylamino)-1,3,5-triazin-2-yl]aminomethyl)cyclohexyl]methyl-1-naphthalenesulfonamide, N1-({4-[({4-(isopropylamino)-6-1 (4-methoxyphenethyl)amino]-1,3,5-triazin-2-yl}amino)methyl]cyclohexyl}methyl)-1-naphthalenesulfonamide, N1-{[4-({[4-(dimethylamino)-6-(isopropylamino)-1,3,5-triazin-2-yl]amino}methyl)cyclohexyl]methyl}-1-naphthalenesulfonamide, N1-[4-([4-[ethyl(methyl)amino]-6-(isopropylamino)-1,3,5-triazin-2-yl]aminomethyl)cyclohexyl]methyl-1-naphthalenesulfonamide, N1-[4-([4-(diethylamino)-6-(isopropylamino)-1,3,5-triazin-2-yl]aminomethyl)cyclohexyl]methyl-1-naphthalenesulfonamide, N1-[4-([4-(isopropylamino)-6-tetrahydro-1H-1-pyrrolyl-1,3,5-triazin-2-yl]aminomethyl)cyclohexyl]methyl-1-naphthalenesulfonamide, N1-(4-[(4-(isopropylamino)-6-[(2S)-2-(methoxymethyl)tetrahydro-1H-1-pyrrolyl]-1,3,5-triazin-2-ylamino)methyl]cyclohexylmethyl)-1-naphthalenesulfonamide, N1-{[4-({[4-(isopropylamino)-6-piperidino-1,3,5-triazin-2-yl]amino}methyl)cyclohexyl]methyl}-1-naphthalenesulfonamide, N1-4-([4-(isopropylamino)-6-(2-methylpiperidino)-1,3,5-triazin-2-yl]aminomethyl)cyclohexyl]methyl-1-naphthalenesulfonamide, N1-[4-([4-(isopropylamino)-6-morpholino-1,3,5-triazin-2-yl]aminomethyl)cyclohexyl]methyl-1-naphthalenesulfonamide, N1-{[4-({[4-[(2R,6S)-2,6-dimethyl-1,4-oxazinan-4-yl]-6-(isopropylamino)-1,3,5-triazin-2-yl]amino}methyl)cyclohexyl]methyl}-1-naphthalenesulfonamide, N1-[4-([4-[(2-hydroxyethyl)(methyl)amino]-6-(isopropylamino)-1,3,5-triazin-2-yl]aminomethyl)cyclohexyl]methyl-1-naphthalenesulfonamide, N1-{[4-({[4-(4-acetylpiperazino)-6-(isopropylamino)-1,3,5-triazin-2-yl]amino}methyl)cyclohexyl]methyl}-1-naphthalenesulfonamide, N1-{[4-({[4-(isopropylamino)-6-(4-isopropylpiperazino)-1,3,5-triazin-2-yl]amino}methyl)cyclohexyl]methyl}-1-naphthalenesulfonamide, N1-[4-([4,6-di(ethylamino)-1,3,5-triazin-2-yl]aminomethyl)cyclohexyl]methyl-4-(tert-butyl)-1-benzenesulfonamide, N1-[4-([4,6-di(ethylamino)-1,3,5-triazin-2-yl]aminomethyl)cyclohexyl]methyl-4-fluoro-1-benzenesulfonamide, N1-[4-([4,6-di (ethylamino)-1,3,5-triazin-2-yl]aminomethyl)cyclohexyl]methyl-2-methoxy-5-methyl-1-benzenesulfonamide, N1-[4-([4,6-di(ethylamino)-1,3,5-triazin-2-yl]aminomethyl)cyclohexyl]methyl-2-fluoro-1-benzenesulfonamide, N1-[4-([4,6-di(ethylamino)-1,3,5-triazin-2-yl]aminomethyl)cyclohexyl]methyl-2-methyl-1-benzenesulfonamide, N3-[4-([4,6-di(ethylamino)-1,3,5-triazin-2-yl]aminomethyl)cyclohexyl]methyl-3-pyridinesulfonamide, N1-[4-([4,6-di(ethylamino)-1,3,5-triazin-2-yl]aminomethyl)cyclohexyl]methyl-4-methoxy-1-benzenesulfonamide, N5-[4-([4,6-di(ethylamino)-1,3,5-triazin-2-yl]aminomethyl)cyclohexyl]methyl-2,4-dimethyl-1,3-oxazole-5-sulfonamide, N2-[4-([4,6-di(ethylamino)-1,3,5-triazin-2-yl]aminomethyl)cyclohexyl]methyl-2-thiophenesulfonamide, N4-[4-([4,6-di(ethylamino)-1,3,5-triazin-2-yl]aminomethyl)cyclohexyl]methyl-1-methyl-1H-4-imidazolesulfonamide, N1-4-([4,6-di(ethylamino)-1,3,5-triazin-2-yl]aminomethyl)cyclohexyl]methyl-4-methyl-1-benzenesulfonamide, N5-[4-([4,6-di(ethylamino)-1,3,5-triazin-2-yl]aminomethyl)cyclohexyl]methyl-2,1,3-benzothiadiazole-5-sulfonamide, N8-[4-([4,6-di(ethylamino)-1,3,5-triazin-2-yl]aminomethyl)cyclohexyl]methyl-8-quinolinesulfonamide-yl]aminomethyl)cyclohexyl]methylmethanesulfonamide N1-[4-([4-(isopropylamino)-6-tetrahydro-1H-1-pyrrolyl-1,3,5-triazin-2-yl]aminomethyl)cyclohexyl]methyl-1-pyrrolidinesulfonamide, N4-[4-([4-(isopropylamino)-6-morpholino-1,3,5-triazin-2-yl]aminomethyl)cyclohexyl]methyl-4-morpholinesulfonamide, N1-[4-([4-(isopropylamino)-6-piperidino-1,3,5-triazin-2-yl]aminomethyl)cyclohexyl]methyl-1-piperidinesulfonamide, N1-[(4-[(4,6-ditetrahydro-1H-1-pyrrolyl-1,3,5-triazin-2-yl)amino]methylcyclohexyl)methyl]-4-(tert-butyl)-1-benzenesulfonamide, N-cyclopropyl-N'-[4-([4-(cyclopropylamino)-6-(isopropylamino)-1,3,5-triazin-2-yl]aminomethyl)cyclohexyl]methylsulfamide, N'-[4-([4-(cyclopropylamino)-6-(isopropylamino)-1,3,5-triazin-2-yl]aminomethyl)cyclohexyl]methyl-N,N-dimethylsulfamide, N1-{[4-({[4-chloro-6-(isopropylamino)-1,3,5-triazin-2-yl]amino}methyl)cyclohexyl]methyl}-1-naphthalenesulfonamide, N'-[(4-[(4,6-dimorpholino-1,3,5-triazin-2-yl)amino]methylcyclohexyl)methyl]-N,N-dimethylsulfamide, N1-[4-([4-chloro-6-(isopropylamino)-1,3,5-triazin-2-yl]aminomethyl)cyclohex yl]methyl-4-(tert-butyl)-1-benzenesulfonamide, N1-[4-([4-(cyclopropylamino)-6-tetrahydro-1H-1-pyrrolyl-1,3,5-triazin-2-yl]aminomethyl)cyclohexyl]methyl-4-fluoro-1-benzenesulfonamide, N'-((4-(((4,6-dichloro-1,3,5-triazin-2-yl)amino)methyl)cyclohexyl)methyl)-N,N-dimethylsulfamide, N1-[(4-[(4,6-ditetrahydro-1H-1-pyrrolyl-1,3,5-triazin-2-yl)amino]methylcyclohexyl)methyl]-2-methoxy-5-methyl-1-benzenesulfonamide, N1-[4-([4-(cyclopropylamino)-6-(2-pyridyl)-1,3,5-triazin-2-l]aminomethyl)cyclohexyl]methyl-4-fluoro-1-benzenesulfonamide, N1-[4-(aminomethyl)cyclohexyl]methyl-4-fluoro-1-benzenesulfonamide, N1-[4-(aminomethyl)cyclohexyl]methyl-4-fluoro-1-benzenesulfonamide, N2, N4-diethyl-N6-[5-(1H-1-pyrazolyl)pentyl]-1,3,5-triazine-2,4,6-triamine N2, N4-diethyl-N6-[3-(1H-1-imidazolyl)propyl]-1,3,5-triazine-2,4,6-triamine N2, N4-diethyl-N6-(2-pyridylmethyl)-1,3,5-triazine-2,4,6-triamine Ref: U.S. Pat. No. 6,340,683

Tricyclic compound Y receptor antagonists, such as:

trans-N2-(4-Dimethylaminosulfonylaminomethyl)cyclohexyl-9-fluoro-5,6-dihydro-4H-benzo[6,7]cyclohepta[d][1,3]thiazol-2-amine;

1-Aza-9-fluoro-4,5-dihydro-2-{5-(dimethylaminosulfonylamino)pentyl}amino-3-thia-benzo[e]azulene;

1-Aza-9-fluoro-2-(5-(2-fluorophenyl)sulfonylamino)pentylamino-4,5-dihydro-3-thia-benzo[e]azulene;

1-Aza-9-fluoro-4,5-dihydro-2-(5-(1-naphthyl)sulfonylamino)-pentylamino-3-thia-benzo[e]azulene;

1-Aza-9-fluoro-4,5-dihydro-2-(4-(methanesulfonylamino)-butyl)amino-3-thia-benzo[e]azulene;

1-Aza-9-fluoro-4,5-dihydro-2-(4-(dimethylaminosulfonyl-amino)butyl)amino-3-thia-benzo[e]azulene;
1-Aza-9-fluoro-2-(4-(2-fluorophenyl)sulfonylamino)buty-lamino-4,5-dihydro-3-thia-benzo[e]azulene-3-thia-benzo[e]azulene;
1-Aza-9-fluoro-4,5-dihydro-2-(4-((2(S)-methoxymethyl)-pyrrolidine-1-yl)sulfonyl)phenylamino-3-thia-benzo[e]azulene;
1-Aza-9-fluoro-4,5-dihydro-2-(5-(methylsulfonylamino)-pentyl)amino-3-thia-benzo[e]azulene;
trans-1-Aza-9-fluoro-4,5-dihydro-2-(4-(methylsulfony-lamino-methyl)cyclohexyl)amino-3-thia-benzo[e]azu-lene;
1-Aza-9-fluoro-4,5-dihydro-2-(5-(2,4-difluorophenyl)sulfo-nylamino)pentylamino-3-thia-benzo[e]azulene;
1-Aza-9-fluoro-4,5-dihydro-2-(5-isopropylsulfonylamino)-pentylamino-3-thia-benzo[e]azulene;
1-Aza-9-fluoro-4,5-dihydro-2-(5-(diethylaminosulfonyl-amino)pentyl)amino-3-thia-benzo[e]azulene;
1-Aza-9-fluoro-4,5-dihydro-2-(5-(2-methoxy-5-methylphe-nyl)sulfonylamino)pentylamino-3-thia-benzo[e]azulene;
1-Aza-2-(5-benzylsulfonylamino)pentylamino-9-fluoro-4,5-dihydro-3-thia-benzo[e]azulene;
1-Aza-2-(5-(3,4-difluorophenyl)sulfonylamino)penty-lamino-9-fluoro-4,5-dihydro-3-thia-benzo[e]azulene;
1-Aza-9-fluoro-4,5-dihydro-2-(5-(4-methoxyphenyl)sulfo-nylamino)pentylamino-3-thia-benzo[e]azulene;
1-Aza-9-fluoro-4,5-dihydro-2-(5-(2-thienyl)sulfony-lamino)-pentylamino-3-thia-benzo[e]azulene;
1-Aza-9-fluoro-2-(5-(2-trifluoroethyl)sulfonylamino)penty-lamino-4,5-dihydro-3-thia-benzo[e]azulene;
1-Aza-9-fluoro-2-(5-ethylsulfonylamino)pentylamino-4,5-dihydro-3-thia-benzo[e]azulene;
1-Aza-2-(4-diethylaminosulfonylamino)butylamino-9-fluoro-4,5-dihydro-3-thia-benzo[e]azulene;
1-Aza-9-fluoro-4,5-dihydro-2-(5-(1-methylimidazol-4-yl)sulfonylamino)pentylamino-3-thia-benzo[e]azulene;
1-Aza-9-fluoro-4,5-dihydro-2-(5-(3,5-dimethylisoxazol-4-yl)sulfonylamino)pentylamino-3-thia-benzo[e]azulene;
1-Aza-9-fluoro-4,5-dihydro-2-(5-aminosulfonylamino)pen-tylamino-3-thia-benzo[e]azulene;
trans-1-aza-9-fluoro-2-(4-(2-fluorophenyl)sulfonylamino-methyl)cyclohexylamino-4,5-dihydro-3-thia-benzo[e]azulene;
trans-1-Aza-9-fluoro-4,5-dihydro-2-{4-(4-methoxyphenyl)-sulfonylaminomethyl}cyclohexylamino-3-thia-benzo[e]azulene;
trans-N2-(4-(2,6-Difluorophenylsulfonyl)aminomethyl)cy-clohexyl-9-fluoro-5,6-dihydro-4H-benzo[6,7]cyclohepta-[d][1,3]-thiazol-2-amine;
trans-1-Aza-2-{4-benzylsulfonylaminomethyl}cyclohexylamino-9-fluoro-4,5-dihydro-3-thia-benzo[e]azulene;
trans-N2-(4-(2-Thienylsulfonyl)aminomethyl)cyclohexyl-9-fluoro-5,6-dihydro-4H-benzo[6,7]cyclohepta[d][1,3]thia-zol-2-amine;
trans-N2-(4-Ethylsulfonylaminomethyl)cyclohexyl-9-fluoro-5,6-dihydro-4H-benzo[6,7]cyclohepta[d][1,3]thia-zol-2-amine;
trans-1-Aza-9-fluoro-4,5-dihydro-2-{4-(1-methylimida-zolyl-4-yl)sulfonylaminomethyl}cyclohexylamino-3-thia-benzo[e]azulene;
trans-1-Aza-9-fluoro-4,5-dihydro-2-{4-(3,5-dimethylisox-azol-4-yl)sulfonylaminomethyl}cyclohexylamino-3-thia-benzo[e]azulene)-cyclohexylamino-3-thia-benzo[e]azu-lene;

trans-1-Aza-9-fluoro-4,5-dihydro-2-(4-diethylaminosulfo-nylamino)-cyclohexylamino-3-thia-benzo[e]azulene;
trans-1-Aza-9-fluoro-4,5-dihydro-2-(4-(4-methoxyphenyl)sulfonylamino)-cyclohexylamino-3-thia-benzo[e]azu-lene;
trans-1-Aza-9-fluoro-4,5-dihydro-2-(4-(2-thienyl)sulfonyl-amino)-cyclohexylamino-3-thia-benzo[e]azulene;
trans-1-Aza-9-fluoro-4,5-dihydro-2-(4-(2,2,2-trifluoro-ethyl)sulfonylamino)-cyclohexylamino-3-thia-benzo[e]azulene;
1-Aza-9-fluoro-4,5-dihydro-2-(4-(2,2,2-trifluoroethyl)-sul-fonylamino)butylamino-3-thia-benzo[e]azulene;
trans-1-Aza-9-fluoro-2-{4-(3,4-difluorophenyl)sulfonyl-aminomethy}cyclohexylamino-4,5-dihydro-3-thia-benzo[e]azulene;
trans-1-Aza-9-fluoro-2-{4-trifluoromethylsulfonylaminomethyl}cyclohexylamino-4,5-dihydro-3-thiabenzo[e]-azulene;
trans-1-Aza-9-fluoro-2-{4-(2-fluoro)phenylsulfony-lamino}-cyclohexylmethylamino-4,5-dihydro-3-thia-benzo[e]azulene;
trans-N2-(4-Methylsulfonylamino)cyclohexylmethyl-9-fluoro-5,6-dihydro-4H-benzo[6,7]cyclohepta[d][1,3]thia-zol-2-amine: A mixture of trans-N2-(4-amino)cyclohexy-lmethyl-9-fluoro-5,6-dihydro-4H-benzo[6,7]cyclo hepta[d][1,3]thiazol-2-aminedihydrochloride;
trans-N2-(4-Aminosulfonylamino)cyclohexylmethyl-9-fluoro-5,6-dihydro-4H-benzo[6,7]cyclohepta[d][1,3]thia-zol-2-amine;
trans-N2-(4-Amino)cyclohexylmethyl-9-fluoro-5,6-dihy-dro-4H-benzo[6,7]cyclohepta[d][1,3]thiazol-2-amine;
trans-N2-(4-Aminosulfonylamino)cyclohexylmethyl-9-fluoro-5,6-dihydro-4H-benzo[6,7]cyclohepta[d][1,3]thia-zol-2-amine;
9-Fluoro-5,6-dihydro-4H-benzo[6,7]cyclohepta[d][1,3]thia-zol-2-amine: 6-Bromo-3-fluoro-6,7,8,9-tetrahydro-5H-benzo[a]cyclohepten-5-one;
N1-(9-Fluoro-5,6-dihydro-4H-benzo[6,7]cyclohepta[d][1,3]thiazol-2-yl)-5-bromopentanamide;
1-5-[(9-Fluoro-5,6-dihydro-4H-benzo[6,7]cyclohepta[d][1,3]-thiazol-2-yl)amino]-5-oxopentyl-1,2-triazadien-2-ium;
N1-(9-fluoro-5,6-dihydro-4H-benzo[6,7]cyclohepta[d][1,3]thiazol-2-yl)-5-aminopentanamide;
N1-(9-fluoro-5,6-dihydro-4H-benzo[6,7]cyclohepta[d][1,3]thiazol-2-yl)-5-[(methylsulfonyl)amino]pentanamide;
trans-N2-(4-Aminosulfonylaminomethyl)cyclohexyl-4,5-dihydro-benzo[2,3]oxepino[4,5-d][1,3]thiazol-2-amine;
trans-N2-(4-Methylsulfonylaminomethyl)cyclohexyl-4,5-dihydro-benzo[2,3]oxepino[4,5-d][1,3]thiazol-2-amine;
trans-1-Aza-4,5-dihydro-2-{4-(2-methoxy-5-methyl)phe-nyl-sulfonylaminomethyl}cyclohexylamino-6-oxa-3-thia-benzo[e]azulene;
N1-(9-Fluoro-5,6-dihydro-4H-benzo[6,7]cyclohepta[d][1,3]-thiazol-2-yl)-5-[(2-methoxy-5-methylphenyl)sulfo-nyl]-aminopentanamide;
N1-(9-fluoro-5,6-dihydro-4H-benzo[6,7]cyclohepta[d][1,3]-thiazol-2-yl)-5-aminopentanamide;
trans-N2-(4-Methylsulfonylamino)cyclohexylmethyl-4,5-dihydro-benzo[2,3]oxepino[4,5-d][1,3]thiazol-2-amine;
trans-1-Aza-4,5-dihydro-2-{4-(2-methoxy-5-methylphe-nyl)-sulfonylamino}cyclohexylmethylamino-6-oxa-3-thia-benzo[e]azulene;
trans-N2-(4-Ethylsulfonylamino)cyclohexylmethyl-9-fluoro-5,6-dihydro-4H-benzo[6,7]cyclohepta[d][1,3]thia-zol-2-amine;

trans-1-Aza-9-fluoro-4,5-dihydro-2-{4-isopropylsulfonylamino}cyclohexylmethylamino-3-thia-benzo[e]azulene;

trans-1-Aza-9-fluoro-4,5-dihydro-2-(4-(3-pyridylsulfonylamino)cyclohexyl)amino-3-thia-benzo[e]azulene;

1-Aza-9-fluoro-4,5-dihydro-2-(5-(3-pyridyl)sulfonylamino)pentylamino-3-thia-benzo[e]azulene;

1-Aza-9-fluoro-4,5-dihydro-2-(4-(3-pyridyl)sulfonylamino)butylamino-3-thia-benzo[e]azulene;

1-Aza-9-fluoro-4,5-dihydro-2-{2-(2-methylsulfonylamino)ethoxy}ethylamino-3-thia-benzo[e]azulene;

1-Aza-9-fluoro-4,5-dihydro-2-{2-[2-(2-methoxy-5-methylphenyl)sulfonylamino]ethoxy}ethylamino-3-thia-benzo[e]azulene;

trans-1-Aza-9-fluoro-4,5-dihydro-2-(4-(3-pyridyl)sulfonylaminomethyl)cyclohexylamino-3-thia-benzo[e]azulene;

trans-N2-(4-Ethylsulfonylamino)cyclohexylmethyl-8-methoxy-4,5-dihydro-benzo[2,3]oxepino[4,5-d][1,3]thiazol-2-amine;

trans-1-Aza-4,5-dihydro-8-methoxy-2-{4-methylsulfonylamino)cyclohexylmethylamino-6-oxa-3-thia-benzo[e]azulene;

trans-1-Aza-9-fluoro-4,5-dihydro-2-{4-(3-pyridyl)sulfonylamino}cyclohexylmethylamino-3-thia-benzo[e]azulene;

trans-1-Aza-4,5-dihydro-9-methoxy-2-{4-methylsulfonylamino}cyclohexylmethylamino-6-oxa-3-thia-benzo[e]azulene;

trans-N2-(4-Ethylsulfonylamino)cyclohexylmethyl-9-methoxy-4,5-dihydro-benzo[2,3]oxepino[4,5-d][1,3]thiazol-2-amine;

trans-N2-(4-Methylsulfonylamino)cyclohexylmethyl-7-methoxy-4,5-dihydro-benzo[2,3]oxepino[4,5-d][1,3]thiazol-2-amine hydrochloride;

trans-1-Aza-4,5-dihydro-7-methoxy-2-{4-dimethylaminosulfonylamino}cyclohexylmethylamino-6-oxa-3-thia-benzo[e]azulene;

trans-N2-(4-Dimethylphosphonylamino)cyclohexylmethyl-9-fluoro-5,6-dihydro-4H-benzo[6,7]cyclohepta[d][1,3]thiazol-2-amine;

trans-N2-(4-Ethoxycarbonylamino)cyclohexylmethyl-9-fluoro-5,6-dihydro-4H-benzo[6,7]cyclohepta[d][1,3]thiazol-2-amine hydrochloride;

1-Aza-9-fluoro-4,5-dihydro-2-(2-(2-isopropylsulfonylamino)-ethoxy)ethylamino-3-thia-benzo[e]-azulene;

2-(4-Methylsulfonylaminomethyl)cyclohexylamino-4H-chromeno[4,3-d]thiazole;

trans-1-Aza-4,5-dihydro-8-methoxy-2-(4-methylsulfonylamino)cyclohexylmethylamino-3-thia-benzo[e]-azulene;

trans-1-Aza-4,5-dihydro-8-methoxy-2-(4-methylsulfonylamino-methyl)cyclohexylamino-3-thia-benzo[e]-azulene;

trans-1-Aza-4,5-dihydro-2-(4-isopropylsulfonylaminomethyl)-cyclohexylamino-8-methoxy-3-thia-benzo[e]-azulene;

trans-1-Aza-4,5-dihydro-2-(4-methylsulfonylaminomethyl)-cyclohexylamino-7-methoxy-3-thia-benzo[e]-azulene;

trans-1-Aza-4,5-dihydro-2-(4-ethylcarbonylaminomethyl)-cyclohexylamino-9-fluoro-3-thia-benzo[e]azulen;

trans-1-Aza-9-fluoro-4,5-dihydro-2-(4-(4-morpholinyl)-sulfonylaminomethyl)cyclohexylamino-3-thia-benzo[e]azulene;

trans-1-Aza-9-fluoro-4,5-dihydro-2-(4-(2-methoxy)ethoxycarbonylaminomethyl)cyclohexylamino-3-thia-benzo[e]azulene 2-methoxyethyl N-(t4-[(9-fluoro-5,6-dihydro-4H-benzo[6,7]-cyclohepta[d][1,3]thiazol-2-yl)amino]cyclohexyl}methyl)-carbamate;

tert-butyl N-[(4-{[(benzoylamino)carbothioyl]amino}cyclohexyl)methyl]carbamate;

tert-butyl-N-({4-[(aminocarbothioyl)amino]cyclohexyl}-methyl)carbamate; 6-Bromo-3-fluoro-6,7,8,9-tetrahydro-5H-benzo[a]cyclohepten-5-one;

tert-Butyl-N-({4-[(9-fluoro-5,6-dihydro-4H-benzo[6,7]-cyclohepta-[d][1,3]thiazol-2-yl)amino]cyclohexyl}methyl)-carbamate;

trans-N2-[4-(Aminomethyl)cyclohexyl]-9-fluoro-5,6-dihydro-4H-benzo[6,7]cyclohepta[d][1,3]thiazol-2-amine;

trans-1-Aza-9-fluoro-4,5-dihydro-2-(4-(2-methoxy)ethoxycarbonylaminomethyl)cyclohexylamino-3-thia-benzo[e]azulene 2-methoxyethyl N-({4-[(9-fluoro-5,6-dihydro-4H-benzo[6,7]cyclohepta[d][1,3]thiazol-2-yl)amino]cyclohexyl}-methyl)carbamate;

trans-N2-(4-(1-Morpholinylsulfonylaminomethyl)cyclohexyl-8-methoxy-5,6-dihydro-4H-benzo[6,7]cyclohepta[d][1,3]thiazol-2-amine hydrochloride;

3-({4-[(9-fluoro-5,6-dihydro-4H-benzo[6,7]cyclohepta[d][1,3]thiazol-2-yl)amino]cyclohexyl}methyl)-1,3-oxazolan-2-one;

2-chloroethyl-N-({4-[(9-fluoro-5,6-dihydro-4H-benzo[6,7]-cyclohepta[d][1,3]thiazol-2-yl)amino]cyclohexyl}methyl)-carbamate;

3-({4-[(9-Fluoro-5,6-dihydro-4H-benzo[6,7]cyclohepta[d][1,3]thiazol-2-yl)amino]cyclohexyl}methyl)-1,3-oxazolan-2-one;

N1-({4-[(9-fluoro-5,6-dihydro-4H-benzo[6,7]cyclohepta-[d][1,3]thiazol-2-yl)amino]cyclohexyl}methyl)-2-methoxyacetamide;

N1-({4-[(9-fluoro-5,6-dihydro-4H-benzo[6,7]-cyclohepta-[d][1,3]thiazol-2-yl)amino]cyclohexyl}methyl)acetamide;

trans-1-Aza-9-fluoro-4,5-dihydro-2-(4-(N-propylformamido)-methyl)cyclohexylamino-3-thia-benzo[e]azulene;

trans-1-Aza-9-fluoro-4,5-dihydro-2-(4-(N-isopropylformamido)methyl)cyclohex ylamino-3-thia-benzo[e]azulene;

N1-{4-[(4,5-dihydrobenzo[2,3]oxepino[4,5-d][1,3]thiazol-2-ylamino)methyl]cyclohexyl}-2-methoxyacetamide;

Benzyl-N-(4-{[(aminocarbothioyl)amino]methyl}cyclohexyl)-carbamate;

Benzyl-N-{4-[(4,5-dihydrobenzo[2,3]oxepino[4,5-d][1,3]-thiazol-2-ylamino)methyl]cyclohexyl}carbamate;

N2-[(4-aminocyclohexyl)methyl]-4,5-dihydrobenzo[2,3]oxepino[4,5-d][1,3]thiazol-2-amine N-{[4-(4,5-Dihydrobenzo[2,3]oxepino[4,5-d][1,3]thiazol-2-ylamino)cyclohexyl]methyl}-N-propylformamide;

N1-{[4-(4,5-Dihydrobenzo[2,3]oxepino[4,5-d][1,3]thiazol-2-ylamino)cyclohexyl]methyl}propanamide;

N2-{4-[(Propylamino)methyl]cyclohexyl}-4,5-dihydrobenzo-[2,3]oxepino[4,5-d][1,3]thiazol-2-amine;

N-{[4-(4,5-dihydrobenzo[2,3]oxepino[4,5-d][1,3]thiazol-2-ylamino)cyclohexyl]methyl}-N-propylformamide;

N-{4-[(4,5-dihydrobenzo[2,3]oxepino[4,5-d][1,3]thiazol-2-ylamino)methyl]cyclohexyl}-N-(2-methoxyethyl)formamide;

N2-({4-[(2-methoxyethyl)amino]cyclohexyl}methyl)-4,5-dihydrobenzo[2,3]oxepino[4,5-d][1,3]thiazol-2-amine;

N-{4-[(4,5-dihydrobenzo[2,3]oxepino[4,5-d][1,3]thiazol-2-ylamino)methyl]cyclohexyl}-N-(2-methoxyethyl)formamide;

trans-1-Aza-2-(4-(n-(ethyl)formamido)cyclohexyl)methylamino-4,5-dihydro-6-oxa-3-thia-benzo[e]azulene;

trans-2-(4-Acetamido)cyclohexylmethylamino-1-aza-4,5-dihydro-6-oxa-3-thia-benzo[e]azulene;

Benzyl-N-[4-({[(benzoylamino)carbothioyl]amino}methyl)-cyclohexyl]carbamate;
Benzyl-N-(4-{[(aminocarbothioyl)amino]methyl}cyclohexyl)-carbamate;
Benzyl-N-{4-[(4,5-dihydrobenzo[2,3]oxepino[4,5-d][1,3]-thiazol-2-ylamino)methyl]cyclohexyl}carbamate;
N2-[(4-aminocyclohexyl)methyl]-4,5-dihydrobenzo[2,3]-oxepino[4,5-d][1,3]thiazol-2-amine
N1-{4-[(4,5-dihydrobenzo[2,3]oxepino[4,5-d][1,3]-thiazol-2-ylamino)methyl]cyclohexyl}acetamide;
N2-{[4-(Ethylamino)cyclohexyl]methyl}-4,5-dihydrobenzo-[2,3]oxepino[4,5-d][1,3]thiazol-2-amine;
N-{4-[(4,5-Dihydrobenzo[2,3]oxepino[4,5-d][1,3]thiazol-2-ylamino)methyl]cyclohexyl}-N-ethylformamide; N-(4-[(4,5-Dihydrobenzo[2,3]oxepino[4,5-d][1,3]thiazol-2-ylamino)methyl]cyclohexyl}-N-propylformamide;
N2-{[4-(propylamino)cyclohexyl]methyl}-4,5-dihydrobenzo-[2,3]oxepino[4,5-d][1,3]thiazol-2-amine;
N-{4-[(4,5-Dihydrobenzo[2,3]oxepino[4,5-d][1,3]thiazol-2-ylamino)methyl]cyclohexyl}-N-propylformamide;
N1-{4-[(9-fluoro-5,6-dihydro-4H-benzo[6,7]cyclohepta[d][1,3]thiazol-2-yl)amino]benzyl}-2-methoxyacetamide;
N-{4-[(9-Fluoro-5,6-dihydro-4H-benzo[6,7]cyclohepta[d][1,3]thiazol-2-yl)amino]benzyl}methanesulfonamide;
N2-[4-(Aminomethyl)phenyl]-9-fluoro-5,6-dihydro-4H-benzo[6,7]cyclohepta[d][1,3]thiazol-2-amine
Ref: U.S. Pat. No. 6,225,330
Bicyclic compound Y receptor antagonists, such as:
2-(5-Diethylaminosulfonylamino)pentylamino-4-(2-pyridyl)-thiazole hydrogen chloride
4-(2-Pyridyl)-2-(5-(2-thienyl)sulfonylaminopentyl)-aminothiazole hydrogen chloride
2-(5-(2-Fluorophenyl)sulfonylamino)pentylamino-4-(2-pyridyl)-thiazole hydrogen chloride
2-(5-(4-Methoxyphenyl)sulfonylamino)pentylamino-4-(2-pyridyl)thiazole hydrogen chloride
2-(5-(3,5-Dimethylisoxazol-4-yl)sulfonylamino)pentylamino-4-(2-pyridyl)thiazole hydrogen chloride
2-(5-(3,4-Difluorophenyl)sulfonylamino)pentylamino-4-(2-pyridyl)thiazole hydrogen chloride
2-(5-(2-Methoxy-5-methylphenyl)sulfonylamino)pentylamino-4-(2-pyridyl)thiazole hydrogen chloride
2-(5-(Benzylsulfonylamino)pentylamino-4-(2-pyridyl)thiazole hydrogen chloride
2-(5-(Ethylsulfonylamino)pentyl)amino-4-(2-pyridyl)thiazole hydrogen chloride
2-(5-(Trifluoromethylsulfonylamino)pentyl)amino-4-(2-pyridyl)thiazole hydrogen chloride
2-(5-(Aminosulfonylamino)pentyl)amino-4-(2-pyridyl)thiazole hydrogen chloride
2-(5-(2-Fluorophenyl)sulfonylamino)pentylamino-4-(3-pyridyl)thiazole hydrogen chloride
2-(5-(3,5-Dimethylisoxazol-4-yl)sulfonylamino)pentylamino-4-(3-pyridyl)thiazole hydrogen chloride
2-(5-(2-Methoxy-5-methyl)phenylsulfonylamino)pentylamino-4-(3-pyridyl)thiazole hydrogen chloride
2-(5-(2-Fluoro)phenylsulfonylamino)pentylamino-4-(4-pyridyl)thiazole hydrogen chloride
2-(5-(3,5-Dimethylisoxazol-4-yl)sulfonylamino)pentylamino-4-(4-pyridyl)thiazole hydrogen chloride 2-(5-(2-Methoxy-5-methyl)phenylsulfonylamino)pentylamino-4-(4-pyridyl)thiazole hydrogen chloride N1-{5-[(4-Benzo[b]thiophen-2-yl-1,3-thiazol-2-yl)amino]-pentyl}-2-methoxy-5-methyl-1-benzenesulfonamide
N1-(5-{[4-(5-Chloro-3-methylbenzo[b]thiophen-2-yl)-1,3-thiazol-2-yl]amino}pentyl)-2-methoxy-5-methyl-1-benzene-sulfonamide
N1-(4-{[4-(5-Phenyl-3-isoxazolyl)-1,3-thiazol-2-yl)amino}-pentyl)-2-methoxy-5-methyl-1-benzenesulfonamide
N1-(5-{[4-(3-Thienyl)-1,3-thiazol-2-yl]amino}pentyl)-2-methoxy-5-methyl-1-benzenesulfonamide
N1-[5-({4-[1-(Phenylsulfonyl)-1H-3-pyrrolyl]-1,3-thiazol-2-yl}amino)pentyl]-2-methoxy-5-methyl-1-benzene-sulfonamide trans-N8-[(4-{[4-(3-Phenyl-5-isoxazolyl)-1,3-thiazol-2-yl]amino}cyclohexyl)methyl]-8-quinolinesulfonamide
N,N-Dimethyl-N'-(5-{[4-(3-Thienyl)-1,3-thiazol-2-yl]amino}pentyl)sulfamide
trans-2-(4-(2-Methoxy-5-methylphenyl)sulfonylamino)cyclohexylmethylamino-4-(2-pyridyl)thiazole dihydrogen chloride
trans-2-(4-(2-Fluorophenyl)sulfonylamino)cyclohexylmethyl-amino-4-(2-pyridyl)thiazole dihydrogen chloride
trans-2-(4-(3,5-Dimethyl-4-isoxazolyl)sulfonylamino)cyclohexylmethylamino-4-(2-pyridyl)thiazole dihydrogen chloride
trans-2-(4-(2-Fluorophenyl)sulfonylamino)cyclohexylmethyl-amino-4-(3-pyridyl)thiazole dihydrogen chloride
trans-2-(4-(2-Methoxy-5-methylphenyl)sulfonylamino)cyclohexylmethylamino-4-(4-pyridyl)thiazole dihydrogen chloride
N1-(5-[4-(1,3-thiazol-2-yl)-1,3-thiazol-2-yl]aminopentyl)-2-methoxy-5-methyl-1-benzenesulfonamide
trans-N1-[(4-[4-(2,5-Dimethyl-1,3-thiazol-4-yl)-1,3-thiazol-2-yl]aminocyclohexyl)methyl]-2-methoxy-5-methyl-1-benzenesulfonamide
trans-N,N-dimethyl-N'-[(4-[4-(-1,3-thiazol-2-yl)-1,3-thiazol-2-yl]aminocyclohexyl)methyl]sulfamide
N,N-Dimethyl-N'-(5-{[4-(2-thienyl)-1,3-thiazol-2-yl]amino}-pentyl)sulfamide
N1-(5-{[4-(2-Thienyl)-1,3-thiazol-2-yl]amino}pentyl)-2-methoxy-5-methyl-1-benzenesulfonamide
N1-(5-[4-(2,5-Dimethyl-1,3-thiazol-4-yl)-1,3-thiazol-2-yl]aminopentyl)-2-methoxy-5-methyl-1-benzenesulfonamide
N1-(5-[4-(2,5-Dimethyl-1,3-thiazol-4-yl)-1,3-thiazol-2-yl]aminopentyl)-4-fluoro-1-benzenesulfonamide
N1-(5-[4-(1,3-Thiazol-2-yl)-1,3-thiazol-2-yl]aminopentyl)-4-fluoro-1-benzenesulfonamide
N'-(5-[4-(2,5-Dimethyl-1,3-thiazol-4-yl)-1,3-thiazol-2-yl]aminopentyl)-N,N-dimethylsulfamide
trans-N1-[(4-[4-(2,5-dimethyl-1,3-thiazol-4-yl])-1,3-thiazol-2-yl]aminocyclohexyl)methyl]-4-fluoro-1-benzene-sulfonamide
trans-N'-[(4-[4-(2,5-dimethyl-1,3-thiazol-4-yl)-1,3-thiazol-2-yl]aminocyclohexyl)methyl]-N,N-dimethylsulfamide
trans-N'-[4-([5-(2,5-Dimethyl-1,3-thiazol-4-yl)-1,3-thiazol-2-yl]aminomethyl)cyclohexyl]methyl-N,N-dimethyl-sulfamide
trans-N4-[4-([4-(2,5-Dimethyl-1,3-thiazol-4-yl)-1,3-thiazol-2-yl]aminomethyl)cyclohexyl]methyl-4-morpholine-sulfonamide
trans-N-[4-([4-(2,5-Dimethyl-1,3-thiazol-4-yl)-1,3-thiazol-2-yl]aminomethyl)cyclohexyl]-N-(2-methoxyethyl)formamide
trans-N-[4-([4-(2,5-Dimethyl-1,3-thiazol-4-yl)-1,3-thiazol-2-yl]aminomethyl)cyclohexyl]-N-isopropylformamide
Ref: U.S. Pat. No. 6,218,408
N-aralkylaminotetralin Y receptor antagonist, such as:
rac-cis-1-(Phenylmethyl)-6-methoxy-N-(2-(3,4-dimethoxyphenyl)ethyl)-1,2,3,4-tetrahydro-2-naphthalenamine;

rac-cis-1-(Phenylmethyl)-6-methoxy-N-(2-(3-indolyl) ethyl)-1,2,3,4-tetrahydro-2-naphthalenamine hemifumarate;
rac-cis-1-(Phenylmethyl)-N-(4-fluorophenylmethyl)-1,2,3,4-tetrahydro-2-naphthalenamine monohydrobromide;
rac-cis-1-(Phenylmethyl)-N-(2-methoxyphenylmethyl)-1,2,3,4-tetrahydro-2-naphthalenamine;
rac-cis-1-(Phenylmethyl)-N-(2-methoxyphenylmethyl)-1,2,3,4-tetrahydro-2-naphthalenamine monohydrobromide;
rac-cis-1-(4-Fluorophenylmethyl)-N-(2-methoxyphenylmethyl)-1,2,3,4-tetrahydro-2-naphthalenamine monohydrobromide;
rac-trans-1-(4-Fluorophenylmethyl)-N-(2-methoxyphenylmethyl)-1,2,3,4-tetrahydro-2-naphthalenamine monooxalate;
rac-cis-1-(Phenylmethyl)-N-(4-fluorophenylmethyl)-1,2,3,4-tetrahydro-2-naphthalenamine monohydrobromide;
rac-cis-1-(Phenylmethyl)-7-methoxy-N-(2-methoxyphenylmethyl)-1,2,3,4-tetrahydro-2-naphthalenamine monohydrobromide;
rac-trans-1-(4-Fluorophenylmethyl)-N-(2-(3-indolyl)ethyl)-1,2,3,4-tetrahydro-2-naphthalenamine monooxalate;
rac-cis-1-(Phenylmethyl)-N-(2-methoxyphenyl-2-oxomethyl)-1,2,3,4-tetrahydro-2-naphthalenamine monohydrobromide;
rac-cis-1-(Phenylmethyl)-7-methoxy-N-(2-(3-indolyl) ethyl)-1,2,3,4-tetrahydro-2-naphthalenamine 0.8 fumarate 0.8 methanol 0.2 hydrate;
rac-trans-1-(Phenylmethyl)-7-methoxy-N-(2(3-indolyl) ethyl)-1,2,3,4-tetrahydro-2-naphthalenamine monooxalate;
rac-cis-1-(2-Naphthylmethyl)-N-(2-(3-indolyl)ethyl)-1,2,3,4-tetrahydro-2-naphthalenamine hemifumarate methanol;
rac-trans-1-(2-Naphthylmethyl)-N-(2-(3-indolyl)ethyl)-1,2,3,4-tetrahydro-2-naphthalenamine monooxalate;
rac-cis-1-(2-Naphthylmethyl)-N-(2-methoxyphenylmethyl)-1,2,3,4-tetrahydro-2-naphthalenamine monohydrobromide;
rac-cis-1-(Phenylmethyl)-N-(2-methoxyphenyl-2-oxoethyl)-1,2,3,4-tetrahydro-2-naphthalenamine;
rac-cis-1-(4-Fluorophenylmethyl)-N-(3-phenylpropyl)-1,2,3,4-tetrahydro-2-naphthalenamine monohydrobromide;
rac-cis-1-(3-pyridylmethyl)-N-(2-(3,4-dimethoxyphenyl) ethyl-1,2,3,4-tetrahydro-2-naphthalenamine monohydrobromide
Ref: U.S. Pat. No. 6,201,025
Amide derivative Y receptor antagonist:
Ref: U.S. Pat. No. 6,048,900
N-substituted aminotetralin Y receptor antagonist, such as:
rac-[1α,2α(trans)]-N-[[[[[1,2,3,4-tetrahydro-6-methoxy-1-(phenylmethyl)-2-naphthalenyl]amino]methyl]4-cyclohexyl]methyl]2-naphthalenesulfonamide; rac-[1α,2α(trans)]-N-[[[[[1,2,3,4-tetrahydro-6-methoxy-1-(phenylmethyl)-2-naphthalenyl]amino]-5-pentyl]2-naphthalenesulfonamide;
rac-[1α,2α(trans)]-N-[[[[[1,2,3,4-tetrahydro-6-methoxy-1-(3-pyridinylmethyl)-2-naphthalenyl]amino]methyl]-4-cyclohexyl]methyl]2-naphthalenesulfonamide;
rac-[1α,2α(trans)]-N-[[[[[1,2,3,4-tetrahydro-6-fluoro-1-(phenylmethyl)-2-naphthalenyl]amino]methyl]-4-cyclohexyl]methyl]2-fluorobenzenesulfonamide; rac-[1α,2α(trans)]-N-[[[[[1,2,3,4-tetrahydro-6-fluoro-1-phenyl-2-naphthalenyl]amino]methyl]-4-cyclohexyl]methyl]2-naphthalenesulfonamide; rac-[1α,2α(trans)]-N-[[[[1,2,3,4-tetrahydro-6-methoxy-1-(1-propene-3-yl)-2-naphthalenyl]amino]methyl]4-cyclohexyl]methyl]benzenesulfonamide;
rac-[1α,2α(trans)]-N-[[[[[1,2,3,4-tetrahydro-6-methoxy-1-(3-hydroxypropyl)-2-naphthalenyl]amino]methyl]-4-cyclohexyl]methyl]benzenesulfonamide;
rac-[1α,2α(trans)]-N-[[[[[1,2,3,4-tetrahydro-6-methoxy-1-(n-propyl)-2-naphthalenyl]amino]methyl]-4-cyclohexyl] methyl]benzenesulfonamide.
Ref: U.S. Pat. No. 6,140,354
4-phenyl-1,4-dihydropyrimidinone Derivative Y Receptor Antagonist:
Ref: U.S. Pat. No. 5,889,016
Piperidine derivative dihydropyridine Y receptor antagonist:
4-Dihydro-[3-[[[[3-[4-(3-methoxyphenyl)-1-piperidinyl] propyl]amino]carbonyl]amino]phenyl]-2,6-dimethyl-3,5-pyridinedicarboxylic acid, dimethyl ester;
1,4-Dihydro-4-[3-[[[[3-[4-hydroxy-4-(3-methoxyphenyl)piperidin-1-yl]propyl]amino]carbonyl]amino]phenyl]-2,6-dimethyl-3,5-pyridine dicarboxylic acid, dimethyl ester;
1,4-Dihydro-4-[3-[[[[3-[4-(2-methoxyphenyl)piperidin-1-yl]propyl]amino]carbonyl]amino]phenyl]-2,6-dimethyl-3,5-pyridine dicarboxylic acid, dimethyl ester;
1,4-Dihydro-4-[3-[[[[3-(4-phenylpiperidin-1-yl)propyl] amino]carbonyl]amino]phenyl]-2,6-dimethyl-3,5-pyridinedicarboxylic acid, dimethyl ester;
1,4-Dihydro-4-[3-[[[[3-(4-hydroxy-4-phenylpiperidin-1-yl) propyl]amino]carbonyl]amino]phenyl]-2,6-dimethyl-3,5-pyridine dicarboxylic acid, dimethyl ester;
1,4-Dihydro-2,6-dimethyl-4-[3-[[[[3-[4-[3-(2-propynyloxy) phenyl]-1-piperidinyl]propyl]amino]carbonyl]amino] phenyl]-3,5-pyridinedicarboxylic acid, dimethyl ester;
1,4-Dihydro-4-[3-[[[[3-[4-cyano-4-phenylpiperidin-1-yl] propyl]amino]carbonyl]amino]phenyl]-2,6-dimethyl-3,5-pyridine dicarboxylic acid, dimethyl ester;
1,4-Dihydro-4-[3-[[[[3-[4-(3-hydroxyphenyl)piperidin-1-yl] propyl]amino]carbonyl]amino]phenyl]-2,6-dimethyl-3,5-pyridine dicarboxylic acid, dimethyl ester;
1,4-Dihydro-4-[3-[[[[3-[4-naphthalen-1-ylpiperidin-1-yl] propyl]amino]carbonyl]amino]phenyl]-2,6-dimethyl-3,5-pyridine dicarboxylic acid, dimethyl ester;
4-[3-[[[[3-[4-(1,1'-Biphenyl-3-yl)piperidin-1-yl]propyl] amino]carbonyl]amino]phenyl]-1,4-dihydro-2,6-dimethyl-3,5-pyridine dicarboxylic acid, dimethyl ester;
1,4-Dihydro-4-[3-[[[[3-[4-(phenylmethyl)-piperidin-1-yl] propyl]amino]carbonyl]amino]phenyl-2,6-dimethyl-3,5-pyridinedicarboxylic acid, dimethyl ester;
4-[3-[[[[3-(4-cyclohexyl-1-piperidinyl)propyl]amino]carbonyl]amino]phenyl]-1,4-dihydro-2,6-dimethyl-3,5-pyridinedicarboxylic acid, dimethyl ester;
1,4-dihydro-4-[3-[[[[3-[4-hydroxy-4-(2-phenoxyphenyl)-1-piperidinyl]propyl]amino]carbonyl]amino]phenyl]-2,6-dimethyl-3,5-pyridinedicarboxylic acid, dimethyl ester;
1,4-Dihydro-4-[3-[[[[3-(4-phenyl-1-piperidinyl)propyl] amino]carbonyl]amino]phenyl]-2,6-dimethyl-3,5-pyridinedicarboxylic acid, ethyl methyl ester;
1,4-Dihydro-4-[3-[[[[3-[(4-phenylmethyl)-1-piperidinyl] propyl]amino]carbonyl]amino]phenyl]-2,6-dimethyl-3,5-pyridinedicarboxylic acid, ethyl methyl ester;
1,4-Dihydro-4-[3-[[[3-[4-hydroxy-4-(2-methoxyphenyl)-piperidin-1-yl]propyl]amino]carbonyl]amino]phenyl]-2,6-dimethyl-3,5-pyridinedicarboxylic acid, ethyl methyl ester;
1,4-Dihydro-4-[3-[[[[3-[4-hydroxy-4-(3-methoxyphenyl)-piperidin-1-yl]propyl]amino]carbonyl]amino]phenyl]-2,6-dimethyl-3,5-pyridinedicarboxylic acid, ethyl methyl ester;
1,4-Dihydro-2,6-dimethyl-4-[3-[[[[3-[4-[3-(2-propoxy)phenyl]-1-piperidinyl]-propyl]amino]carbonyl]amino]phenyl]3,5-pyridinedicarboxylic acid, dimethyl ester;

1,4-Dihydro-4-[3-[[[[2-[4-(3-methoxyphenyl)-1-piperidinyl]ethyl]amino]carbonyl]amino]phenyl]-2,6-dimethyl-3,5-pyridinedicarboxylic acid, dimethyl ester hydrochloride;
1,4-Dihydro-4-[3-[[[[4-[4-(3-methoxyphenyl)-1-piperidinyl]butyl]amino]carbonyl]amino]phenyl]-2,6-dimethyl-3,5-pyridinedicarboxylic acid, dimethyl ester hydrochloride;
1,4-Dihydro-4-[3-[[[[3-[4-(3-methoxyphenyl)-1-piperidinyl]propyl]methylamino]carbonyl]amino]phenyl]-2,6-dimethyl-3,5-pyridinedicarboxylic acid, dimethyl ester hydrochloride;
4-Dihydro-4-[3-[[[[3-[1,2,3,6-tetrahydro-4-(3-methoxyphenyl)pyridin-1-yl]propyl]amino]carbonyl]amino]phenyl]-2,6-dimethyl-3,5-pyridine dicarboxylic acid, dimethyl ester;
1,4-Dihydro-4-[3-[[[[3-(1,2,3,6-tetrahydro-4-phenylpyridin-1-yl)propyl]amino]carbonyl]amino]phenyl]-2,6-dimethyl-3,5-pyridine dicarboxylic acid, dimethyl ester;
1,4-Dihydro-4-[3-[[[3-[1,2,3,6-tetrahydro-4-(3-hydroxyphenyl)pyridine]propyl]amino]carbonyl]amino]phenyl]-2,6-dimethyl-3,5-pyridine dicarboxylic acid, dimethyl ester;
1,4-Dihydro-4-[3-[[[[3-[1,2,3,6-tetrahydro-4-(1-naphthalenyl)-1-pyridinyl]propyl]amino]carbonyl]amino]phenyl]-2,6-dimethyl-3,5-pyridinedicarboxylic acid, dimethyl ester;
1,4-Dihydro-4-[3-[[3-(4-phenylpiperidin-1-yl)-1-oxo-1-propyl]amino]phenyl]-2,6-dimethyl-3,5-pyridinedicarboxylic acid, dimethyl ester; 1,4-Dihydro-4-[3-[[4-(4-phenylpiperidin-1-yl)-1-oxo-1-butyl]amino]phenyl]-2,6-dimethyl-3,5-pyridinedicarboxylic acid, dimethyl ester;
1,4-Dihydro-4-[3-[[5-(4-phenylpiperidin-1-yl)-1-oxo-1-pentyl]amino]phenyl]-2,6-dimethyl-3,5-pyridinedicarboxylic acid, dimethyl ester; 1,4-Dihydro-4-[3-[[6-(4-phenylpiperidin-1-yl)-1-oxo-1-hexyl]amino]phenyl]-2,6-dimethyl-3,5-pyridinedicarboxylic acid, dimethyl ester;
1,4-Dihydro-4-[3-[[5-(4-hydroxy-4-phenylpiperidin-1-yl)-1-oxo-1-pentyl]amino]phenyl]-2,6-dimethyl-3,5-pyridinedicarboxylic acid, dimethyl ester; 1,4-Dihydro-4-[3-[[5-(4-cyano-4-phenylpiperidin-1-yl)-1-oxo-1-pentyl]amino]phenyl]-2,6-dimethyl-3,5-pyridinedicarboxylic acid, dimethyl ester;
1,4-Dihydro-4-[3-[[[4-[4-(3-methoxyphenyl)-1-piperidinyl]butyl]carbonyl]amino]phenyl]-2,6-dimethyl-3,5-pyridinedicarboxylic acid, dimethyl ester;
1,4-dihydro-4-[3-[[[[3-[4-(3-methoxyphenyl)-1-piperidinyl]propyl]oxy]carbonyl]amino]phenyl]-2,6-dimethyl-3,5-pyridinedicarboxylic acid, dimethyl ester hydrochloride;
1,4-Dihydro-4-[3-[[[[3-[4-(3-methoxyphenyl)piperidin-1-yl]propyl]amino]carbonyl]amino]phenyl]-2,6-dimethyl-3,5-pyridinedicarboxylic acid, dimethyl ester;
1,4-Dihydro-4-[3-[[[[3-[4-(2-methoxyphenyl)piperidin-1-yl]propyl]amino]carbonyl]amino]phenyl]-2,6-dimethyl-3,5-pyridinedicarboxylic acid, dimethyl ester;
1,4-Dihydro-4-[3-[[[[3-[4-(3-hydroxyphenyl)piperidin-1-yl]propyl]amino]carbonyl]amino]phenyl]-2,6-dimethyl-3,5-pyridinedicarboxylic acid, dimethyl ester;
1,4-Dihydro-4-[3-[[[[3-[4-naphthalenylpiperidin-1-yl]propyl]amino]carbonyl]amino]phenyl]-2,6-dimethyl-3,5-pyridinedicarboxylic acid, dimethyl ester;
4-[3-[[[[3-(4-cyclohexyl-1-piperidinyl)propyl]amino]carbonyl]amino]phenyl]-1,4-dihydro-2,6-dimethyl-3,5-pyridinedicarboxylic acid, dimethyl ester;
1,4-Dihydro-4-[3-[[[[3-[1,2,3,6-tetrahydro-4-(3-methoxyphenyl)pyridin-1-yl]propyl]amino]carbonyl]amino]phenyl]-2,6-dimethyl-3,5-pyridinedicarboxylic acid, dimethyl ester;
1,4-Dihydro-4-[3-[[[3-[1,2,3,6-tetrahydro-4-(1-naphthalenyl)pyridin-1-yl]propyl]amino]carbonyl]amino]phenyl-2,6-dimethyl-3,5-pyridinedicarboxylic acid, dimethyl ester.
Ref: U.S. Pat. No. 5,668,151

The invention is illustrated by the following non-limiting Examples.

EXAMPLES

Example 1

Material and Methods

Generation of POMC-EGFP mice: The EGFP cassette contains its own Kozak consensus translation initiation site along with SV40 polyadenylation signals downstream of the EGFP coding sequences directing proper processing of the 3' end of the EGFP mRNA. The EGFP cassette was introduced by standard techniques into the 5' untranslated region of exon 2 of a mouse Pomc genomic clone containing 13 kb of 5' and 2 kb of 3' flanking sequences (Young et al., *J Neurosci* 18, 6631-40, 1998). The transgene was microinjected into pronuclei of one-cell stage embryos of C57BL/6J mice (Jackson Laboratories) as described (Young et al., *J Neurosci* 18, 6631-40, 1998). One founder was generated and bred to wildtype C57BL/6J to produce $N_1$ hemizygous mice. In addition, $N_2$ and subsequent generations of mice homozygous for the transgene were also generated. The mice are fertile and have normal growth and development.

Immunofluorescence and GFP co-localization: Anesthetized mice were perfused transcardially with 4% paraformaldehyde and free-floating brain sections prepared with a vibratome. Sections were processed for immunofluorescence and colocalization of GFP fluorescence using standard techniques. Primary antisera and their final dilutions were rabbit anti-β-endorphin, 1:2500 v/v; rabbit anti-NPY, 1:25,000 v/v (Alanex Corp.); rabbit anti-ACTH, 1:2000 v/v; and mouse anti-TH, 1:1000 v/v (Incstar). After rinsing, sections were incubated with 10 mg/ml biotinylated horse anti-mouse/rabbit IgG (Vector Laboratories) followed by Cy-3 conjugated streptavidin, 1:500 v/v (Jackson Immunoresearch Laboratories). Photomicrographs were taken on a Zeiss Axioscop using FITC and RITC filter sets (Chroma Technology Corp.).

Electrophysiology (Example 2): 200 μm thick coronal slices were cut from the ARC of four-week old male POMC-EGFP mice. Slices were maintained in (in mM) [NaCl, 126; KCl, 2.5; $MgCl_2$, 1.2; $CaCl_2.2H_2O$, 2.4; $NaH_2PO_4.H_2O$, 1.2; $NaHCO_3$, 21.4; Glucose, 11.1] (Krebs) at 35° C. and saturated with 95% $O_2$ 5% $CO_2$ for 1 hour (hr) prior to recordings. Recordings were made in Krebs at 35° C. Slices were visualized on an Axioskop FS2 (Zeiss) through standard infra red optics and using epifluorescence through a FITC filter set (see FIG. 1c). Whole cell recordings were made from fluorescent neurons using an Axopatch 1D amplifier (Axon Instruments) and Clampex 7 (Axon Instruments). Resting membrane potentials were determined using an event detection protocol on a PowerLab system (AD Instruments, Mountain View, Calif.) to average expanded traces of the membrane potential. Drugs were applied to the bath over the times indicated. The resting membrane potential was stable for up to an hour in cells treated with Krebs alone. I-V relationships for the Met-Enk currents were established using a step protocol; (−60 mV holding potential, sequentially pulsed (40 ms) from −120 to −50 mV, cells were returned to −60 mV for 2 s between voltage steps). The protocol was repeated after Met Enk addition. The net current was the difference between the two I-V relationships. This protocol was repeated in Krebs with 6.5 mM K$^+$. I-V relationships to identify the postsynaptic leptin current were performed similarly with slow voltage ramps (5 mV/s from −100 to −20 mV) before and 10 minutes after the addition of leptin (100 nM). GABAergic IPSCs were recorded using a CsCl internal electrode solution (in mM) [CsCl, 140; Hepes, 10; MgCl$_2$, 5; Bapta, 1; (Mg)-ATP, 5; (Na)GTP, 0.3]. Both mini IPSCs and large amplitude (presumably multisynaptic) IPSCs were observed in the untreated slices. TTX (1 µM) abolished large IPSCs. Data were acquired before and after addition of drug for the times indicated on the figures at a −50 mV holding potential in 2 s. sweeps every 4 s. Mini postsynaptic currents were analyzed using Axograph 4 (Axon Instruments). IPSCs and excitatory postsynaptic currents (EPSCS) were distinguished on the basis of their decay constants; additionally picrotoxin (100 µM) blocked all IPSCs. POMC neurons receive a low EPSC tone and the frequency was not modulated by any of the treatments described here.

Immunostaining for light and electron microscopy. Double immunocytochemistry for NPY and POMC using different color diaminobenzidine(DAB) chromogens was carried out on fixed mouse hypothalami according to published protocols (Horvath et al., *Neuroscience* 51, 391-9, 1992). For electron microscopy, preembedding immunostaining for β-endorphin was using an ABC Elite kit (Vector Laboratories) and a DAB reaction followed by post-embedding labeling of GABA and NPY using rabbit anti-GABA, 1:1000 v/v and gold conjugated (10 nm) goat anti-rabbit IgG or sheep anti-NPY and gold conjugated (25 nm) goat anti-sheep IgG. Finally, sections were contrasted with saturated uranyl acetate (10 minutes) and lead citrate (20-30 s) and examined using a Philips CM-10 electron microscope.

Animals: Male Pomc-EGFP mice were studied at 5-6 weeks of age and were generated as described above. Male mice aged 8-12 weeks and between 20-30 g bodyweight were kept under controlled temperature (21-23° C.) and light conditions (lights on 06:00-18:00) with ad libitum access to water and food except where stated. All studies were performed in the early light-phase (0700-0800).

Intraperitoneal injections: Mice were accustomed to IP injection by injections of 0.5 ml saline on the two days prior to study. For all studies, animals received an IP injection of either PYY$_{3-36}$ or saline in 100 µl.

Electrophysiology. Whole cell patch clamp recordings were made from POMC neurons in the hypothalamus of 180 µm thick coronal slices from Pomc-EGFP mice, as previously reported (Cowley et al., *Nature* 411, 480-484, 2001). "Loose cell-attached" recordings were made using extracellular buffer in the electrode solution, and maintaining seal resistance between 3-5 Mohm throughout the recording. Firing rates were analyzed using mini-analysis protocols (Mini-Analysis, Jaejin Software, NJ). Vehicle controls were used in this system, previously validated for the electrophysiological actions of neuropeptides (Cowley et al., *Nature* 411, 480-484, 2001). Data were analyzed by ANOVA, Neuman-Keuls posthoc comparison, and Wilcoxon Signed Rank Test.

C-fos expression: C-fos expression was measured in Pomc-EGFP mice 2 hours after IP administration of saline or PYY$_{3-36}$ (5 µg/100 g) using standard immunohistochemical techniques (Hoffman et al., *Front. Neuroendocrinol.* 14, 173-213, 1993). Data were obtained from 5 mice in each group. For the Pomc-EGFP mice 5 anatomically matched arcuate nucleus sections (Franklin et al., *The Mouse Brain in Stereotaxic Coordinates* (Academic Press, San Diego, 1997) were counted from each animal, and images acquired using a Leica TSC confocal microscope (Grove et al., *Neuroscience* 100, 731-40, 2000).

Measurements of Energy Expenditure: To determine the actions of PYY on energy expenditure the OXYMAX system (Columbus Instruments, Columbus, Ohio) is utilized with rodents following PYY injection into a treatment cohort. This system is also utilized with rodents following a saline injection (control cohort). The equipment measures O$_2$ consumption and CO$_2$ production; the efficiency with which the body produces CO$_2$ from O$_2$ gives a reliable index of caloric or metabolic efficiency. A similar system is used with human volunteers.

Example 2

Neural Network in the Arcuate Nucleus

A strain of transgenic mice was generated expressing green fluorescent protein (EGFP Clontech), under the transcriptional control of mouse Pomc genomic sequences that include a region located between −13 kb and −2 kb required for accurate neuronal expression (Young et al., *J Neurosci* 18, 6631-40, 1998) (FIG. 1*a*). Bright green fluorescence (509 nm) was seen in the two CNS regions where POMC is produced: the ARC and the nucleus of the solitary tract. Under ultraviolet (450-480 nm) excitation POMC neurons were clearly distinguished from adjacent, non-fluorescent neurons (FIG. 1*b*) visualized under infrared optics. Double immunofluorescence revealed >99% cellular co-localization of EGFP and POMC peptides within the ARC (FIG. 1*c*). There was close apposition of both tyrosine hydroxylase (TH)- and NPY-stained terminals on EGFP-expressing POMC neurons, but no evidence of co-localization of the TH or NPY immunoreactivity with EGFP. Total fluorescent cell counts performed on coronal hypothalamic sections revealed 3148±62 (mean±SEM: n=3) POMC-EGFP neurons distributed through the entire ARC (Franklin et al., *The Mouse Brain in Stereotaxic Coordinates* (Academic Press, San Diego, 1997) (FIG. 1*d*). POMC neurons in the mouse are located both medially and ventrally within the ARC, in contrast to a predominantly lateral position in the rat ARC.

POMC-EGFP neurons in hypothalamic slices had a resting membrane potential of −40 to −45 mV and exhibited frequent spontaneous action potentials. The non-selective opioid agonist met-enkephalin (Met-Enk: 30 µM; Sigma) caused a rapid (35-40 s), reversible hyperpolarization (10-20 mV) of the membrane potential of POMC cells (n=10) and prevented spontaneous action potential generation (FIG. 2*a*). In normal (2.5 mM K$^+$) Krebs buffer, the reversal-potential of the inwardly-rectifying opioid current was approximately −90 mV, while in 6.5 mM K$^+$ Krebs the reversal-potential was shifted to approximately −60 mV (n=3: FIG. 2*b*). The µ opioid receptor (MOP-R) antagonist CTAP (1 µM; Phoenix Pharmaceuticals) completely prevented the current induced by Met-Enk in POMC cells (n=3: FIG. 2*c*). These characteristics indicate the opioid current was due to activation of MOP-R and increased ion conductance through G protein coupled, inwardly-rectifying potassium channels (GIRK) (Kelly et al., *Neuroendocrinology* 52, 268-75, 1990). The similar opioid responses in EGFP-labeled POMC neurons to that of guinea pig (Kelly et al., *Neuroendocrinology* 52, 268-75, 1990) or mouse (Slugg et al., *Neuroendocrinology* 72, 208-17, 2000). POMC cells, identified by post-recording immunohistochemistry, suggests that expression of the EGFP transgene does not compromise either expression of receptors nor their coupling to second messenger systems in POMC neurons.

Figure 3:
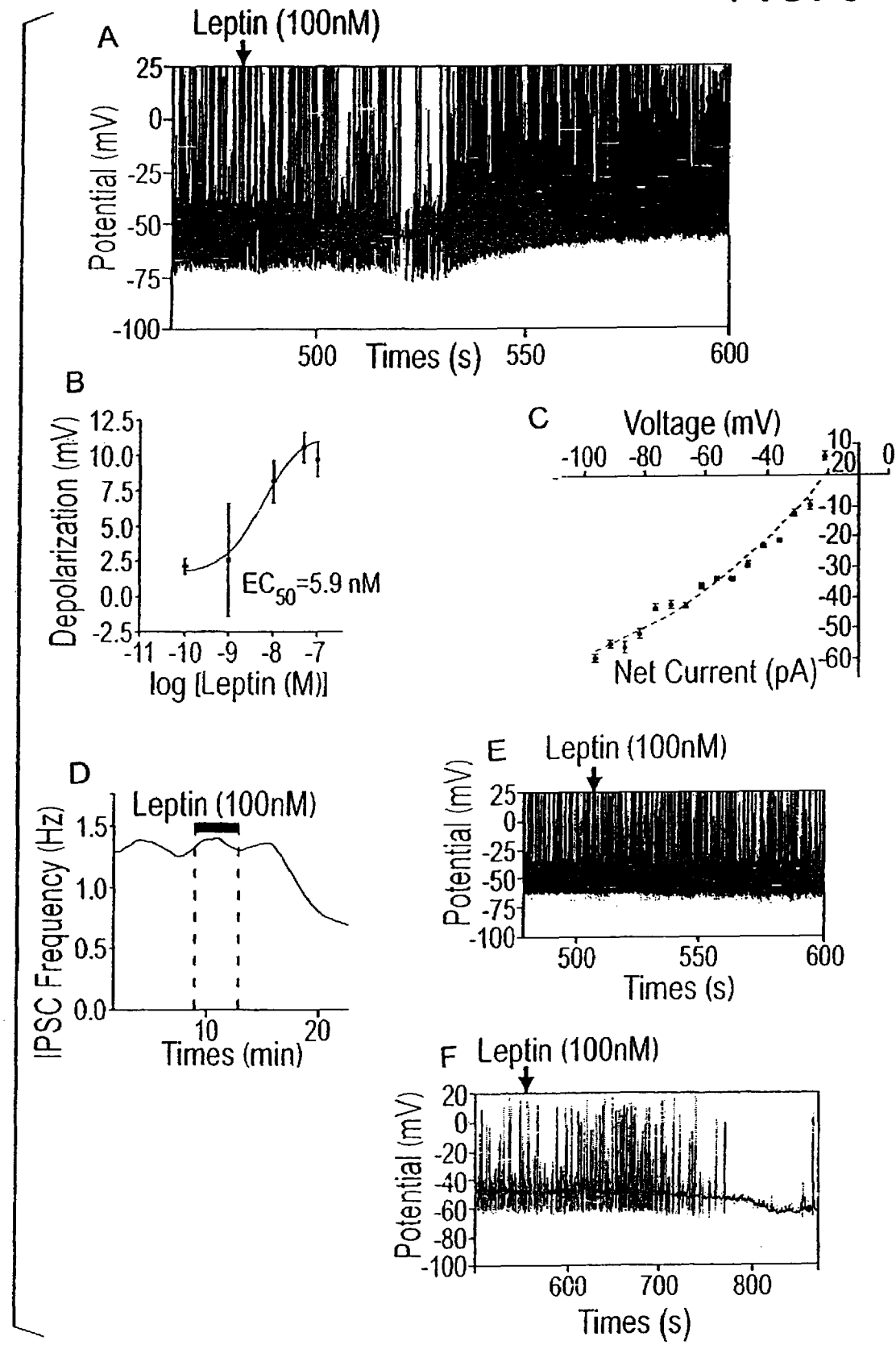
FIG. 3 are tracings and graphs demonstrating that leptin depolarizes POMC neurons via a non-specific cation channel, and decreases GABAergic tone onto POMC cells.

Next, the direct effects of leptin on identified POMC cells in slice preparations were investigated. Leptin (0.1-100 nM)

depolarized 72 of 77 POMC cells by 3-30 mV (FIG. 3a; mean±SEM depolarization at 100 nM leptin=9.7±1.2 mV, n=45) within 2-10 minutes, in a concentration responsive manner (FIG. 3b). There were two components to the depolarization and neither were fully reversible within 40 minutes. Firstly, the depolarization was due to a small inward current which reversed at approximately −20 mV (FIG. 3c), suggesting the involvement of a non-specific cation channel (Powis et al., Am J Physiol 274, R1468-72, 1998). Secondly, leptin treatment decreased the GABAergic tone onto POMC cells. GABAergic inhibitory postsynaptic currents (IPSCs) were observed in POMC cells and leptin (100 nM) decreased their frequency by 25% (FIG. 3d) in 5 out of 15 cells suggesting that it acted presynaptically to reduce GABA release (leptin had no effect on IPSCs in 10 out of 15 POMC neurons). The effect on IPSC frequency occurred with a similar lag to the effect on membrane potential. Thus, leptin not only directly depolarizes POMC neurons but also acts at GABAergic nerve terminals to reduce the release of GABA onto POMC neurons, allowing them to adopt a more depolarized resting potential. The consistent depolarization of POMC cells by leptin was specific because leptin had no effect on 5 of 13 adjacent non-fluorescent cells tested (FIG. 3e), while it hyperpolarized 5 (FIG. 3f) and depolarized 3 other non-POMC neurons in the ARC. The electrophysiological effects of leptin reported here are consistent with leptin's biological actions; leptin rapidly causes release of α-MSH from rat hypothalami (Kim et al., J Clin Invest 105, 1005-11, 2000), presumably by activating POMC neurons.

Figure 4:
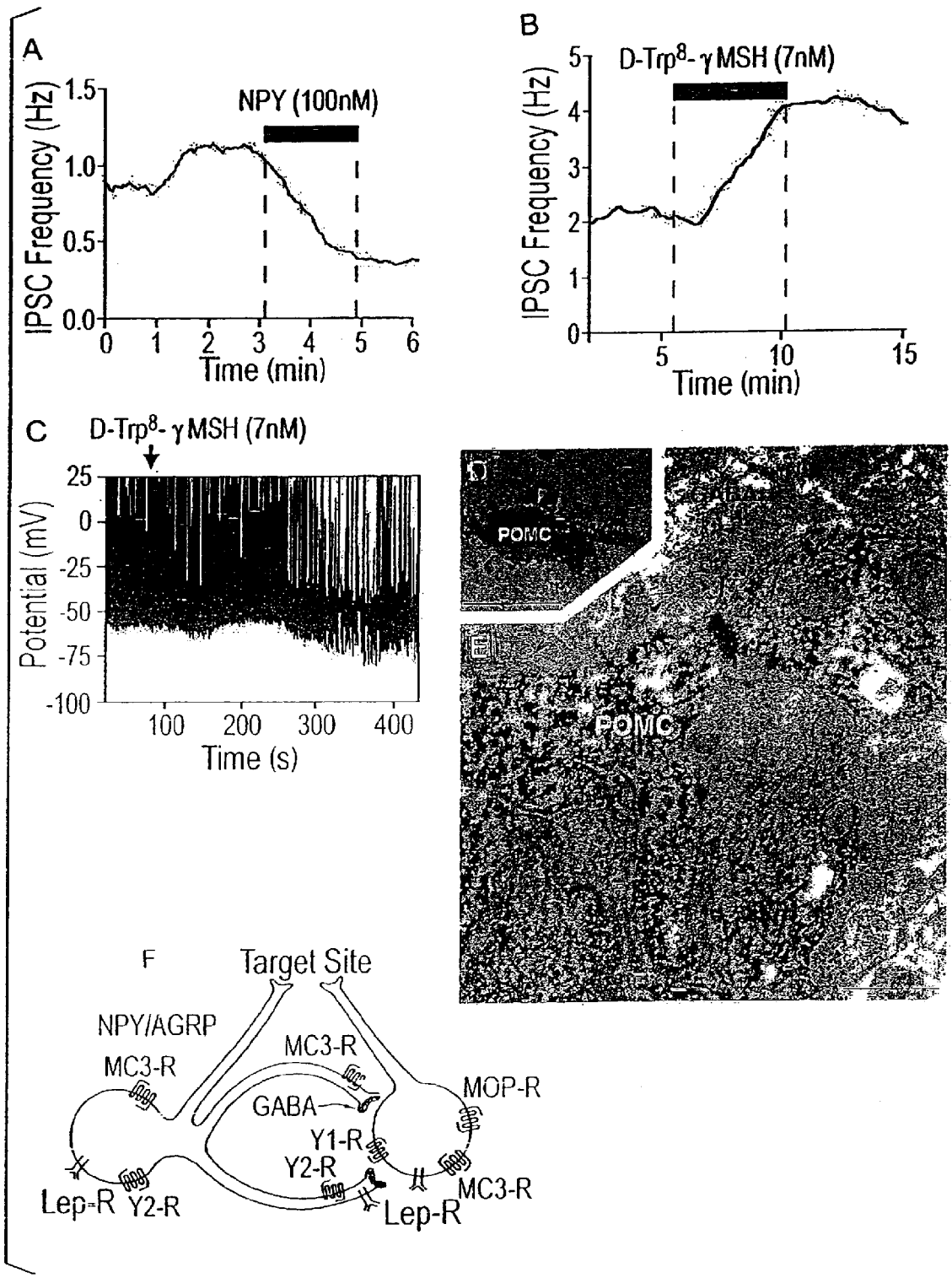
FIG. 4 is a set of images showing that the GABAergic inputs to POMC cells are from NPY neurons that co-express GABA.

Previous reports of neuronal hyperpolarization by leptin (Glaum et al., Mol Pharmacol 50, 230-5, 1996; Spanswick et al., Nature 390, 521-5, 1997), and the demonstrated co-localization of GABA and NPY (Horvath et al., Brain Res 756, 283-6, 1997) within subpopulations of ARC neurons, suggested that leptin hyperpolarizes NPY/GABA cells that directly innervate POMC neurons, and thus reduces GABAergic drive onto POMC cells. Both the leptin and NPY Y2 receptors are expressed on NPY neurons in the ARC (Hakansson et al., J Neurosci 18, 559-72, 1998; Broberger et al., Neuroendocrinology 66, 393-408, 1997). Furthermore, activation of Y2 receptors inhibits NPY release from NPY neurons (King et al., J Neurochem 73, 641-6, 1999), and presumably would also diminish GABA release from NPY/GABA terminals. This provides an alternative pharmacological approach, independent of leptin, to test the hypothesized innervation of POMC neurons by GABAergic NPY neurons. Indeed, NPY (100 nM; Bachem) decreased the frequency of GABAergic IPSCs by 55% within 3 minutes, in all 12 POMC cells tested (FIG. 4a). Both NPY and leptin still inhibited IPSCs in the presence of tetrodotoxin (TTX) (6 of 6 and 3 of 5 cells respectively), indicating that some of the inhibition of IPSCs was occurring through direct effects at presynaptic nerve terminals. POMC neurons express the NPY Y1 receptor (Broberger et al., Neuroendocrinology 66, 393-408, 1997) and NPY also hyperpolarized all POMC neurons tested, by an average of 9±6 mV (n=3).

Another pharmacological test to confirm the origin of GABAergic innervation on POMC neurons from NPY/GABA terminals was to test the effect of the recently characterized and highly selective MC3-R agonist D-Trp$^8$-γMSH (Grieco et al., J Med Chem 43, 4998-5002, 2000) on local GABA release. D-Trp$^8$-γMSH (7 nM) increased the frequency of GABAergic IPSCs (280±90%) recorded from 3 of 4 POMC neurons (FIG. 4b). It had no effect on one cell. The positive effect of MC3-R activation, together with the negative effects of NPY and leptin, demonstrate the dynamic range of the NPY/GABA synapse onto POMC neurons and point to the important role of this synapse in modulating signal flow within the ARC. D-Trp$^8$-γMSH (7 nM) also hyperpolarized (−5.5±2.4 mV) 9 of 15 POMC neurons tested and decreased the frequency of action potentials (FIG. 4c); the remaining cells showed no significant response to D-Trp$^8$-γMSH. These effects could be due entirely to increased GABA release onto the POMC cells, or could be due to an additional postsynaptic action of D-Trp$^8$-γMSH on POMC neurons, approximately half of which also express the MC3-R (Bagnol et al., J Neurosci (Online) 19, RC26, 1999). Thus, MC3-R acts in a similar autoreceptor manner to MOP-Rs on POMC neurons, diminishing POMC neuronal activity in response to elevated POMC peptides.

To further determine that the IPSCs in POMC neurons were due to local innervation by NPY/GABA cells, multi-label immunohistochemistry was performed using light and electron microscopy. Although independent NPY (Csiffary et al., Brain Res 506, 215-22, 1990) and GABA (Horvath et al., Neuroscience 51, 391-9, 1992) innervation of POMC cells has been reported, co-localization of NPY and GABA in nerve terminals forming synapses onto POMC cells has not been shown. Similar to the rat (Csiffary et al., Brain Res 506, 215-22, 1990), a dense innervation of POMC cells by NPY axon terminals was detected in the mouse (FIG. 4d). Electron microscopy confirmed the coexpression of NPY and GABA in axon terminals and revealed that these boutons established synapses on the perikarya of all 15 ARC POMC neurons analyzed (representative example, FIG. 4e).

A detailed model of regulation of this circuit shows dual mechanisms of leptin action in the ARC, interactions between NPY/GABA and POMC neurons, and autoregulatory feedback from opioid and melanocortin peptides as well as NPY (FIG. 4f). In this model, leptin directly depolarizes the POMC neurons and simultaneously hyperpolarizes the somata of NPY/GABA neurons, and diminishes release from NPY/GABA terminals. This diminished GABA release disinhibits the POMC neurons, and result in an activation of POMC neurons and an increased frequency of action potentials.

Example 3

Administration of PYY Inhibits Food Intake

The effect of PYY on feeding in rats, and mice has been established (Batterham et al., Nature 418:450, 2002).

Example 4

PYY Administration Affects c-fos Expression

Figure 5:
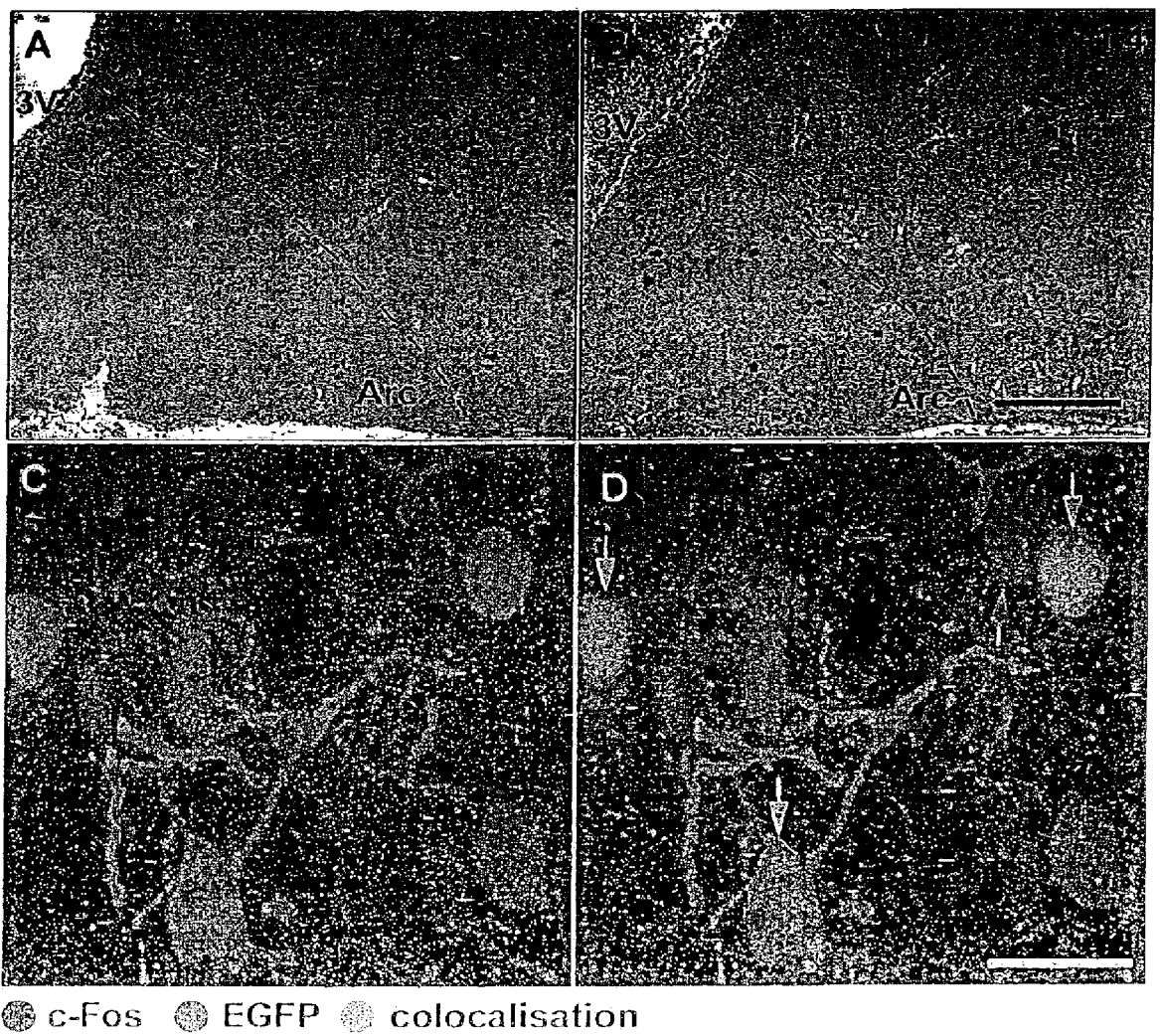
FIG. 5 is a set of digital images of c-fos expression in Pomc-EGFP mice.

To investigate whether this inhibition of food intake involved a hypothalamic pathway, c-fos expression was examined in the arcuate nucleus, an important center of feeding control (Schwartz et al., Nature 404, 661-671, 2000; Cowley et al., Nature 411, 480-484, 2001), following a single IP injection of $PYY_{3-36}$ (FIG. 5). There was a 2-fold increase in the number of cells positive for c-fos in the lateral arcuate of the rat ($PYY_{3-36}$=168±2, saline=82.7±5, n=3, P<0.0001). Likewise in Pomc-EGFP-transgenic mice (Cowley et al., Nature 411, 480-484, 2001) IP administration of $PYY_{3-36}$ resulted in a 1.8-fold increase in the number of arcuate cells positive for c-fos (FIG. 5b), compared with saline control animals (FIG. 5a) ($PYY_{3-36}$=250±40, saline=137±15, n=5, P<0.05). IP $PYY_{3-36}$ caused a 2.6 fold increase in the proportion of POMC neurons that express c-fos ($PYY_{3-36}$=20.4±2.9%, saline=8±1.4%, n=5, P<0.006) (FIGS. 5c and d). These observations show that $PYY_{3-36}$ can act via the arcuate nucleus Example 5

Y2 Receptors

The electrophysiological response of hypothalamic POMC neurons to administration of both $PYY_{3-36}$ and Y2A was examined. The effect of PYY on feeding in rats and mice has been established (Batterham et al., Nature 418:450, 2002). POMC neurons were identified using mice with targeted expression of green fluorescent protein in POMC neurons (Cowley et al., Nature 411, 480-484, 2001). $PYY_{3-36}$ disinhibited the POMC neurons, resulting in a significant depolarization of 19 of the 22 POMC neurons tested (FIG. 6a inset) (10.3±2.1 mV depolarization, n=22, P<0.0003). A similar depolarization was seen with Y2A (8.7±1.8 mV depolarization, n=9, P<0.002). The depolarization caused by $PYY_{3-36}$ stimulated a significant increase in the frequency of action potentials in POMC neurons (FIG. 6a) (93% increase over control, P<0.05, n=22). In the whole cell mode the effect of $PYY_{3-36}$ was sometimes reversed upon washout, but only after a long latency (30 minutes). A similar washout of leptin effects upon these neurons was observed.

Figure 6:
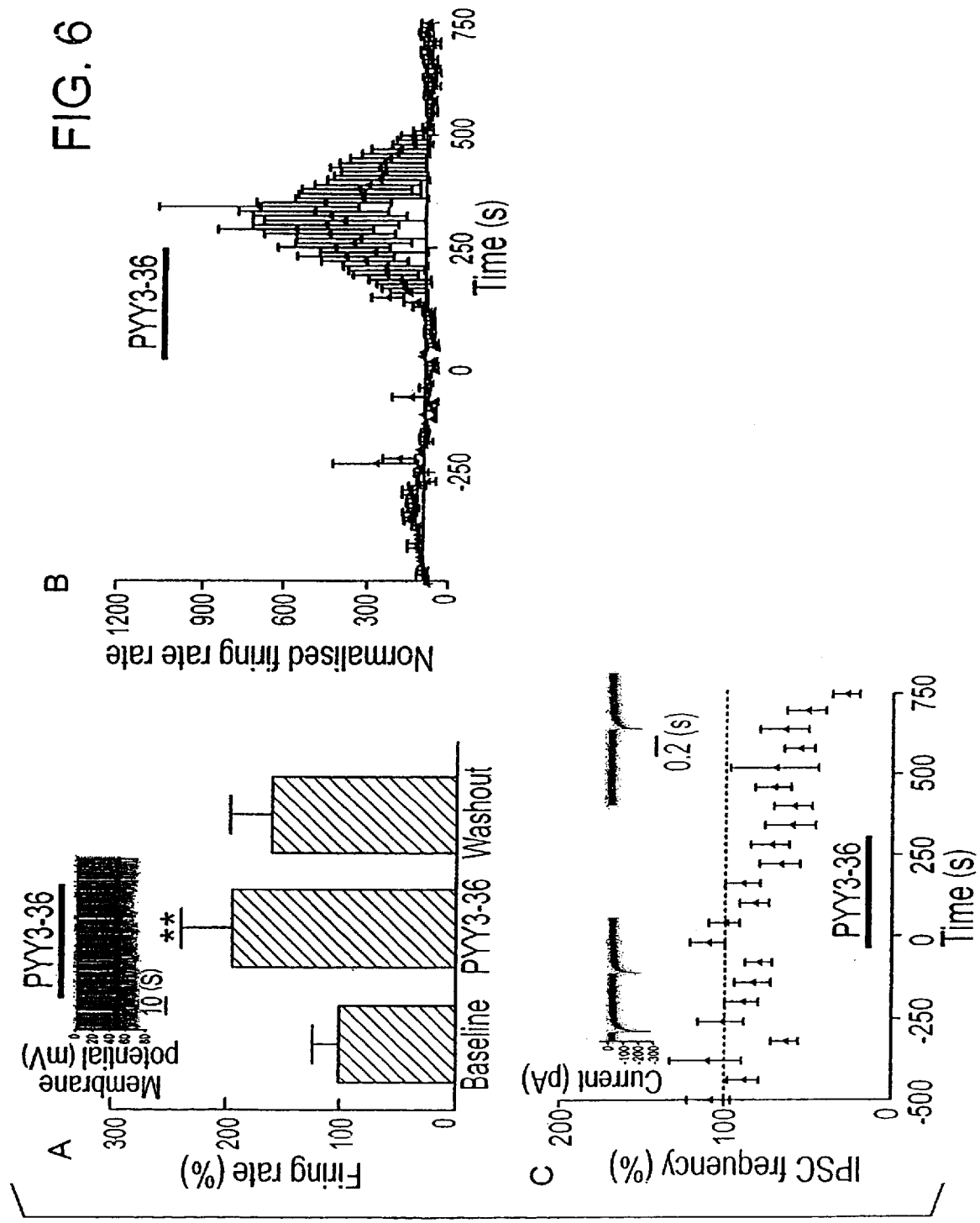
FIG. 6 is a set of images relating to the electrophysiological responses to PYY$_{3-36}$ and Y2A.

To exclude effects of cellular rundown, or seal deterioration, the effects of $PYY_{3-36}$ in the "loose cell-attached" (or extracellular) configuration was examined. $PYY_{3-36}$ caused a reversible 5-fold increase in the frequency of action potentials in loose cell-attached recordings of POMC neurons (FIG. 6b). This increase in firing rate occurred with the same latency as $PYY_{3-36}$ reduced the frequency of inhibitory postsynaptic currents (IPSCs) onto all 13 POMC neurons tested (FIG. 6c) (51.9±9.2% reduction, n=13, P<0.0001), indicating a reduced frequency of GABA release onto POMC neurons. Interestingly, the firing rate of POMC neurons returned to basal, in spite of continued inhibition of IPSCs. A similar effect upon IPSC frequency was seen with Y2A (44.4±9.3% reduction, n=8, P<0.004) suggesting this effect to be via Y2R. $PYY_{3-36}$ (25 nM) caused a hyperpolarization (5.2±1.16 mV, P<0.004, n=5) of unidentified, but presumably NPY-containing, non-POMC, neurons in the arcuate nucleus. There is a tonic GABAergic inhibition of POMC neurons by NPY neurons (Cowley et al., Nature 411, 480-484, 2001) and these results suggest that $PYY_{3-36}$ acts by inhibiting NPY neurons, thus decreasing this GABAergic tone and consequentially disinhibiting POMC neurons. The effect of Y2A on peptide secretion was also examined using hypothalamic explants (Kim et al., J. Clin. Invest. 105, 1005-11, 2000). Y2A significantly decreased NPY release, with a concomitant increase in A-MSH release from hypothalamic explants (Batterham et al., Nature 418:450, 2002). Taken together these observations show that $PYY_{3-36}$ modulates both the NPY and melanocortin systems in the arcuate nucleus.

Example 6

Human Studies

The effect of PYY on feeding in humans has been established (Batterham et al., Nature 418:450, 2002).

Example 7

Generation of Additional Lines of Transgenic Mice

A strain of transgenic mice has been generated that expresses green fluorescent protein under the transcriptional control of the mouse POMC genomic sequences, including a region located between −13 kilobases (kb) and −2 kb that is required for accurate neuronal expression (see above, e.g. Example 2, and Cowley et al., Nature 411:480, 2001, which is herein incorporated by reference). Additional lines of transgenic mice were then generated. The starting material for these experiments was either a 4 kb fragment of the rat POMC gene extending from a position approximately −4000 base pairs (bp) 5' to the transcriptional start site through to position +64 in the first exon or a 10 kb mouse genomic clone including approximately 2 kb of 5' flanking sequences. The complete POMC gene is composed of 3 exons and 2 introns, and approximately 2 kb of 3' flanking sequences (see Rubinstein et al., Neuroendocrinol. 58:373, 1993, herein incorporated by reference).

A cosmid genomic library was constructed from 129S6 strain mouse genomic DNA partially cut with the EcoRI restriction endonuclease. This library was screened with probes generated from the original 10 kb mouse POMC clone. This screen resulted in the isolation of several overlapping POMC genomic clones, which were used to construct a transgene vector for microinjection that included approximately 13 kb of 5' flanking sequences, the 6 kb POMC gene, and 8 kb of 3' flanking sequences for a total size of 27 kb. An artificial oligonucleotide sequence was introduced into exon 3 of the coding sequence to permit the unequivocal identification and quantification of mRNA transcribed from the transgene compared to the endogenous mouse POMC gene. Two additional transgenes were constructed, one that was truncated at the −2 kb side 5' to the POMC gene and the other that was truncated at the +2 kb side 3' to the POMC gene (see Young et al., J. Neurosci. 18:6631, 1998, herein incorporated by reference). Expression studies in this line of transgenic mice demonstrated that DNA sequences between −13 and −2 kb 5' to the POMC gene are necessary for eutopic, neuron-specific expression in the arcuate nucleus of the hypothalamus and the nucleus of the tractus solitarius. However, all the transgenes were appropriately expressed in the pituitary gland, consistent with the location of pituitary-specific DNA regulatory elements within the proximal −400 bp of the POMC promoter.

Figure 7:
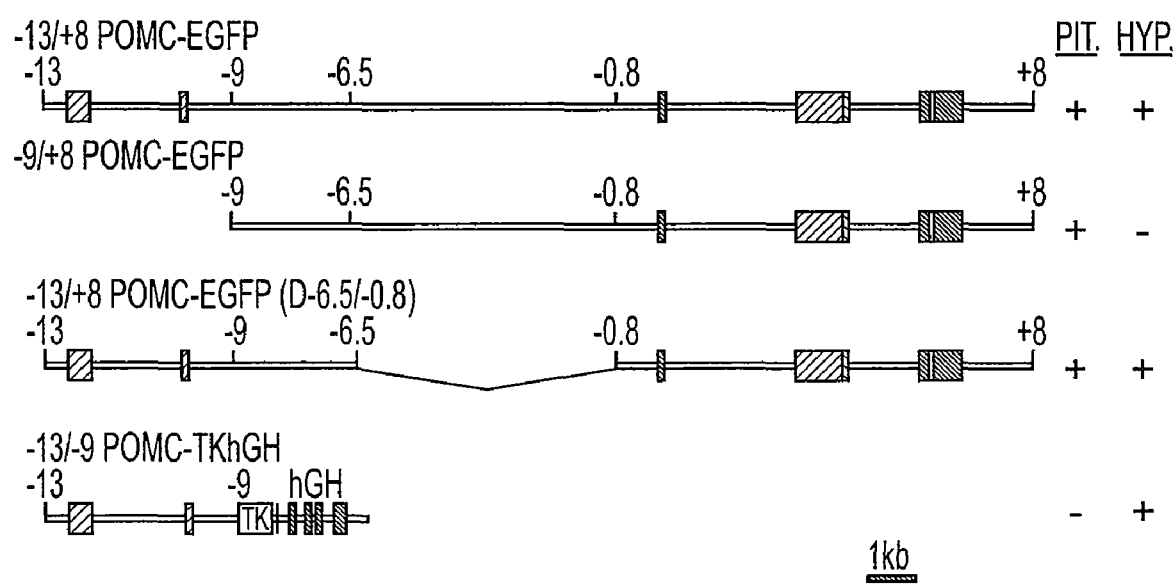
FIG. 7 is a schematic diagram of transgenes carrying variable lengths or deletions of 5' flanking sequences of the mouse POMC gene. The EGFP gene was inserted into the second exon immediately before the site of translational initiation. A polyadenylation signal from the large T antigen of the SV40 virus was included immediately adjacent and 3' to the EGFP gene. Black boxes are mouse POMC exons. Open boxes, EGFP. Striped boxes are nPOMC1 and nPOMC2 sites. The white box is the TK minimal promoter in front of the hGH structural gene. Right: Plus signs indicate that the transgene is expressed correctly in POMC pituitary cells or in POMC hypothalamic neurons and minus signs indicate the absence of expression.

An additional series of transgenes containing the EGFP reporter gene were constructed as illustrated in FIG. 7. Truncation of the 5' flanking sequences to position −9 kb resulted in a loss of neuronal expression, but did not affect pituitary expression, suggesting that the essential neuron-specific regulatory elements are contained in the 4 kb between nucleotide positions −13 and −9 kb. Furthermore, an internal deletion of genomic 5' flanking genomic sequences between positions −6.5 to −0.8 did not affect the positive transgene expression in either hypothalamic neurons (see FIG. 8a for a representative histologic section illustrating the robust expression of the fluorescent protein in arcuate neurons) or the pituitary cells. This suggests the position independence of the neural regulatory elements relative to the basal promoter. Virtually every transgenic strain produced with the distal 4 kb of regulatory elements displayed a high penetrance of reporter transgene expression in the neurons of the arcuate nucleus, suggesting that the transcriptional regulatory elements contained within the 4 kb of DNA sequence are insulated from the effects of random chromosomal integration position in common with known locus-control type enhancer elements.

Figure 8:
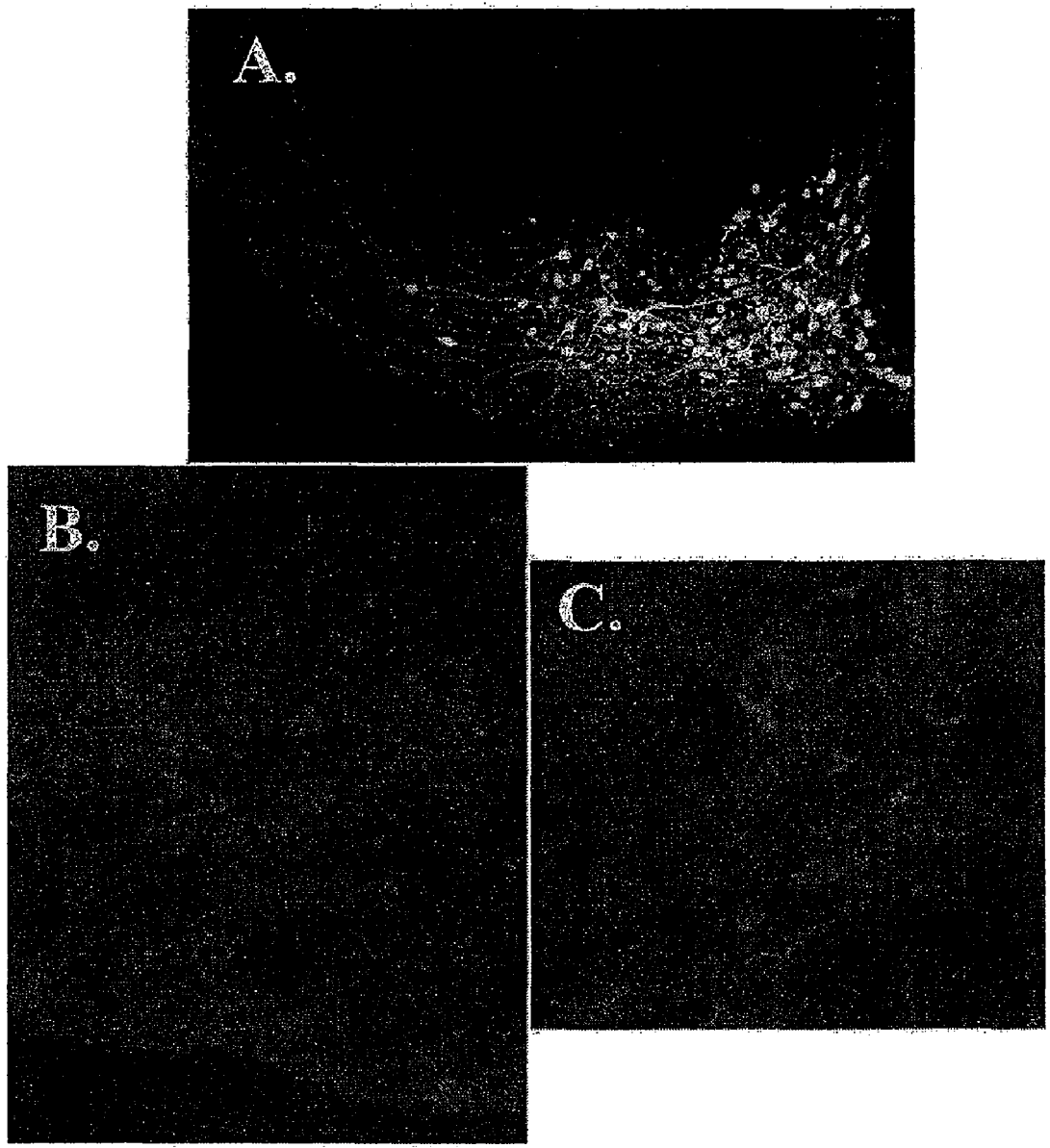
FIG. 8 is a set of digital images of sections of the arcuate nucleus.

A transgene containing the distal 4 kb of mouse POMC 5' genomic sequences between −13 and −9 kb to a minimal herpes simplex viral thymidine kinase (TK) promoter and human growth hormone reporter transgene (FIGS. 8b and 8c)

was produced, and transengic mice carrying this construct were generated. This region of the mouse POMC genomic sequences conferred hypothalamic arcuate neuronal-specific expression of the human growth hormone marker.

The minimal TK promoter has been used previously in conjunction with proximal pituitary-specific POMC regulatory elements (see Liu, et al 1992). In these studies, no intrinsic capacity of the TK promoter to cause reporter gene expression in POMC cells of transgenic mice was observed. Thus, expression of the hGH marker in these transgenic mice indicate that the 4 kb of distal mouse POMC genomic sequences contain a classically defined position- and promoter-independent transcriptional enhancer with specific activity for targeting high-level gene expression to POMC neurons, but not pituitary cells, in vivo.

Figure 9:
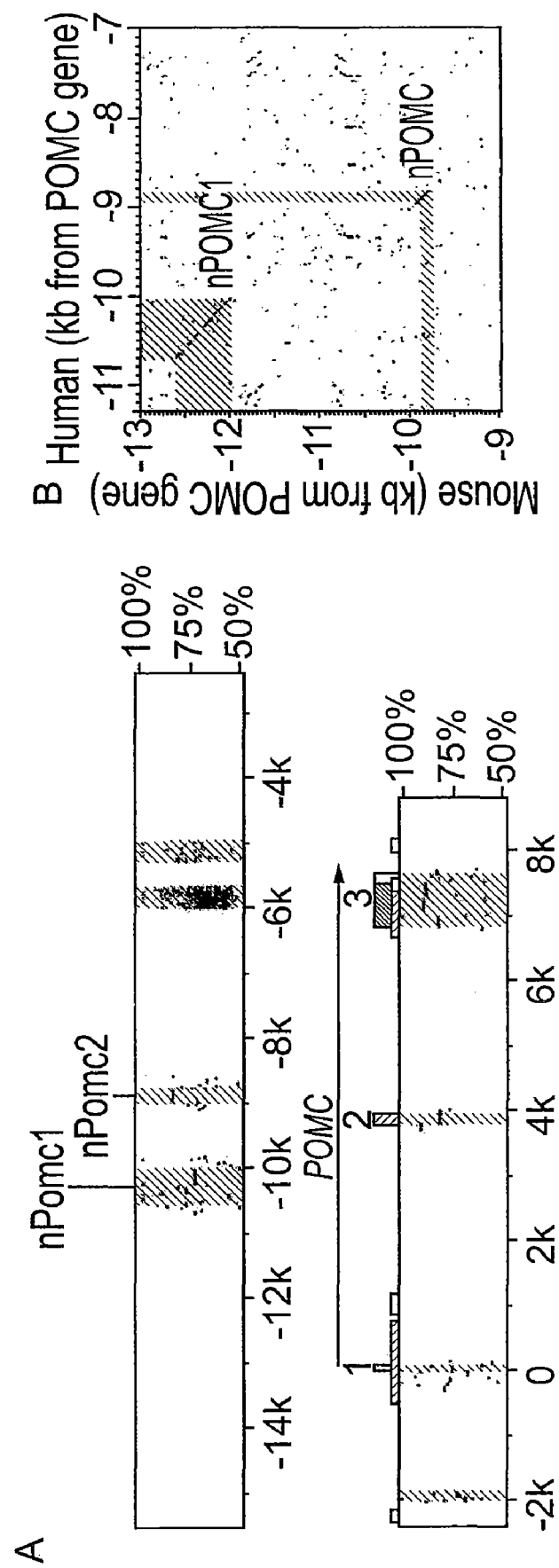
FIG. 9 is a set of diagrams showing sequence alignments.

The complete nucleotide sequence of the 4 kb of 129S6 substrain mouse POMC genomic DNA was obtained from the cosmid clones. A multiple alignment sequence comparison was performed with a public human data base BAC sequence containing the human POMC gene on chromosome 2 using the web-based program PIP Maker (Percentage Identity Plot) and the program named Dotter. The two programs, which use a completely different sequence comparison algorithm, found the same two highly conserved regions between mouse and human 5' flanking POMC gene sequences (FIG. 9). These two homology islands have been termed nPOMC1 and nPOMC2 for neural POMC regulatory elements 1 and 2.

FIG. 10 illustrates a sequence alignment of the nPOMC1 and nPOMC2 elements from a variety of mammalian species. In addition to the primary sequence, the distance between both sites to the TATA box is also conserved in the human and mouse POMC genes. The nPOMC1 site extends for approximately 450 bp with an overall mouse/human similarity of 65% having a 190 bp core with a maximal conservation of 80% (the human and bovine similarity is even higher, at 85%). This core is at −10.5 and −12.2 kb from the human and mouse TATA box, respectively. The core is located 1.7 or 2.3 kb upstream of human and mouse nPOMC2, respectively. The site nPOMC2 has a 153 bp region from which 138 are identical between mouse and human (90% of similarity). It is located at −8.9 and −9.9 kb from the human and mouse TATA box, respectively.

Without being bound by theory, these two small and highly conserved areas, embedded within several kb of heterogeneous genomic sequences, resemble the exon-intron differences within the transcriptional unit. Interestingly, the similarities between mouse and human exon 1, 2 and 3 of 64%, 87% and 82%, respectively, are not higher than the interspecies identity for nPOMC1 and nPOMC2 (FIG. 9).

A Clustall comparison of 280 bp of the proximal human and mouse POMC promoters show 68% of similarity in a region that contains all cis-acting elements necessary for basal (e.g. TATA and GC boxes) and pituitary specific expression (e.g. T-Pit, Ptx1 and PP1). Using degenerate oligonucleotide primers to amplify corresponding genomic regions from other mammalian species and sequencing of the PCR fragments, it was confirmed that nPOMC1 and nPOMC2 are also highly conserved in bovine, hamster, and rabbit genomic DNA. In addition, a bovine genomic library was screened using the bovine nPOMC1 PCR fragment as a radiolabeled probe. One of the positive phage clones also contains nPOMC2 and POMC exon 1 indicating that these two regulatory regions are syntenic with the TATA box within 15 kb, similar to the human and mouse. An internal portion of bovine nPOMC2 that was amplified from this clone shows 90% similarity with the human. The sequence of the rat nPOMC1 was obtained from a BLAST comparison of the draft genome project and is highly similar to the mouse sequence. Furthermore, the 129 mouse POMC genomic sequence is nearly identical to the C57BL/6J POMC genomic sequence now available on the public genomic data bases. The nucleotide sequences spanning the nPOMC1 and nPOMC2 elements together with the precise nucleotide positions on human chromosome 2 and mouse chromosome 12 are shown in FIG. 11. BLAST analyses indicate that the complete nPOMC1 and nPOMC2 elements are previously unidentified and uncharacterized sequences and appear to be unique to the POMC gene locus. Thus, one of skill in the art can readily generate transgenic mice carrying a transgene including any of these regions of the POMC gene, operably linked to a marker (such as, but not limited to, growth hormone or GFP).

The adipostatic hormone leptin not only activates POMC neurons but also stimulates transcription of the POMC gene in the hypothalamus presumably through a JAK kinase/STAT3-dependent pathway. The web-based program Mat Inspector was used to localize STAT3 DNA binding sites within 11.5 kb of 5' flanking regions of the human POMC gene. Eight sites were detected that share high homology with the consensus core TTCCNGGAA. Interestingly, only one site entirely matches this consensus sequence and it is located within the highly conserved nPOMC1 site and 50 bp downstream of another STAT3-like site (FIG. 10). This similarity suggests that nPOMC1 may be a leptin-responsive element within the POMC gene. The sites are slightly less well conserved in the other genomic sequences available. Another potentially interesting short DNA sequence present in the 5' half of nPOMC1 that is 100% identical among all five mammalian species is CTAATGGATGTGCATTA (SEQ ID NO: 352). Excluding the 5° C., the remaining 16 nucleotides contain an imperfect (12/16) palindrome that could be a symmetrical DNA-protein binding site.

As disclosed herein, a number of lines of transgenic mice have been produced that carry a number of transgenes that including a POMC regulatory region operably linked to nucleic acid sequence encoding a marker. Histological sections can readily be prepared from these, or other lines of transgenic mice carrying a POMC regulatory region operably linked to a nucleic acid sequence encoding a marker. These sections can be used to screen agents, such as chemical compounds, proteins, small molecules or salts, in order to identify an agent that affects caloric intake, food intake, or appetite, as described herein.

Example 8

Exemplary Screening Protocol

Coronal slices, from about 140 to about 400 μm thick, containing neurons form the ARC of mice carrying a POMC gene or regulatory element operably linked to a maker, wherein the marker is expressed in the POMC neurons in the ARC. In one embodiment, suitable sections are produced from a male, four week old mouse expressing GFP from the POMC promoter, such as one of the lines of mice disclosed herein. It should be noted that the age and sex of the animal is not a limitation, as female mice as well as older and younger mice can be used. These sections are then incubated with an agent of interest, and an electrophysiological parameter of the POMC neurons is measured. A change in this electrophysiological parameter indicates that the agent affects caloric intake, food intake, appetite and/or energy expenditure.

In one example, 180 μm thick slices of the ARC are maintained in (in mM) [NaCl, 126; KCl, 2.5; $MgCl_2$, 1.2; $CaCl_2 2H_2O$, 2.4; $NaH_2PO_4 \cdot H_2O$, 1.2; $NaHCO_3$, 21.4; Glucose, 11.1] (Krebs) at 35° C. and saturated with 95% $O_2$ 5% $CO_2$ for 1 hour (hr) prior to recordings. Recordings are made in Krebs at 35° C. Slices are visualized on an Axioskop FS2 (Zeiss) through standard infra red optics and using epifluorescence through a FITC filter set (see FIG. 1c). Whole cell or loose cell attached recordings are made from fluorescent neurons using an Axopatch iD amplifier (Axon Instruments) and Clampex 7 (Axon Instruments).

Resting membrane potentials and action potential frequencies are determined using an event detection protocol on a PowerLab system (AD Instruments, Mountain View, Calif.) to average expanded traces of the membrane potential. Alternatively, an event detection software package, such as Synaptosoft (Gaegin software), is used to plot instantaneous frequencies. Agents are applied to the bath over a specific time period, such as but not limited to, about one to about 15 minutes. The resting membrane potential is stable for up to an hour in cells treated with Krebs alone.

Current to voltage (I-V) relationships are established using a step protocol; (−60 mV holding potential, sequentially pulsed (40 ms) from −120 to −50 mV, cells were returned to −60 mV for 2 s between voltage steps). The protocol is repeated after addition of an agent of interest. The net current is the difference between the two I-V relationships are used to confirm that the agent is exerting a postsynaptic effect. Similarly slow voltage ramps (5 mV/s from −100 to −20 mV) before and 10 minutes after the addition of the agent (such as, but not limited to, a concentration of 1 nM-10 mM, e.g. at 100 nM) can be used to determine if a postsynaptic effect is occurring.

GABAergic IPSCs are recorded using a CsCl internal electrode solution (in mM) [CsCl, 140; Hepes, 10; $MgCl_2$, 5; Bapta, 1; (Mg)-ATP, 5; (Na)GTP, 0.3]. Addition of blockers of excitatory currents are used to allow the analysis of IPSC frequency in isolation. Both mini IPSCs and large amplitude (presumably multisynaptic) IPSCs are observed in the untreated slices. TTX (1 mM) abolishes large IPSCs. Data is acquired before and after addition of agent at, for example, a −50 mV holding potential in 2 seconds sweeps every 4 seconds. Mini postsynaptic currents are analyzed using Axograph 4 (Axon Instruments) or Synaptosoft. IPSCs and excitatory postsynaptic currents (EPSCs) are distinguished on the basis of their decay constants and sensitivity to specific blocking agents; picrotoxin (100 mM) blocks IPSCs.

Exemplary parameters that can be analyzed are:

1. Analyzing membrane potential in POMC neurons as compared to a control, such as a POMC neuron in an untreated section or a section incubated with a control agent. This allows assessment of whether an agent increases or decreases the activity of POMC neurons.

2. Analyzing action potential firing rate in POMC neurons as compared to a control, such as a POMC neuron in an untreated section or a section incubated with a control agent. This allows assessment of whether an agent increases or decreases the activity of POMC neurons.

3. Analyzing IPSC frequency onto POMC neurons as compared to a control, such as an untreated section or a section incubated with a control agent. This allows assessment of whether an agent increases or decreases the activity of NPY neurons.

Any change in one or more of these parameters identifies the agent as affecting caloric intake, appetite, food intake, and/or energy expenditure when a therapeutically effective amount of the agent is administered to a subject. Thus, in one embodiment, these data are interpreted by determining the effect of the agent on the activity of POMC neurons (as shown by membrane potential or action potential firing rate) and/or NPY/AGRP neurons (as shown by the IPSC frequency in POMC neurons). Agents that increase the activity of NPY neurons and/or decrease the activity of POMC neurons will increase caloric intake, food intake and/or appetite, and decrease energy expenditure. Agents which decrease the activity of NPY neurons and/or increase the activity of POMC neurons will decrease caloric intake, food intake and/or appetite and/or increase energy expenditure.

Example 9

In Vitro Assessment of Ghrelin, a Known Appetite Stimulant

Slices are of the ARC from POMC-EGFP mice (see Example 1 for a description of the animals) were maintained in (in mM) [NaCl, 126; KCl, 2.5; $MgCl_2$, 1.2; $CaCl_2.2H_2O$, 2.4; $NaH_2PO_4.H_2O$, 1.2; $NaHCO_3$, 21.4; Glucose, 11.1] (Krebs) at 35° C. and saturated with 95% $O_2$ 5% $CO_2$ for 1 hour (hr) prior to recordings. Recordings were made in Krebs at 35° C. Slices were visualized on an Axioskop FS2 (Zeiss) through standard infra red optics and using epifluorescence through a FITC filter set. Whole cell (FIGS. 12a and 12b) or loose cell attached (FIG. 12c) recordings were made from fluorescent neurons using an Axopatch 1D amplifier (Axon Instruments) and Clampex 7 (Axon Instruments).

GABAergic IPSCs were recorded using a CsCl internal electrode solution (in mM) [CsCl, 140; Hepes, 10; $MgCl_2$, 5; Bapta, 1; (Mg)-ATP, 5; (Na)GTP, 0.3]. Addition of blockers of excitatory currents allowed the analysis of IPSC frequency in isolation. Both mini IPSCs and large amplitude (presumably multisynaptic) IPSCs were observed in the untreated slices. TTX (1 mM) abolished large IPSCs. Data was acquired before and after addition of agent at a −50 mV holding potential in 2 second sweeps every 4 seconds. Picrotoxin (100 mM) blocked all IPSCs.

Figure 12:
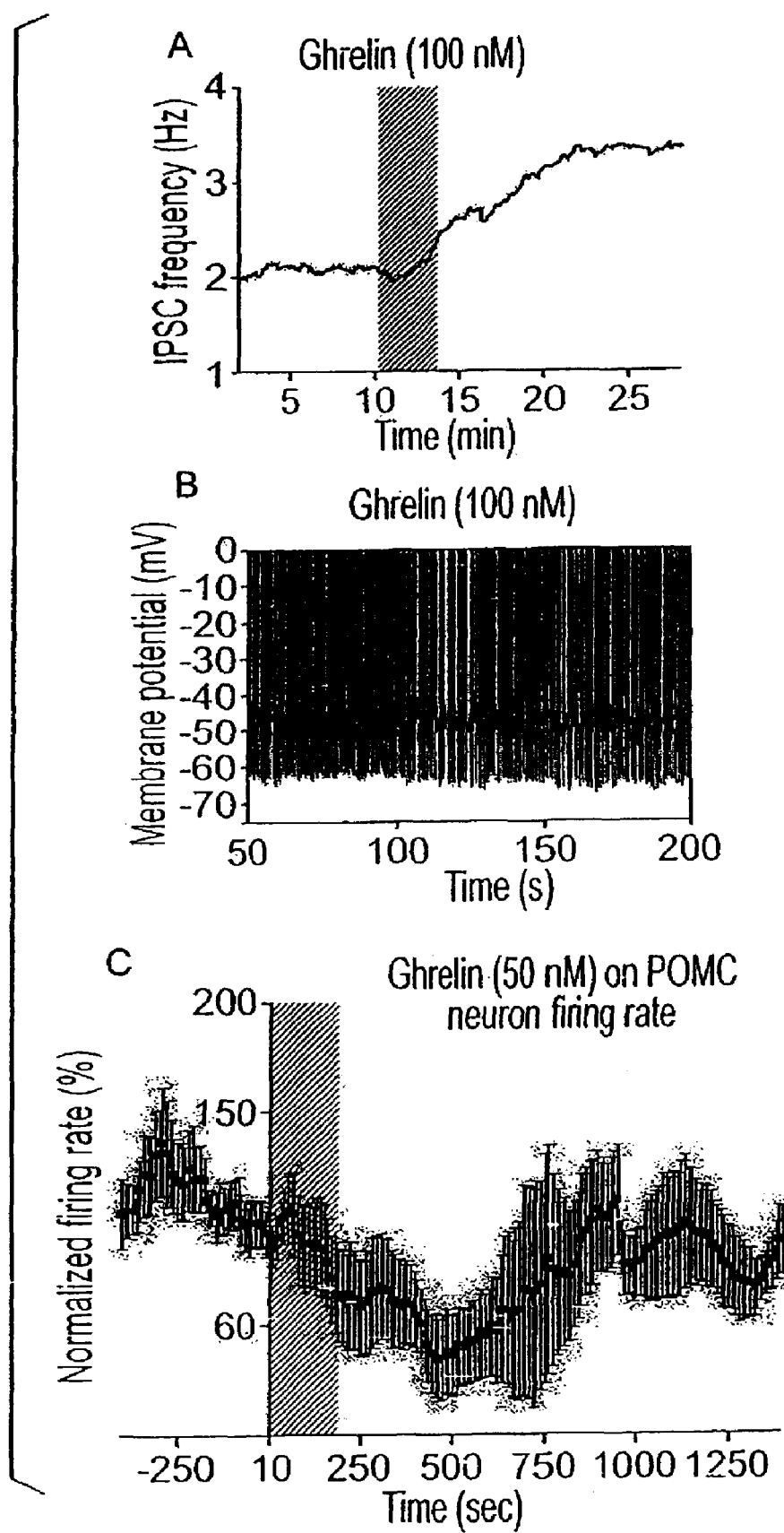
FIG. 12 is a set of graphs demonstrating that Ghrelin increases the secretory activity of NPY neurons onto POMC neurons, hyperpolarizes POMC neurons, and decreases the frequency of action potentials in POMC neurons.

IPSC frequencies were analyzed using Synaptosoft (Gaegin software), to determine instantaneous IPSC frequencies (FIG. 12a). Resting membrane potentials are determined using an event detection protocol on a PowerLab system (AD Instruments, Mountain View, Calif.) to average expanded traces of the membrane potential (FIG. 12b). Action potential firing rates were determined in loose cell attached mode and the recorded data was analyzed using synaptosoft to determine instantaneous frequencies. Ghrelin (50 nM) was applied to the bath over three minutes. The resting membrane potential was stable for up to an hour in cells treated with Krebs alone.

The results of the addition of ghrelin on IPSC frequency of POMC neurons are shown in FIG. 12a. An increase in the frequency of IPSCs in POMC neurons was detected. This is caused by NPY neurons. Thus an increase in the activity of NPY neurons is demonstrated. FIG. 12b shows the effect of ghrelin on the resting membrane potential of POMC neurons. Gherlin hyperpolarized POMC neurons, mean 1.47±0.7 mV; p<0.03. The activity of POMC neurons was decreased by the addition of ghrelin. FIG. 12c shows the action potential firing rate in POMC neurons. The activity of POMC neurons was inhibited by ghrelin. Thus, ghrelin, an agent known to increase feeding, caloric intake, and appetite, and decrease energy expenditure, decreases the resting membrane potential (FIG. 12b) and action potential firing rate of POMC neurons (by 50%, see FIG. 12c), increases the frequency of IPSCs in POMC neurons (FIG. 12a) and increases the activity of NPY neurons.

Example 10

In-vitro Assessment of Fenfluramine, a Known Appetite Suppressant and Weight Loss Agent Slices are of the ARC from POMC-EGFP expressing transgenic mice (Batterham et al., Nature 418:450, 2002) were maintained in (in mM) [NaCl, 126; KCl, 2.5; MgCl$_2$, 1.2; CaCl$_2$.2H$_2$O, 2.4; NaH$_2$PO$_4$.H$_2$O, 1.2; NaHCO$_3$, 21.4; Glucose, 11.1] (Krebs) at 35° C. and saturated with 95% O$_2$ 5% CO$_2$ for 1 hour (hr) prior to recordings. Recordings were made in Krebs at 35° C. Slices were visualized on an Axioskop FS2 plus (Zeiss) through standard infra red optics and using epifluorescence through a endow-GFP filter set (Chroma Technology Corp). Whole cell or loose cell attached recordings (both were used, results from whole cell recordings are shown in FIG. 13b; results from loose cell attached are shown in FIG. 13a) were made from fluorescent neurons using an Axopatch 200B amplifier (Axon Instruments) and Clampex 8 (Axon Instruments).

Figure 13:
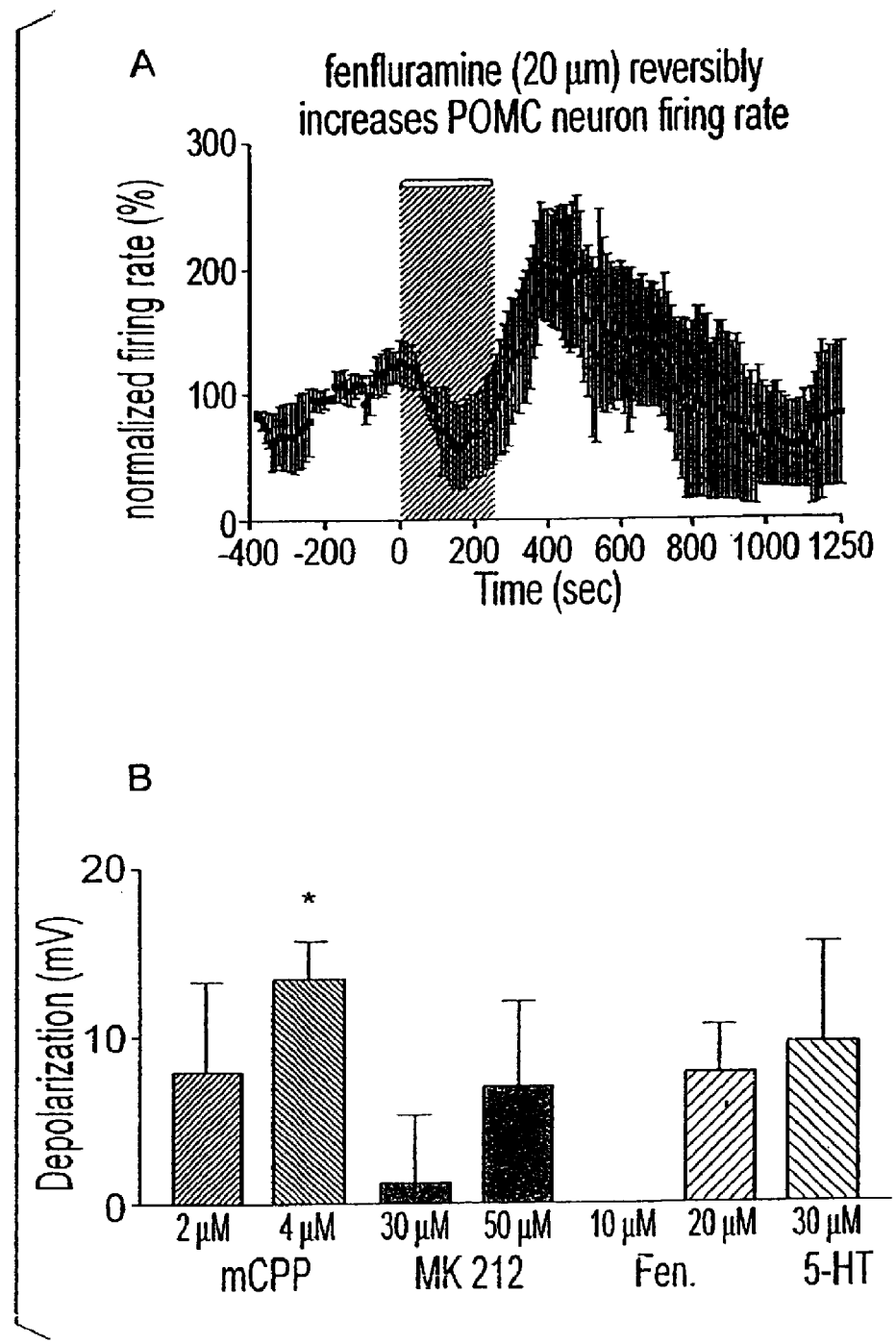
FIG. 13 is a set of graphs demonstrating that fenfluramine (d-FEN) increases the frequency of action potentials and depolarizes POMC neurons.

Action potential firing rates were determined in loose cell attached mode and the recorded data was analyzed using synaptosoft to determine instantaneous frequencies (FIG. 13a). Resting membrane potentials and depolarizations were determined using an event detection protocol on a PowerLab system (AD Instruments, Mountain View, Calif.) to average expanded traces of the membrane potential (FIG. 13b) Serotonin receptor agonists were applied to the bath at the specified concentrations over four minutes. The resting membrane potential was stable for up to an hour in cells treated with Krebs alone.

Fenfluramine (20 μM) caused a two fold increase in the frequency of action potentials in POMC neurons (FIG. 13a; n=3). Thus fenfluramine increased the activity of POMC neurons. In separate experiments Fenfluramine also depolarized POMC neurons (FIG. 13b) in a dose dependent manner. Thus, by another test Fenfluramine increases the activity of POMC neurons. The non-selective serotonin receptor agonist serotonin (5-HT) also increased the resting membrane potential (depolarized) POMC neurons. The effect of serotonin and fenfluramine on POMC neurons is likely mediated by the 5-HT 2C R because 5-HT 2C R selective agonists mCPP and MK 212 also depolarized POMC neurons (FIG. 13b).

It will be apparent that the precise details of the methods or compositions described may be varied or modified without departing from the spirit of the described invention. We claim all such modifications and variations that fall within the scope and spirit of the claims below.

---

The invention claimed is:

1. A method for screening for an agent that affects food intake, comprising
contacting a proopiomelanocortin neuron with an agent to be tested, wherein the proopiomelanocortin neuron is in a histological section of an arcuate nucleus, wherein proopiomelanocortin neurons in the histological section express a heterologous marker that distinguishes the proopiomelanocortin neurons from other cells in the histological section and wherein the agent to be tested is a polypeptide, a cytokine, a small molecule, a peptidomimetic, a chemical compound or an antibody;
assaying for a change in the action potential firing rate and the resting membrane potential of the proopiomelanocortin neuron in the histological section as compared to a control, wherein the control is (a) an action potential firing rate and resting membrane potential of a proopiomelanocortin neuron in the histological section of the arcuate nucleus contacted with buffer in the absence of a test agent or (b) an action potential firing rate and the resting membrane potential of the proopiomelanocortin neuron prior to contacting the histological section with the agent; and
wherein the agent is identified as being correlated with increased food intake when the agent decreases the resting membrane potential of the proopiomelanocortin neuron and decreases the action potential firing rate of the proopiomelanocortin neuron as compared to the control, and wherein the agent is identified as being correlated with decreased food intake when the agent increases the resting membrane potential of the proopiomelanocortin neuron and increases the action potential firing rate of the proopiomelanocortin neuron as compared to the control.

2. The method of claim 1, wherein the agent specifically binds a receptor found on the proopiomelanocortin neuron.

3. The method of claim 1, wherein the agent specifically binds a melanocortin receptor or a μ-opioid receptor on a proopiomelanocortin neuron.

4. The method of claim 3, wherein the agent specifically binds a melanocortin 3 receptor on a proopiomelanocortin neuron.

5. The method of claim 1, wherein the agent specifically binds a leptin receptor on a proopiomelanocortin neuron.

6. The method of claim 5, wherein the agent is an agent which specifically binds the Y2 receptor.

7. The method of claim 1, wherein the heterologous marker is a fluorescent protein.

8. The method of claim 7, wherein the fluorescent protein is green fluorescent protein.

9. The method of claim 1, wherein the assaying for a change in the action potential firing rate and the resting membrane potential of the proopiomelanocortin neuron in the histological section comprises:
obtaining a first whole cell recording from the proopiomelanocortin neuron prior to contacting the histological section with the agent; and
obtaining a second whole cell recording from the proopiomelanocortin neuron after contacting the histological section with the agent; and
comparing the first whole cell recording and the second whole cell recording to assay for the change.

10. The method of claims 1, wherein assaying for a change in the resting membrane potential and the action potential firing rate of the proopiomelanocortin neuron in the histological section comprises:
determining a resting membrane potential and the action potential firing rate of the proopiomelanocortin neuron prior to contacting the histological section with the agent to provide a control value;
determining the resting membrane potential and the action potential firing rate of the propiomelanocoritn neuron after contacting the histological section with the agent to provide a test value; and
measuring the difference between the control value and the test value for each of the action potential firing rate and the resting membrane potential,
wherein a decrease in the test value as compared to the control value for the action potential firing rate and the resting membrane potential indicates that the agent is correlated with increased food intake and wherein an increase in the test value as compared to the control value for the action potential firing rate and the resting membrane potential indicates that the agent is correlated with a decrease in food intake.

11. The method of claim 1, wherein the heterologous marker is expressed from a transgene and the transgene comprises a nucleic acid encoding the heterologous marker operably linked to a proopiomelanocortin regulatory nucleic acid sequence, wherein the proopiomelanocortin regulatory nucleic acid sequence directs expression of the heterologous marker in the arcuate nucleus.

12. The method of claim 1, wherein the assaying for a change in the resting membrane potential and the action potential firing rate of a proopiomelanocortin neuron in the histological section comprises:
obtaining a first loose cell attached patch recording from the proopiomelanocortin neuron prior to contacting the histological section with the agent; and
obtaining a second loose cell attached patch recording from the proopiomelanocortin neuron after contacting the histological section with the agent; and
comparing the first loose cell attached patch recording and the second loose cell attached patch recording to assay for the change in the resting membrane potential and the action potential firing rate.

13. The method of claim 1, wherein assessing the resting membrane potential or the action potential firing rate comprises the use of a whole cell recording.

14. The method of claim 1, wherein a decrease of about 2 to about 50 mV in the resting membrane potential indicates that the agent is correlated with increased food intake, and wherein an increase of about 2 to about 50 mV in the resting membrane potential indicates that the agent is correlated with decreased food intake.

15. The method of claim 1, wherein at least a one-fold decrease in the action potential firing rate indicates the agent in correlated with increased food intake, and wherein at least a one fold increase in the action potential firing rate indicates that the agent is correlated with decreased food intake.

* * * * *

SEQUENCE LISTING

```
<160> NUMBER OF SEQ ID NOS: 352

<210> SEQ ID NO 1
<211> LENGTH: 36
<212> TYPE: PRT
<213> ORGANISM: Homo sapiens

<400> SEQUENCE: 1

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 2
<211> LENGTH: 36
<212> TYPE: PRT
<213> ORGANISM: Homo sapiens

<400> SEQUENCE: 2

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 3
<211> LENGTH: 36
<212> TYPE: PRT
<213> ORGANISM: Homo sapiens

<400> SEQUENCE: 3

Ala Ser Leu Glu Pro Glu Tyr Pro Gly Asp Asn Ala Thr Pro Glu Gln
1               5                   10                  15
```

Met Ala Gln Tyr Ala Ala Glu Leu Arg Arg Tyr Ile Asn Met Leu Thr
                20                  25                  30

Arg Pro Arg Tyr
        35

<210> SEQ ID NO 4
<211> LENGTH: 3
<212> TYPE: PRT
<213> ORGANISM: Homo sapiens

<400> SEQUENCE: 4

Ala Ala Ala
1

<210> SEQ ID NO 5
<211> LENGTH: 36
<212> TYPE: PRT
<213> ORGANISM: Rattus sp.

<400> SEQUENCE: 5

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
                20                  25                  30

Arg Gln Arg Tyr
        35

<210> SEQ ID NO 6
<211> LENGTH: 36
<212> TYPE: PRT
<213> ORGANISM: Sus sp.

<400> SEQUENCE: 6

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
                20                  25                  30

Arg Gln Arg Tyr
        35

<210> SEQ ID NO 7
<211> LENGTH: 36
<212> TYPE: PRT
<213> ORGANISM: Cavia porcellus

<400> SEQUENCE: 7

Tyr Pro Ser Lys Pro Glu Ala Pro Gly Ser Asp Ala Ser Pro Glu Glu
1               5                   10                  15

Leu Ala Arg Tyr Tyr Ala Ser Leu Arg His Tyr Leu Asn Leu Val Thr
                20                  25                  30

Arg Gln Arg Tyr
        35

<210> SEQ ID NO 8
<211> LENGTH: 36
<212> TYPE: PRT
<213> ORGANISM: Rana sp.

<400> SEQUENCE: 8

Tyr Pro Pro Lys Pro Glu Asn Pro Gly Glu Asp Ala Ser Pro Glu Glu
1               5                   10                  15

Met Thr Lys Tyr Leu Thr Ala Leu Arg His Tyr Ile Asn Leu Val Thr

```
                    20                  25                  30

Arg Gln Arg Tyr
        35

<210> SEQ ID NO 9
<211> LENGTH: 36
<212> TYPE: PRT
<213> ORGANISM: Raja sp.

<400> SEQUENCE: 9

Tyr Pro Pro Lys Pro Glu Asn Pro Gly Asp Ala Ala Pro Glu Glu
1               5                   10                  15

Leu Ala Lys Tyr Tyr Ser Ala Leu Arg His Tyr Ile Asn Leu Ile Thr
                20                  25                  30

Arg Gln Arg Tyr
        35

<210> SEQ ID NO 10
<211> LENGTH: 36
<212> TYPE: PRT
<213> ORGANISM: Dogfish sp.

<400> SEQUENCE: 10

Tyr Pro Pro Lys Pro Glu Asn Pro Gly Glu Asp Ala Pro Glu Glu
1               5                   10                  15

Leu Ala Lys Tyr Tyr Ser Ala Leu Arg His Tyr Ile Asn Leu Ile Thr
                20                  25                  30

Arg Gln Arg Tyr
        35

<210> SEQ ID NO 11
<211> LENGTH: 36
<212> TYPE: PRT
<213> ORGANISM: Lampetra sp.

<400> SEQUENCE: 11

Phe Pro Pro Lys Pro Asp Asn Pro Gly Asp Asn Ala Ser Pro Glu Gln
1               5                   10                  15

Met Ala Arg Tyr Lys Ala Ala Val Arg His Tyr Ile Asn Leu Ile Thr
                20                  25                  30

Arg Gln Arg Tyr
        35

<210> SEQ ID NO 12
<211> LENGTH: 36
<212> TYPE: PRT
<213> ORGANISM: Petromyzontidae gen. sp.

<400> SEQUENCE: 12

Met Pro Pro Lys Pro Asp Asn Pro Ser Pro Asp Ala Ser Pro Glu Glu
1               5                   10                  15

Leu Ser Lys Tyr Met Leu Ala Val Arg Asn Tyr Ile Asn Leu Ile Thr
                20                  25                  30

Arg Gln Arg Tyr
        35

<210> SEQ ID NO 13
<211> LENGTH: 36
<212> TYPE: PRT
<213> ORGANISM: Rattus sp.

<400> SEQUENCE: 13
```

```
Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 14
<211> LENGTH: 36
<212> TYPE: PRT
<213> ORGANISM: Oryctolagus cuniculus

<400> SEQUENCE: 14

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 15
<211> LENGTH: 36
<212> TYPE: PRT
<213> ORGANISM: Canis familiaris

<400> SEQUENCE: 15

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 16
<211> LENGTH: 36
<212> TYPE: PRT
<213> ORGANISM: Sus sp.

<400> SEQUENCE: 16

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
            35

<210> SEQ ID NO 17
<211> LENGTH: 36
<212> TYPE: PRT
<213> ORGANISM: Bos taurus

<400> SEQUENCE: 17

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
            35

<210> SEQ ID NO 18
```

```
<211> LENGTH: 36
<212> TYPE: PRT
<213> ORGANISM: Ovis aries

<400> SEQUENCE: 18

Tyr Pro Ser Lys Pro Asp Asn Pro Gly Asp Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
            35

<210> SEQ ID NO 19
<211> LENGTH: 36
<212> TYPE: PRT
<213> ORGANISM: Cavia porcellus

<400> SEQUENCE: 19

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 20
<211> LENGTH: 36
<212> TYPE: PRT
<213> ORGANISM: Avian

<400> SEQUENCE: 20

Tyr Pro Ser Lys Pro Asp Ser Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 21
<211> LENGTH: 36
<212> TYPE: PRT
<213> ORGANISM: Rana sp.

<400> SEQUENCE: 21

Tyr Pro Ser Lys Pro Asp Asn Pro Gly Glu Asp Ala Pro Ala Glu Asp
1               5                   10                  15

Met Ala Lys Tyr Tyr Ser Ala Leu Arg His Tyr Ile Asn Leu Ile Thr
            20                  25                  30

Arg Gln Arg Tyr
            35

<210> SEQ ID NO 22
<211> LENGTH: 36
<212> TYPE: PRT
<213> ORGANISM: Carassius auratus

<400> SEQUENCE: 22

Tyr Pro Thr Lys Pro Asp Asn Pro Gly Glu Gly Ala Pro Ala Glu Glu
1               5                   10                  15

Leu Ala Lys Tyr Tyr Ser Ala Leu Arg His Tyr Ile Asn Leu Ile Thr
            20                  25                  30
```

```
Arg Gln Arg Tyr
        35

<210> SEQ ID NO 23
<211> LENGTH: 36
<212> TYPE: PRT
<213> ORGANISM: Dogfish sp.

<400> SEQUENCE: 23

Tyr Pro Ser Lys Pro Asp Asn Pro Gly Glu Gly Ala Pro Ala Glu Asp
1               5                   10                  15

Leu Ala Lys Tyr Tyr Ser Ala Leu Arg His Tyr Ile Asn Leu Ile Thr
            20                  25                  30

Arg Gln Arg Tyr
        35

<210> SEQ ID NO 24
<211> LENGTH: 36
<212> TYPE: PRT
<213> ORGANISM: Lampetra sp.

<400> SEQUENCE: 24

Pro Pro Asn Lys Pro Asp Ser Pro Gly Glu Asp Ala Pro Ala Glu Asp
1               5                   10                  15

Leu Ala Arg Tyr Leu Ser Ala Val Arg His Tyr Ile Asn Leu Ile Thr
            20                  25                  30

Arg Gln Arg Tyr
        35

<210> SEQ ID NO 25
<211> LENGTH: 36
<212> TYPE: PRT
<213> ORGANISM: Ovis aries

<400> SEQUENCE: 25

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 26
<211> LENGTH: 36
<212> TYPE: PRT
<213> ORGANISM: Sus sp.

<400> SEQUENCE: 26

Ala Pro Leu Glu Pro Val Tyr Pro Gly Asp Asp Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 27
<211> LENGTH: 36
<212> TYPE: PRT
<213> ORGANISM: Canis familiaris

<400> SEQUENCE: 27

Ala Pro Leu Glu Pro Val Tyr Pro Gly Asp Asp Ala Thr Pro Glu Gln
```

```
                 1               5                  10                 15
Met Ala Gln Tyr Ala Ala Glu Leu Arg Arg Tyr Ile Asn Met Leu Thr
                20                  25                 30

Arg Pro Arg Tyr
        35

<210> SEQ ID NO 28
<211> LENGTH: 36
<212> TYPE: PRT
<213> ORGANISM: Felis catus

<400> SEQUENCE: 28

Ala Pro Leu Glu Pro Val Tyr Pro Gly Asp Asn Ala Thr Pro Glu Gln
 1               5                  10                 15

Met Ala Gln Tyr Ala Ala Glu Leu Arg Arg Tyr Ile Asn Met Leu Thr
                20                  25                 30

Arg Pro Arg Tyr
        35

<210> SEQ ID NO 29
<211> LENGTH: 36
<212> TYPE: PRT
<213> ORGANISM: Bos taurus

<400> SEQUENCE: 29

Ala Pro Leu Glu Pro Glu Tyr Pro Gly Asp Asn Ala Thr Pro Glu Gln
 1               5                  10                 15

Met Ala Gln Tyr Ala Ala Glu Leu Arg Arg Tyr Ile Asn Met Leu Thr
                20                  25                 30

Arg Pro Arg Tyr
        35

<210> SEQ ID NO 30
<211> LENGTH: 36
<212> TYPE: PRT
<213> ORGANISM: Rattus sp.

<400> SEQUENCE: 30

Ala Pro Leu Glu Pro Met Tyr Pro Gly Asp Tyr Ala Thr His Glu Gln
 1               5                  10                 15

Arg Ala Gln Tyr Glu Thr Gln Leu Arg Arg Tyr Ile Asn Thr Leu Thr
                20                  25                 30

Arg Pro Arg Tyr
        35

<210> SEQ ID NO 31
<211> LENGTH: 36
<212> TYPE: PRT
<213> ORGANISM: Mus musculus

<400> SEQUENCE: 31

Ala Pro Leu Glu Pro Met Tyr Pro Gly Asp Tyr Ala Thr Pro Glu Gln
 1               5                  10                 15

Met Ala Gln Tyr Glu Thr Gln Leu Arg Arg Tyr Ile Asn Thr Leu Thr
                20                  25                 30

Arg Pro Arg Tyr
        35

<210> SEQ ID NO 32
<211> LENGTH: 37
<212> TYPE: PRT
```

<213> ORGANISM: Cavia porcellus

<400> SEQUENCE: 32

Ala Pro Leu Glu Pro Val Tyr Pro Gly Asp Asn Ala Thr Pro Glu Gln
1               5                   10                  15
Gln Met Ala Gln Tyr Ala Ala Glu Met Arg Arg Tyr Ile Asn Met Leu
            20                  25                  30
Thr Arg Pro Arg Tyr
        35

<210> SEQ ID NO 33
<211> LENGTH: 36
<212> TYPE: PRT
<213> ORGANISM: Gallus gallus

<400> SEQUENCE: 33

Gly Pro Ser Gln Pro Thr Tyr Pro Gly Asp Asp Ala Pro Val Glu Asp
1               5                   10                  15
Leu Ile Arg Phe Tyr Asn Asp Leu Gln Gln Tyr Leu Asn Val Val Thr
            20                  25                  30
Arg His Arg Tyr
        35

<210> SEQ ID NO 34
<211> LENGTH: 36
<212> TYPE: PRT
<213> ORGANISM: Alligator sp.

<400> SEQUENCE: 34

Thr Pro Leu Gln Pro Lys Tyr Pro Gly Asp Gly Ala Pro Val Glu Asp
1               5                   10                  15
Leu Ile Gln Phe Tyr Asn Asp Leu Gln Gln Tyr Leu Asn Val Val Thr
            20                  25                  30
Arg Pro Arg Phe
        35

<210> SEQ ID NO 35
<211> LENGTH: 36
<212> TYPE: PRT
<213> ORGANISM: Rana catesbeiana

<400> SEQUENCE: 35

Ala Pro Ser Glu Pro His His Pro Gly Asp Gln Ala Thr Pro Asp Gln
1               5                   10                  15
Leu Ala Gln Tyr Tyr Ser Asp Leu Tyr Gln Tyr Ile Thr Phe Ile Thr
            20                  25                  30
Arg Pro Arg Phe
        35

<210> SEQ ID NO 36
<211> LENGTH: 12
<212> TYPE: PRT
<213> ORGANISM: Artificial Sequence
<220> FEATURE:
<223> OTHER INFORMATION: Polypeptide variation

<400> SEQUENCE: 36

Lys His Tyr Leu Asn Leu Val Thr Arg Gln Arg Tyr
1               5                   10

<210> SEQ ID NO 37
<211> LENGTH: 12

```
<212> TYPE: PRT
<213> ORGANISM: Artificial Sequence
<220> FEATURE:
<223> OTHER INFORMATION: Polypeptide variation

<400> SEQUENCE: 37

Arg His Thr Leu Asn Leu Val Thr Arg Gln Arg Tyr
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: Polypeptide variation

<400> SEQUENCE: 38

Arg His Phe Leu Asn Leu Val Thr Arg Gln Arg Tyr
 1               5                  10

<210> SEQ ID NO 39
<211> LENGTH: 12
<212> TYPE: PRT
<213> ORGANISM: Artificial Sequence
<220> FEATURE:
<223> OTHER INFORMATION: Polypeptide variation

<400> SEQUENCE: 39

Arg His Tyr Ile Asn Leu Val Thr Arg Gln Arg Tyr
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: Polypeptide variation

<400> SEQUENCE: 40

Arg His Tyr Val Asn Leu Val Thr Arg Gln Arg Tyr
 1               5                  10

<210> SEQ ID NO 41
<211> LENGTH: 12
<212> TYPE: PRT
<213> ORGANISM: Artificial Sequence
<220> FEATURE:
<223> OTHER INFORMATION: Polypeptide variation

<400> SEQUENCE: 41

Arg His Tyr Leu Gln Leu Val Thr Arg Gln Arg Tyr
 1               5                  10

<210> SEQ ID NO 42
<211> LENGTH: 12
<212> TYPE: PRT
<213> ORGANISM: Artificial Sequence
<220> FEATURE:
<223> OTHER INFORMATION: Polypeptide variation

<400> SEQUENCE: 42

Arg His Tyr Leu Asn Ile Val Thr Arg Gln Arg Tyr
 1               5                  10

<210> SEQ ID NO 43
<211> LENGTH: 12
<212> TYPE: PRT
<213> ORGANISM: Artificial Sequence
```

```
<220> FEATURE:
<223> OTHER INFORMATION: Polypeptide variation

<400> SEQUENCE: 43

Arg His Tyr Leu Asn Val Val Thr Arg Gln Arg Tyr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Polypeptide variation

<400> SEQUENCE: 44

Arg His Tyr Leu Asn Leu Ile Thr Arg Gln Arg Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Polypeptide variation

<400> SEQUENCE: 45

Arg His Tyr Leu Asn Leu Leu Thr Arg Gln Arg Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Polypeptide variation

<400> SEQUENCE: 46

Arg His Tyr Leu Asn Leu Val Ser Arg Gln Arg Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Polypeptide variation

<400> SEQUENCE: 47

Arg His Tyr Leu Asn Leu Val Thr Lys Gln Arg Tyr
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Polypeptide variation

<400> SEQUENCE: 48

Arg His Tyr Leu Asn Leu Val Thr Arg Asn Arg Tyr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Polypeptide variation
```

```
<400> SEQUENCE: 49

Arg His Tyr Leu Asn Leu Val Thr Arg Gln Lys Tyr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Polypeptide variation

<400> SEQUENCE: 50

Arg His Tyr Leu Asn Leu Val Thr Arg Gln Arg Thr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Polypeptide variation

<400> SEQUENCE: 51

Arg His Tyr Leu Asn Leu Val Thr Arg Gln Arg Phe
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Polypeptide variation

<400> SEQUENCE: 52

Lys His Thr Leu Asn Leu Val Thr Arg Gln Arg Tyr
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Polypeptide variation

<400> SEQUENCE: 53

Lys His Phe Leu Asn Leu Val Thr Arg Gln Arg Tyr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Polypeptide variation

<400> SEQUENCE: 54

Lys His Tyr Ile Asn Leu Val Thr Arg Gln Arg Tyr
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Polypeptide variation

<400> SEQUENCE: 55
```

Lys His Tyr Val Asn Leu Val Thr Arg Gln Arg Tyr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Polypeptide variation

<400> SEQUENCE: 56

Lys His Tyr Leu Gln Leu Val Thr Arg Gln Arg Tyr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Polypeptide variation

<400> SEQUENCE: 57

Lys His Tyr Leu Asn Ile Val Thr Arg Gln Arg Tyr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Polypeptide variation

<400> SEQUENCE: 58

Lys His Tyr Leu Asn Val Val Thr Arg Gln Arg Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Polypeptide variation

<400> SEQUENCE: 59

Lys His Tyr Leu Asn Leu Ile Thr Arg Gln Arg Tyr
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Polypeptide variation

<400> SEQUENCE: 60

Lys His Tyr Leu Asn Leu Leu Thr Arg Gln Arg Tyr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Polypeptide variation

<400> SEQUENCE: 61

Lys His Tyr Leu Asn Leu Val Ser Arg Gln Arg Tyr

```
<210> SEQ ID NO 62
<211> LENGTH: 12
<212> TYPE: PRT
<213> ORGANISM: Artificial Sequence
<220> FEATURE:
<223> OTHER INFORMATION: Polypeptide variation

<400> SEQUENCE: 62

Lys His Tyr Leu Asn Leu Val Thr Lys Gln Arg Tyr
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Polypeptide variation

<400> SEQUENCE: 63

Lys His Tyr Leu Asn Leu Val Thr Arg Asn Arg Tyr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Polypeptide variation

<400> SEQUENCE: 64

Lys His Tyr Leu Asn Leu Val Thr Arg Gln Lys Tyr
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Polypeptide variation

<400> SEQUENCE: 65

Lys His Tyr Leu Asn Leu Val Thr Arg Gln Arg Thr
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Polypeptide variation

<400> SEQUENCE: 66

Lys His Tyr Leu Asn Leu Val Thr Arg Gln Arg Phe
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Polypeptide variation

<400> SEQUENCE: 67

Arg His Thr Ile Asn Leu Val Thr Arg Gln Arg Tyr
1               5                   10
```

<210> SEQ ID NO 68
<211> LENGTH: 12
<212> TYPE: PRT
<213> ORGANISM: Artificial Sequence
<220> FEATURE:
<223> OTHER INFORMATION: Polypeptide variation

<400> SEQUENCE: 68

Arg His Thr Val Asn Leu Val Thr Arg Gln Arg Tyr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Polypeptide variation

<400> SEQUENCE: 69

Arg His Thr Leu Gln Leu Val Thr Arg Gln Arg Tyr
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Polypeptide variation

<400> SEQUENCE: 70

Arg His Thr Leu Asn Ile Val Thr Arg Gln Arg Tyr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Polypeptide variation

<400> SEQUENCE: 71

Arg His Thr Leu Asn Val Val Thr Arg Gln Arg Tyr
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Polypeptide variation

<400> SEQUENCE: 72

Arg His Thr Leu Asn Leu Ile Thr Arg Gln Arg Tyr
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Polypeptide variation

<400> SEQUENCE: 73

Arg His Thr Leu Asn Leu Leu Thr Arg Gln Arg Tyr
1               5                   10

<210> SEQ ID NO 74

```
<211> LENGTH: 12
<212> TYPE: PRT
<213> ORGANISM: Artificial Sequence
<220> FEATURE:
<223> OTHER INFORMATION: Polypeptide variation

<400> SEQUENCE: 74

Arg His Thr Leu Asn Leu Val Ser Arg Gln Arg Tyr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Polypeptide variation

<400> SEQUENCE: 75

Arg His Thr Leu Asn Leu Val Thr Lys Gln Arg Tyr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Polypeptide variation

<400> SEQUENCE: 76

Arg His Thr Leu Asn Leu Val Thr Arg Asn Arg Tyr
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Polypeptide variation

<400> SEQUENCE: 77

Arg His Thr Leu Asn Leu Val Thr Arg Gln Lys Tyr
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Polypeptide variation

<400> SEQUENCE: 78

Arg His Thr Leu Asn Leu Val Thr Arg Gln Arg Thr
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Polypeptide variation

<400> SEQUENCE: 79

Arg His Thr Leu Asn Leu Val Thr Arg Gln Arg Phe
1               5                   10

<210> SEQ ID NO 80
<211> LENGTH: 12
<212> TYPE: PRT
```

<213> ORGANISM: Artificial Sequence
<220> FEATURE:
<223> OTHER INFORMATION: Polypeptide variation

<400> SEQUENCE: 80

Arg His Phe Ile Asn Leu Val Thr Arg Gln Arg Tyr
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Polypeptide variation

<400> SEQUENCE: 81

Arg His Phe Val Asn Leu Val Thr Arg Gln Arg Tyr
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Polypeptide variation

<400> SEQUENCE: 82

Arg His Phe Leu Gln Leu Val Thr Arg Gln Arg Tyr
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Polypeptide variation

<400> SEQUENCE: 83

Arg His Phe Leu Asn Ile Val Thr Arg Gln Arg Tyr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Polypeptide variation

<400> SEQUENCE: 84

Arg His Phe Leu Asn Val Val Thr Arg Gln Arg Tyr
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Polypeptide variation

<400> SEQUENCE: 85

Arg His Phe Leu Asn Leu Ile Thr Arg Gln Arg Tyr
1               5                   10

<210> SEQ ID NO 86
<211> LENGTH: 12
<212> TYPE: PRT
<213> ORGANISM: Artificial Sequence
<220> FEATURE:

<223> OTHER INFORMATION: Polypeptide variation

<400> SEQUENCE: 86

Arg His Phe Leu Asn Leu Leu Thr Arg Gln Arg Tyr
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Polypeptide variation

<400> SEQUENCE: 87

Arg His Phe Leu Asn Leu Val Ser Arg Gln Arg Tyr
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Polypeptide variation

<400> SEQUENCE: 88

Arg His Phe Leu Asn Leu Val Thr Lys Gln Arg Tyr
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Polypeptide variation

<400> SEQUENCE: 89

Arg His Phe Leu Asn Leu Val Thr Arg Asn Arg Tyr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Polypeptide variation

<400> SEQUENCE: 90

Arg His Phe Leu Asn Leu Val Thr Arg Gln Lys Tyr
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Polypeptide variation

<400> SEQUENCE: 91

Arg His Phe Leu Asn Leu Val Thr Arg Gln Arg Thr
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Polypeptide variation

```
<400> SEQUENCE: 92

Arg His Phe Leu Asn Leu Val Thr Arg Gln Arg Phe
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Polypeptide variation

<400> SEQUENCE: 93

Arg His Tyr Leu Gln Ile Val Thr Arg Gln Arg Tyr
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Polypeptide variation

<400> SEQUENCE: 94

Arg His Tyr Leu Gln Val Val Thr Arg Gln Arg Tyr
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Polypeptide variation

<400> SEQUENCE: 95

Arg His Tyr Leu Gln Leu Ile Thr Arg Gln Arg Tyr
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Polypeptide variation

<400> SEQUENCE: 96

Arg His Tyr Leu Gln Leu Leu Thr Arg Gln Arg Tyr
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Polypeptide variation

<400> SEQUENCE: 97

Arg His Tyr Leu Gln Leu Val Ser Arg Gln Arg Tyr
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Polypeptide variation

<400> SEQUENCE: 98
```

Arg His Tyr Leu Gln Leu Val Thr Lys Gln Arg Tyr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Polypeptide variation

<400> SEQUENCE: 99

Arg His Tyr Leu Gln Leu Val Thr Arg Asn Arg Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Polypeptide variation

<400> SEQUENCE: 100

Arg His Tyr Leu Gln Leu Val Thr Arg Gln Lys Tyr
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Polypeptide variation

<400> SEQUENCE: 101

Arg His Tyr Leu Gln Leu Val Thr Arg Gln Arg Thr
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Polypeptide variation

<400> SEQUENCE: 102

Arg His Tyr Leu Gln Leu Val Thr Arg Gln Arg Phe
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Polypeptide variation

<400> SEQUENCE: 103

Arg His Tyr Leu Asn Ile Ile Thr Arg Gln Arg Tyr
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Polypeptide variation

<400> SEQUENCE: 104

Arg His Tyr Leu Asn Ile Leu Thr Arg Gln Arg Tyr
1               5                   10

```
<210> SEQ ID NO 105
<211> LENGTH: 12
<212> TYPE: PRT
<213> ORGANISM: Artificial Sequence
<220> FEATURE:
<223> OTHER INFORMATION: Polypeptide variation

<400> SEQUENCE: 105

Arg His Tyr Leu Asn Ile Val Ser Arg Gln Arg Tyr
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Polypeptide variation

<400> SEQUENCE: 106

Arg His Tyr Leu Asn Ile Val Thr Lys Gln Arg Tyr
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Polypeptide variation

<400> SEQUENCE: 107

Arg His Tyr Leu Asn Ile Val Thr Arg Asn Arg Tyr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Polypeptide variation

<400> SEQUENCE: 108

Arg His Tyr Leu Asn Ile Val Thr Arg Gln Lys Tyr
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Polypeptide variation

<400> SEQUENCE: 109

Arg His Tyr Leu Asn Ile Val Thr Arg Gln Arg Thr
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Polypeptide variation

<400> SEQUENCE: 110

Arg His Tyr Leu Asn Ile Val Thr Arg Gln Arg Phe
1               5                   10
```

<210> SEQ ID NO 111
<211> LENGTH: 12
<212> TYPE: PRT
<213> ORGANISM: Artificial Sequence
<220> FEATURE:
<223> OTHER INFORMATION: Polypeptide variation

<400> SEQUENCE: 111

Arg His Tyr Leu Asn Val Ile Thr Arg Gln Arg Tyr
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Polypeptide variation

<400> SEQUENCE: 112

Arg His Tyr Leu Asn Val Leu Thr Arg Gln Arg Tyr
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Polypeptide variation

<400> SEQUENCE: 113

Arg His Tyr Leu Asn Val Val Ser Arg Gln Arg Tyr
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Polypeptide variation

<400> SEQUENCE: 114

Arg His Tyr Leu Asn Val Val Thr Lys Gln Arg Tyr
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Polypeptide variation

<400> SEQUENCE: 115

Arg His Tyr Leu Asn Val Val Thr Arg Asn Arg Tyr
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Polypeptide variation

<400> SEQUENCE: 116

Arg His Tyr Leu Asn Val Val Thr Arg Gln Lys Tyr
1               5                   10

<210> SEQ ID NO 117
<211> LENGTH: 12

```
<212> TYPE: PRT
<213> ORGANISM: Artificial Sequence
<220> FEATURE:
<223> OTHER INFORMATION: Polypeptide variation

<400> SEQUENCE: 117

Arg His Tyr Leu Asn Val Val Thr Arg Gln Arg Thr
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Polypeptide variation

<400> SEQUENCE: 118

Arg His Tyr Leu Asn Val Val Thr Arg Gln Arg Phe
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Polypeptide variation

<400> SEQUENCE: 119

Arg His Tyr Leu Asn Leu Ile Ser Arg Gln Arg Tyr
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Polypeptide variation

<400> SEQUENCE: 120

Arg His Tyr Leu Asn Leu Ile Thr Lys Gln Arg Tyr
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Polypeptide variation

<400> SEQUENCE: 121

Arg His Tyr Leu Asn Leu Ile Thr Arg Asn Arg Tyr
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Polypeptide variation

<400> SEQUENCE: 122

Arg His Tyr Leu Asn Leu Ile Thr Arg Gln Lys Tyr
1               5                   10

<210> SEQ ID NO 123
<211> LENGTH: 12
<212> TYPE: PRT
<213> ORGANISM: Artificial Sequence
```

```
<220> FEATURE:
<223> OTHER INFORMATION: Polypeptide variation

<400> SEQUENCE: 123

Arg His Tyr Leu Asn Leu Ile Thr Arg Gln Arg Thr
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Polypeptide variation

<400> SEQUENCE: 124

Arg His Tyr Leu Asn Leu Ile Thr Arg Gln Arg Phe
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Polypeptide variation

<400> SEQUENCE: 125

Arg His Tyr Leu Asn Leu Leu Ser Arg Gln Arg Tyr
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Polypeptide variation

<400> SEQUENCE: 126

Arg His Tyr Leu Asn Leu Leu Thr Lys Gln Arg Tyr
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Polypeptide variation

<400> SEQUENCE: 127

Arg His Tyr Leu Asn Leu Leu Thr Arg Asn Arg Tyr
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Polypeptide variation

<400> SEQUENCE: 128

Arg His Tyr Leu Asn Leu Leu Thr Arg Gln Lys Tyr
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Polypeptide variation
```

```
<400> SEQUENCE: 129

Arg His Tyr Leu Asn Leu Leu Thr Arg Gln Arg Thr
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Polypeptide variation

<400> SEQUENCE: 130

Arg His Tyr Leu Asn Leu Leu Thr Arg Gln Arg Phe
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Polypeptide variation

<400> SEQUENCE: 131

Arg His Tyr Leu Asn Leu Val Ser Lys Gln Arg Tyr
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Polypeptide variation

<400> SEQUENCE: 132

Arg His Tyr Leu Asn Leu Val Ser Arg Asn Arg Tyr
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Polypeptide variation

<400> SEQUENCE: 133

Arg His Tyr Leu Asn Leu Val Ser Arg Gln Lys Tyr
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Polypeptide variation

<400> SEQUENCE: 134

Arg His Tyr Leu Asn Leu Val Ser Arg Gln Arg Thr
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Polypeptide variation

<400> SEQUENCE: 135
```

```
Arg His Tyr Leu Asn Leu Val Ser Arg Gln Arg Tyr
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Polypeptide variation

<400> SEQUENCE: 136

Arg His Tyr Leu Asn Leu Val Thr Lys Asn Arg Tyr
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Polypeptide variation

<400> SEQUENCE: 137

Arg His Tyr Leu Asn Leu Val Thr Lys Gln Lys Tyr
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Polypeptide variation

<400> SEQUENCE: 138

Arg His Tyr Leu Asn Leu Val Thr Lys Gln Arg Thr
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Polypeptide variation

<400> SEQUENCE: 139

Arg His Tyr Leu Asn Leu Val Thr Lys Gln Arg Phe
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Polypeptide variation

<400> SEQUENCE: 140

Arg His Tyr Leu Asn Leu Val Thr Arg Asn Lys Tyr
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Polypeptide variation

<400> SEQUENCE: 141

Arg His Tyr Leu Asn Leu Val Thr Arg Asn Arg Thr
```

```
<210> SEQ ID NO 142
<211> LENGTH: 12
<212> TYPE: PRT
<213> ORGANISM: Artificial Sequence
<220> FEATURE:
<223> OTHER INFORMATION: Polypeptide variation

<400> SEQUENCE: 142

Arg His Tyr Leu Asn Leu Val Thr Arg Asn Arg Phe
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Polypeptide variation

<400> SEQUENCE: 143

Arg His Tyr Leu Asn Leu Val Thr Arg Gln Lys Thr
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Polypeptide variation

<400> SEQUENCE: 144

Arg His Tyr Leu Asn Leu Val Thr Arg Gln Lys Phe
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Polypeptide variation

<400> SEQUENCE: 145

Leu Arg His Tyr Leu Asn Leu Val Thr Arg Gln Arg Tyr
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Polypeptide variation

<400> SEQUENCE: 146

Ile Arg His Tyr Leu Asn Leu Val Thr Arg Gln Arg Tyr
1               5                   10

<210> SEQ ID NO 147
<211> LENGTH: 13
<212> TYPE: PRT
<213> ORGANISM: Artificial Sequence
<220> FEATURE:
<223> OTHER INFORMATION: Polypeptide variation

<400> SEQUENCE: 147

Val Arg His Tyr Leu Asn Leu Val Thr Arg Gln Arg Tyr
1               5                   10
```

```
<210> SEQ ID NO 148
<211> LENGTH: 14
<212> TYPE: PRT
<213> ORGANISM: Artificial Sequence
<220> FEATURE:
<223> OTHER INFORMATION: Polypeptide variation

<400> SEQUENCE: 148

Ser Leu Arg His Tyr Leu Asn Leu Val Thr Arg Gln Arg Tyr
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Polypeptide variation

<400> SEQUENCE: 149

Thr Leu Arg His Tyr Leu Asn Leu Val Thr Arg Gln Arg Tyr
1               5                   10

<210> SEQ ID NO 150
<211> LENGTH: 15
<212> TYPE: PRT
<213> ORGANISM: Artificial Sequence
<220> FEATURE:
<223> OTHER INFORMATION: Polypeptide variation

<400> SEQUENCE: 150

Ala Ser Leu Arg His Tyr Leu Asn Leu Val Thr Arg Gln Arg Tyr
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Polypeptide variation

<400> SEQUENCE: 151

Ser Ser Leu Arg His Tyr Leu Asn Leu Val Thr Arg Gln Arg Tyr
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Polypeptide variation

<400> SEQUENCE: 152

Tyr Ala Ser Leu Arg His Tyr Leu Asn Leu Val Thr Arg Gln Arg Tyr
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Polypeptide variation

<400> SEQUENCE: 153

Thr Ala Ser Leu Arg His Tyr Leu Asn Leu Val Thr Arg Gln Arg Tyr
1               5                   10                  15

<210> SEQ ID NO 154
```

```
<211> LENGTH: 16
<212> TYPE: PRT
<213> ORGANISM: Artificial Sequence
<220> FEATURE:
<223> OTHER INFORMATION: Polypeptide variation

<400> SEQUENCE: 154

Phe Ala Ser Leu Arg His Tyr Leu Asn Leu Val Thr Arg Gln Arg Tyr
1               5                   10                  15

<210> SEQ ID NO 155
<211> LENGTH: 17
<212> TYPE: PRT
<213> ORGANISM: Artificial Sequence
<220> FEATURE:
<223> OTHER INFORMATION: Polypeptide variation

<400> SEQUENCE: 155

Tyr Tyr Ala Ser Leu Arg His Tyr Leu Asn Leu Val Thr Arg Gln Arg
1               5                   10                  15

Tyr

<210> SEQ ID NO 156
<211> LENGTH: 17
<212> TYPE: PRT
<213> ORGANISM: Artificial Sequence
<220> FEATURE:
<223> OTHER INFORMATION: Polypeptide variation

<400> SEQUENCE: 156

Thr Tyr Ala Ser Leu Arg His Tyr Leu Asn Leu Val Thr Arg Gln Arg
1               5                   10                  15

Tyr

<210> SEQ ID NO 157
<211> LENGTH: 17
<212> TYPE: PRT
<213> ORGANISM: Artificial Sequence
<220> FEATURE:
<223> OTHER INFORMATION: Polypeptide variation

<400> SEQUENCE: 157

Phe Tyr Ala Ser Leu Arg His Tyr Leu Asn Leu Val Thr Arg Gln Arg
1               5                   10                  15

Tyr

<210> SEQ ID NO 158
<211> LENGTH: 18
<212> TYPE: PRT
<213> ORGANISM: Artificial Sequence
<220> FEATURE:
<223> OTHER INFORMATION: Polypeptide variation

<400> SEQUENCE: 158

Arg Tyr Tyr Ala Ser Leu Arg His Tyr Leu Asn Leu Val Thr Arg Gln
1               5                   10                  15

Arg Tyr

<210> SEQ ID NO 159
<211> LENGTH: 18
<212> TYPE: PRT
<213> ORGANISM: Artificial Sequence
<220> FEATURE:
<223> OTHER INFORMATION: Polypeptide variation

<400> SEQUENCE: 159
```

Lys Tyr Tyr Ala Ser Leu Arg His Tyr Leu Asn Leu Val Thr Arg Gln
1               5                   10                  15

Arg Tyr

<210> SEQ ID NO 160
<211> LENGTH: 19
<212> TYPE: PRT
<213> ORGANISM: Artificial Sequence
<220> FEATURE:
<223> OTHER INFORMATION: Polypeptide variation

<400> SEQUENCE: 160

Asn Arg Tyr Tyr Ala Ser Leu Arg His Tyr Leu Asn Leu Val Thr Arg
1               5                   10                  15

Gln Arg Tyr

<210> SEQ ID NO 161
<211> LENGTH: 19
<212> TYPE: PRT
<213> ORGANISM: Artificial Sequence
<220> FEATURE:
<223> OTHER INFORMATION: Polypeptide variation

<400> SEQUENCE: 161

Gln Arg Tyr Tyr Ala Ser Leu Arg His Tyr Leu Asn Leu Val Thr Arg
1               5                   10                  15

Gln Arg Tyr

<210> SEQ ID NO 162
<211> LENGTH: 20
<212> TYPE: PRT
<213> ORGANISM: Artificial Sequence
<220> FEATURE:
<223> OTHER INFORMATION: Polypeptide variation

<400> SEQUENCE: 162

Leu Asn Arg Tyr Tyr Ala Ser Leu Arg His Tyr Leu Asn Leu Val Thr
1               5                   10                  15

Arg Gln Arg Tyr
            20

<210> SEQ ID NO 163
<211> LENGTH: 20
<212> TYPE: PRT
<213> ORGANISM: Artificial Sequence
<220> FEATURE:
<223> OTHER INFORMATION: Polypeptide variation

<400> SEQUENCE: 163

Ile Asn Arg Tyr Tyr Ala Ser Leu Arg His Tyr Leu Asn Leu Val Thr
1               5                   10                  15

Arg Gln Arg Tyr
            20

<210> SEQ ID NO 164
<211> LENGTH: 20
<212> TYPE: PRT
<213> ORGANISM: Artificial Sequence
<220> FEATURE:
<223> OTHER INFORMATION: Polypeptide variation

<400> SEQUENCE: 164

Val Asn Arg Tyr Tyr Ala Ser Leu Arg His Tyr Leu Asn Leu Val Thr
1               5                   10                  15

Arg Gln Arg Tyr
            20

<210> SEQ ID NO 165
<211> LENGTH: 21
<212> TYPE: PRT
<213> ORGANISM: Artificial Sequence
<220> FEATURE:
<223> OTHER INFORMATION: Polypeptide variation

<400> SEQUENCE: 165

Glu Leu Asn Arg Tyr Tyr Ala Ser Leu Arg His Tyr Leu Asn Leu Val
1               5                   10                  15

Thr Arg Gln Arg Tyr
            20

<210> SEQ ID NO 166
<211> LENGTH: 21
<212> TYPE: PRT
<213> ORGANISM: Artificial Sequence
<220> FEATURE:
<223> OTHER INFORMATION: Polypeptide variation

<400> SEQUENCE: 166

Asp Leu Asn Arg Tyr Tyr Ala Ser Leu Arg His Tyr Leu Asn Leu Val
1               5                   10                  15

Thr Arg Gln Arg Tyr
            20

<210> SEQ ID NO 167
<211> LENGTH: 22
<212> TYPE: PRT
<213> ORGANISM: Artificial Sequence
<220> FEATURE:
<223> OTHER INFORMATION: Polypeptide variation

<400> SEQUENCE: 167

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 168
<211> LENGTH: 22
<212> TYPE: PRT
<213> ORGANISM: Artificial Sequence
<220> FEATURE:
<223> OTHER INFORMATION: Polypeptide variation

<400> SEQUENCE: 168

Asp Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 169
<211> LENGTH: 23
<212> TYPE: PRT
<213> ORGANISM: Artificial Sequence
<220> FEATURE:
<223> OTHER INFORMATION: Polypeptide variation

<400> SEQUENCE: 169

Pro Glu Glu Leu Asn Arg Tyr Tyr Ala Ser Leu Arg His Tyr Leu Asn
1               5                   10                  15

Leu Val Thr Arg Gln Arg Tyr
            20

<210> SEQ ID NO 170
<211> LENGTH: 24
<212> TYPE: PRT
<213> ORGANISM: Artificial Sequence
<220> FEATURE:
<223> OTHER INFORMATION: Polypeptide variation

<400> SEQUENCE: 170

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 171
<211> LENGTH: 24
<212> TYPE: PRT
<213> ORGANISM: Artificial Sequence
<220> FEATURE:
<223> OTHER INFORMATION: Polypeptide variation

<400> SEQUENCE: 171

Thr Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 172
<211> LENGTH: 25
<212> TYPE: PRT
<213> ORGANISM: Artificial Sequence
<220> FEATURE:
<223> OTHER INFORMATION: Polypeptide variation

<400> SEQUENCE: 172

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 173
<211> LENGTH: 25
<212> TYPE: PRT
<213> ORGANISM: Artificial Sequence
<220> FEATURE:
<223> OTHER INFORMATION: Polypeptide variation

<400> SEQUENCE: 173

Ser Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 174
<211> LENGTH: 26
<212> TYPE: PRT
<213> ORGANISM: Artificial Sequence
<220> FEATURE:
<223> OTHER INFORMATION: Polypeptide variation

<400> SEQUENCE: 174

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 175
<211> LENGTH: 26
<212> TYPE: PRT
<213> ORGANISM: Artificial Sequence
<220> FEATURE:
<223> OTHER INFORMATION: Polypeptide variation

<400> SEQUENCE: 175

Glu Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 176
<211> LENGTH: 27
<212> TYPE: PRT
<213> ORGANISM: Artificial Sequence
<220> FEATURE:
<223> OTHER INFORMATION: Polypeptide variation

<400> SEQUENCE: 176

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 177
<211> LENGTH: 27
<212> TYPE: PRT
<213> ORGANISM: Artificial Sequence
<220> FEATURE:
<223> OTHER INFORMATION: Polypeptide variation

<400> SEQUENCE: 177

Asp Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 178
<211> LENGTH: 28
<212> TYPE: PRT
<213> ORGANISM: Artificial Sequence
<220> FEATURE:
<223> OTHER INFORMATION: Polypeptide variation

<400> SEQUENCE: 178

Gly Glu Asp Ala Ser Pro Glu Glu Leu Asn Arg Tyr Tyr Ala Ser Leu
1               5                   10                  15

Arg His Tyr Leu Asn Leu Val Thr Arg Gln Arg Tyr
            20                  25

<210> SEQ ID NO 179
<211> LENGTH: 29
<212> TYPE: PRT
<213> ORGANISM: Artificial Sequence
<220> FEATURE:
<223> OTHER INFORMATION: Polypeptide variation

<400> SEQUENCE: 179

Pro Gly Glu Asp Ala Ser Pro Glu Glu Leu Asn Arg Tyr Tyr Ala Ser
1               5                   10                  15

Leu Arg His Tyr Leu Asn Leu Val Thr Arg Gln Arg Tyr
            20                  25

<210> SEQ ID NO 180
<211> LENGTH: 30
<212> TYPE: PRT
<213> ORGANISM: Artificial Sequence
<220> FEATURE:
<223> OTHER INFORMATION: Polypeptide variation

<400> SEQUENCE: 180

Ala Pro Gly Glu Asp Ala Ser Pro Glu Glu Leu Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: Polypeptide variation

<400> SEQUENCE: 181

Ser Pro Gly Glu Asp Ala Ser Pro Glu Glu Leu Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 182
<211> LENGTH: 31
<212> TYPE: PRT
<213> ORGANISM: Artificial Sequence
<220> FEATURE:
<223> OTHER INFORMATION: Polypeptide variation

<400> SEQUENCE: 182

Glu Ala Pro Gly Glu Asp Ala Ser Pro Glu Glu Leu Asn Arg Tyr Tyr
1               5                   10                  15

Ala Ser Leu Arg His Tyr Leu Asn Leu Val Thr Arg Gln Arg Tyr
            20                  25                  30

<210> SEQ ID NO 183
<211> LENGTH: 31
<212> TYPE: PRT
<213> ORGANISM: Artificial Sequence
<220> FEATURE:
<223> OTHER INFORMATION: Polypeptide variation

<400> SEQUENCE: 183

Asp Ala Pro Gly Glu Asp Ala Ser Pro Glu Glu Leu Asn Arg Tyr Tyr
1               5                   10                  15

Ala Ser Leu Arg His Tyr Leu Asn Leu Val Thr Arg Gln Arg Tyr
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: Polypeptide variation

<400> SEQUENCE: 184

Pro Glu Ala Pro Gly Glu Asp Ala Ser Pro Glu Glu Leu Asn Arg Tyr
1               5                   10                  15

Tyr Ala Ser Leu Arg His Tyr Leu Asn Leu Val Thr Arg Gln Arg Tyr
            20                  25                  30

<210> SEQ ID NO 185
<211> LENGTH: 33
<212> TYPE: PRT
<213> ORGANISM: Artificial Sequence
<220> FEATURE:
<223> OTHER INFORMATION: Polypeptide variation

<400> SEQUENCE: 185

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 186
<211> LENGTH: 33
<212> TYPE: PRT
<213> ORGANISM: Artificial Sequence
<220> FEATURE:
<223> OTHER INFORMATION: Polypeptide variation

<400> SEQUENCE: 186

Arg Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 187
<211> LENGTH: 33
<212> TYPE: PRT
<213> ORGANISM: Artificial Sequence
<220> FEATURE:
<223> OTHER INFORMATION: Polypeptide variation

<400> SEQUENCE: 187

Gln Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 188
<211> LENGTH: 33
<212> TYPE: PRT
<213> ORGANISM: Artificial Sequence
<220> FEATURE:
<223> OTHER INFORMATION: Polypeptide variation

<400> SEQUENCE: 188

Asn Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 189
<211> LENGTH: 34
<212> TYPE: PRT

```
<213> ORGANISM: Artificial Sequence
<220> FEATURE:
<223> OTHER INFORMATION: Polypeptide variation

<400> SEQUENCE: 189

Leu Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 190
<211> LENGTH: 34
<212> TYPE: PRT
<213> ORGANISM: Artificial Sequence
<220> FEATURE:
<223> OTHER INFORMATION: Polypeptide variation

<400> SEQUENCE: 190

Val Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 191
<211> LENGTH: 13
<212> TYPE: PRT
<213> ORGANISM: Artificial Sequence
<220> FEATURE:
<223> OTHER INFORMATION: Polypeptide variation

<400> SEQUENCE: 191

Leu Lys His Tyr Leu Asn Leu Val Thr Arg Gln Arg Tyr
1               5                   10

<210> SEQ ID NO 192
<211> LENGTH: 14
<212> TYPE: PRT
<213> ORGANISM: Artificial Sequence
<220> FEATURE:
<223> OTHER INFORMATION: Polypeptide variation

<400> SEQUENCE: 192

Ser Leu Lys His Tyr Leu Asn Leu Val Thr Arg Gln Arg Tyr
1               5                   10

<210> SEQ ID NO 193
<211> LENGTH: 15
<212> TYPE: PRT
<213> ORGANISM: Artificial Sequence
<220> FEATURE:
<223> OTHER INFORMATION: Polypeptide variation

<400> SEQUENCE: 193

Ala Ser Leu Lys His Tyr Leu Asn Leu Val Thr Arg Gln Arg Tyr
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Polypeptide variation

<400> SEQUENCE: 194
```

Tyr Ala Ser Leu Lys His Tyr Leu Asn Leu Val Thr Arg Gln Arg Tyr
1               5                   10                  15

<210> SEQ ID NO 195
<211> LENGTH: 17
<212> TYPE: PRT
<213> ORGANISM: Artificial Sequence
<220> FEATURE:
<223> OTHER INFORMATION: Polypeptide variation

<400> SEQUENCE: 195

Tyr Tyr Ala Ser Leu Lys His Tyr Leu Asn Leu Val Thr Arg Gln Arg
1               5                   10                  15

Tyr

<210> SEQ ID NO 196
<211> LENGTH: 18
<212> TYPE: PRT
<213> ORGANISM: Artificial Sequence
<220> FEATURE:
<223> OTHER INFORMATION: Polypeptide variation

<400> SEQUENCE: 196

Arg Tyr Tyr Ala Ser Leu Lys His Tyr Leu Asn Leu Val Thr Arg Gln
1               5                   10                  15

Arg Tyr

<210> SEQ ID NO 197
<211> LENGTH: 19
<212> TYPE: PRT
<213> ORGANISM: Artificial Sequence
<220> FEATURE:
<223> OTHER INFORMATION: Polypeptide variation

<400> SEQUENCE: 197

Asn Arg Tyr Tyr Ala Ser Leu Lys His Tyr Leu Asn Leu Val Thr Arg
1               5                   10                  15

Gln Arg Tyr

<210> SEQ ID NO 198
<211> LENGTH: 20
<212> TYPE: PRT
<213> ORGANISM: Artificial Sequence
<220> FEATURE:
<223> OTHER INFORMATION: Polypeptide variation

<400> SEQUENCE: 198

Leu Asn Arg Tyr Tyr Ala Ser Leu Lys His Tyr Leu Asn Leu Val Thr
1               5                   10                  15

Arg Gln Arg Tyr
            20

<210> SEQ ID NO 199
<211> LENGTH: 21
<212> TYPE: PRT
<213> ORGANISM: Artificial Sequence
<220> FEATURE:
<223> OTHER INFORMATION: Polypeptide variation

<400> SEQUENCE: 199

Glu Leu Asn Arg Tyr Tyr Ala Ser Leu Lys His Tyr Leu Asn Leu Val
1               5                   10                  15

Thr Arg Gln Arg Tyr
            20

```
<210> SEQ ID NO 200
<211> LENGTH: 22
<212> TYPE: PRT
<213> ORGANISM: Artificial Sequence
<220> FEATURE:
<223> OTHER INFORMATION: Polypeptide variation

<400> SEQUENCE: 200

Glu Glu Leu Asn Arg Tyr Tyr Ala Ser Leu Lys His Tyr Leu Asn Leu
1               5                   10                  15

Val Thr Arg Gln Arg Tyr
            20

<210> SEQ ID NO 201
<211> LENGTH: 23
<212> TYPE: PRT
<213> ORGANISM: Artificial Sequence
<220> FEATURE:
<223> OTHER INFORMATION: Polypeptide variation

<400> SEQUENCE: 201

Pro Glu Glu Leu Asn Arg Tyr Tyr Ala Ser Leu Lys His Tyr Leu Asn
1               5                   10                  15

Leu Val Thr Arg Gln Arg Tyr
            20

<210> SEQ ID NO 202
<211> LENGTH: 23
<212> TYPE: PRT
<213> ORGANISM: Artificial Sequence
<220> FEATURE:
<223> OTHER INFORMATION: Polypeptide variation

<400> SEQUENCE: 202

Ser Glu Glu Leu Asn Arg Tyr Tyr Ala Ser Leu Lys His Tyr Leu Asn
1               5                   10                  15

Leu Val Thr Arg Gln Arg Tyr
            20

<210> SEQ ID NO 203
<211> LENGTH: 24
<212> TYPE: PRT
<213> ORGANISM: Artificial Sequence
<220> FEATURE:
<223> OTHER INFORMATION: Polypeptide variation

<400> SEQUENCE: 203

Ala Ser Glu Glu Leu Asn Arg Tyr Tyr Ala Ser Leu Lys His Tyr Leu
1               5                   10                  15

Asn Leu Val Thr Arg Gln Arg Tyr
            20

<210> SEQ ID NO 204
<211> LENGTH: 25
<212> TYPE: PRT
<213> ORGANISM: Artificial Sequence
<220> FEATURE:
<223> OTHER INFORMATION: Polypeptide variation

<400> SEQUENCE: 204

Asp Ala Ser Glu Glu Leu Asn Arg Tyr Tyr Ala Ser Leu Lys His Tyr
1               5                   10                  15

Leu Asn Leu Val Thr Arg Gln Arg Tyr
            20                  25
```

<210> SEQ ID NO 205
<211> LENGTH: 26
<212> TYPE: PRT
<213> ORGANISM: Artificial Sequence
<220> FEATURE:
<223> OTHER INFORMATION: Polypeptide variation

<400> SEQUENCE: 205

Glu Asp Ala Ser Glu Glu Leu Asn Arg Tyr Tyr Ala Ser Leu Lys His
1               5                   10                  15

Tyr Leu Asn Leu Val Thr Arg Gln Arg Tyr
            20                  25

<210> SEQ ID NO 206
<211> LENGTH: 28
<212> TYPE: PRT
<213> ORGANISM: Artificial Sequence
<220> FEATURE:
<223> OTHER INFORMATION: Polypeptide variation

<400> SEQUENCE: 206

Gly Glu Asp Ala Ser Pro Glu Glu Leu Asn Arg Tyr Tyr Ala Ser Leu
1               5                   10                  15

Lys His Tyr Leu Asn Leu Val Thr Arg Gln Arg Tyr
            20                  25

<210> SEQ ID NO 207
<211> LENGTH: 29
<212> TYPE: PRT
<213> ORGANISM: Artificial Sequence
<220> FEATURE:
<223> OTHER INFORMATION: Polypeptide variation

<400> SEQUENCE: 207

Pro Gly Glu Asp Ala Ser Pro Glu Glu Leu Asn Arg Tyr Tyr Ala Ser
1               5                   10                  15

Leu Lys His Tyr Leu Asn Leu Val Thr Arg Gln Arg Tyr
            20                  25

<210> SEQ ID NO 208
<211> LENGTH: 29
<212> TYPE: PRT
<213> ORGANISM: Artificial Sequence
<220> FEATURE:
<223> OTHER INFORMATION: Polypeptide variation

<400> SEQUENCE: 208

Ala Pro Gly Glu Asp Ala Ser Glu Glu Leu Asn Arg Tyr Tyr Ala Ser
1               5                   10                  15

Leu Lys His Tyr Leu Asn Leu Val Thr Arg Gln Arg Tyr
            20                  25

<210> SEQ ID NO 209
<211> LENGTH: 30
<212> TYPE: PRT
<213> ORGANISM: Artificial Sequence
<220> FEATURE:
<223> OTHER INFORMATION: Polypeptide variation

<400> SEQUENCE: 209

Glu Ala Pro Gly Glu Asp Ala Ser Glu Glu Leu Asn Arg Tyr Tyr Ala
1               5                   10                  15

Ser Leu Lys His Tyr Leu Asn Leu Val Thr Arg Gln Arg Tyr
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: Polypeptide variation

<400> SEQUENCE: 210

Pro Glu Ala Pro Gly Glu Asp Ala Ser Pro Glu Glu Leu Asn Arg Tyr
1               5                   10                  15

Tyr Ala Ser Leu Lys His Tyr Leu Asn Leu Val Thr Arg Gln Arg Tyr
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Polypeptide variation

<400> SEQUENCE: 211

Lys Pro Glu Ala Pro Gly Glu Asp Ala Ser Glu Glu Leu Asn Arg Tyr
1               5                   10                  15

Tyr Ala Ser Leu Lys His Tyr Leu Asn Leu Val Thr Arg Gln Arg Tyr
            20                  25                  30

<210> SEQ ID NO 212
<211> LENGTH: 33
<212> TYPE: PRT
<213> ORGANISM: Artificial Sequence
<220> FEATURE:
<223> OTHER INFORMATION: Polypeptide variation

<400> SEQUENCE: 212

Ile Lys Pro Glu Ala Pro Gly Glu Asp Ala Ser Glu Glu Leu Asn Arg
1               5                   10                  15

Tyr Tyr Ala Ser Leu Lys His Tyr Leu Asn Leu Val Thr Arg Gln Arg
            20                  25                  30

Tyr

<210> SEQ ID NO 213
<211> LENGTH: 13
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: ACETYLATION

<400> SEQUENCE: 213

Leu Arg His Tyr Ile Asn Leu Ile Thr Arg Gln Arg Tyr
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: ACETYLATION -continued

```
<400> SEQUENCE: 214

Leu Arg His Tyr Leu Asn Leu Leu Thr Arg Gln Arg Tyr
1               5                   10

<210> SEQ ID NO 215
<211> LENGTH: 13
<212> TYPE: PRT
<213> ORGANISM: Artificial Sequence
<220> FEATURE:
<223> OTHER INFORMATION: Polypeptide variation

<400> SEQUENCE: 215

Leu Arg His Tyr Leu Asn Leu Leu Thr Arg Gln Arg Tyr
1               5                   10

<210> SEQ ID NO 216
<211> LENGTH: 24
<212> TYPE: PRT
<213> ORGANISM: Artificial Sequence
<220> FEATURE:
<223> OTHER INFORMATION: Polypeptide variation

<400> SEQUENCE: 216

Pro Ala Glu Asp Leu Ala Gln Tyr Ala Ala Glu Leu Arg His Tyr Leu
1               5                   10                  15

Asn Leu Leu Thr Arg Gln Arg Tyr
            20

<210> SEQ ID NO 217
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: H
<220> FEATURE:
<221> NAME/KEY: MOD_RES
<222> LOCATION: (20)..(20)
<223> OTHER INFORMATION: AMIDATION

<400> SEQUENCE: 217

Leu Ala Arg Tyr Tyr Ser Ala Leu Arg His Tyr Ile Asn Leu Ile Thr
1               5                   10                  15

Arg Gln Arg Tyr
            20

<210> SEQ ID NO 218
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 218

Met Ala Arg Tyr Tyr Ser Ala Leu Arg His Tyr Ile Asn Leu Ile Thr
1               5                   10                  15

Arg Gln Arg Tyr
```

```
<210> SEQ ID NO 219
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 219

Ala Arg Tyr Tyr Ser Ala Leu Arg His Phe Ile Asn Leu Ile Thr Arg
1               5                   10                  15

Gln Arg Tyr

<210> SEQ ID NO 220
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is D-Ala
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 220

Xaa Ala Arg Tyr Tyr Ser Ala Leu Arg His Tyr Ile Asn Leu Ile Thr
1               5                   10                  15

Arg Gln Arg Tyr
            20

<210> SEQ ID NO 221
<211> LENGTH: 18
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (18)..(18)
<223> OTHER INFORMATION: AMIDATION

<400> SEQUENCE: 221

Arg Tyr Tyr Ser Ala Leu Arg His Tyr Ile Asn Leu Ile Thr Arg Gln
1               5                   10                  15

Arg Tyr

<210> SEQ ID NO 222
<211> LENGTH: 20
<212> TYPE: PRT
```

-continued

```
<213> ORGANISM: Artificial Sequence
<220> FEATURE:
<223> OTHER INFORMATION: Polypeptide variation
<220> FEATURE:
<221> NAME/KEY: MISC-FEATURE
<222> LOCATION: (1)..(1)
<223> OTHER INFORMATION: Xaa is Nle
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 222

Xaa Ala Arg Tyr Tyr Ser Ala Leu Arg His Tyr Ile Asn Leu Ile Thr
1               5                   10                  15

Arg Gln Arg Tyr
            20

<210> SEQ ID NO 223
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MISC_FEATURE
<222> LOCATION: (1)..(1)
<223> OTHER INFORMATION: Xaa is D-Ser
<220> FEATURE:
<221> NAME/KEY: MOD_RES
<222> LOCATION: (19)..(19)
<223> OTHER INFORMATION: AMIDATION

<400> SEQUENCE: 223

Xaa Arg Tyr Tyr Ser Ala Leu Arg His Tyr Ile Asn Leu Ile Thr Arg
1               5                   10                  15

Gln Arg Tyr

<210> SEQ ID NO 224
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 224

Ala Ala Arg Tyr Ser His Ala Leu Arg His Tyr Ile Asn Leu Ile Thr
1               5                   10                  15

Arg Gln Arg Tyr
            20

<210> SEQ ID NO 225
<211> LENGTH: 19
<212> TYPE: PRT
<213> ORGANISM: Artificial Sequence
```

```
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MISC_FEATURE
<222> LOCATION: (1)..(1)
<223> OTHER INFORMATION: Xaa is D-Ile
<220> FEATURE:
<221> NAME/KEY: MOD_RES
<222> LOCATION: (19)..(19)
<223> OTHER INFORMATION: AMIDATION

<400> SEQUENCE: 225

Xaa Arg Tyr Tyr Ser Ala Leu Arg His Tyr Ile Asn Leu Ile Thr Arg
1               5                   10                  15

Gln Arg Tyr

<210> SEQ ID NO 226
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (20)..(20)
<223> OTHER INFORMATION: AMIDATION
<220> FEATURE:
<221> NAME/KEY: MOD_RES
<222> LOCATION: (1)..(1)
<223> OTHER INFORMATION: ACETYLATION

<400> SEQUENCE: 226

Arg Ala Arg Tyr Tyr Ser Ala Leu Arg His Tyr Ile Asn Leu Ile Thr
1               5                   10                  15

Arg Gln Arg Tyr
            20

<210> SEQ ID NO 227
<211> LENGTH: 18
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (18)..(18)
<223> OTHER INFORMATION: AMIDATION

<400> SEQUENCE: 227

Gln Tyr Tyr Ser Ala Leu Arg His Tyr Ile Asn Leu Ile Thr Arg Gln
1               5                   10                  15

Arg Tyr

<210> SEQ ID NO 228
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
```

```
<220> FEATURE:
<221> NAME/KEY: MOD_RES
<222> LOCATION: (19)..(19)
<223> OTHER INFORMATION: AMIDATION

<400> SEQUENCE: 228

Ala Arg Phe Tyr Ser Ala Leu Arg His Tyr Ile Asn Leu Ile Thr Arg
1               5                   10                  15

Gln Arg Tyr

<210> SEQ ID NO 229
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is MeLeu
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 229

Xaa Ala Arg Tyr Tyr Ser Ala Leu Arg His Tyr Ile Asn Leu Ile Thr
1               5                   10                  15

Arg Gln Arg Tyr
            20

<210> SEQ ID NO 230
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION
<220> FEATURE:
<221> NAME/KEY: MOD_RES
<222> LOCATION: (1)..(1)
<223> OTHER INFORMATION: METHYLATION

<400> SEQUENCE: 230

Leu Ala Arg Tyr Tyr Ser Ala Leu Arg His Tyr Ile Asn Leu Ile Thr
1               5                   10                  15

Arg Gln Arg Tyr
            20

<210> SEQ ID NO 231
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is desamino
<220> FEATURE:
```

```
<221> NAME/KEY: MOD_RES
<222> LOCATION: (19)..(19)
<223> OTHER INFORMATION: AMIDATION

<400> SEQUENCE: 231

Xaa Ala Arg Tyr Tyr Ser Ala Leu Arg His Tyr Ile Asn Leu Ile Thr
1               5                   10                  15

Arg Gln Arg Tyr
            20

<210> SEQ ID NO 232
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (19)..(19)
<223> OTHER INFORMATION: AMIDATION
<220> FEATURE:
<221> NAME/KEY: MOD_RES
<222> LOCATION: (1)..(1)
<223> OTHER INFORMATION: FORMYLATION

<400> SEQUENCE: 232

Ala Arg Tyr Tyr Ser Glu Leu Arg Arg Tyr Ile Asn Leu Ile Thr Arg
1               5                   10                  15

Gln Arg Tyr

<210> SEQ ID NO 233
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is Nva
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 233

Xaa Ala Arg Tyr Ala Ser Ala Leu Arg His Tyr Leu Asn Leu Ile Thr
1               5                   10                  15

Arg Gln Arg Tyr
            20

<210> SEQ ID NO 234
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 234
```

```
Ala Arg Tyr Tyr Thr Gln Leu Arg His Tyr Ile Asn Leu Ile Thr Arg
1               5                   10                  15

Gln Arg Tyr

<210> SEQ ID NO 235
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: desamino
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 235

Leu Ala Arg Tyr Tyr Ser Asn Leu Arg His Tyr Ile Asn Val Ile Thr
1               5                   10                  15

Arg Gln Arg Tyr
            20

<210> SEQ ID NO 236
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 236

Ala Arg Tyr Tyr Asp Ser Leu Arg His Tyr Ile Asn Thr Ile Thr Arg
1               5                   10                  15

Gln Arg Tyr

<210> SEQ ID NO 237
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 237

Ala Arg Tyr Tyr Ser Ala Leu Gln His Tyr Ile Asn Leu Leu Thr Arg
1               5                   10                  15

Pro Arg Tyr
```

```
<210> SEQ ID NO 238
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 238

Leu Ala Arg Tyr Tyr Ser Ala Leu Arg Gln Tyr Arg Asn Leu Ile Thr
1               5                   10                  15

Arg Gln Arg Phe
            20

<210> SEQ ID NO 239
<211> LENGTH: 18
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (18)..(18)
<223> OTHER INFORMATION: AMIDATION

<400> SEQUENCE: 239

Arg Tyr Tyr Ala Ser Leu Arg His Tyr Leu Asn Leu Val Thr Arg Gln
1               5                   10                  15

Arg Phe

<210> SEQ ID NO 240
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 240

Ser Arg Tyr Tyr Ala Ser Leu Arg His Tyr Leu Asn Leu Val Thr Arg
1               5                   10                  15

Gln Arg Tyr

<210> SEQ ID NO 241
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (19)..(19)
<223> OTHER INFORMATION: AMIDATION

<400> SEQUENCE: 241

Ser Arg Tyr Tyr Ala Ser Leu Arg His Phe Leu Asn Leu Val Thr Arg
1               5                   10                  15
Gln Arg Tyr

<210> SEQ ID NO 242
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is Nle
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 242

Xaa Ala Arg Tyr Tyr Asn Ala Leu Arg His Phe Ile Asn Leu Ile Thr
1               5                   10                  15
Arg Gln Arg Tyr
            20

<210> SEQ ID NO 243
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is D-Ala
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 243

Xaa Arg Tyr Glu Ser Ala Leu Arg His Tyr Ile Asn Leu Ile Thr Arg
1               5                   10                  15
His Arg Tyr

<210> SEQ ID NO 244
<211> LENGTH: 21
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (21)..(21)
<223> OTHER INFORMATION: AMIDATION
<220> FEATURE:
```

```
<221> NAME/KEY: MISC_FEATURE
<222> LOCATION: (1)..(1)
<223> OTHER INFORMATION: Xaa is Bz

<400> SEQUENCE: 244

Xaa Leu Ala Arg Tyr Tyr Ser Ala Leu Arg His Tyr Ile Asn Leu Ile
1               5                   10                  15

Thr Arg Pro Arg Phe
            20

<210> SEQ ID NO 245
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 245

Ala Leu Tyr Tyr Ser Ala Leu Arg His Phe Val Asn Leu Ile Thr Arg
1               5                   10                  15

Gln Arg Tyr

<210> SEQ ID NO 246
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is D-Ala
<220> FEATURE:
<221> NAME/KEY: MOD_RES
<222> LOCATION: (19)..(19)
<223> OTHER INFORMATION: AMIDATION

<400> SEQUENCE: 246

Xaa Arg Tyr Tyr Ser Ala Leu Arg His Tyr Val Asn Leu Ile Phe Arg
1               5                   10                  15

Gln Arg Tyr

<210> SEQ ID NO 247
<211> LENGTH: 18
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MISC_FEATURE
<222> LOCATION: (1)..(1)
<223> OTHER INFORMATION: Xaa is MeSer
<220> FEATURE:
<221> NAME/KEY: MOD_RES
<222> LOCATION: (18)..(18)
<223> OTHER INFORMATION: AMIDATION

<400> SEQUENCE: 247
```

```
Xaa Tyr Tyr Ser Ala Leu Arg His Tyr Ile Asn Met Ile Thr Arg Gln
1               5                   10                  15

Arg Phe

<210> SEQ ID NO 248
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 248

Arg Ile Arg Tyr Tyr Ser Ala Leu Arg His Phe Ile Asn Leu Ile Thr
1               5                   10                  15

Arg Gln Arg Phe
            20

<210> SEQ ID NO 249
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminal is bonded to -H
<220> FEATURE:
<221> NAME/KEY: MOD_RES
<222> LOCATION: (20)..(20)
<223> OTHER INFORMATION: AMIDATION

<400> SEQUENCE: 249

Leu Ser Arg Tyr Tyr Ser Ala Leu Arg His Phe Ile Asn Leu Ile Thr
1               5                   10                  15

Arg Gln Arg Tyr
            20

<210> SEQ ID NO 250
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (19)..(19)
<223> OTHER INFORMATION: AMIDATION
<220> FEATURE:
<221> NAME/KEY: MISC_FEATURE
<222> LOCATION: (1)..(1)
<223> OTHER INFORMATION: Xaa is MeIle

<400> SEQUENCE: 250

Xaa Arg Tyr Tyr Ser Ala Leu Gln His Phe Ile Asn Leu Ile Thr Arg
1               5                   10                  15

Gln Arg Tyr

<210> SEQ ID NO 251
<211> LENGTH: 19
<212> TYPE: PRT
```

```
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is D-Ser
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 251

Xaa Arg Tyr Tyr Ser Ala Leu Arg His Tyr Ile Asn Leu Ile Thr Arg
1               5                   10                  15

Gln Arg Phe

<210> SEQ ID NO 252
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (20)..(20)
<223> OTHER INFORMATION: AMIDATION

<400> SEQUENCE: 252

Met Ala Arg Tyr Tyr Ser Asp Leu Arg Arg Tyr Ile Asn Leu Ile Thr
1               5                   10                  15

Arg Gln Arg Tyr
            20

<210> SEQ ID NO 253
<211> LENGTH: 19
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MOD_RES
<222> LOCATION: (19)..(19)
<223> OTHER INFORMATION: AMIDATION

<400> SEQUENCE: 253

Ala Arg Tyr Tyr Ser Glu Leu Arg His Tyr Ile Ile Leu Ile Thr Arg
1               5                   10                  15

Gln Arg Tyr

<210> SEQ ID NO 254
<211> LENGTH: 20
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
```

```
<223> OTHER INFORMATION: Xaa is D-Ala
<220> FEATURE:
<221> NAME/KEY: MOD_RES
<222> LOCATION: (20)..(20)
<223> OTHER INFORMATION: AMIDATION

<400> SEQUENCE: 254

Xaa Ala Arg Tyr Tyr Ser Ala Leu Arg His Tyr Ile Asn Leu Ile Thr
1               5                   10                  15

Arg Gln Arg Tyr
            20

<210> SEQ ID NO 255
<211> LENGTH: 15
<212> TYPE: PRT
<213> ORGANISM: Artificial Sequence
<220> FEATURE:
<223> OTHER INFORMATION: Polypeptide variation

<400> SEQUENCE: 255

Ala Ser Leu Arg His Trp Leu Asn Leu Val Thr Arg Gln Arg Tyr
1               5                   10                  15

<210> SEQ ID NO 256
<211> LENGTH: 35
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (25)..(25)
<223> OTHER INFORMATION: Xaa is im-DNP-HIS; 2,2-diphenylalanine
      Hisitidine
<220> FEATURE:
<221> NAME/KEY: MOD_RES
<222> LOCATION: (35)..(35)
<223> OTHER INFORMATION: AMIDATION

<400> SEQUENCE: 256

Tyr Pro Ala Lys Glu Ala Pro Gly Glu Asp Ala Ser Pro Glu Glu Leu
1               5                   10                  15

Ser Thr Tyr Tyr Ala Ser Leu Arg Xaa Tyr Leu Asn Leu Val Thr Arg
            20                  25                  30

Glx Arg Tyr
        35

<210> SEQ ID NO 257
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (15)..(15)
<223> OTHER INFORMATION: AMIDATION

<400> SEQUENCE: 257

Ala Ser Leu Arg His Tyr Leu Asn Leu Val Thr Arg Gln Arg Tyr
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Polypeptide variation
<220> FEATURE:
```

```
<221> NAME/KEY: MOD_RES
<222> LOCATION: (15)..(15)
<223> OTHER INFORMATION: AMIDATION

<400> SEQUENCE: 258

Ala Ser Leu Arg His Tyr Leu Asn Leu Val Ala Arg Gln Arg Tyr
 1               5                  10                  15

<210> SEQ ID NO 259
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (15)..(15)
<223> OTHER INFORMATION: AMIDATION

<400> SEQUENCE: 259

Ala Ala Leu Arg His Tyr Leu Asn Leu Val Ala Arg Gln Arg Tyr
 1               5                  10                  15

<210> SEQ ID NO 260
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (15)..(15)
<223> OTHER INFORMATION: AMIDATION

<400> SEQUENCE: 260

Ala Ser Leu Arg His Tyr Glu Asn Leu Val Thr Arg Gln Arg Tyr
 1               5                  10                  15

<210> SEQ ID NO 261
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MISC_FEATURE
<222> LOCATION: (13)..(13)
<223> OTHER INFORMATION: Xaa is Ornithine
<220> FEATURE:
<221> NAME/KEY: MOD_RES
<222> LOCATION: (15)..(15)
<223> OTHER INFORMATION: AMIDATION

<400> SEQUENCE: 261

Ala Ser Leu Arg His Tyr Leu Asn Leu Val Thr Arg Xaa Arg Tyr
 1               5                  10                  15

<210> SEQ ID NO 262
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (5)..(5)
<223> OTHER INFORMATION: Xaa is p.Cl.Pro; 4-chlorophenylalanine
<220> FEATURE:
```

```
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 262

Ala Ser Leu Arg Xaa Tyr Leu Asn Leu Val Thr Arg Gln Arg Tyr
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 263

Ala Ser Leu Arg His Tyr Glu Asn Leu Val Thr Arg Gln Arg Tyr
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (15)..(15)
<223> OTHER INFORMATION: Xaa is N-Me-Tyr

<400> SEQUENCE: 264

Ala Ser Leu Arg His Phe Glu Asn Leu Val Thr Arg Gln Arg Xaa
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (13)..(13)
<223> OTHER INFORMATION: Xaa is Ornithine
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
```

```
<222> LOCATION: (15)..(15)
<223> OTHER INFORMATION: Xaa is N-Me-Tyr

<400> SEQUENCE: 265

Ala Ser Leu Arg His Tyr Glu Asn Leu Val Thr Arg Xaa Arg Xaa
 1               5                  10                  15

<210> SEQ ID NO 266
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: LIPID
<222> LOCATION: (1)..(1)
<223> OTHER INFORMATION: N-alpha-myristoyl
<220> FEATURE:
<221> NAME/KEY: MOD_RES
<222> LOCATION: (15)..(15)
<223> OTHER INFORMATION: AMIDATION

<400> SEQUENCE: 266

Ala Ser Leu Arg His Tyr Leu Asn Leu Val Thr Arg Gln Arg Tyr
 1               5                  10                  15

<210> SEQ ID NO 267
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-alpha-naphthateneacetyl
<220> FEATURE:
<221> NAME/KEY: MOD_RES
<222> LOCATION: (15)..(15)
<223> OTHER INFORMATION: AMIDATION

<400> SEQUENCE: 267

Ala Ser Leu Arg His Tyr Leu Asn Leu Val Thr Arg Gln Arg Tyr
 1               5                  10                  15

<210> SEQ ID NO 268
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (15)..(15)
<223> OTHER INFORMATION: Xaa is N-Me-Tyr
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (13)..(13)
<223> OTHER INFORMATION: Xaa is Ornithine

<400> SEQUENCE: 268

Ala Ser Leu Arg His Phe Glu Asn Leu Val Thr Arg Xaa Arg Xaa
 1               5                  10                  15
```

```
<210> SEQ ID NO 269
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 269

Ala Ser Leu Arg His Tyr Leu Asn Leu Val Thr Arg Gln Arg Tyr
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (6)..(6)
<223> OTHER INFORMATION: Xaa is 3-benzothienylalanine
<220> FEATURE:
<221> NAME/KEY: MOD_RES
<222> LOCATION: (7)..(7)
<223> OTHER INFORMATION: N-alpha-ACETYLATION
<220> FEATURE:
<221> NAME/KEY: MOD_RES
<222> LOCATION: (1)..(1)
<223> OTHER INFORMATION: N-alpha-ACETYLATION

<400> SEQUENCE: 270

Ala Ser Leu Arg His Xaa Leu Asn Leu Val Thr Arg Gln Arg Tyr
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: Xaa is 4,4'-biphenylalanine
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (16)..(16)
<223> OTHER INFORMATION: AMIDATION

<400> SEQUENCE: 271

Xaa Ala Ser Leu Arg His Tyr Leu Asn Leu Val Thr Arg Gln Arg Tyr
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
```

```
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (6)..(6)
<223> OTHER INFORMATION: Xaa is 3-benzothienyalanine

<400> SEQUENCE: 272

Ala Ser Leu Arg His Xaa Leu Asn Leu Val Thr Arg Gln Arg Tyr
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (6)..(6)
<223> OTHER INFORMATION: Xaa is 3-benzothienyalanine

<400> SEQUENCE: 273

Ala Ser Leu Arg His Xaa Leu Asn Leu Val Thr Arg Gln Arg Tyr
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 274

Ala Ser Leu Arg His Trp Leu Asn Leu Val Thr Arg Gln Arg Tyr
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 275

Ala Ser Leu Arg His Trp Leu Asn Leu Val Thr Arg Gln Arg Tyr
```

-continued

```
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (6)..(6)
<223> OTHER INFORMATION: Xaa is 2-thienylalanine

<400> SEQUENCE: 276

Ala Ser Leu Arg Asn Xaa Leu Asn Leu Val Thr Arg Gln Arg Tyr
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (6)..(6)
<223> OTHER INFORMATION: Xaa is tetrahydroisoquinoline

<400> SEQUENCE: 277

Ala Ser Leu Arg His Xaa Leu Asn Leu Val Thr Arg Gln Arg Tyr
1               5                   10                  15

<210> SEQ ID NO 278
<211> LENGTH: 3
<212> TYPE: PRT
<213> ORGANISM: Homo sapiens

<400> SEQUENCE: 278

Ala Ala Ala
1

<210> SEQ ID NO 279
<211> LENGTH: 11
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (11)..(11)
<223> OTHER INFORMATION: AMIDATION

<400> SEQUENCE: 279
```

His Phe Leu Asn Leu Val Thr Arg Gln Arg Tyr
1               5                   10

<210> SEQ ID NO 280
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (15)..(15)
<223> OTHER INFORMATION: AMIDATION
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: Xaa is 2-thienylalanine

<400> SEQUENCE: 280

Ala Ser Leu Arg His Phe Leu Asn Leu Val Thr Arg Gln Arg Xaa
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (16)..(16)
<223> OTHER INFORMATION: AMIDATION
<220> FEATURE:
<221> NAME/KEY: MISC_FEATURE
<222> LOCATION: (6)..(6)
<223> OTHER INFORMATION: Xaa is 4-Thiazolylalanine

<400> SEQUENCE: 281

Ala Ser Leu Arg His Xaa Phe Leu Asn Leu Val Thr Arg Gln Arg Tyr
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (16)..(16)
<223> OTHER INFORMATION: AMIDATION
<220> FEATURE:
<221> NAME/KEY: MISC_FEATURE
<222> LOCATION: (6)..(6)
<223> OTHER INFORMATION: Xaa is 4-Thiazolylalanine

<400> SEQUENCE: 282

Ala Ser Leu Arg His Xaa Phe Leu Asn Leu Val Thr Arg Gln Arg Tyr
1               5                   10                  15

```
<210> SEQ ID NO 283
<211> LENGTH: 3
<212> TYPE: PRT
<213> ORGANISM: Homo sapiens

<400> SEQUENCE: 283

Ala Ala Ala
1

<210> SEQ ID NO 284
<211> LENGTH: 3
<212> TYPE: PRT
<213> ORGANISM: Homo sapiens

<400> SEQUENCE: 284

Ala Ala Ala
1

<210> SEQ ID NO 285
<211> LENGTH: 3
<212> TYPE: PRT
<213> ORGANISM: Homo sapiens

<400> SEQUENCE: 285

Ala Ala Ala
1

<210> SEQ ID NO 286
<211> LENGTH: 3
<212> TYPE: PRT
<213> ORGANISM: Homo sapiens

<400> SEQUENCE: 286

Ala Ala Ala
1

<210> SEQ ID NO 287
<211> LENGTH: 3
<212> TYPE: PRT
<213> ORGANISM: Homo sapiens

<400> SEQUENCE: 287

Ala Ala Ala
1

<210> SEQ ID NO 288
<211> LENGTH: 3
<212> TYPE: PRT
<213> ORGANISM: Homo sapiens

<400> SEQUENCE: 288

Ala Ala Ala
1

<210> SEQ ID NO 289
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
```

```
<400> SEQUENCE: 289

Phe Ser Leu Arg Asn Phe Leu Asn Leu Val Thr Arg Gln Arg Tyr
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 290

Tyr Ser Leu Arg His Phe Leu Asn Leu Val Thr Arg Gln Arg Tyr
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 291

Ala Ser Leu Arg His Tyr Trp Asn Leu Val Thr Arg Gln Arg Tyr
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 292

Ala Ser Leu Arg His Tyr Leu Asn Trp Val Thr Arg Gln Arg Tyr
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
```

```
<220> FEATURE:
<221> NAME/KEY: MOD_RES
<222> LOCATION: (15)..(15)
<223> OTHER INFORMATION: AMIDATION

<400> SEQUENCE: 293

Ala Ser Leu Arg Ala Phe Leu Asn Leu Val Thr Arg Gln Arg Tyr
1               5                   10                  15

<210> SEQ ID NO 294
<211> LENGTH: 14
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (14)..(14)
<223> OTHER INFORMATION: AMIDATION
<220> FEATURE:
<221> NAME/KEY: MISC_FEATURE
<222> LOCATION: (5)..(5)
<223> OTHER INFORMATION: Xaa is 3'-benzothienylalanine

<400> SEQUENCE: 294

Ala Ser Leu Arg Xaa Leu Asn Leu Val Thr Arg Gln Arg Tyr
1               5                   10

<210> SEQ ID NO 295
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 295

Ala Ser Leu Arg His Phe Leu Asn Leu Val Thr Arg Gln Arg Tyr
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 296

Ala Ser Leu Arg His Phe Leu Asn Leu Val Thr Arg Gln Arg Phe
1               5                   10                  15

<210> SEQ ID NO 297
<211> LENGTH: 15
```

```
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (11)..(11)
<223> OTHER INFORMATION: Xaa is D-Trp
<220> FEATURE:
<221> NAME/KEY: MOD_RES
<222> LOCATION: (11)..(11)
<223> OTHER INFORMATION: AMIDATION
<220> FEATURE:
<221> NAME/KEY: MOD_RES
<222> LOCATION: (11)..(11)
<223> OTHER INFORMATION: N-alpha-ACETYLATION

<400> SEQUENCE: 297

Ala Ser Leu Arg His Phe Leu Asn Leu Val Xaa Arg Gln Arg Tyr
1               5                   10                  15

<210> SEQ ID NO 298
<211> LENGTH: 13
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (13)..(13)
<223> OTHER INFORMATION: AMIDATION
<220> FEATURE:
<221> NAME/KEY: MISC_FEATURE
<222> LOCATION: (1)..(1)
<223> OTHER INFORMATION: N-terminus is bonded to CH3CO-

<400> SEQUENCE: 298

Leu Arg His Tyr Leu Asn Leu Leu Thr Arg Gln Arg Tyr
1               5                   10

<210> SEQ ID NO 299
<211> LENGTH: 13
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (13)..(13)
<223> OTHER INFORMATION: AMIDATION
<220> FEATURE:
<221> NAME/KEY: MISC_FEATURE
<222> LOCATION: (1)..(1)
<223> OTHER INFORMATION: N-terminus is bonded to CH3CO-

<400> SEQUENCE: 299

Leu Arg His Tyr Ile Asn Leu Ile Thr Arg Gln Arg Tyr
1               5                   10

<210> SEQ ID NO 300
<211> LENGTH: 13
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: AMIDATION
<220> FEATURE:
<221> NAME/KEY: MOD_RES
<222> LOCATION: (13)..(13)
<223> OTHER INFORMATION: AMIDATION
```

```
<400> SEQUENCE: 300

Leu Arg His Tyr Leu Asn Leu Leu Thr Arg Gln Arg Tyr
1               5                   10

<210> SEQ ID NO 301
<211> LENGTH: 13
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: AMIDATION
<220> FEATURE:
<221> NAME/KEY: MOD_RES
<222> LOCATION: (13)..(13)
<223> OTHER INFORMATION: AMIDATION

<400> SEQUENCE: 301

Leu Arg His Tyr Ile Asn Leu Ile Thr Arg Gln Arg Tyr
1               5                   10

<210> SEQ ID NO 302
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (15)..(15)
<223> OTHER INFORMATION: Xaa is a pseudopeptide bond consisting of
      --CH2--NH--
<220> FEATURE:
<221> NAME/KEY: MISC_FEATURE
<222> LOCATION: (14)..(14)
<223> OTHER INFORMATION: Xaa is a pseudopeptide bond consisting of
      --CH2--NH--
<220> FEATURE:
<221> NAME/KEY: MISC_FEATURE
<222> LOCATION: (10)..(10)
<223> OTHER INFORMATION: Xaa is Norvaline
<220> FEATURE:
<221> NAME/KEY: MISC_FEATURE
<222> LOCATION: (3)..(3)
<223> OTHER INFORMATION: Xaa is Norleucine
<220> FEATURE:
<221> NAME/KEY: MISC_FEATURE
<222> LOCATION: (7)..(7)
<223> OTHER INFORMATION: Xaa is Norleucine
<220> FEATURE:
<221> NAME/KEY: MISC_FEATURE
<222> LOCATION: (9)..(9)
<223> OTHER INFORMATION: Xaa is Norleucine

<400> SEQUENCE: 302

Ala Ser Xaa Arg His Trp Xaa Asn Xaa Xaa Thr Arg Gln Xaa Xaa
1               5                   10                  15

<210> SEQ ID NO 303
<211> LENGTH: 15
<212> TYPE: PRT
<213> ORGANISM: Artificial Sequence
<220> FEATURE:
<223> OTHER INFORMATION: Polypeptide variation
```

```
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (15)..(15)
<223> OTHER INFORMATION: Xaa is a pseudopeptide bond consisting of
      --CH2--NH--
<220> FEATURE:
<221> NAME/KEY: MISC_FEATURE
<222> LOCATION: (14)..(14)
<223> OTHER INFORMATION: Xaa is a pseudopeptide bond consisting of
      --CH2--NH--
<220> FEATURE:
<221> NAME/KEY: MISC_FEATURE
<222> LOCATION: (3)..(3)
<223> OTHER INFORMATION: Xaa is Norleucine
<220> FEATURE:
<221> NAME/KEY: MISC_FEATURE
<222> LOCATION: (7)..(7)
<223> OTHER INFORMATION: Xaa is Norleucine
<220> FEATURE:
<221> NAME/KEY: MISC_FEATURE
<222> LOCATION: (10)..(10)
<223> OTHER INFORMATION: Xaa is Norvaline

<400> SEQUENCE: 303

Ala Ser Xaa Arg His Trp Xaa Asn Trp Xaa Thr Arg Gln Xaa Xaa
1               5                   10                  15

<210> SEQ ID NO 304
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (15)..(15)
<223> OTHER INFORMATION: Xaa is a pseudopeptide bond consisting of
      --CH2--NH--
<220> FEATURE:
<221> NAME/KEY: MISC_FEATURE
<222> LOCATION: (14)..(14)
<223> OTHER INFORMATION: Xaa is a pseudopeptide bond consisting of
      --CH2--NH--
<220> FEATURE:
<221> NAME/KEY: MISC_FEATURE
<222> LOCATION: (3)..(3)
<223> OTHER INFORMATION: Xaa is Norleucine
<220> FEATURE:
<221> NAME/KEY: MISC_FEATURE
<222> LOCATION: (7)..(7)
<223> OTHER INFORMATION: Xaa is Norleucine
<220> FEATURE:
<221> NAME/KEY: MISC_FEATURE
<222> LOCATION: (9)..(9)
<223> OTHER INFORMATION: Xaa is Norleucine
<220> FEATURE:
<221> NAME/KEY: MISC_FEATURE
<222> LOCATION: (10)..(10)
<223> OTHER INFORMATION: Xaa is Norvaline

<400> SEQUENCE: 304
```

```
Ala Ser Xaa Arg His Phe Xaa Asn Xaa Xaa Thr Arg Gln Xaa Xaa
1               5                   10                  15

<210> SEQ ID NO 305
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (15)..(15)
<223> OTHER INFORMATION: Xaa is a pseudopeptide bond consisting of
      --CH2--NH--
<220> FEATURE:
<221> NAME/KEY: MISC_FEATURE
<222> LOCATION: (14)..(14)
<223> OTHER INFORMATION: Xaa is a pseudopeptide bond consisting of
      --CH2--NH--
<220> FEATURE:
<221> NAME/KEY: MISC_FEATURE
<222> LOCATION: (3)..(3)
<223> OTHER INFORMATION: Xaa is Norleucine
<220> FEATURE:
<221> NAME/KEY: MISC_FEATURE
<222> LOCATION: (7)..(7)
<223> OTHER INFORMATION: Xaa is Norleucine
<220> FEATURE:
<221> NAME/KEY: MISC_FEATURE
<222> LOCATION: (10)..(10)
<223> OTHER INFORMATION: Xaa is Norvaline

<400> SEQUENCE: 305

Ala Ser Xaa Arg His Phe Xaa Asn Trp Xaa Thr Arg Gln Xaa Xaa
1               5                   10                  15

<210> SEQ ID NO 306
<211> LENGTH: 12
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (12)..(12)
<223> OTHER INFORMATION: AMIDATION
<220> FEATURE:
<221> NAME/KEY: MISC_FEATURE
<222> LOCATION: (12)..(12)
<223> OTHER INFORMATION: Xaa is a pseudopeptide bond consiting of
      --CH2--NH--
<220> FEATURE:
<221> NAME/KEY: MISC_FEATURE
<222> LOCATION: (11)..(11)
<223> OTHER INFORMATION: Xaa is a pseudopeptide bond consiting of
      --CH2--NH--

<400> SEQUENCE: 306

Arg His Tyr Leu Asn Trp Val Thr Arg Gln Xaa Xaa
1               5                   10

<210> SEQ ID NO 307
<211> LENGTH: 12
```

```
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (12)..(12)
<223> OTHER INFORMATION: AMIDATION

<400> SEQUENCE: 307

Arg His Tyr Leu Asn Trp Val Thr Arg Gln Arg Tyr
1               5                   10

<210> SEQ ID NO 308
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (14)..(14)
<223> OTHER INFORMATION: Xaa is a psuedopeptide bond consisting of
      --CH2--NH2
<220> FEATURE:
<221> NAME/KEY: MISC_FEATURE
<222> LOCATION: (15)..(15)
<223> OTHER INFORMATION: Xaa is a psuedopeptide bond consisting of
      --CH2--NH2
<220> FEATURE:
<221> NAME/KEY: MISC_FEATURE
<222> LOCATION: (7)..(7)
<223> OTHER INFORMATION: Xaa is Norleucine
<220> FEATURE:
<221> NAME/KEY: MISC_FEATURE
<222> LOCATION: (10)..(10)
<223> OTHER INFORMATION: Xaa is Norvaline

<400> SEQUENCE: 308

Ala Ser Leu Arg His Tyr Xaa Asn Trp Xaa Thr Arg Gln Xaa Xaa
1               5                   10                  15

<210> SEQ ID NO 309
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION
<220> FEATURE:
<221> NAME/KEY: MISC_FEATURE
<222> LOCATION: (15)..(15)
<223> OTHER INFORMATION: Xaa is a pseudopeptide bond consisting of
      --CH2--NH2--
<220> FEATURE:
<221> NAME/KEY: MISC_FEATURE
<222> LOCATION: (14)..(14)
```

```
<223> OTHER INFORMATION: Xaa is a pseudopeptide bond consisting of
      --CH2--NH2--
<220> FEATURE:
<221> NAME/KEY: MISC_FEATURE
<222> LOCATION: (3)..(3)
<223> OTHER INFORMATION: Xaa is Norleucine
<220> FEATURE:
<221> NAME/KEY: MISC_FEATURE
<222> LOCATION: (7)..(7)
<223> OTHER INFORMATION: Xaa is Norleucine
<220> FEATURE:
<221> NAME/KEY: MISC_FEATURE
<222> LOCATION: (10)..(10)
<223> OTHER INFORMATION: Xaa is Norvaline

<400> SEQUENCE: 309

Ala Ser Xaa Arg His Tyr Xaa Asn Trp Xaa Thr Arg Gln Xaa Xaa
1               5                   10                  15

<210> SEQ ID NO 310
<211> LENGTH: 9
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (9)..(9)
<223> OTHER INFORMATION: bonded to -OCH3
<220> FEATURE:
<221> NAME/KEY: MISC_FEATURE
<222> LOCATION: (1)..(1)
<223> OTHER INFORMATION: N-terminus is bonded to -H

<400> SEQUENCE: 310

Ile Asn Pro Ile Tyr Arg Leu Arg Tyr
1               5

<210> SEQ ID NO 311
<211> LENGTH: 9
<212> TYPE: PRT
<213> ORGANISM: Artificial Sequence
<220> FEATURE:
<223> OTHER INFORMATION: Polypeptide variation
<220> FEATURE:
<221> NAME/KEY: DISULFID
<222> LOCATION: (4)..(4)
<223> OTHER INFORMATION: Sequence is linked to identical sequence by a
      disulfide bond
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MISC_FEATURE
<222> LOCATION: (9)..(9)
<223> OTHER INFORMATION: C-terminus is bonded to -NH2

<400> SEQUENCE: 311

Ile Asn Pro Cys Tyr Arg Leu Arg Tyr
1               5

<210> SEQ ID NO 312
<211> LENGTH: 6
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (6)..(6)
<223> OTHER INFORMATION: C-terminus is bonded to -OCH3
<220> FEATURE:
<221> NAME/KEY: DISULFID
```

```
<222> LOCATION: (1)..(1)
<223> OTHER INFORMATION: sequence is linked to an identical sequence
<220> FEATURE:
<221> NAME/KEY: MISC_FEATURE
<222> LOCATION: (1)..(1)
<223> OTHER INFORMATION: N-terminus is bonded to -H

<400> SEQUENCE: 312

Cys Tyr Arg Leu Arg Tyr
1               5

<210> SEQ ID NO 313
<211> LENGTH: 8
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MISC_FEATURE
<222> LOCATION: (3)..(4)
<223> OTHER INFORMATION: Connected by --NH---CH--CO--
<220> FEATURE:
<221> NAME/KEY: MISC_FEATURE
<222> LOCATION: (3)..(4)
<223> OTHER INFORMATION: Identical peptide chains are connected by
      --(CH2)4-- at the -CH of --NH--CH--CO--

<400> SEQUENCE: 313

Ile Asn Pro Tyr Arg Leu Arg Tyr
1               5

<210> SEQ ID NO 314
<211> LENGTH: 10
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminus is bonded to -H
<220> FEATURE:
<221> NAME/KEY: MISC_FEATURE
<222> LOCATION: (5)..(5)
<223> OTHER INFORMATION: C-terminus is bonded to -OCH3

<400> SEQUENCE: 314

Tyr Arg Leu Arg Tyr Tyr Arg Leu Arg Tyr
1               5                   10

<210> SEQ ID NO 315
<211> LENGTH: 34
<212> TYPE: PRT
<213> ORGANISM: Artificial Sequence
<220> FEATURE:
<223> OTHER INFORMATION: Polypeptide variation
<220> FEATURE:
<221> NAME/KEY: DISULFID
<222> LOCATION: (18)..(22)
<223> OTHER INFORMATION:

<400> SEQUENCE: 315

Ser Lys Pro Asp Asn Pro Gly Glu Asp Ala Pro Ala Glu Asp Met Ala
1               5                   10                  15

Arg Cys Tyr Ser Ala Cys Arg His Tyr Ile Asn Leu Ile Thr Arg Gln
            20                  25                  30

Arg Tyr
```

<210> SEQ ID NO 316
<211> LENGTH: 12
<212> TYPE: PRT
<213> ORGANISM: Artificial Sequence
<220> FEATURE:
<223> OTHER INFORMATION: Polypeptide variation

<400> SEQUENCE: 316

Arg His Tyr Leu Asn Leu Ile Gly Arg Gln Arg Tyr
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (3)..(7)
<223> OTHER INFORMATION: ACETYLATION

<400> SEQUENCE: 317

Arg His Gly Leu Asn Leu Leu Gly Arg Gln Arg Tyr
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Polypeptide variation

<400> SEQUENCE: 318

Tyr Ile Asn Leu Ile Tyr Arg Leu Arg Tyr
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Polypeptide variation

<400> SEQUENCE: 319

His Tyr Ile Asn Leu Ile Tyr Arg Leu Arg Tyr
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Polypeptide variation

<400> SEQUENCE: 320

Arg His Tyr Ile Asn Leu Ile Tyr Arg Leu Arg Tyr
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Polypeptide variation

<400> SEQUENCE: 321

```
Tyr Ile Asn Leu Leu Tyr Arg Gln Arg Tyr
1               5                   10

<210> SEQ ID NO 322
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MISC_FEATURE
<222> LOCATION: (5)..(5)
<223> OTHER INFORMATION: Xaa is 6-amino hexanoic acid

<400> SEQUENCE: 322

Tyr Pro Ser Leu Xaa Tyr Ile Asn Leu Ile Tyr Arg Leu Arg Tyr
1               5                   10                  15

<210> SEQ ID NO 323
<211> LENGTH: 9
<212> TYPE: PRT
<213> ORGANISM: Artificial Sequence
<220> FEATURE:
<223> OTHER INFORMATION: Polypeptide variation

<400> SEQUENCE: 323

Ile Asn Leu Ile Tyr Arg Leu Arg Tyr
1               5

<210> SEQ ID NO 324
<211> LENGTH: 12
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (12)..(12)
<223> OTHER INFORMATION: AMIDATION

<400> SEQUENCE: 324

Arg His Phe Leu Asn Leu Val Thr Arg Gln Arg Tyr
1               5                   10

<210> SEQ ID NO 325
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 325

Ala Ser Leu Arg His Phe Leu Asn Leu Val Thr Arg Gln Arg Tyr
1               5                   10                  15

<210> SEQ ID NO 326
<211> LENGTH: 15
<212> TYPE: PRT
<213> ORGANISM: Artificial Sequence
```

```
<220> FEATURE:
<223> OTHER INFORMATION: Polypeptide variation
<220> FEATURE:
<221> NAME/KEY: MISC_FEATURE
<222> LOCATION: (1)..(1)
<223> OTHER INFORMATION: N-terminal is bonded to -H
<220> FEATURE:
<221> NAME/KEY: MOD_RES
<222> LOCATION: (15)..(15)
<223> OTHER INFORMATION: AMIDATION

<400> SEQUENCE: 326

Ala Ser Leu Arg His Phe Leu Asn Leu Val Thr Arg Gln Arg Tyr
1               5                   10                  15

<210> SEQ ID NO 327
<211> LENGTH: 9
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (9)..(9)
<223> OTHER INFORMATION: AMIDATION
<220> FEATURE:
<221> NAME/KEY: MOD_RES
<222> LOCATION: (1)..(1)
<223> OTHER INFORMATION: N-alpha-ACETYLATION

<400> SEQUENCE: 327

Ala Ser Leu Arg Thr Arg Gln Arg Tyr
1               5

<210> SEQ ID NO 328
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MISC_FEATURE
<222> LOCATION: (6)..(6)
<223> OTHER INFORMATION: Xaa is 2-thienylalanine
<220> FEATURE:
<221> NAME/KEY: MOD_RES
<222> LOCATION: (15)..(15)
<223> OTHER INFORMATION: AMIDATION

<400> SEQUENCE: 328

Ala Ser Leu Arg His Xaa Leu Asn Leu Val Thr Arg Gln Arg Tyr
1               5                   10                  15

<210> SEQ ID NO 329
<211> LENGTH: 15
<212> TYPE: PRT
<213> ORGANISM: Artificial Sequence
<220> FEATURE:
<223> OTHER INFORMATION: Polypeptide variation
<220> FEATURE:
<221> NAME/KEY: MOD_RES
<222> LOCATION: (1)..(1)
<223> OTHER INFORMATION: N-alpha-ACETYLATION
<220> FEATURE:
<221> NAME/KEY: MOD_RES
<222> LOCATION: (15)..(15)
<223> OTHER INFORMATION: AMIDATION

<400> SEQUENCE: 329
```

Tyr Ser Leu Arg His Phe Leu Asn Leu Val Thr Arg Gln Arg Tyr
1               5                   10                  15

<210> SEQ ID NO 330
<211> LENGTH: 5
<212> TYPE: PRT
<213> ORGANISM: Artificial Sequence
<220> FEATURE:
<223> OTHER INFORMATION: Polypeptide variation

<400> SEQUENCE: 330

Asp Asp Asp Asp Tyr
1               5

<210> SEQ ID NO 331
<211> LENGTH: 3
<212> TYPE: PRT
<213> ORGANISM: Artificial Sequence
<220> FEATURE:
<223> OTHER INFORMATION: Polypeptide variation

<400> SEQUENCE: 331

Gly Pro Arg
1

<210> SEQ ID NO 332
<211> LENGTH: 3
<212> TYPE: PRT
<213> ORGANISM: Artificial Sequence
<220> FEATURE:
<223> OTHER INFORMATION: Polypeptide variation

<400> SEQUENCE: 332

Ala Gly Gly
1

<210> SEQ ID NO 333
<211> LENGTH: 5
<212> TYPE: PRT
<213> ORGANISM: Artificial Sequence
<220> FEATURE:
<223> OTHER INFORMATION: Polypeptide variation

<400> SEQUENCE: 333

His Pro Phe His Leu
1               5

<210> SEQ ID NO 334
<211> LENGTH: 34
<212> TYPE: PRT
<213> ORGANISM: Homo sapiens

<400> SEQUENCE: 334

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
                20                  25                  30

Arg Tyr

<210> SEQ ID NO 335
<211> LENGTH: 34
<212> TYPE: PRT
<213> ORGANISM: Artificial Sequence
<220> FEATURE:
<223> OTHER INFORMATION: Polypeptide variation

<400> SEQUENCE: 335

```
Ser Lys Pro Asp Asn Pro Gly Glu Asp Ala Pro Ala Glu Asp Met Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 336
<211> LENGTH: 204
<212> TYPE: DNA
<213> ORGANISM: Homo sapiens

<400> SEQUENCE: 336
ggagactgag ctgagtgcct gtaaaaaggc cacttcaagc cccctccacg cagccattgt      60
tgggtctgga ggaaggagga ccgctcggaa gcttctgaat gccgcccgt  gatgcactca     120 ctaatggatg tgcattagtg gcgtccttcc tggccaccac gtcactctcc ctacctcaac    180
tgctggctgg agaactccgc attc                                            204

<210> SEQ ID NO 337
<211> LENGTH: 190
<212> TYPE: DNA
<213> ORGANISM: Bos taurus
<220> FEATURE:
<221> NAME/KEY: misc_feature
<222> LOCATION: (146)..(146)
<223> OTHER INFORMATION: n is any nucleotide

<400> SEQUENCE: 337
ggggactgag ctgagtgcct gttaaaaagg ccacttcagc cccttccatg cagcctttgt      60
tggctcgaga ggaaggagga tggttccggg ggcctctgaa tgcacctaat ggatgtgcat    120
tatcagcgtc cttcctggcc actgcnggca ctctccccac ctccacccct ggctggagaa    180
ctcagcattc                                                            190

<210> SEQ ID NO 338
<211> LENGTH: 189
<212> TYPE: DNA
<213> ORGANISM: Mesocricetus sp.

<400> SEQUENCE: 338
gggactgagc tgagtgcctg taaaaaggcc acttcaagcc ccattgtggg gatagcagca     60
ggtgggcatg tctgcgcttt gaatgcctct tccctgatgc actgcgctaa tggatgtgca    120
ttaacggcgt ccttcctggc cactgtgtct acctcccttc cccaggcccc gatggagaac    180
tccgcattc                                                             189

<210> SEQ ID NO 339
<211> LENGTH: 191
<212> TYPE: DNA
<213> ORGANISM: Mus musculus

<400> SEQUENCE: 339
tgggactgag ctgagtgcct gtaaaaaggc cacttcaagc cccattgtgg ggacagcagc     60
aggtgggcaa gtttgagctt tgaatgcctc ttcccgtgat gcactacgct aatggatgtg    120
cattaacagt gtccttcctg ccaccgcat cgctcgcctt tcctcaggcc ctgctggaga    180
actctgcatt c                                                          191

<210> SEQ ID NO 340
<211> LENGTH: 184
```

```
<212> TYPE: DNA
<213> ORGANISM: Rattus sp.

<400> SEQUENCE: 340
agggactgag ctgagtgcct gtaaaaaggc cacttcaagc cccattgtgg ggccagcagc       60
aggtgggcaa gtctgagctt tgaatgcctc ttcccatgat gcattgcgct aatggatgtg      120
cattaacagt gtccttcctc cattgctctc ttttccttag accctgctgg agaactctgc      180
attc                                                                   184

<210> SEQ ID NO 341
<211> LENGTH: 408
<212> TYPE: DNA
<213> ORGANISM: Homo sapiens

<400> SEQUENCE: 341
ttctggaaaa gtagcagtca tgctcgagcc cctaacaaag gcctgtcccc cacaaaagga       60
ccattatgac caccgctgag tcagaatggt ggccgctggc acctgagctc tgtctggaaa      120
gagcggcagc agggacgtca tctagcagag cctggtgtgt ctgttatgtc cacaacatct      180
tcagcaaaga cactacttcc aggaagtcta cttggattgc agaggcgcaa gccttcattg      240
tgaaaaaagg gcttgggata aggagtggtt ctaaaagaat acatgtggct ccacatggca      300
atatacccag gtgtaataag ctcagggtaa gagagaacct gccattgctg atgcaggact      360
gtgcacacaa acttacaggc tctctactgg ggtgtcccat ggaactgg                   408

<210> SEQ ID NO 342
<211> LENGTH: 387
<212> TYPE: DNA
<213> ORGANISM: Mus musculus

<400> SEQUENCE: 342
cctgaggaag ggcagcagtc agtgcctaaa ggccccagaa tggggccatt gtggtcatca       60
ctgagtcaca ctagtgacta ctggcacctg agctcagtct ggagtaagtg gtttcaggga      120
cgtcatctgg gagagtctgg tgcgagtcta acgtccagga catttcagc aaagactgca      180 cctccaggaa gtccattctg actgcccaga acaaaccct cattttgaaa agagagtttg      240
ggctaaggca agcttgggaa agggcacaaa aggctctgcg gaggaacacg cctacgcctt      300
gatccaggga acaagagtgg gatgttctaa cagccttgca ccacgccacg ccacgccatt      360
gcgatggcat tagtgctgcg tgtagga                                          387

<210> SEQ ID NO 343
<211> LENGTH: 385
<212> TYPE: DNA
<213> ORGANISM: Rattus sp.

<400> SEQUENCE: 343
cctgaggaag agcagcagtc agtgcctgag ggcctcacaa agggcccatt gtggtcctca       60
ctgagtcaga ctggtgactg ctggcacccg agctcagtct ggagtaagtg gttgcaggga      120
cgtcatccgc gagagtctgg tgtgactcta atatccagga catcttcagc aaagactgca      180
cctccaggaa gtccattctg actgcccaga acaaaccct cattttgaaa agagcgtttg      240
agctaaggca agcttgggaa agggcacaag aggctctgca gaagaacacg cctacgcctt      300
gagccaggga acaagagcgt gatgttctaa cgcagggccc tgcgtcacac ggccttgcac      360
cacaccattc catcatgatg caatg                                            385
```

```
<210> SEQ ID NO 344
<211> LENGTH: 231
<212> TYPE: DNA
<213> ORGANISM: Homo sapiens

<400> SEQUENCE: 344
ggctgctgca ctaatgcgcg cattagtgga taaaagcagt ctcaagggtc tcttcacgag      60
gtccctttgg ctggaataaa gcaaattaaa accccattca aggtcaatt gaaatctctt     120 tcattccagt tctctgcaca aattgattcc tctttgccct tgaggtcaaa ccgaaggctg     180
gtgaagtagc ccagctgcag tgctgcatga gagaagctca atgaaaaggc t             231

<210> SEQ ID NO 345
<211> LENGTH: 136
<212> TYPE: DNA
<213> ORGANISM: Bos taurus

<400> SEQUENCE: 345
ggataaaagc ggtctcaagg gtctcttcat gaggctcctt tggctgtaat aaagcaaatt      60
aaaaccccat tcaaaggtca attgaaatcg cttccattcc cattctttgc acaaattgat     120
tcctctttgc ccttga                                                     136

<210> SEQ ID NO 346
<211> LENGTH: 226
<212> TYPE: DNA
<213> ORGANISM: Mus musculus

<400> SEQUENCE: 346
ggctactgtg ctaatacatg cattagtgga tgaaagccgt ctcaaggggc tcttcaccag      60 ggcccctttgg ctgtaataaa gcaaattaaa accccatcca aggtcaatt gaaatctctt     120 tcattcttct tctccacaca aattgattcc tctttgccct tgaggttgca ctgaatgcca     180
taaaggggcc cagctgtagc tggatgggaa cagcctgaaa atggct                    226

<210> SEQ ID NO 347
<211> LENGTH: 136
<212> TYPE: DNA
<213> ORGANISM: Oryctolagus cuniculus

<400> SEQUENCE: 347
ggataaaagc tgtctcaagg ggctcttcac cgtggccctt tggctgtaat aaagcaaatt      60
aaaaccccat tcgaaggtca attgaaatct ctttcattcc acttctccac acaaattgat     120
tcctctttgc ccttga                                                     136

<210> SEQ ID NO 348
<211> LENGTH: 435
<212> TYPE: DNA
<213> ORGANISM: Mus musculus

<400> SEQUENCE: 348
gactgagctg agtgcctgta aaaaggccac ttcaagcccc attgtgggga cagcagcagg      60
tgggcaagtc tgagctttga atgcctcttc ccgtgatgca ctacgctaat ggatgtgcat     120
taacagtgtc cttcctggcc accgcatcgc tcgcctttcc tcaggccctg ctggagaact     180
ctgcattcct gaggaagggc agcagtcagt gcctaaaggc cccagaatgg ggccattgtg     240
gtcatcactg agtcacacta gtgactactg gcacctgagc tcagtctgga gtaagtggtt     300
tcagggacgt catctgggag agtctggtgc gagtctaacg tccaggacat ttcagcaaa     360 gactgcacct ccaggaagtc cattctgact gcccagaaac aaaccctcat tttgaaaaga    420
```

```
gagtttgggc taagg                                                       435

<210> SEQ ID NO 349
<211> LENGTH: 464
<212> TYPE: DNA
<213> ORGANISM: Homo sapiens

<400> SEQUENCE: 349
gactgagctg agtgcctgta aaaaggccac ttcaagcccc ctccacgcag ccattgttgg        60
gtctggagga aggaggaccg ctcggaagct tctgaatgcc gccctgtgat gcactcacta       120
atggatgtgc attagtggcg tccttcctgg ccaccacgtc actctcccta cctcaactgc       180
tggctggaga actccgcatt cttctggaaa agtagcagtc atgctcgagc ccctaacaaa       240
ggcctgtccc ccacaaaagg accattatga ccaccgctga gtcagaatgg tggccgctgg       300
cacctgagct ctgtctggaa agagcggcag cagggacgtc atctagcaga gcctggtgtg       360
tctgttatgt ccacaacatc ttcagcaaag acactacttc caggaagtct acttggattg       420
cagaggcgca agccttcatt gtgaaaaaag ggcttgggat aagg                       464

<210> SEQ ID NO 350
<211> LENGTH: 236
<212> TYPE: DNA
<213> ORGANISM: Mus musculus

<400> SEQUENCE: 350
ggctggggtg ggctactgtg ctaatacatg cattagtgga tgaaagccgt ctcaaggggc        60
tcttcaccag ggccctttgg ctgtaataaa gcaaattaaa accccatcca aggtcaatt       120 gaaatctctt tcattcttct ctccacaca aattgattcc tctttgccct tgaggttgca        180
ctgaatgcca taagggggcc cagctgtagc tggatgggaa cagcctgaaa atggct          236

<210> SEQ ID NO 351
<211> LENGTH: 231
<212> TYPE: DNA
<213> ORGANISM: Homo sapiens

<400> SEQUENCE: 351
ggctgctgca ctaatgcgcg cattagtgga taaaagcagt ctcaagggtc tcttcacgag        60 gtcccttttgg ctggaataaa gcaaattaaa accccattca aggtcaatt gaaatctctt       120 tcattccagt tctctgcaca aattgattcc tctttgccct tgaggtcaaa ccgaaggctg       180
gtgaagtagc ccagctgcag tgctgcatga gagaagctca atgaaaaggc t               231

<210> SEQ ID NO 352
<211> LENGTH: 17
<212> TYPE: DNA
<213> ORGANISM: Unknown
<220> FEATURE:
<223> OTHER INFORMATION: Homologous among Homo sapiens, Bos taurus,
      Oryctolagus cuniculus, Mus musculus, and Mesocricetus sp.

<400> SEQUENCE: 352
ctaatggatg tgcatta                                                      17
```